(12) United States Patent
McGinness et al.

(10) Patent No.: US 12,077,785 B2
(45) Date of Patent: Sep. 3, 2024

(54) CHIMERIC ANTIGEN RECEPTOR POLYPEPTIDES IN COMBINATION WITH TRANS METABOLISM MOLECULES MODULATING KREBS CYCLE AND THERAPEUTIC USES THEREOF

(71) Applicant: SOTIO BIOTECH INC., Boston, MA (US)

(72) Inventors: Kathleen McGinness, Cambridge, MA (US); Seth Ettenberg, Cambridge, MA (US); Luke Barron, Cambridge, MA (US); Michael Fray, Cambridge, MA (US); Charles Wilson, Cambridge, MA (US); Gregory Motz, Cambridge, MA (US)

(73) Assignee: SOTIO BIOTECH INC., Boston, MA (US)

( * ) Notice: Subject to any disclaimer, the term of this patent is extended or adjusted under 35 U.S.C. 154(b) by 485 days.

(21) Appl. No.: 17/268,345

(22) PCT Filed: Aug. 14, 2019

(86) PCT No.: PCT/US2019/046550
§ 371 (c)(1),
(2) Date: Feb. 12, 2021

(87) PCT Pub. No.: WO2020/037066
PCT Pub. Date: Feb. 20, 2020

(65) Prior Publication Data
US 2021/0332334 A1    Oct. 28, 2021

Related U.S. Application Data

(60) Provisional application No. 62/718,579, filed on Aug. 14, 2018, provisional application No. 62/718,491, filed on Aug. 14, 2018.

(51) Int. Cl.
| | | |
|---|---|---|
| *C12N 9/04* | (2006.01) | |
| *A61K 35/17* | (2015.01) | |
| *A61K 48/00* | (2006.01) | |
| *A61P 35/00* | (2006.01) | |
| *C07K 14/705* | (2006.01) | |
| *C07K 14/725* | (2006.01) | |
| *C07K 16/30* | (2006.01) | |
| *C12N 9/06* | (2006.01) | |
| *C12N 9/10* | (2006.01) | |
| *C12N 9/80* | (2006.01) | |
| *C12N 9/88* | (2006.01) | |

(52) U.S. Cl.
CPC .......... *C12N 9/0006* (2013.01); *A61K 35/17* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 16/303* (2013.01); *C12N 9/0016* (2013.01); *C12N 9/1096* (2013.01); *C12N 9/80* (2013.01); *C12N 9/88* (2013.01); *C12Y 101/01037* (2013.01); *C12Y 101/01042* (2013.01); *C12Y 104/01002* (2013.01); *C12Y 206/01001* (2013.01); *C12Y 206/01002* (2013.01); *C12Y 206/01052* (2013.01); *C12Y 305/01002* (2013.01); *C12Y 401/01032* (2013.01); *A61K 48/00* (2013.01); *C07K 2319/02* (2013.01); *C07K 2319/03* (2013.01)

(58) Field of Classification Search
CPC ...... C12N 9/0006; C12N 9/1096; C12N 9/80; C12N 2510/00; C12N 5/0638; C12N 15/62; A61K 35/17; C07K 14/7051; C07K 14/70521; C07K 2319/02; C07K 2319/03; C07K 14/705; C12Y 101/01037; C12Y 101/01042; C12Y 104/01002; C12Y 206/01052; C12Y 305/01002; C12Y 101/01041; C12Y 104/01003; C12Y 104/01004; C12Y 401/01049; C12Y 101/01095; C12Y 206/01015
See application file for complete search history.

(56) References Cited

U.S. PATENT DOCUMENTS

| | | | |
|---|---|---|---|
| 4,650,764 A | 3/1987 | Temin et al. | |
| 4,777,127 A | 10/1988 | Suni et al. | |
| 4,980,289 A | 12/1990 | Temin et al. | |
| 5,124,263 A | 6/1992 | Temin et al. | |

(Continued)

FOREIGN PATENT DOCUMENTS

| | | |
|---|---|---|
| EP | 0345242 A2 | 12/1989 |
| GB | 2200651 A | 8/1988 |

(Continued)

OTHER PUBLICATIONS

O'Sullivan, David, et al. "Targeting T cell metabolism for therapy" Trends in immunology, vol. 36, No. 2, pp. 71-80, Feb. 1, 2015.

(Continued)

*Primary Examiner* — Iqbal H Chowdhury
(74) *Attorney, Agent, or Firm* — Mintz, Levin, Cohn, Ferris, Glovsky and Popeo, P.C.

(57) ABSTRACT

Disclosed herein are genetically engineered hematopoietic cells, which express one or more Krebs cycle modulating polypeptides, and optionally a chimeric receptor polypeptide (e.g., an antibody-coupled T cell receptor (ACTR) polypeptide or a chimeric antigen receptor (CAR) polypeptide) capable of binding to a target antigen of interest. Also disclosed herein are uses of the engineered hematopoietic cells for inhibiting cells expressing a target antigen in a subject in need thereof.

23 Claims, 20 Drawing Sheets
Specification includes a Sequence Listing.

(56) References Cited

U.S. PATENT DOCUMENTS

| | | | |
|---|---|---|---|
| 5,219,740 | A | 6/1993 | Miller et al. |
| 5,399,346 | A | 3/1995 | Anderson et al. |
| 6,194,191 | B1 | 2/2001 | Zhang et al. |
| 7,052,906 | B1 | 5/2006 | Lawson et al. |
| 7,435,596 | B2 | 10/2008 | Campana et al. |
| 8,026,097 | B2 | 9/2011 | Campana et al. |
| 8,673,860 | B2 | 3/2014 | Schellenberger et al. |
| 10,138,479 | B2 | 11/2018 | Kimmelman et al. |
| 2014/0017213 | A1 | 1/2014 | Li et al. |
| 2014/0106449 | A1 | 4/2014 | June et al. |
| 2015/0139943 | A1 | 5/2015 | Campana et al. |
| 2017/0137783 | A1 | 5/2017 | Bedoya et al. |
| 2017/0281683 | A1 | 10/2017 | Heczey et al. |
| 2018/0142035 | A1 | 5/2018 | Lobb et al. |

FOREIGN PATENT DOCUMENTS

| | | |
|---|---|---|
| WO | 9007936 A1 | 7/1990 |
| WO | 9102805 A2 | 3/1991 |
| WO | 9303769 A1 | 3/1993 |
| WO | 93 10218 A1 | 5/1993 |
| WO | 9311230 A1 | 6/1993 |
| WO | 9319191 A1 | 9/1993 |
| WO | 9325234 A1 | 12/1993 |
| WO | 9325698 A1 | 12/1993 |
| WO | 9403622 A1 | 2/1994 |
| WO | 9412649 A2 | 6/1994 |
| WO | 9428938 A1 | 12/1994 |
| WO | 9500655 A1 | 1/1995 |
| WO | 9507358 A1 | 3/1995 |
| WO | 9511984 A2 | 5/1995 |
| WO | 9809271 A1 | 3/1998 |
| WO | 9958572 A1 | 11/1999 |
| WO | 0032776 A2 | 6/2000 |
| WO | 2006006693 A1 | 1/2006 |
| WO | 2013040557 A2 | 3/2013 |
| WO | 2013/177426 A2 | 11/2013 |
| WO | 2015058018 A1 | 4/2015 |
| WO | WO 2016/040441 A1 | 3/2016 |
| WO | WO 2016/049459 A1 | 3/2016 |
| WO | 2017/079703 A1 | 5/2017 |
| WO | 2017161333 A1 | 9/2017 |
| WO | 2017180989 A2 | 10/2017 |
| WO | WO 2018/140960 A1 | 8/2018 |
| WO | WO 2020/010110 A1 | 1/2020 |
| WO | WO 2020/097346 A1 | 5/2020 |

OTHER PUBLICATIONS

Ho et al., Phosphoenolpyruvate Is a Metabolic Checkpoint of Anti-tumor T Cell Responses. Cell. Sep. 10, 2015;162(6):1217-28. Epub Aug. 27, 2015.

Ligtenberg et al., Coexpressed Catalase Protects Chimeric Antigen Receptor-Redirected T Cells as well as Bystander Cells from Oxidative Stress-Induced Loss of Antitumor Activity. J Immunol. Jan. 15, 2016;196(2):759-66. Epub Dec. 16, 2015.

Beezhold et al., Targeting immuno-metabolism to improve anti-cancer therapies. Cancer Lett. Feb. 1, 2018;414:127-135. Epub Nov. 8, 2017.

Mills et al., Mitochondria are the powerhouses of immunity. Nat Immunol. Apr. 18, 2017;18(5):488-498.

Altman et al. (2016) "From Krebs to Clinic: Glutamine Metabolism to Cancer Therapy", Nature Reviews Cancer, 16 (10):619-634.

Altschul et al. (Oct. 5, 1990) "Basic Local Alignment Search Tool", Journal of Molecular Biology, 215(3):403-410.

Altschul et al. (Sep. 1, 1997) "Gapped BLAST and PSI-BLAST: A New Generation of Protein Database Search Programs", Nucleic Acids Research, 25(17):3389-3402.

Bailis et al. (2019) "Distinct Modes of Mitochondrial Metabolism Uncouple T Cell Differentiation and Function", Nature, 571(7765):403-407.

Baumhoer et al. (2008) "Glypican 3 Expression in Human Non-neoplastic, Preneoplastic, and Neoplastic Tissues", American Society for Clinical Pathology, 129:899-906.

Bengsch et al. (2016) "Bioenergetic Insufficiencies Due to Metabolic Alterations Regulated by the Inhibitory Receptor PD-1 Are an Early Driver of CD8(+) T Cell Exhaustion", Immunity, 45(2):358-373.

Brentjens et al. (2013) "CD 19-Targeted T Cells Rapidly Induce Molecular Remissions in 8-Adults with Chemotherapy-Refractory Acute Lymphoblastic Leukemia", Science Translational Medicine, 5(177):177ra38 (19 pages).

Brentjens et al. (Feb. 10, 2003) "Eradication of Systemic B-Cell Tumors by Genetically Targeted Human T Lymphocytes Co-Stimulated by CD80 and Interleukin-15", Nature Medicine, 9(3):279-286.

Brentjens et al. (Nov. 3, 2011) "Safety and Persistence of Adoptively Transferred Autologous Cd 19-targeted T Cells in Patients with Relapsed or Chemotherapy Refractory B-cell Leukemias", Blood, 118(18):4817-4828.

Cao et al. (2016) "Design of Switchable Chimeric Antigen Receptor T Cells Targeting Breast Cancer", Angewandte Chemie, 55(26):7520-7524.

Cartellieri et al. (2016) "Switching Car T Cells on and Off: a Novel Modular Platform For Retargeting of T Cells to AML Blasts", Blood Cancer Journal, 6(8):e458 (8 pages).

Chang et al. (Sep. 2015) "Metabolic Competition in the Tumor Microenvironment Is a Driver of Cancer Progression", Cell, 162(6):1229-1241.

Chen et al. (2018) "Combining Expression of GPC3 in Tumors and CD 16 on NK Cells from Peripheral Blood to Identify Patients Responding to Codriturumab", Oncotarget, 9(12):10436-10444.

Cho et al. (2018) "Universal Chimeric Antigen Receptors for Multiplexed and Logical Control of T Cell Responses", Cell, 173(6):1426-1438.

Cooper et al. (Feb. 2003) "T-Cell Clones Can Be Rendered Specific for CD 19: Toward the Selective Augmentation of the Graft-Versus-B-Lineage Leukemia Effect", Blood, 101(4):1637-1644.

Cretenet et al. (2016) "Cell Surface Glut1 Levels Distinguish Human CD4 and CD8 T Lymphocyte Subsets with Distinct Effector Functions", Scientific Reports, 6:24129 (13 pages).

Curran et al. (2012) "Chimeric Antigen Receptors for T Cell Immunotherapy: Current Understanding and Future Directions", Journal Gene Medicine, 14(6):405-415.

Daberkow et al. (2003) "Monocarboxylate Transporter 1 Mediates Biotin Uptake in Human Peripheral Blood Mononuclear Cells", Journal of Nutrition, 133(9):2703-2706.

Eshhar et al. (Jan. 1993) "Specific Activation and Targeting of Cytotoxic Lymphocytes Through Chimeric Single Chains Consisting of Antibody-Binding Domains and The y or C Subunits of the Immunoglobulin and T-cell Receptors", Proceedings of the National Academy of Sciences of the United States of America, 90(2):720-724.

Haji-Fatahaliha et al. (2016) "CAR-Modified T-Cell Therapy for Cancer: An Updated Review", Artificial Cells, Nanomedicine, and Biotechnology, 44(6):1339-1349.

Fehniger et al. (2001) "Ontogeny and Expansion of Human Natural Killer Cells: Clinical Implications", International Reviews of Immunology, 20(3-4):503-534.

Freemerman et al. (Mar. 14, 2014) "Metabolic Reprogramming of Macrophages Glucose Transporter 1 (GLUT1)-Mediated Glucose Metabolism Drives a Proinflammatory Phenotype", Journal of Biological Chemistry, 289(11):7884-7896.

Zhao et al. (2007) "Functional Properties and Genomics of Glucose Transporters", Current Genomics, 8(2):113-128.

Gao et al. (2014) "Development of T Cells Redirected to Glypican-3 for the Treatment of Hepatocellular Carcinoma", Clinical Cancer Research : An Official Journal of the American Association for Cancer Research, 20(24):6418-28.

Geiger et al. (May 15, 1999) "The TCR C-Chain Immunoreceptor Tyrosine-Based Activation Motifs Are Sufficient for the Activation and Differentiation of Primary T Lymphocytes", The Journal of Immunology, 162(10):5931-5939.

(56) References Cited

OTHER PUBLICATIONS

Goodwin et al. (2017) "The Distinct Metabolic Phenotype of Lung Squamous Cell Carcinoma Defines Selective Vulnerability to Glycolytic Inhibition", Nature Communications, 8:15503 (16 pages).
Guo et al. (2020) "Glypican-3: A New Target for Diagnosis and Treatment of Hepatocellular Carcinoma", Journal of Cancer, 11(8):2008-2021.
Harada et al. (2004) "A Wilms Tumor Cell Line, HFWT, Can Greatly Stimulate Proliferation of CD56+ Human Natural Killer Cells and Their Novel Precursors in Blood Mononuclear Cells", Experimental Hematology, 32(7):614-621.
Harada et al. (2002) "Selective Expansion of Human Natural Killer Cells from Peripheral Blood Mononuclear Cells by the Cell Line, HFWT", Japanese Journal of Cancer Research, 93(3):313-319.
Hickman et al. (2022) "BOXR 1030, an Anti-GPC3 CAR With Exogenous GOT2 Expression, Shows Enhanced T Cell Metabolism and Improved Anti-Cell Line Derived Tumor Xenograft Activity", PLoS One, 17(5):e0266980 (25 pages).
Houten et al. (2010) "A General Introduction to the Biochemistry of Mitochondrial Fatty Acid B-Oxidation", Journal of Inherited Metabolic Disease, 33(5):469-477.
Hu et al. (2016) "Energy Metabolism Plays a Critical Role in Stem Cell Maintenance and Differentiation", International Journal of Molecular Sciences, 17(2):253 (15 pages).
Ikeda et al. (2014) "Japanese Phase I Study of GC33, A Humanized Antibody Against Glypican-3 for Advanced Hepatocellular Carcinoma", Cancer Science, 105(4):455-462.
Imai et al. (2004) "Chimeric Receptors with 4-1 BB Signaling Capacity Provoke Potent Cytotoxicity Against Acute Lymphoblastic Leukemia", Leukemia, 18(4):676-684.
Irving et al. (2017) "Engineering Chimeric Antigen Receptor T-Cells for Racing in Solid Tumors: Don't Forget the Fuel", Frontiers in Immunology, 8:267 (19 pages).
Ishiguro et al. (2017) "An Anti-Glypican 3/CD3 Bispecific T Cell-Redirecting Antibody for Treatment of Solid Tumors", Science Translational Medicine, 9(410):eaal4291 (14 pages).
Jacob et al. (2008) "Glucose Uptake Is Limiting in T Cell Activation and Requires CD28-Mediated Akt-Dependent and Independent Pathwaysl", The Journal of Immunology, 180(7):4476-4486.
Jena et al. (2010) "Redirecting T-Cell Specificity by Introducing a Tumor-Specific Chimeric Antigen Receptor", Blood, 116(7):1035-1044.
Johnson et al. (2018) "Distinct Regulation of Th17 and Th 1 Cell Differentiation by Glutaminase-Dependent Metabolism", Cell, 175(7):1780-1795.
Zhao et al. (Oct. 12, 2015) "Structural Design of Engineered Costimulation Determines Tumor Rejection Kinetics and Persistence of CAR T Cells", Cancer Cell, 28(4):415-428.
Karlin et al. (Jun. 15, 1993) "Applications and Statistics for Multiple High-scoring Segments in Molecular Sequences", Proceedings of the National Academy of Sciences of the United States of America, 90( 12):5873-5877.
Karlin et al. (Mar. 1, 1990) "Methods for Assessing the Statistical Significance of Molecular Sequence Features by Using General Scoring Schemes", Proceedings of the National Academy of Sciences United States of America, 87(6):2264-2268.
Kawalekar et al. (2016) "Distinct Signaling of Coreceptors Regulates Specific Metabolism Pathways and Impacts Memory Development in Car T Cells", Immunity, 44(2):380-390.
Kim et al. (2001) "Analysis of FcγRIII and IgG Fc Polymorphism Reveals Functional and Evolutionary Implications of Protein-Protein Interaction", Journal of Molecular Evolution, 53(1):1-9.
Kim et al. (2011) "High Cleavage Efficiency of a 2A Peptide Derived from Porcine Teschovirus-1 in Human Cell Lines, Zebrafish and Mice", Plos One, 6(4):e 18556 (8 pages).
Kim et al. (2015) "Redirection of Genetically Engineered CAR-T Cells Using Bifunctional Small Molecules", Journal of the American Chemical Society, 137(8):2832-2835.
Kishton et al. (2017) "Metabolic Regulation of T Cell Longevity and Function in Tumor Immunotherapy", Cell Metabolism, 26(1):94-109.
Klein et al. (Jun. 11, 1976) "Properties of the k562 Cell Line, Derived from a Patient with Chronic Myeloid Leukemia", International Journal of Cancer, 18:421-431.
Kochenderfer et al. (Mar. 22, 2012) "B-Cell Depletion and Remissions of Malignancy along with Cytokine- Associated Toxicity in a Clinical Trial of Anti-CD 19 Chimeric-Antigen-Receptor-Transduced T Cells", Blood, 119(12):2709-2720.
Kudo et al. (Jan. 1, 2014) "T Lymphocytes Expressing a CD 16 Signaling Receptor Exert Antibody-Dependent Cancer Cell Killing", Cancer Research, 74(1):93-103.
Kuo et al. (Aug. 1, 1993) "Efficient Gene Transfer Into Primary Murine Lymphocytes Obviating the Need for Drug Selection", Blood, 82(3):845-852.
Lee et al. (Jun. 4, 2015) "A Protein Kinase C Phosphorylation Motif in GLUT 1 Affects Glucose Transport and is Mutated in GLUT 1 Deficiency Syndrome", Molecular Cell, 58: 845-853.
Ligtenberg Maarten A. (Aug. 28, 2015) "Strengthening the Pillars of Cancer Immunotherapy", Thesis for Doctoral degree (Ph.D.), Karolinska Institutet, 178 pages.
Lohmueller et al. (2018) "mSA2 Affinity-Enhanced Biotin-Binding Car T Cells for Universal Tumor Targeting", Oncoimmunology, 7(1): e1368604 (6 pages).
Lozzio et al. (Mar. 1975) "Human Chronic Myelogenous Leukemia Cell-Line With Positive Philadelphia Chromosome", Blood, 45(3):321-334 (1 page).
Ma et al. (Jan. 12, 2016) "Versatile Strategy for Controlling the Specificity and Activity of Engineered T Cells", PNAS, E450-E458.
Macintyre et al. (2014) "The Glucose Transporter Glut1 Is Selectively Essential for CD4 T Cell Activation and Effector Function", Cell Metabolism, 20(1):61-72.
Mann et al. (May 1983) "Construction of a Retrovirus Packaging Mutant and Its Use to Produce Helper-Free Defective Retrovirus", Cell, 33:153-159.
Markowitz et al. (Apr. 1988) "A Safe Packaging Line for Gene Transfer: Separating Viral Genes on Two Different Plasmids", Journal of Virology, 62(4):1120-1124.
Moek et al. (Sep. 2018) "Glypican 3 Overexpression across a Broad Spectrum of Tumor Types Discovered with Functional Genomic mRNA Profiling of a Large Cancer Database", The American Journal of Pathology, 188 (9):1973-1981.
Nakamura et al. (Jan. 19, 2018) "Pharmacokinetic Dynamic Relationships", British Journal of Clinical Pharmacology, 84:944-951.
Neal et al. (Aug. 17, 2017) "The Basics of Artificial Antigen Presenting Cells in T Cell-Based Cancer Immunotherapies", J Immunol Res Ther., 2(1): 68-79.
Ortiz et al. (Feb. 26, 2019) "Immunotherapeutic Targeting of GPC3 in Pediatric Solid Embryonal Tumors", Frontiers in Oncology, 9(108):8 pages.
Palmer et al. (2015) "Glucose Metabolism Regulates T Cell Activation, Differentiation, and Functions", Frontiers in Immunology, 6:1 (7 pages).
Patel et al. (Jul. 30, 2019) "Targeting Metabolism to Regulate Immune Responses in Autoimmunity and Cancer", Nature Reviews | Drug Discovery, 20 pages.
Porter et al. (Aug. 25, 2011) "Chimeric Antigen Receptor-Modified T Cells in Chronic Lymphoid Leukemia", The New England Journal of Medicine, 365(8):725-733.
Patel et al. (Nov. 2008) "Virus-Specific T Cells Engineered to Coexpress Tumor-Specific Receptors: Persistence and Antitumor Activity in Individuals with Neuroblastoma", Nature Medicine, 14(11):1264-1270.
Rabinovich et al. (Oct. 2006) "Synthetic Messenger RNA as a Tool for Gene Therapy", Human Gene Therapy, 17:1027-1035.
Rodgers et al. (Jan. 12, 2016) "Switch-Mediated Activation and Retargeting of CAR-T Cells for B-Cell Malignancies", PNAS, 113(4):E459-E468.
Sade-Feldman et al. (Nov. 1, 2018) "Defining T Cell States Associated with Response to Checkpoint Immunotherapy in Melanoma", Cell, 175(4):998-1013.

(56) References Cited

OTHER PUBLICATIONS

Sawada et al. (Jul. 1, 2012) "Phase I Trial of a Glypican-3-Derived Peptide Vaccine for Advanced Hepatocellular Carcinoma: Immunologic Evidence and Potential for Improving Overall Survival", Clinical Cancer Research, 18(13):3686-3696.
Scharping et al. (Aug. 16, 2016) "The Tumor Microenvironment Represses T Cell Mitochondrial Biogenesis to Drive Intratumoral T Cell Metabolic Insufficiency and Dysfunction", Immunity, 45(2):374-388.
Shi et al. (2020) "Chimeric Antigen Receptor-Glypican-3 T-Cell Therapy for Advanced Hepatocellular Carcinoma: Results of Phase I Trials", Clinical Cancer Research, 26:3979-3989.
Shin et al. (2004) "Glucose Transporter GLUT8 Translocation in Neurons Is Not Insulin Responsive", Journal of Neuroscience Research, 75:835-844.
Siska et al. (2017) "Mitochondrial Dysregulation and Glycolytic Insufficiency Functionally Impair CD8 T Cells Infiltrating Human Renal Cell Carcinoma", JCI Insight, 2(12):e93411 (13 pages).
Siska et al. (Aug. 10, 2016) "Suppression of Glut1 and Glucose Metabolism by Decreased Akt/mTORC1 Signaling Drives T Cell Impairment in B Cell Leukemia", The Journal of Immunology, 197:2532-2540.
Son et al. (Apr. 4, 2013) "Glutamine Supports Pancreatic Cancer Growth through a Kras-Regulated Metabolic Pathway", Nature, 496(7443):101-105.
Tahmasebi et al. (Jun. 4, 2019) "Solid Tumors Challenges and New Insights of CAR T Cell Engineering", Stem Cell Reviews and Reports, 18 pages.
Takeuchi et al. (Mar. 31, 2009) "Biochemistry, Physiology, and Genetics of GPAT, AGPAT, and Lipin Enzymes in Triglyceride Synthesis", American Journal of Physiology-Endocrinology and Metabolism, 296:E1195-E1209.
Tamada et al. (Dec. 1, 2012) "Redirecting Gene-Modified T Cells toward Various Cancer Types Using Tagged Antibodies", Clinical Cancer Research, 18(23):6436-6445.
Till et al. (Apr. 26, 2012) "CD20-Specific Adoptive Immunotherapy for Lymphoma using a Chimeric Antigen Receptor with both CD28 and 4-1BB Domains: Pilot Clinical Trial Results", Blood, 119(17):3940-3950.
Turtle et al. (2010) "Artificial Antigen Presenting Cells for Use in Adoptive Immunotherapy", Journal of Cancer, 16(4):374-381.
Zhu et al. (Feb. 15, 2013) "First-in-Man Phase I Study of GC33, a Novel Recombinant Humanized Antibody Against Glypican-3, in Patients with Advanced Hepatocellular Carcinoma", Clinical Cancer Research, 19(4):920-928.
Wiig et al. (Sep. 12, 2002) "Isolation of Interstitial Fluid from Rat Mammary Tumors by a Centrifugation Method", The American Journal of Physiology—Heart and Circulatory Physiology, 284:H416-H424.
Xu et al. (Apr. 30, 2019) "A Metabolism Toolbox for CAR T Therapy", Frontiers in Oncology, 9(322):15 pages.
Ying et al. (Jun. 2019) "A Safe and Potent Anti-CD19 CAR T Cell Therapy", Nature Medicine, 25(6):947-953.
Zhang et al. (Feb. 10, 2016) "Starved and Asphyxiated: How can cD8+ T Cells within a Tumor Microenvironment Prevent Tumor Progression", Frontier in Immunology, 7(32):7 pages.

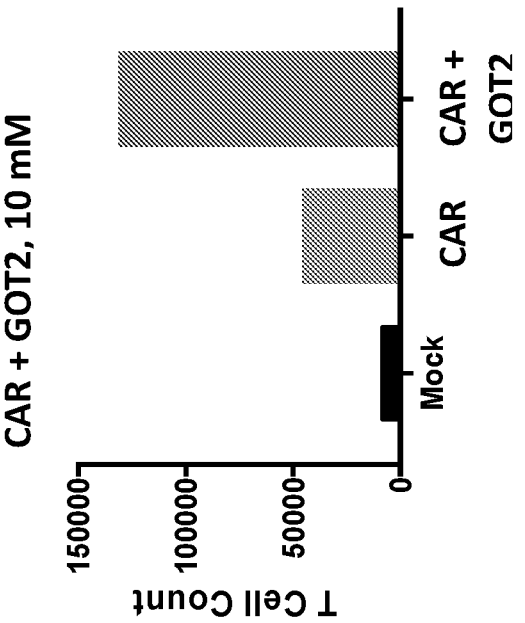
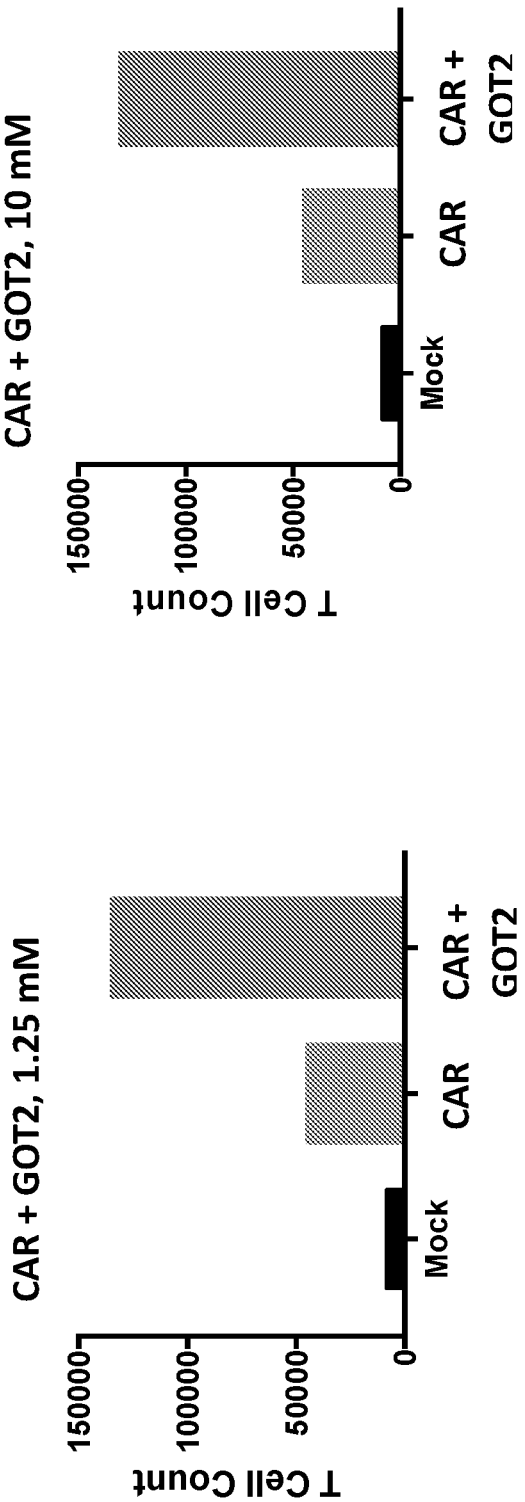

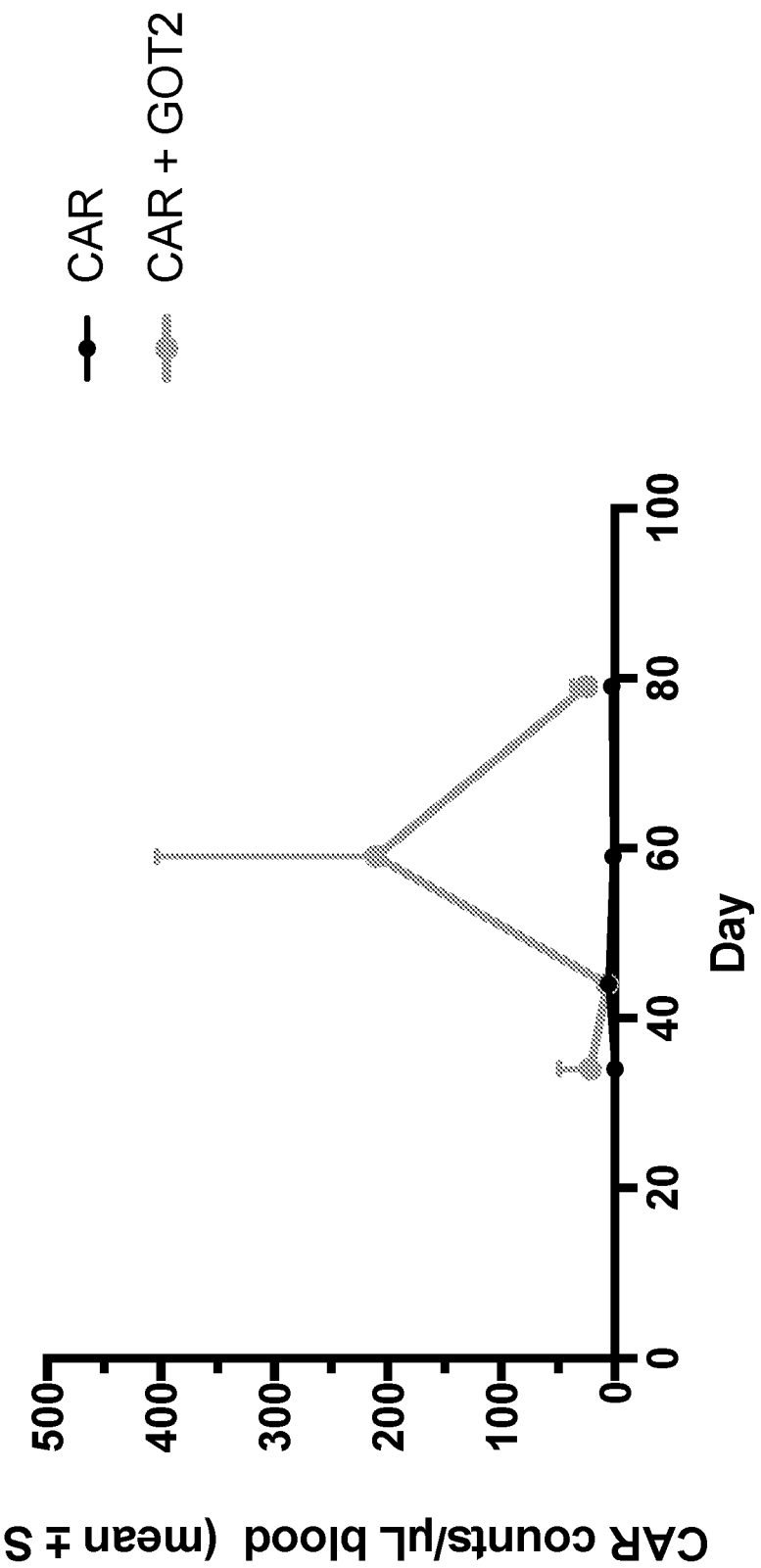

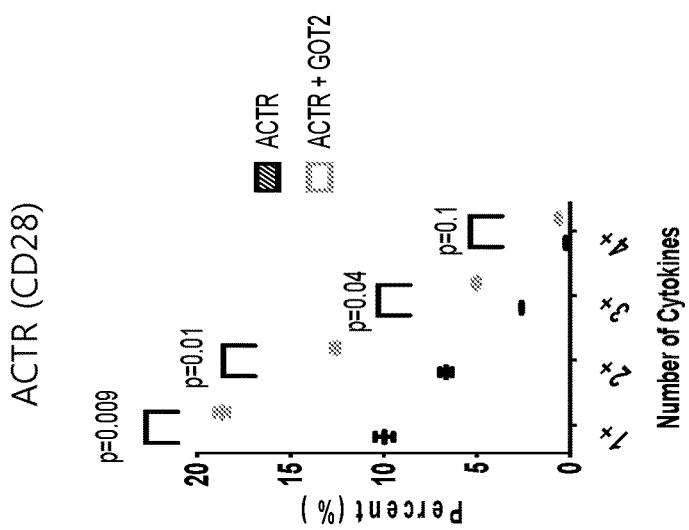
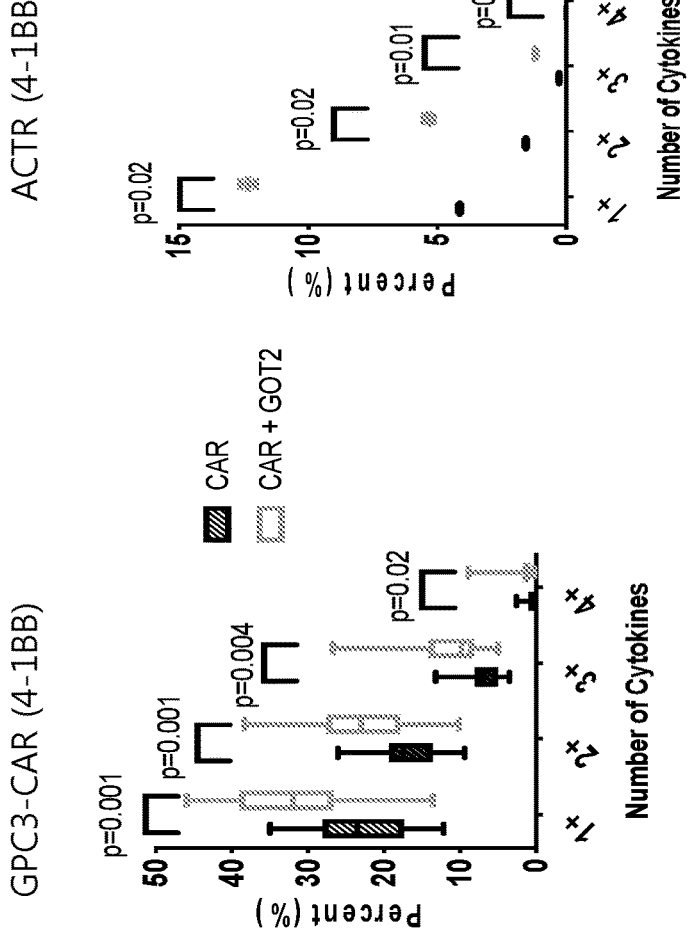
Figure 11A Figure 11B Figure 11C

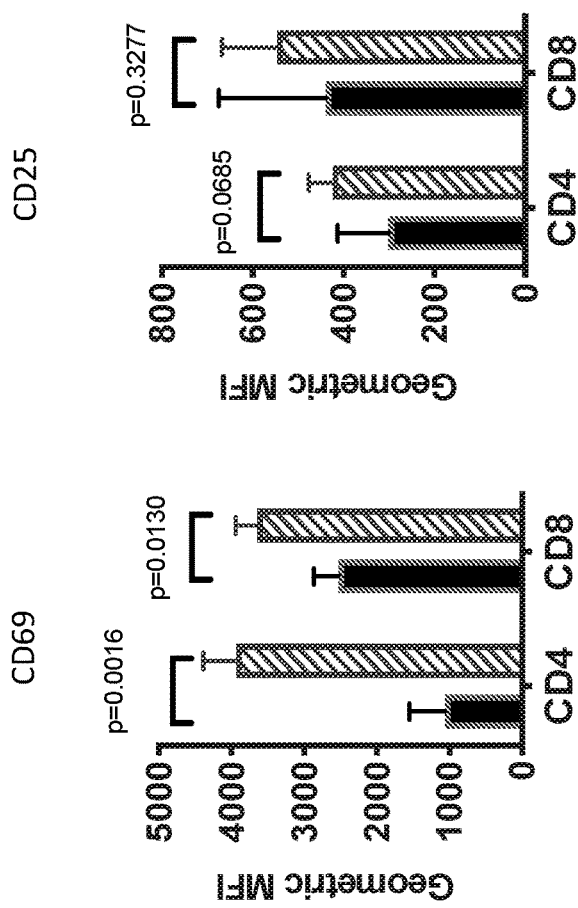
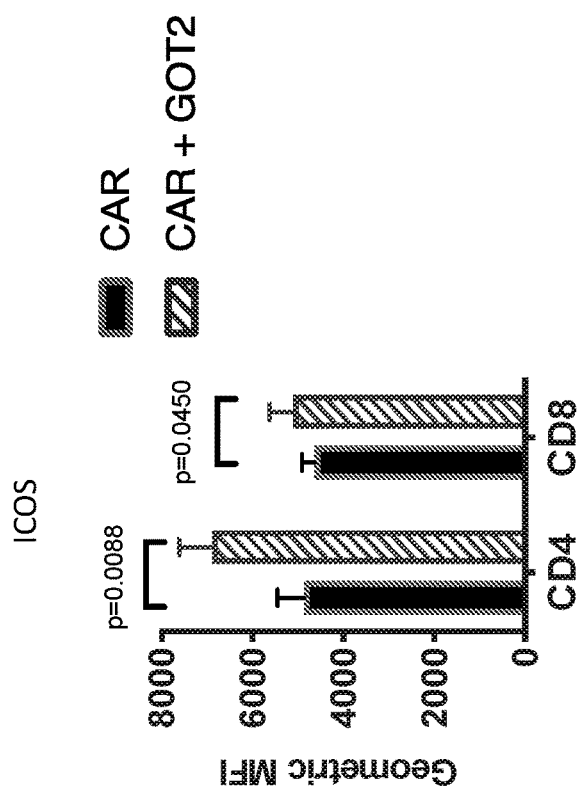
Figure 17A Figure 17B Figure 17C

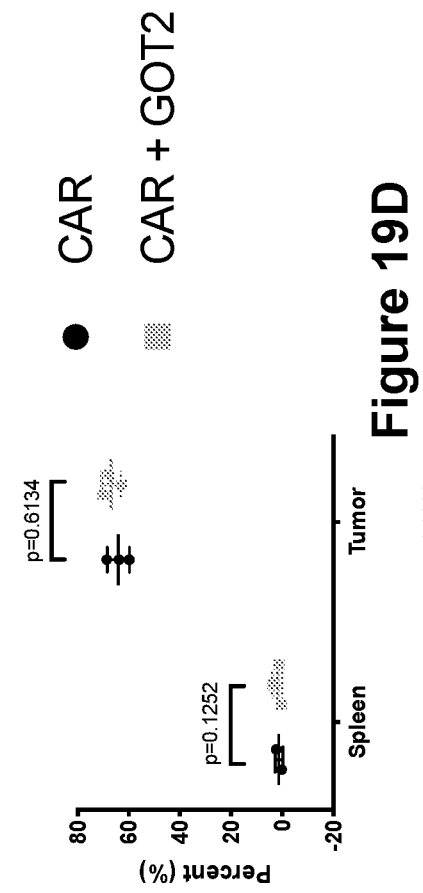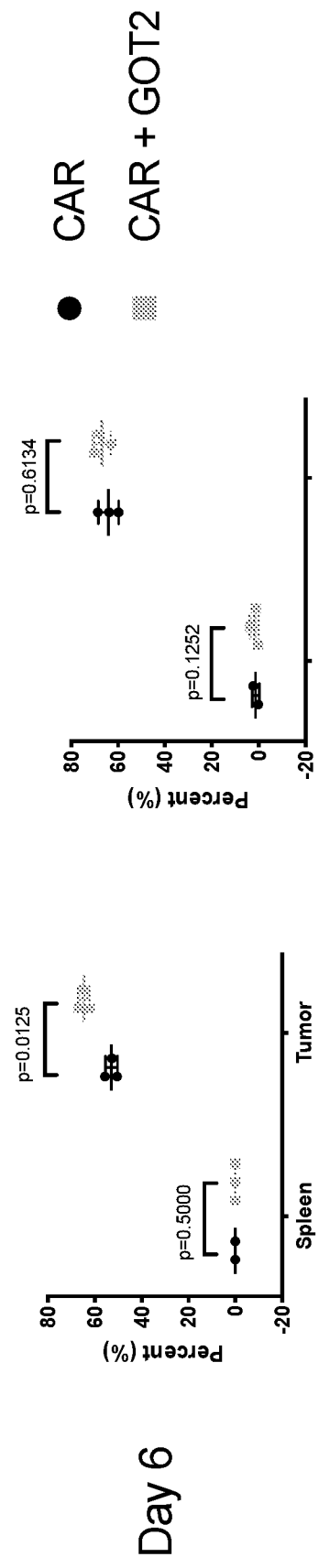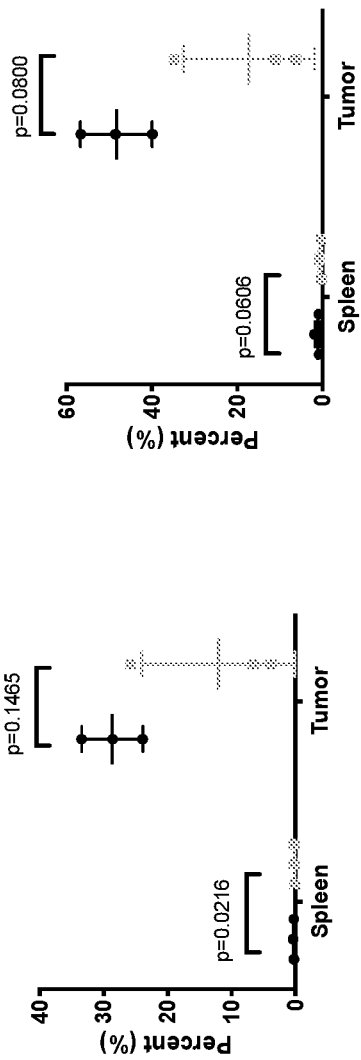
Figure 19A Figure 19B Figure 19C Figure 19D

SEQUENCE LISTING

<160> NUMBER OF SEQ ID NOS: 107

<210> SEQ ID NO 1
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 1

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
```

```
                355                 360                 365
Met Gly Gly Lys Pro Arg Arg Lys Asn Pro Gln Glu Gly Leu Tyr Asn
            370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 2
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 2

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ile Ser Phe Phe Leu Ala Leu Thr Ser Thr Ala Leu Leu
            260                 265                 270

Phe Leu Leu Phe Phe Leu Thr Leu Arg Phe Ser Val Val Lys Arg Gly
```

```
                    275                 280                 285
Lys Arg Gly Arg Lys Leu Leu Tyr Ile Phe Lys Gln Pro Phe Met
                290                 295                 300
Arg Pro Val Gln Thr Thr Gln Glu Glu Asp Gly Cys Ser Cys Arg Phe
305                 310                 315                 320
Pro Glu Glu Glu Gly Gly Cys Glu Leu Arg Val Lys Phe Ser Arg
                    325                 330                 335
Ser Ala Asp Ala Pro Ala Tyr Gln Gln Gly Gln Asn Gln Leu Tyr Asn
                340                 345                 350
Glu Leu Asn Leu Gly Arg Arg Glu Glu Tyr Asp Val Leu Asp Lys Arg
                355                 360                 365
Arg Gly Arg Asp Pro Glu Met Gly Gly Lys Pro Arg Arg Lys Asn Pro
                370                 375                 380
Gln Glu Gly Leu Tyr Asn Glu Leu Gln Lys Asp Lys Met Ala Glu Ala
385                 390                 395                 400
Tyr Ser Glu Ile Gly Met Lys Gly Glu Arg Arg Arg Gly Lys Gly His
                    405                 410                 415
Asp Gly Leu Tyr Gln Gly Leu Ser Thr Ala Thr Lys Asp Thr Tyr Asp
                420                 425                 430
Ala Leu His Met Gln Ala Leu Pro Pro Arg
                435                 440
```

<210> SEQ ID NO 3
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 3

```
Met Ala Leu Pro Val Thr Ala Leu Leu Leu Pro Leu Ala Leu Leu Leu
1               5                   10                  15
His Ala Ala Arg Pro Gly Met Arg Thr Glu Asp Leu Pro Lys Ala Val
                20                  25                  30
Val Phe Leu Glu Pro Gln Trp Tyr Arg Val Leu Glu Lys Asp Ser Val
                35                  40                  45
Thr Leu Lys Cys Gln Gly Ala Tyr Ser Pro Glu Asp Asn Ser Thr Gln
50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
                100                 105                 110
Trp Leu Leu Leu Gln Ala Pro Arg Trp Val Phe Lys Glu Glu Asp Pro
                115                 120                 125
Ile His Leu Arg Cys His Ser Trp Lys Asn Thr Ala Leu His Lys Val
                130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
                180                 185                 190
Ile Thr Ile Thr Gln Gly Leu Ala Val Ser Thr Ile Ser Ser Phe Phe
```

```
            195                 200                 205
Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Ala Val His Thr Arg Gly Leu Asp Phe Ala
                245                 250                 255

Cys Asp Phe Trp Val Leu Val Val Val Gly Gly Val Leu Ala Cys Tyr
                260                 265                 270

Ser Leu Leu Val Thr Val Ala Phe Ile Ile Phe Trp Val Arg Ser Lys
                275                 280                 285

Lys Arg Gly Arg Lys Lys Leu Leu Tyr Ile Phe Lys Gln Pro Phe Met
290                 295                 300

Arg Pro Val Gln Thr Thr Gln Glu Glu Asp Gly Cys Ser Cys Arg Phe
305                 310                 315                 320

Pro Glu Glu Glu Glu Gly Gly Cys Glu Leu Arg Val Lys Phe Ser Arg
                325                 330                 335

Ser Ala Asp Ala Pro Ala Tyr Gln Gln Gly Gln Asn Gln Leu Tyr Asn
                340                 345                 350

Glu Leu Asn Leu Gly Arg Arg Glu Glu Tyr Asp Val Leu Asp Lys Arg
                355                 360                 365

Arg Gly Arg Asp Pro Glu Met Gly Gly Lys Pro Arg Arg Lys Asn Pro
370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
                420                 425                 430

Ala Leu His Met Gln Ala Leu Pro Pro Arg
                435                 440

<210> SEQ ID NO 4
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 4

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
                35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65              70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
```

```
                115                 120                 125
Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Ile Ala Leu Val Thr Ser Gly Ala Leu Leu Ala Val Leu
            260                 265                 270

Gly Ile Thr Gly Tyr Phe Leu Met Asn Arg Lys Arg Gly Arg Lys Lys
            275                 280                 285

Leu Leu Tyr Ile Phe Lys Gln Pro Phe Met Arg Pro Val Gln Thr Thr
            290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
            370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 5
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 5

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
```

```
                35                  40                  45
Thr Leu Lys Cys Gln Gly Ala Tyr Ser Pro Glu Asp Asn Ser Thr Gln
 50                  55                  60

Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
                115                 120                 125

Ile His Leu Arg Cys His Ser Trp Lys Asn Thr Ala Leu His Lys Val
                130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
                195                 200                 205

Pro Pro Gly Tyr Gln Thr Thr Thr Pro Ala Pro Arg Pro Pro Thr Pro
                210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Leu Ala Ala Leu Leu Ala Leu Ala Ala Leu Leu Ala
                260                 265                 270

Leu Leu Ala Ala Leu Leu Ala Arg Ser Lys Lys Arg Gly Arg Lys Lys
                275                 280                 285

Leu Leu Tyr Ile Phe Lys Gln Pro Phe Met Arg Pro Val Gln Thr Thr
                290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
                355                 360                 365

Met Gly Gly Lys Pro Arg Arg Lys Asn Pro Gln Glu Gly Leu Tyr Asn
                370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
                420                 425                 430

Leu Pro Pro Arg
            435

<210> SEQ ID NO 6
```

<211> LENGTH: 428
<212> TYPE: PRT
<213> ORGANISM: Artificial Sequence
<220> FEATURE:
<223> OTHER INFORMATION: Synthetic polypeptide

<400> SEQUENCE: 6

```
Met Ala Leu Pro Val Thr Ala Leu Leu Leu Pro Leu Ala Leu Leu Leu
1               5                   10                  15

His Ala Ala Arg Pro Gln Ala Ala Pro Pro Lys Ala Val Leu Lys
            20                  25                  30

Leu Glu Pro Pro Trp Ile Asn Val Leu Gln Glu Asp Ser Val Thr Leu
        35                  40                  45

Thr Cys Gln Gly Ala Arg Ser Pro Glu Ser Asp Ser Ile Gln Trp Phe
    50                  55                  60

His Asn Gly Asn Leu Ile Pro Thr His Thr Gln Pro Ser Tyr Arg Phe
65                  70                  75                  80

Lys Ala Asn Asn Asn Asp Ser Gly Glu Tyr Thr Cys Gln Thr Gly Gln
                85                  90                  95

Thr Ser Leu Ser Asp Pro Val His Leu Thr Val Leu Ser Glu Trp Leu
            100                 105                 110

Val Leu Gln Thr Pro His Leu Glu Phe Gln Glu Gly Glu Thr Ile Met
        115                 120                 125

Leu Arg Cys His Ser Trp Lys Asp Lys Pro Leu Val Lys Val Thr Phe
130                 135                 140

Phe Gln Asn Gly Lys Ser Gln Lys Phe Ser His Leu Asp Pro Thr Phe
145                 150                 155                 160

Ser Ile Pro Gln Ala Asn His Ser His Ser Gly Asp Tyr His Cys Thr
                165                 170                 175

Gly Asn Ile Gly Tyr Thr Leu Phe Ser Ser Lys Pro Val Thr Ile Thr
            180                 185                 190

Val Gln Val Pro Ser Met Gly Ser Ser Ser Pro Met Gly Thr Thr Thr
        195                 200                 205

Pro Ala Pro Arg Pro Pro Thr Pro Ala Pro Thr Ile Ala Ser Gln Pro
    210                 215                 220

Leu Ser Leu Arg Pro Glu Ala Cys Arg Pro Ala Ala Gly Gly Ala Val
225                 230                 235                 240

His Thr Arg Gly Leu Asp Phe Ala Cys Asp Ile Tyr Ile Trp Ala Pro
                245                 250                 255

Leu Ala Gly Thr Cys Gly Val Leu Leu Leu Ser Leu Val Ile Thr Leu
            260                 265                 270

Tyr Cys Lys Arg Gly Arg Lys Lys Leu Leu Tyr Ile Phe Lys Gln Pro
        275                 280                 285

Phe Met Arg Pro Val Gln Thr Thr Gln Glu Glu Asp Gly Cys Ser Cys
    290                 295                 300

Arg Phe Pro Glu Glu Glu Glu Gly Gly Cys Glu Leu Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
            340                 345                 350

Lys Arg Arg Gly Arg Asp Pro Glu Met Gly Gly Lys Pro Arg Arg Lys
        355                 360                 365

Asn Pro Gln Glu Gly Leu Tyr Asn Glu Leu Gln Lys Asp Lys Met Ala
    370                 375                 380
```

```
Glu Ala Tyr Ser Glu Ile Gly Met Lys Gly Glu Arg Arg Gly Lys
385                 390                 395                 400

Gly His Asp Gly Leu Tyr Gln Gly Leu Ser Thr Ala Thr Lys Asp Thr
                405                 410                 415

Tyr Asp Ala Leu His Met Gln Ala Leu Pro Pro Arg
            420                 425
```

<210> SEQ ID NO 7
<211> LENGTH: 435
<212> TYPE: PRT
<213> ORGANISM: Artificial Sequence
<220> FEATURE:
<223> OTHER INFORMATION: Synthetic polypeptide

<400> SEQUENCE: 7

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Leu Leu His Ser Asp Tyr Met Asn Met Thr Pro Arg Arg Pro Gly Pro
    290                 295                 300

Thr Arg Lys His Tyr Gln Pro Tyr Ala Pro Pro Arg Asp Phe Ala Ala
305                 310                 315                 320
```

```
Tyr Arg Ser Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Gly Arg Asp Pro Glu Met
        355                 360                 365

Gly Gly Lys Pro Arg Arg Lys Asn Pro Gln Glu Gly Leu Tyr Asn Glu
370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
                420                 425                 430

Pro Pro Arg
        435

<210> SEQ ID NO 8
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 8

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240
```

```
Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Ala Leu Tyr Leu Leu Arg
        275                 280                 285

Arg Asp Gln Arg Leu Pro Pro Asp Ala His Lys Pro Pro Gly Gly Gly
    290                 295                 300

Ser Phe Arg Thr Pro Ile Gln Glu Glu Gln Ala Asp Ala His Ser Thr
305                 310                 315                 320

Leu Ala Lys Ile Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 9
<211> LENGTH: 477
<212> TYPE: PRT
<213> ORGANISM: Artificial Sequence
<220> FEATURE:
<223> OTHER INFORMATION: Synthetic polypeptide

<400> SEQUENCE: 9

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160
```

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Leu Leu His Ser Asp Tyr Met Asn Met Thr Pro Arg Arg Pro Gly Pro
    290                 295                 300

Thr Arg Lys His Tyr Gln Pro Tyr Ala Pro Pro Arg Asp Phe Ala Ala
305                 310                 315                 320

Tyr Arg Ser Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Glu Gly Gly Cys Glu Leu Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475

<210> SEQ ID NO 10
<211> LENGTH: 391
<212> TYPE: PRT
<213> ORGANISM: Artificial Sequence
<220> FEATURE:
<223> OTHER INFORMATION: Synthetic polypeptide

<400> SEQUENCE: 10

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
 50                  55                  60

Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Tyr Ile Trp Ala Pro Leu Ala Gly Thr Cys
210                 215                 220

Gly Val Leu Leu Leu Ser Leu Val Ile Thr Leu Tyr Cys Lys Arg Gly
225                 230                 235                 240

Arg Lys Lys Leu Leu Tyr Ile Phe Lys Gln Pro Phe Met Arg Pro Val
                245                 250                 255

Gln Thr Thr Gln Glu Glu Asp Gly Cys Ser Cys Arg Phe Pro Glu Glu
            260                 265                 270

Glu Glu Gly Gly Cys Glu Leu Arg Val Lys Phe Ser Arg Ser Ala Asp
        275                 280                 285

Ala Pro Ala Tyr Gln Gln Gly Gln Asn Gln Leu Tyr Asn Glu Leu Asn
290                 295                 300

Leu Gly Arg Arg Glu Glu Tyr Asp Val Leu Asp Lys Arg Arg Gly Arg
305                 310                 315                 320

Asp Pro Glu Met Gly Gly Lys Pro Arg Arg Lys Asn Pro Gln Glu Gly
                325                 330                 335

Leu Tyr Asn Glu Leu Gln Lys Asp Lys Met Ala Glu Ala Tyr Ser Glu
            340                 345                 350

Ile Gly Met Lys Gly Glu Arg Arg Arg Gly Lys Gly His Asp Gly Leu
        355                 360                 365

Tyr Gln Gly Leu Ser Thr Ala Thr Lys Asp Thr Tyr Asp Ala Leu His
370                 375                 380

Met Gln Ala Leu Pro Pro Arg
385                 390

<210> SEQ ID NO 11
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 11

Met Ala Leu Pro Val Thr Ala Leu Leu Leu Pro Leu Ala Leu Leu Leu
 1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
            195                 200                 205

Pro Pro Gly Tyr Gln Gly Gly Ser Pro Ala Gly Ser Pro Thr Ser Thr
210                 215                 220

Glu Glu Gly Thr Ser Glu Ser Ala Thr Pro Glu Ser Gly Pro Gly Thr
225                 230                 235                 240

Ser Thr Glu Pro Ser Glu Gly Ser Ala Pro Gly Ser Pro Ala Gly Ser
                245                 250                 255

Pro Thr Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
            275                 280                 285

Leu Leu Tyr Ile Phe Lys Gln Pro Phe Met Arg Pro Val Gln Thr Thr
            290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
            370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

```
Leu Pro Pro Arg
        435
```

<210> SEQ ID NO 12
<211> LENGTH: 435
<212> TYPE: PRT
<213> ORGANISM: Artificial Sequence
<220> FEATURE:
<223> OTHER INFORMATION: Synthetic polypeptide

<400> SEQUENCE: 12

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Gly Gly His Ser Asp Tyr Met Asn Met Thr Pro Arg Arg Pro Gly Pro
    290                 295                 300

Thr Arg Lys His Tyr Gln Pro Tyr Ala Pro Pro Arg Asp Phe Ala Ala
305                 310                 315                 320

Tyr Arg Ser Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350
```

```
Glu Glu Tyr Asp Val Leu Asp Lys Arg Arg Gly Arg Asp Pro Glu Met
            355                 360                 365

Gly Gly Lys Pro Arg Arg Lys Asn Pro Gln Glu Gly Leu Tyr Asn Glu
370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
            420                 425                 430

Pro Pro Arg
        435

<210> SEQ ID NO 13
<211> LENGTH: 477
<212> TYPE: PRT
<213> ORGANISM: Artificial Sequence
<220> FEATURE:
<223> OTHER INFORMATION: Synthetic polypeptide

<400> SEQUENCE: 13

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270
```

```
Leu Leu Ser Leu Val Ile Thr Leu Tyr Cys Arg Ser Lys Arg Ser Arg
            275                 280                 285

Gly Gly His Ser Asp Tyr Met Asn Met Thr Pro Arg Arg Pro Gly Pro
        290                 295                 300

Thr Arg Lys His Tyr Gln Pro Tyr Ala Pro Pro Arg Asp Phe Ala Ala
305                 310                 315                 320

Tyr Arg Ser Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
            340                 345                 350

Cys Arg Phe Pro Glu Glu Glu Gly Gly Cys Glu Leu Arg Val Lys
        355                 360                 365

Phe Ser Arg Ser Ala Asp Ala Pro Ala Tyr Gln Gln Gly Gln Asn Gln
370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
            435                 440                 445

Lys Gly His Asp Gly Leu Tyr Gln Gly Leu Ser Thr Ala Thr Lys Asp
        450                 455                 460

Thr Tyr Asp Ala Leu His Met Gln Ala Leu Pro Pro Arg
465                 470                 475

<210> SEQ ID NO 14
<211> LENGTH: 437
<212> TYPE: PRT
<213> ORGANISM: Artificial Sequence
<220> FEATURE:
<223> OTHER INFORMATION: Synthetic polypeptide

<400> SEQUENCE: 14

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160
```

-continued

```
Asp Phe Tyr Ile Pro Lys Ala Thr Leu Lys Asp Ser Gly Ser Tyr Phe
            165                 170                 175

Cys Arg Gly Leu Val Gly Ser Lys Asn Val Ser Ser Glu Thr Val Asn
        180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Met Ala Leu Ile Val Leu Gly Gly Val Ala Gly Leu Leu Leu
            260                 265                 270

Phe Ile Gly Leu Gly Ile Phe Phe Cys Val Arg Lys Arg Gly Arg Lys
        275                 280                 285

Lys Leu Leu Tyr Ile Phe Lys Gln Pro Phe Met Arg Pro Val Gln Thr
            290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
            340                 345                 350

Arg Arg Glu Glu Tyr Asp Val Leu Asp Lys Arg Arg Gly Arg Asp Pro
        355                 360                 365

Glu Met Gly Gly Lys Pro Arg Arg Lys Asn Pro Gln Glu Gly Leu Tyr
            370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
            435

<210> SEQ ID NO 15
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 15

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80
```

Ile Asp Ala Ala Thr Val Asp Asp Ser Gly Glu Tyr Arg Cys Gln Thr
            85                  90                  95

Asn Leu Ser Thr Leu Ser Asp Pro Val Gln Leu Glu Val His Ile Gly
        100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205

Pro Pro Gly Tyr Gln Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Met Ala Leu Ile Val Leu Gly Val Ala Gly Leu Leu Leu
                260                 265                 270

Phe Ile Gly Leu Gly Ile Phe Phe Cys Val Arg Arg Ser Lys Arg Ser
            275                 280                 285

Arg Gly Gly His Ser Asp Tyr Met Asn Met Thr Pro Arg Arg Pro Gly
    290                 295                 300

Pro Thr Arg Lys His Tyr Gln Pro Tyr Ala Pro Pro Arg Asp Phe Ala
305                 310                 315                 320

Ala Tyr Arg Ser Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
        370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 16
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 16

-continued

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
    195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Cys Tyr Ile Leu Asp Ala Ile Leu Phe Leu Tyr Gly Ile
            260                 265                 270

Val Leu Thr Leu Leu Tyr Cys Arg Leu Lys Lys Arg Gly Arg Lys Lys
    275                 280                 285

Leu Leu Tyr Ile Phe Lys Gln Pro Phe Met Arg Pro Val Gln Thr Thr
290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
    355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
```

420                 425                 430

Leu Pro Pro Arg
        435

<210> SEQ ID NO 17
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 17

Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
    195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Leu Leu Leu Ile Leu Leu Gly Val Leu Ala Gly Val Leu Ala
            260                 265                 270

Thr Leu Ala Ala Leu Leu Ala Arg Ser Lys Arg Gly Arg Lys Lys
    275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg

```
            340                 345                 350
Arg Glu Glu Tyr Asp Val Leu Asp Lys Arg Gly Arg Asp Pro Glu
            355                 360                 365
Met Gly Gly Lys Pro Arg Arg Lys Asn Pro Gln Glu Gly Leu Tyr Asn
370                 375                 380
Glu Leu Gln Lys Asp Lys Met Ala Glu Ala Tyr Ser Glu Ile Gly Met
385                 390                 395                 400
Lys Gly Glu Arg Arg Arg Gly Lys Gly His Asp Gly Leu Tyr Gln Gly
                405                 410                 415
Leu Ser Thr Ala Thr Lys Asp Thr Tyr Asp Ala Leu His Met Gln Ala
                420                 425                 430
Leu Pro Pro Arg
                435

<210> SEQ ID NO 18
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 18

Met Ala Leu Pro Val Thr Ala Leu Leu Leu Pro Leu Ala Leu Leu Leu
1               5                   10                  15
His Ala Ala Arg Pro Gly Met Arg Thr Glu Asp Leu Pro Lys Ala Val
                20                  25                  30
Val Phe Leu Glu Pro Gln Trp Tyr Arg Val Leu Glu Lys Asp Ser Val
            35                  40                  45
Thr Leu Lys Cys Gln Gly Ala Tyr Ser Pro Glu Asp Asn Ser Thr Gln
    50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
                100                 105                 110
Trp Leu Leu Leu Gln Ala Pro Arg Trp Val Phe Lys Glu Glu Asp Pro
            115                 120                 125
Ile His Leu Arg Cys His Ser Trp Lys Asn Thr Ala Leu His Lys Val
    130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
                180                 185                 190
Ile Thr Ile Thr Gln Gly Leu Ala Val Ser Thr Ile Ser Ser Phe Phe
            195                 200                 205
Pro Pro Gly Tyr Gln Thr Thr Thr Pro Ala Pro Arg Pro Pro Thr Pro
    210                 215                 220
Ala Pro Thr Ile Ala Ser Gln Pro Leu Ser Leu Arg Pro Glu Ala Cys
225                 230                 235                 240
Arg Pro Ala Ala Gly Gly Ala Val His Thr Arg Gly Leu Asp Phe Ala
                245                 250                 255
Cys Asp Ile Thr Leu Gly Leu Leu Val Ala Gly Val Leu Val Leu Leu
```

```
                       260                 265                 270
Val Ser Leu Gly Val Ala Ile His Leu Cys Lys Arg Gly Arg Lys Lys
            275                 280                 285

Leu Leu Tyr Ile Phe Lys Gln Pro Phe Met Arg Pro Val Gln Thr Thr
        290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 19
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 19

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
```

180                 185                 190
Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
            245                 250                 255

Cys Asp Val Ser Phe Cys Leu Val Met Val Leu Leu Phe Ala Val Asp
            260                 265                 270

Thr Gly Leu Tyr Phe Ser Val Lys Thr Asn Lys Arg Gly Arg Lys Lys
            275                 280                 285

Leu Leu Tyr Ile Phe Lys Gln Pro Phe Met Arg Pro Val Gln Thr Thr
            290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
            325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
            370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
            405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 20
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 20

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
            85                  90                  95

Asn Leu Ser Thr Leu Ser Asp Pro Val Gln Leu Glu Val His Ile Gly

```
            100                 105                 110
Trp Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205

Pro Pro Gly Tyr Gln Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Val Ala Ala Ile Leu Gly Leu Gly Leu Val Leu Gly Leu Leu
                260                 265                 270

Gly Pro Leu Ala Ile Leu Leu Ala Leu Tyr Lys Arg Gly Arg Lys Lys
            275                 280                 285

Leu Leu Tyr Ile Phe Lys Gln Pro Phe Met Arg Pro Val Gln Thr Thr
290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
                340                 345                 350

Arg Glu Glu Tyr Asp Val Leu Asp Lys Arg Arg Gly Arg Asp Pro Glu
                355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
                420                 425                 430

Leu Pro Pro Arg
        435

<210> SEQ ID NO 21
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 21

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
```

-continued

```
            20                  25                  30
Val Phe Leu Glu Pro Gln Trp Tyr Arg Val Leu Glu Lys Asp Ser Val
            35                  40                  45
Thr Leu Lys Cys Gln Gly Ala Tyr Ser Pro Glu Asp Asn Ser Thr Gln
        50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
            100                 105                 110
Trp Leu Leu Leu Gln Ala Pro Arg Trp Val Phe Lys Glu Glu Asp Pro
        115                 120                 125
Ile His Leu Arg Cys His Ser Trp Lys Asn Thr Ala Leu His Lys Val
    130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
            180                 185                 190
Ile Thr Ile Thr Gln Gly Leu Ala Val Ser Thr Ile Ser Ser Phe Phe
        195                 200                 205
Pro Pro Gly Tyr Gln Thr Thr Thr Pro Ala Pro Arg Pro Pro Thr Pro
    210                 215                 220
Ala Pro Thr Ile Ala Ser Gln Pro Leu Ser Leu Arg Pro Glu Ala Cys
225                 230                 235                 240
Arg Pro Ala Ala Gly Gly Ala Val His Thr Arg Gly Leu Asp Phe Ala
                245                 250                 255
Cys Asp Leu Cys Tyr Leu Leu Asp Gly Ile Leu Phe Ile Tyr Gly Val
            260                 265                 270
Ile Leu Thr Ala Leu Phe Leu Arg Val Lys Lys Arg Gly Arg Lys Lys
        275                 280                 285
Leu Leu Tyr Ile Phe Lys Gln Pro Phe Met Arg Pro Val Gln Thr Thr
    290                 295                 300
Gln Glu Glu Asp Gly Cys Ser Cys Arg Phe Pro Glu Glu Glu Glu Gly
305                 310                 315                 320
Gly Cys Glu Leu Arg Val Lys Phe Ser Arg Ser Ala Asp Ala Pro Ala
                325                 330                 335
Tyr Gln Gln Gly Gln Asn Gln Leu Tyr Asn Glu Leu Asn Leu Gly Arg
            340                 345                 350
Arg Glu Glu Tyr Asp Val Leu Asp Lys Arg Arg Gly Arg Asp Pro Glu
        355                 360                 365
Met Gly Gly Lys Pro Arg Arg Lys Asn Pro Gln Glu Gly Leu Tyr Asn
    370                 375                 380
Glu Leu Gln Lys Asp Lys Met Ala Glu Ala Tyr Ser Glu Ile Gly Met
385                 390                 395                 400
Lys Gly Glu Arg Arg Arg Gly Lys Gly His Asp Gly Leu Tyr Gln Gly
                405                 410                 415
Leu Ser Thr Ala Thr Lys Asp Thr Tyr Asp Ala Leu His Met Gln Ala
            420                 425                 430
Leu Pro Pro Arg
        435
```

<210> SEQ ID NO 22
<211> LENGTH: 441
<212> TYPE: PRT
<213> ORGANISM: Artificial Sequence
<220> FEATURE:
<223> OTHER INFORMATION: Synthetic polypeptide

<400> SEQUENCE: 22

```
Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Val Met Ser Val Ala Thr Ile Val Ile Val Asp Ile Cys Ile
            260                 265                 270

Thr Gly Gly Leu Leu Leu Leu Val Tyr Tyr Trp Ser Lys Asn Arg Lys
        275                 280                 285

Arg Gly Arg Lys Lys Leu Leu Tyr Ile Phe Lys Gln Pro Phe Met Arg
    290                 295                 300

Pro Val Gln Thr Thr Gln Glu Glu Asp Gly Cys Ser Cys Arg Phe Pro
305                 310                 315                 320

Glu Glu Glu Glu Gly Gly Cys Glu Leu Arg Val Lys Phe Ser Arg Ser
                325                 330                 335

Ala Asp Ala Pro Ala Tyr Gln Gln Gly Gln Asn Gln Leu Tyr Asn Glu
            340                 345                 350

Leu Asn Leu Gly Arg Arg Glu Glu Tyr Asp Val Leu Asp Lys Arg Arg
        355                 360                 365
```

```
Gly Arg Asp Pro Glu Met Gly Gly Lys Pro Arg Arg Lys Asn Pro Gln
    370                 375                 380

Glu Gly Leu Tyr Asn Glu Leu Gln Lys Asp Lys Met Ala Glu Ala Tyr
385                 390                 395                 400

Ser Glu Ile Gly Met Lys Gly Glu Arg Arg Arg Gly Lys Gly His Asp
                405                 410                 415

Gly Leu Tyr Gln Gly Leu Ser Thr Ala Thr Lys Asp Thr Tyr Asp Ala
            420                 425                 430

Leu His Met Gln Ala Leu Pro Pro Arg
            435                 440

<210> SEQ ID NO 23
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 23

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
    195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Gly Phe Leu Phe Ala Glu Ile Val Ser Ile Phe Val Leu Ala
            260                 265                 270

Val Gly Val Tyr Phe Ile Ala Gly Gln Asp Lys Arg Gly Arg Lys Lys
    275                 280                 285
```

Leu Leu Tyr Ile Phe Lys Gln Pro Phe Met Arg Pro Val Gln Thr Thr
            290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 24
<211> LENGTH: 437
<212> TYPE: PRT
<213> ORGANISM: Artificial Sequence
<220> FEATURE:
<223> OTHER INFORMATION: Synthetic polypeptide

<400> SEQUENCE: 24

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Gly Ile Ile Val Thr Asp Val Ile Ala Thr Leu Leu Leu Ala
                260                 265                 270

Leu Gly Val Phe Cys Phe Ala Gly His Glu Thr Lys Arg Gly Arg Lys
            275                 280                 285

Lys Leu Leu Tyr Ile Phe Lys Gln Pro Phe Met Arg Pro Val Gln Thr
            290                 295                 300

Thr Gln Glu Glu Asp Gly Cys Ser Cys Arg Phe Pro Glu Glu Glu Glu
305                 310                 315                 320

Gly Gly Cys Glu Leu Arg Val Lys Phe Ser Arg Ser Ala Asp Ala Pro
                325                 330                 335

Ala Tyr Gln Gln Gly Gln Asn Gln Leu Tyr Asn Glu Leu Asn Leu Gly
                340                 345                 350

Arg Arg Glu Glu Tyr Asp Val Leu Asp Lys Arg Arg Gly Arg Asp Pro
            355                 360                 365

Glu Met Gly Gly Lys Pro Arg Arg Lys Asn Pro Gln Glu Gly Leu Tyr
370                 375                 380

Asn Glu Leu Gln Lys Asp Lys Met Ala Glu Ala Tyr Ser Glu Ile Gly
385                 390                 395                 400

Met Lys Gly Glu Arg Arg Arg Gly Lys Gly His Asp Gly Leu Tyr Gln
                405                 410                 415

Gly Leu Ser Thr Ala Thr Lys Asp Thr Tyr Asp Ala Leu His Met Gln
            420                 425                 430

Ala Leu Pro Pro Arg
            435

<210> SEQ ID NO 25
<211> LENGTH: 435
<212> TYPE: PRT
<213> ORGANISM: Artificial Sequence
<220> FEATURE:
<223> OTHER INFORMATION: Synthetic polypeptide

<400> SEQUENCE: 25

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205

Pro Pro Gly Tyr Gln Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Val Ile Gly Phe Arg Ile Leu Leu Lys Val Ala Gly Phe
                260                 265                 270

Asn Leu Leu Met Thr Leu Arg Leu Trp Lys Arg Gly Arg Lys Lys Leu
            275                 280                 285

Leu Tyr Ile Phe Lys Gln Pro Phe Met Arg Pro Val Gln Thr Thr Gln
    290                 295                 300

Glu Glu Asp Gly Cys Ser Cys Arg Phe Pro Glu Glu Glu Gly Gly
305                 310                 315                 320

Cys Glu Leu Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Arg Gly Arg Asp Pro Glu Met
        355                 360                 365

Gly Gly Lys Pro Arg Arg Lys Asn Pro Gln Glu Gly Leu Tyr Asn Glu
    370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
            420                 425                 430

Pro Pro Arg
    435

<210> SEQ ID NO 26
<211> LENGTH: 438
<212> TYPE: PRT
<213> ORGANISM: Artificial Sequence
<220> FEATURE:
<223> OTHER INFORMATION: Synthetic polypeptide

<400> SEQUENCE: 26

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

```
Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                    85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ile Val Ala Val Val Ile Ala Thr Ala Val Ala Ala Ile
                260                 265                 270

Val Ala Ala Val Val Ala Leu Ile Tyr Cys Arg Lys Lys Arg Gly Arg
            275                 280                 285

Lys Lys Leu Leu Tyr Ile Phe Lys Gln Pro Phe Met Arg Pro Val Gln
            290                 295                 300

Thr Thr Gln Glu Glu Asp Gly Cys Ser Cys Arg Phe Pro Glu Glu Glu
305                 310                 315                 320

Glu Gly Gly Cys Glu Leu Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Arg Gly Arg Asp
            355                 360                 365

Pro Glu Met Gly Gly Lys Pro Arg Arg Lys Asn Pro Gln Glu Gly Leu
            370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
            420                 425                 430

Gln Ala Leu Pro Pro Arg
            435
```

<210> SEQ ID NO 27
<211> LENGTH: 436

-continued

```
<212> TYPE: PRT
<213> ORGANISM: Artificial Sequence
<220> FEATURE:
<223> OTHER INFORMATION: Synthetic polypeptide

<400> SEQUENCE: 27

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Val Leu Phe Tyr Leu Ala Val Gly Ile Met Phe Leu Val Asn
            260                 265                 270

Thr Val Leu Trp Val Thr Ile Arg Lys Glu Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380
```

```
Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
            405                 410                 415

Leu Ser Thr Ala Thr Lys Asp Thr Tyr Asp Ala Leu His Met Gln Ala
        420                 425                 430

Leu Pro Pro Arg
        435

<210> SEQ ID NO 28
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 28

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ile Ile Leu Val Gly Thr Ala Val Ile Ala Met Phe Phe
            260                 265                 270

Trp Leu Leu Leu Val Ile Ile Leu Arg Thr Lys Arg Gly Arg Lys Lys
        275                 280                 285

Leu Leu Tyr Ile Phe Lys Gln Pro Phe Met Arg Pro Val Gln Thr Thr
290                 295                 300
```

```
Gln Glu Glu Asp Gly Cys Ser Cys Arg Phe Pro Glu Glu Glu Gly
305                 310                 315                 320

Gly Cys Glu Leu Arg Val Lys Phe Ser Arg Ser Ala Asp Ala Pro Ala
            325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
            405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 29
<211> LENGTH: 432
<212> TYPE: PRT
<213> ORGANISM: Artificial Sequence
<220> FEATURE:
<223> OTHER INFORMATION: Synthetic polypeptide

<400> SEQUENCE: 29

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
    115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
    210                 215                 220
```

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
            245                 250                 255

Cys Asp Leu Gly Trp Leu Cys Leu Leu Leu Pro Ile Pro Leu Ile
            260                 265                 270

Val Trp Val Lys Arg Lys Lys Arg Gly Arg Lys Lys Leu Leu Tyr Ile
        275                 280                 285

Phe Lys Gln Pro Phe Met Arg Pro Val Gln Thr Thr Gln Glu Glu Asp
        290                 295                 300

Gly Cys Ser Cys Arg Phe Pro Glu Glu Glu Gly Gly Cys Glu Leu
305                 310                 315                 320

Arg Val Lys Phe Ser Arg Ser Ala Asp Ala Pro Ala Tyr Gln Gln Gly
            325                 330                 335

Gln Asn Gln Leu Tyr Asn Glu Leu Asn Leu Gly Arg Arg Glu Glu Tyr
                340                 345                 350

Asp Val Leu Asp Lys Arg Arg Gly Arg Asp Pro Glu Met Gly Gly Lys
            355                 360                 365

Pro Arg Arg Lys Asn Pro Gln Glu Gly Leu Tyr Asn Glu Leu Gln Lys
            370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430

<210> SEQ ID NO 30
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 30

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

```
Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Ala Ile Tyr Cys Ile Gly Val Phe Leu Ile Ala Cys Met
            260                 265                 270

Val Val Thr Val Ile Leu Cys Arg Met Lys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 31
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 31

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80
```

Ile Asp Ala Ala Thr Val Asp Asp Ser Gly Glu Tyr Arg Cys Gln Thr
            85                  90                  95

Asn Leu Ser Thr Leu Ser Asp Pro Val Gln Leu Glu Val His Ile Gly
        100                 105                 110

Trp Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Phe Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 32
<211> LENGTH: 476
<212> TYPE: PRT
<213> ORGANISM: Artificial Sequence
<220> FEATURE:
<223> OTHER INFORMATION: Synthetic polypeptide

<400> SEQUENCE: 32

```
-continued

Met Ala Leu Pro Val Thr Ala Leu Leu Leu Pro Leu Ala Leu Leu Leu
1               5                   10                  15

His Ala Ala Arg Pro Gln Val Asp Thr Thr Lys Ala Val Ile Thr Leu
            20                  25                  30

Gln Pro Pro Trp Val Ser Val Phe Gln Glu Glu Thr Val Thr Leu His
        35                  40                  45

Cys Glu Val Leu His Leu Pro Gly Ser Ser Ser Thr Gln Trp Phe Leu
    50                  55                  60

Asn Gly Thr Ala Thr Gln Thr Ser Thr Pro Ser Tyr Arg Ile Thr Ser
65                  70                  75                  80

Ala Ser Val Asn Asp Ser Gly Glu Tyr Arg Cys Gln Arg Gly Leu Ser
                85                  90                  95

Gly Arg Ser Asp Pro Ile Gln Leu Glu Ile His Arg Gly Trp Leu Leu
            100                 105                 110

Leu Gln Val Ser Ser Arg Val Phe Thr Glu Gly Glu Pro Leu Ala Leu
        115                 120                 125

Arg Cys His Ala Trp Lys Asp Lys Leu Val Tyr Asn Val Leu Tyr Tyr
    130                 135                 140

Arg Asn Gly Lys Ala Phe Lys Phe Phe His Trp Asn Ser Asn Leu Thr
145                 150                 155                 160

Ile Leu Lys Thr Asn Ile Ser His Asn Gly Thr Tyr His Cys Ser Gly
                165                 170                 175

Met Gly Lys His Arg Tyr Thr Ser Ala Gly Ile Ser Val Thr Val Lys
            180                 185                 190

Glu Leu Phe Pro Ala Pro Val Leu Asn Ala Ser Val Thr Ser Pro Leu
        195                 200                 205

Leu Glu Gly Asn Leu Val Thr Leu Ser Cys Glu Thr Lys Leu Leu Leu
    210                 215                 220

Gln Arg Pro Gly Leu Gln Leu Tyr Phe Ser Phe Tyr Met Gly Ser Lys
225                 230                 235                 240

Thr Leu Arg Gly Arg Asn Thr Ser Ser Glu Tyr Gln Ile Leu Thr Ala
                245                 250                 255

Arg Arg Glu Asp Ser Gly Leu Tyr Trp Cys Glu Ala Ala Thr Glu Asp
            260                 265                 270

Gly Asn Val Leu Lys Arg Ser Pro Glu Leu Glu Leu Gln Val Leu Gly
        275                 280                 285

Leu Gln Leu Pro Thr Pro Val Trp Phe His Ile Tyr Ile Trp Ala Pro
    290                 295                 300

Leu Ala Gly Thr Cys Gly Val Leu Leu Leu Ser Leu Val Ile Thr Leu
305                 310                 315                 320

Tyr Cys Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Arg Val Lys Phe
        355                 360                 365

Ser Arg Ser Ala Asp Ala Pro Ala Tyr Gln Gln Gly Gln Asn Gln Leu
    370                 375                 380

Tyr Asn Glu Leu Asn Leu Gly Arg Arg Glu Glu Tyr Asp Val Leu Asp
385                 390                 395                 400

Lys Arg Arg Gly Arg Asp Pro Glu Met Gly Gly Lys Pro Arg Arg Lys
                405                 410                 415

Asn Pro Gln Glu Gly Leu Tyr Asn Glu Leu Gln Lys Asp Lys Met Ala
```

```
                    420                 425                 430
Glu Ala Tyr Ser Glu Ile Gly Met Lys Gly Glu Arg Arg Gly Lys
                435                 440                 445

Gly His Asp Gly Leu Tyr Gln Gly Leu Ser Thr Ala Thr Lys Asp Thr
    450                 455                 460

Tyr Asp Ala Leu His Met Gln Ala Leu Pro Pro Arg
465                 470                 475

<210> SEQ ID NO 33
<211> LENGTH: 623
<212> TYPE: PRT
<213> ORGANISM: Artificial Sequence
<220> FEATURE:
<223> OTHER INFORMATION: Synthetic polypeptide

<400> SEQUENCE: 33

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
            305                 310                 315                 320
Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Ile Tyr Ile
        435                 440                 445

Trp Ala Pro Leu Ala Gly Thr Cys Gly Val Leu Leu Leu Ser Leu Val
    450                 455                 460

Ile Thr Leu Tyr Cys Lys Arg Gly Arg Lys Lys Leu Leu Tyr Ile Phe
465                 470                 475                 480

Lys Gln Pro Phe Met Arg Pro Val Gln Thr Thr Gln Glu Glu Asp Gly
                485                 490                 495

Cys Ser Cys Arg Phe Pro Glu Glu Glu Glu Gly Gly Cys Glu Leu Arg
            500                 505                 510

Val Lys Phe Ser Arg Ser Ala Asp Ala Pro Ala Tyr Gln Gln Gly Gln
        515                 520                 525

Asn Gln Leu Tyr Asn Glu Leu Asn Leu Gly Arg Arg Glu Glu Tyr Asp
    530                 535                 540

Val Leu Asp Lys Arg Arg Gly Arg Asp Pro Glu Met Gly Gly Lys Pro
545                 550                 555                 560

Arg Arg Lys Asn Pro Gln Glu Gly Leu Tyr Asn Glu Leu Gln Lys Asp
                565                 570                 575

Lys Met Ala Glu Ala Tyr Ser Glu Ile Gly Met Lys Gly Glu Arg Arg
            580                 585                 590

Arg Gly Lys Gly His Asp Gly Leu Tyr Gln Gly Leu Ser Thr Ala Thr
        595                 600                 605

Lys Asp Thr Tyr Asp Ala Leu His Met Gln Ala Leu Pro Pro Arg
    610                 615                 620

<210> SEQ ID NO 34
<211> LENGTH: 510
<212> TYPE: PRT
<213> ORGANISM: Artificial Sequence
<220> FEATURE:
<223> OTHER INFORMATION: Synthetic polypeptide

<400> SEQUENCE: 34

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
```

```
             50                  55                  60
Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
                115                 120                 125

Ile His Leu Arg Cys His Ser Trp Lys Asn Thr Ala Leu His Lys Val
                130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
                195                 200                 205

Pro Pro Gly Tyr Gln Glu Pro Lys Ser Cys Asp Lys Thr His Thr Cys
                210                 215                 220

Pro Gly Gln Pro Arg Glu Pro Gln Val Tyr Thr Leu Pro Pro Ser Arg
225                 230                 235                 240

Asp Glu Leu Thr Lys Asn Gln Val Ser Leu Thr Cys Leu Val Lys Gly
                245                 250                 255

Phe Tyr Pro Ser Asp Ile Ala Val Glu Trp Glu Ser Asn Gly Gln Pro
                260                 265                 270

Glu Asn Asn Tyr Lys Thr Thr Pro Pro Val Leu Asp Ser Asp Gly Ser
                275                 280                 285

Phe Phe Leu Tyr Ser Lys Leu Thr Val Asp Lys Ser Arg Trp Gln Gln
                290                 295                 300

Gly Asn Val Phe Ser Cys Ser Val Met His Glu Ala Leu His Asn His
305                 310                 315                 320

Tyr Thr Gln Lys Ser Leu Ser Leu Ser Pro Gly Lys Ile Tyr Ile Trp
                325                 330                 335

Ala Pro Leu Ala Gly Thr Cys Gly Val Leu Leu Leu Ser Leu Val Ile
                340                 345                 350

Thr Leu Tyr Cys Lys Arg Gly Arg Lys Lys Leu Leu Tyr Ile Phe Lys
                355                 360                 365

Gln Pro Phe Met Arg Pro Val Gln Thr Thr Gln Glu Glu Asp Gly Cys
                370                 375                 380

Ser Cys Arg Phe Pro Glu Glu Glu Glu Gly Gly Cys Glu Leu Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
                435                 440                 445

Arg Lys Asn Pro Gln Glu Gly Leu Tyr Asn Glu Leu Gln Lys Asp Lys
                450                 455                 460

Met Ala Glu Ala Tyr Ser Glu Ile Gly Met Lys Gly Glu Arg Arg Arg
465                 470                 475                 480
```

```
Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
            500                 505                 510

<210> SEQ ID NO 35
<211> LENGTH: 403
<212> TYPE: PRT
<213> ORGANISM: Artificial Sequence
<220> FEATURE:
<223> OTHER INFORMATION: Synthetic polypeptide

<400> SEQUENCE: 35

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Glu Pro Lys Ser Cys Asp Lys Thr His Thr Cys
210                 215                 220

Pro Ile Tyr Ile Trp Ala Pro Leu Ala Gly Thr Cys Gly Val Leu Leu
225                 230                 235                 240

Leu Ser Leu Val Ile Thr Leu Tyr Cys Lys Arg Gly Arg Lys Lys Leu
                245                 250                 255

Leu Tyr Ile Phe Lys Gln Pro Phe Met Arg Pro Val Gln Thr Thr Gln
            260                 265                 270

Glu Glu Asp Gly Cys Ser Cys Arg Phe Pro Glu Glu Glu Glu Gly Gly
        275                 280                 285

Cys Glu Leu Arg Val Lys Phe Ser Arg Ser Ala Asp Ala Pro Ala Tyr
290                 295                 300

Gln Gln Gly Gln Asn Gln Leu Tyr Asn Glu Leu Asn Leu Gly Arg Arg
305                 310                 315                 320

Glu Glu Tyr Asp Val Leu Asp Lys Arg Arg Gly Arg Asp Pro Glu Met
                325                 330                 335
```

```
Gly Gly Lys Pro Arg Arg Lys Asn Pro Gln Glu Gly Leu Tyr Asn Glu
            340                 345                 350

Leu Gln Lys Asp Lys Met Ala Glu Ala Tyr Ser Glu Ile Gly Met Lys
        355                 360                 365

Gly Glu Arg Arg Arg Gly Lys Gly His Asp Gly Leu Tyr Gln Gly Leu
    370                 375                 380

Ser Thr Ala Thr Lys Asp Thr Tyr Asp Ala Leu His Met Gln Ala Leu
385                 390                 395                 400

Pro Pro Arg

<210> SEQ ID NO 36
<211> LENGTH: 421
<212> TYPE: PRT
<213> ORGANISM: Artificial Sequence
<220> FEATURE:
<223> OTHER INFORMATION: Synthetic polypeptide

<400> SEQUENCE: 36

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Phe
225                 230                 235                 240

Ala Cys Asp Ile Tyr Ile Trp Ala Pro Leu Ala Gly Thr Cys Gly Val
                245                 250                 255

Leu Leu Leu Ser Leu Val Ile Thr Leu Tyr Cys Lys Arg Gly Arg Lys
            260                 265                 270

Lys Leu Leu Tyr Ile Phe Lys Gln Pro Phe Met Arg Pro Val Gln Thr
        275                 280                 285
```

```
Thr Gln Glu Glu Asp Gly Cys Ser Cys Arg Phe Pro Glu Glu Glu
    290                 295                 300

Gly Gly Cys Glu Leu Arg Val Lys Phe Ser Arg Ser Ala Asp Ala Pro
305             310                 315                 320

Ala Tyr Gln Gln Gly Gln Asn Gln Leu Tyr Asn Glu Leu Asn Leu Gly
                325                 330                 335

Arg Arg Glu Glu Tyr Asp Val Leu Asp Lys Arg Arg Gly Arg Asp Pro
            340                 345                 350

Glu Met Gly Gly Lys Pro Arg Arg Lys Asn Pro Gln Glu Gly Leu Tyr
            355                 360                 365

Asn Glu Leu Gln Lys Asp Lys Met Ala Glu Ala Tyr Ser Glu Ile Gly
370                 375                 380

Met Lys Gly Glu Arg Arg Arg Gly Lys Gly His Asp Gly Leu Tyr Gln
385             390                 395                 400

Gly Leu Ser Thr Ala Thr Lys Asp Thr Tyr Asp Ala Leu His Met Gln
                405                 410                 415

Ala Leu Pro Pro Arg
            420

<210> SEQ ID NO 37
<211> LENGTH: 406
<212> TYPE: PRT
<213> ORGANISM: Artificial Sequence
<220> FEATURE:
<223> OTHER INFORMATION: Synthetic polypeptide

<400> SEQUENCE: 37

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220
```

-continued

Phe Ala Cys Asp Ile Tyr Ile Trp Ala Pro Leu Ala Gly Thr Cys Gly
225                 230                 235                 240

Val Leu Leu Leu Ser Leu Val Ile Thr Leu Tyr Cys Lys Arg Gly Arg
            245                 250                 255

Lys Lys Leu Leu Tyr Ile Phe Lys Gln Pro Phe Met Arg Pro Val Gln
        260                 265                 270

Thr Thr Gln Glu Glu Asp Gly Cys Ser Cys Arg Phe Pro Glu Glu Glu
    275                 280                 285

Glu Gly Gly Cys Glu Leu Arg Val Lys Phe Ser Arg Ser Ala Asp Ala
290                 295                 300

Pro Ala Tyr Gln Gln Gly Gln Asn Gln Leu Tyr Asn Glu Leu Asn Leu
305                 310                 315                 320

Gly Arg Arg Glu Glu Tyr Asp Val Leu Asp Lys Arg Arg Gly Arg Asp
            325                 330                 335

Pro Glu Met Gly Gly Lys Pro Arg Arg Lys Asn Pro Gln Glu Gly Leu
        340                 345                 350

Tyr Asn Glu Leu Gln Lys Asp Lys Met Ala Glu Ala Tyr Ser Glu Ile
    355                 360                 365

Gly Met Lys Gly Glu Arg Arg Arg Gly Lys Gly His Asp Gly Leu Tyr
370                 375                 380

Gln Gly Leu Ser Thr Ala Thr Lys Asp Thr Tyr Asp Ala Leu His Met
385                 390                 395                 400

Gln Ala Leu Pro Pro Arg
            405

<210> SEQ ID NO 38
<211> LENGTH: 406
<212> TYPE: PRT
<213> ORGANISM: Artificial Sequence
<220> FEATURE:
<223> OTHER INFORMATION: Synthetic polypeptide

<400> SEQUENCE: 38

Met Ala Leu Pro Val Thr Ala Leu Leu Leu Pro Leu Ala Leu Leu Leu
1               5                   10                  15

His Ala Ala Arg Pro Gly Met Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
            85                  90                  95

Asn Leu Ser Thr Leu Ser Asp Pro Val Gln Leu Glu Val His Ile Gly
        100                 105                 110

Trp Leu Leu Leu Gln Ala Pro Arg Trp Val Phe Lys Glu Glu Asp Pro
    115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
            165                 170                 175

```
Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Gly Gly Ser Gly Gly Gly Gly Ser Gly
    210                 215                 220

Gly Gly Gly Ser Ile Tyr Ile Trp Ala Pro Leu Ala Gly Thr Cys Gly
225                 230                 235                 240

Val Leu Leu Leu Ser Leu Val Ile Thr Leu Tyr Cys Lys Arg Gly Arg
                245                 250                 255

Lys Lys Leu Leu Tyr Ile Phe Lys Gln Pro Phe Met Arg Pro Val Gln
                260                 265                 270

Thr Thr Gln Glu Glu Asp Gly Cys Ser Cys Arg Phe Pro Glu Glu Glu
            275                 280                 285

Glu Gly Gly Cys Glu Leu Arg Val Lys Phe Ser Arg Ser Ala Asp Ala
        290                 295                 300

Pro Ala Tyr Gln Gln Gly Gln Asn Gln Leu Tyr Asn Glu Leu Asn Leu
305                 310                 315                 320

Gly Arg Arg Glu Glu Tyr Asp Val Leu Asp Lys Arg Arg Gly Arg Asp
                325                 330                 335

Pro Glu Met Gly Gly Lys Pro Arg Arg Lys Asn Pro Gln Glu Gly Leu
            340                 345                 350

Tyr Asn Glu Leu Gln Lys Asp Lys Met Ala Glu Ala Tyr Ser Glu Ile
        355                 360                 365

Gly Met Lys Gly Glu Arg Arg Arg Gly Lys Gly His Asp Gly Leu Tyr
370                 375                 380

Gln Gly Leu Ser Thr Ala Thr Lys Asp Thr Tyr Asp Ala Leu His Met
385                 390                 395                 400

Gln Ala Leu Pro Pro Arg
                405

<210> SEQ ID NO 39
<211> LENGTH: 421
<212> TYPE: PRT
<213> ORGANISM: Artificial Sequence
<220> FEATURE:
<223> OTHER INFORMATION: Synthetic polypeptide

<400> SEQUENCE: 39

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125
```

```
Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Gly Gly Ser Gly Gly Gly Ser Gly
    210                 215                 220

Gly Gly Gly Ser Gly Gly Gly Ser Gly Gly Gly Ser Gly Gly
225                 230                 235                 240

Gly Gly Ser Ile Tyr Ile Trp Ala Pro Leu Ala Gly Thr Cys Gly Val
                245                 250                 255

Leu Leu Leu Ser Leu Val Ile Thr Leu Tyr Cys Lys Arg Gly Arg Lys
            260                 265                 270

Lys Leu Leu Tyr Ile Phe Lys Gln Pro Phe Met Arg Pro Val Gln Thr
        275                 280                 285

Thr Gln Glu Glu Asp Gly Cys Ser Cys Arg Phe Pro Glu Glu Glu Glu
        290                 295                 300

Gly Gly Cys Glu Leu Arg Val Lys Phe Ser Arg Ser Ala Asp Ala Pro
305                 310                 315                 320

Ala Tyr Gln Gln Gly Gln Asn Gln Leu Tyr Asn Glu Leu Asn Leu Gly
                325                 330                 335

Arg Arg Glu Glu Tyr Asp Val Leu Asp Lys Arg Arg Gly Arg Asp Pro
            340                 345                 350

Glu Met Gly Gly Lys Pro Arg Arg Lys Asn Pro Gln Glu Gly Leu Tyr
        355                 360                 365

Asn Glu Leu Gln Lys Asp Lys Met Ala Glu Ala Tyr Ser Glu Ile Gly
        370                 375                 380

Met Lys Gly Glu Arg Arg Arg Gly Lys Gly His Asp Gly Leu Tyr Gln
385                 390                 395                 400

Gly Leu Ser Thr Ala Thr Lys Asp Thr Tyr Asp Ala Leu His Met Gln
                405                 410                 415

Ala Leu Pro Pro Arg
            420

<210> SEQ ID NO 40
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 40

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60
```

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
            85                  90                  95

Asn Leu Ser Thr Leu Ser Asp Pro Val Gln Leu Glu Val His Ile Gly
        100                 105                 110

Trp Leu Leu Leu Gln Ala Pro Arg Trp Val Phe Lys Glu Glu Asp Pro
    115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Gly Gly Ser Gly Gly Gly Ser Gly
    210                 215                 220

Gly Gly Gly Ser Gly Gly Gly Ser Gly Gly Gly Ser Gly Gly
225                 230                 235                 240

Gly Gly Ser Gly Gly Gly Ser Gly Gly Gly Ser Gly Gly Gly
            245                 250                 255

Gly Ser Ile Tyr Ile Trp Ala Pro Leu Ala Gly Thr Cys Gly Val Leu
        260                 265                 270

Leu Leu Ser Leu Val Ile Thr Leu Tyr Cys Lys Arg Gly Arg Lys Lys
    275                 280                 285

Leu Leu Tyr Ile Phe Lys Gln Pro Phe Met Arg Pro Val Gln Thr Thr
290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435

<210> SEQ ID NO 41
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 41

```
Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Gly Gly Ser Gly Gly Gly Ser Gly
    210                 215                 220

Gly Gly Gly Ser Gly Gly Gly Ser Gly Gly Gly Ser Gly Gly
225                 230                 235                 240

Gly Gly Ser Gly Gly Gly Ser Gly Gly Gly Ser Gly Gly Gly
            245                 250                 255

Gly Ser Gly Gly Gly Ser Gly Gly Gly Ser Gly Gly Gly Gly
        260                 265                 270

Ser Ile Tyr Ile Trp Ala Pro Leu Ala Gly Thr Cys Gly Val Leu Leu
    275                 280                 285

Leu Ser Leu Val Ile Thr Leu Tyr Cys Lys Arg Gly Arg Lys Lys Leu
290                 295                 300

Leu Tyr Ile Phe Lys Gln Pro Phe Met Arg Pro Val Gln Thr Thr Gln
305                 310                 315                 320

Glu Glu Asp Gly Cys Ser Cys Arg Phe Pro Glu Glu Glu Glu Gly Gly
                325                 330                 335

Cys Glu Leu Arg Val Lys Phe Ser Arg Ser Ala Asp Ala Pro Ala Tyr
            340                 345                 350

Gln Gln Gly Gln Asn Gln Leu Tyr Asn Glu Leu Asn Leu Gly Arg Arg
        355                 360                 365

Glu Glu Tyr Asp Val Leu Asp Lys Arg Arg Gly Arg Asp Pro Glu Met
    370                 375                 380

Gly Gly Lys Pro Arg Arg Lys Asn Pro Gln Glu Gly Leu Tyr Asn Glu
385                 390                 395                 400

Leu Gln Lys Asp Lys Met Ala Glu Ala Tyr Ser Glu Ile Gly Met Lys
```

```
            405                 410                 415
Gly Glu Arg Arg Arg Gly Lys Gly His Asp Gly Leu Tyr Gln Gly Leu
            420                 425                 430

Ser Thr Ala Thr Lys Asp Thr Tyr Asp Ala Leu His Met Gln Ala Leu
            435                 440                 445

Pro Pro Arg
    450

<210> SEQ ID NO 42
<211> LENGTH: 451
<212> TYPE: PRT
<213> ORGANISM: Artificial Sequence
<220> FEATURE:
<223> OTHER INFORMATION: Synthetic polypeptide

<400> SEQUENCE: 42

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Ser Pro Ala Gly Ser Pro Thr Ser Thr
    210                 215                 220

Glu Glu Gly Thr Ser Glu Ser Ala Thr Pro Glu Ser Gly Pro Gly Thr
225                 230                 235                 240

Ser Thr Glu Pro Ser Glu Gly Ser Ala Pro Gly Ser Pro Ala Gly Ser
                245                 250                 255

Pro Thr Ser Thr Glu Glu Gly Thr Ser Thr Glu Pro Ser Glu Gly Ser
            260                 265                 270

Ala Ile Tyr Ile Trp Ala Pro Leu Ala Gly Thr Cys Gly Val Leu Leu
        275                 280                 285

Leu Ser Leu Val Ile Thr Leu Tyr Cys Lys Arg Gly Arg Lys Lys Leu
    290                 295                 300

Leu Tyr Ile Phe Lys Gln Pro Phe Met Arg Pro Val Gln Thr Thr Gln
```

```
                305                 310                 315                 320
Glu Glu Asp Gly Cys Ser Cys Arg Phe Pro Glu Glu Glu Gly Gly
                    325                 330                 335

Cys Glu Leu Arg Val Lys Phe Ser Arg Ser Ala Asp Ala Pro Ala Tyr
            340                 345                 350

Gln Gln Gly Gln Asn Gln Leu Tyr Asn Glu Leu Asn Leu Gly Arg Arg
                355                 360                 365

Glu Glu Tyr Asp Val Leu Asp Lys Arg Gly Arg Asp Pro Glu Met
            370                 375                 380

Gly Gly Lys Pro Arg Arg Lys Asn Pro Gln Glu Gly Leu Tyr Asn Glu
385                 390                 395                 400

Leu Gln Lys Asp Lys Met Ala Glu Ala Tyr Ser Glu Ile Gly Met Lys
                405                 410                 415

Gly Glu Arg Arg Arg Gly Lys Gly His Asp Gly Leu Tyr Gln Gly Leu
            420                 425                 430

Ser Thr Ala Thr Lys Asp Thr Tyr Asp Ala Leu His Met Gln Ala Leu
                435                 440                 445

Pro Pro Arg
    450

<210> SEQ ID NO 43
<211> LENGTH: 421
<212> TYPE: PRT
<213> ORGANISM: Artificial Sequence
<220> FEATURE:
<223> OTHER INFORMATION: Synthetic polypeptide

<400> SEQUENCE: 43

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Gly Ser Pro Ala Gly Ser Pro Thr Ser Thr
```

```
            210                 215                 220
Glu Glu Gly Thr Ser Glu Ser Ala Thr Pro Glu Ser Gly Pro Gly Thr
225                 230                 235                 240

Ser Thr Glu Ile Tyr Ile Trp Ala Pro Leu Ala Gly Thr Cys Gly Val
                    245                 250                 255

Leu Leu Leu Ser Leu Val Ile Thr Leu Tyr Cys Lys Arg Gly Arg Lys
                260                 265                 270

Lys Leu Leu Tyr Ile Phe Lys Gln Pro Phe Met Arg Pro Val Gln Thr
            275                 280                 285

Thr Gln Glu Glu Asp Gly Cys Ser Cys Arg Phe Pro Glu Glu Glu Glu
        290                 295                 300

Gly Gly Cys Glu Leu Arg Val Lys Phe Ser Arg Ser Ala Asp Ala Pro
305                 310                 315                 320

Ala Tyr Gln Gln Gly Gln Asn Gln Leu Tyr Asn Glu Leu Asn Leu Gly
                    325                 330                 335

Arg Arg Glu Glu Tyr Asp Val Leu Asp Lys Arg Arg Gly Arg Asp Pro
                340                 345                 350

Glu Met Gly Gly Lys Pro Arg Arg Lys Asn Pro Gln Glu Gly Leu Tyr
            355                 360                 365

Asn Glu Leu Gln Lys Asp Lys Met Ala Glu Ala Tyr Ser Glu Ile Gly
        370                 375                 380

Met Lys Gly Glu Arg Arg Arg Gly Lys Gly His Asp Gly Leu Tyr Gln
385                 390                 395                 400

Gly Leu Ser Thr Ala Thr Lys Asp Thr Tyr Asp Ala Leu His Met Gln
                    405                 410                 415

Ala Leu Pro Pro Arg
                420

<210> SEQ ID NO 44
<211> LENGTH: 406
<212> TYPE: PRT
<213> ORGANISM: Artificial Sequence
<220> FEATURE:
<223> OTHER INFORMATION: Synthetic polypeptide

<400> SEQUENCE: 44

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                    85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
```

```
            145                 150                 155                 160
Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
                195                 200                 205

Pro Pro Gly Tyr Gln Gly Gly Ser Pro Ala Gly Ser Pro Thr Ser Thr
            210                 215                 220

Glu Glu Gly Thr Ile Tyr Ile Trp Ala Pro Leu Ala Gly Thr Cys Gly
225                 230                 235                 240

Val Leu Leu Leu Ser Leu Val Ile Thr Leu Tyr Cys Lys Arg Gly Arg
                245                 250                 255

Lys Lys Leu Leu Tyr Ile Phe Lys Gln Pro Phe Met Arg Pro Val Gln
            260                 265                 270

Thr Thr Gln Glu Glu Asp Gly Cys Ser Cys Arg Phe Pro Glu Glu Glu
                275                 280                 285

Glu Gly Gly Cys Glu Leu Arg Val Lys Phe Ser Arg Ser Ala Asp Ala
290                 295                 300

Pro Ala Tyr Gln Gln Gly Gln Asn Gln Leu Tyr Asn Glu Leu Asn Leu
305                 310                 315                 320

Gly Arg Arg Glu Glu Tyr Asp Val Leu Asp Lys Arg Arg Gly Arg Asp
                325                 330                 335

Pro Glu Met Gly Gly Lys Pro Arg Arg Lys Asn Pro Gln Glu Gly Leu
            340                 345                 350

Tyr Asn Glu Leu Gln Lys Asp Lys Met Ala Glu Ala Tyr Ser Glu Ile
                355                 360                 365

Gly Met Lys Gly Glu Arg Arg Arg Gly Lys Gly His Asp Gly Leu Tyr
            370                 375                 380

Gln Gly Leu Ser Thr Ala Thr Lys Asp Thr Tyr Asp Ala Leu His Met
385                 390                 395                 400

Gln Ala Leu Pro Pro Arg
                405

<210> SEQ ID NO 45
<211> LENGTH: 433
<212> TYPE: PRT
<213> ORGANISM: Artificial Sequence
<220> FEATURE:
<223> OTHER INFORMATION: Synthetic polypeptide

<400> SEQUENCE: 45

Met Leu Arg Leu Leu Leu Ala Leu Asn Leu Phe Pro Ser Ile Gln Val
1               5                   10                  15

Thr Gly Gly Met Arg Thr Glu Asp Leu Pro Lys Ala Val Val Phe Leu
                20                  25                  30

Glu Pro Gln Trp Tyr Arg Val Leu Glu Lys Asp Ser Val Thr Leu Lys
            35                  40                  45

Cys Gln Gly Ala Tyr Ser Pro Glu Asp Asn Ser Thr Gln Trp Phe His
        50                  55                  60

Asn Glu Ser Leu Ile Ser Ser Gln Ala Ser Ser Tyr Phe Ile Asp Ala
65                  70                  75                  80

Ala Thr Val Asp Asp Ser Gly Glu Tyr Arg Cys Gln Thr Asn Leu Ser
                85                  90                  95

Thr Leu Ser Asp Pro Val Gln Leu Glu Val His Ile Gly Trp Leu Leu
```

```
            100                 105                 110
Leu Gln Ala Pro Arg Trp Val Phe Lys Glu Asp Pro Ile His Leu
        115                 120                 125

Arg Cys His Ser Trp Lys Asn Thr Ala Leu His Lys Val Thr Tyr Leu
    130                 135                 140

Gln Asn Gly Lys Gly Arg Lys Tyr Phe His His Asn Ser Asp Phe Tyr
145                 150                 155                 160

Ile Pro Lys Ala Thr Leu Lys Asp Ser Gly Ser Tyr Phe Cys Arg Gly
                    165                 170                 175

Leu Val Gly Ser Lys Asn Val Ser Ser Glu Thr Val Asn Ile Thr Ile
                180                 185                 190

Thr Gln Gly Leu Ala Val Ser Thr Ile Ser Ser Phe Phe Pro Pro Gly
            195                 200                 205

Tyr Gln Thr Thr Thr Pro Ala Pro Arg Pro Pro Thr Pro Ala Pro Thr
        210                 215                 220

Ile Ala Ser Gln Pro Leu Ser Leu Arg Pro Glu Ala Cys Arg Pro Ala
225                 230                 235                 240

Ala Gly Gly Ala Val His Thr Arg Gly Leu Asp Phe Ala Cys Asp Ile
                    245                 250                 255

Tyr Ile Trp Ala Pro Leu Ala Gly Thr Cys Gly Val Leu Leu Leu Ser
                260                 265                 270

Leu Val Ile Thr Leu Tyr Cys Lys Arg Gly Arg Lys Lys Leu Leu Tyr
            275                 280                 285

Ile Phe Lys Gln Pro Phe Met Arg Pro Val Gln Thr Thr Gln Glu Glu
        290                 295                 300

Asp Gly Cys Ser Cys Arg Phe Pro Glu Glu Glu Glu Gly Gly Cys Glu
305                 310                 315                 320

Leu Arg Val Lys Phe Ser Arg Ser Ala Asp Ala Pro Ala Tyr Gln Gln
                    325                 330                 335

Gly Gln Asn Gln Leu Tyr Asn Glu Leu Asn Leu Gly Arg Arg Glu Glu
                340                 345                 350

Tyr Asp Val Leu Asp Lys Arg Arg Gly Arg Asp Pro Glu Met Gly Gly
            355                 360                 365

Lys Pro Arg Arg Lys Asn Pro Gln Glu Gly Leu Tyr Asn Glu Leu Gln
        370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                    405                 410                 415

Ala Thr Lys Asp Thr Tyr Asp Ala Leu His Met Gln Ala Leu Pro Pro
                420                 425                 430

Arg

<210> SEQ ID NO 46
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 46

Met Glu Thr Asp Thr Leu Leu Leu Trp Val Leu Leu Leu Trp Val Pro
1               5                   10                  15

Gly Ser Thr Gly Asp Gly Met Arg Thr Glu Asp Leu Pro Lys Ala Val
                20                  25                  30
```

```
Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                          55                  60

Trp Phe His Asn Glu Ser Leu Ile Ser Ser Gln Ala Ser Ser Tyr Phe
65                      70                  75                  80

Ile Asp Ala Ala Thr Val Asp Asp Ser Gly Glu Tyr Arg Cys Gln Thr
                    85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335

Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
        355                 360                 365

Met Gly Gly Lys Pro Arg Arg Lys Asn Pro Gln Glu Gly Leu Tyr Asn
    370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
        435
```

```
<210> SEQ ID NO 47
<211> LENGTH: 431
<212> TYPE: PRT
<213> ORGANISM: Artificial Sequence
<220> FEATURE:
<223> OTHER INFORMATION: Synthetic polypeptide

<400> SEQUENCE: 47

Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Thr Thr Thr Pro Ala Pro Arg Pro Pro Thr Pro Ala Pro Thr Ile Ala
    210                 215                 220

Ser Gln Pro Leu Ser Leu Arg Pro Glu Ala Cys Arg Pro Ala Ala Gly
225                 230                 235                 240

Gly Ala Val His Thr Arg Gly Leu Asp Phe Ala Cys Asp Ile Tyr Ile
                245                 250                 255

Trp Ala Pro Leu Ala Gly Thr Cys Gly Val Leu Leu Leu Ser Leu Val
            260                 265                 270

Ile Thr Leu Tyr Cys Lys Arg Gly Arg Lys Lys Leu Leu Tyr Ile Phe
        275                 280                 285

Lys Gln Pro Phe Met Arg Pro Val Gln Thr Thr Gln Glu Glu Asp Gly
    290                 295                 300

Cys Ser Cys Arg Phe Pro Glu Glu Glu Glu Gly Gly Cys Glu Leu Arg
305                 310                 315                 320

Val Lys Phe Ser Arg Ser Ala Asp Ala Pro Ala Tyr Gln Gln Gly Gln
                325                 330                 335

Asn Gln Leu Tyr Asn Glu Leu Asn Leu Gly Arg Arg Glu Glu Tyr Asp
            340                 345                 350

Val Leu Asp Lys Arg Arg Gly Arg Asp Pro Glu Met Gly Gly Lys Pro
        355                 360                 365
```

```
Arg Arg Lys Asn Pro Gln Glu Gly Leu Tyr Asn Glu Leu Gln Lys Asp
    370                 375                 380

Lys Met Ala Glu Ala Tyr Ser Glu Ile Gly Met Lys Gly Glu Arg Arg
385                 390                 395                 400

Arg Gly Lys Gly His Asp Gly Leu Tyr Gln Gly Leu Ser Thr Ala Thr
                405                 410                 415

Lys Asp Thr Tyr Asp Ala Leu His Met Gln Ala Leu Pro Pro Arg
                420                 425                 430

<210> SEQ ID NO 48
<211> LENGTH: 432
<212> TYPE: PRT
<213> ORGANISM: Artificial Sequence
<220> FEATURE:
<223> OTHER INFORMATION: Synthetic polypeptide

<400> SEQUENCE: 48

Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Cys Trp Leu Thr Lys Lys
            275                 280                 285

Lys Tyr Ser Ser Ser Val His Asp Pro Asn Gly Glu Tyr Met Phe Met
            290                 295                 300
```

```
Arg Ala Val Asn Thr Ala Lys Lys Ser Arg Leu Thr Asp Val Thr Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
        355                 360                 365

Pro Arg Arg Lys Asn Pro Gln Glu Gly Leu Tyr Asn Glu Leu Gln Lys
    370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
                420                 425                 430

<210> SEQ ID NO 49
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 49

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240
```

```
Arg Pro Ala Ala Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Gln Arg Arg Lys Tyr Arg
            275                 280                 285

Ser Asn Lys Gly Glu Ser Pro Val Glu Pro Ala Glu Pro Cys Arg Tyr
290                 295                 300

Ser Cys Pro Arg Glu Glu Gly Ser Thr Ile Pro Ile Gln Glu Asp
305                 310                 315                 320

Tyr Arg Lys Pro Glu Pro Ala Cys Ser Pro Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
            355                 360                 365

Arg Gly Arg Asp Pro Glu Met Gly Gly Lys Pro Arg Arg Lys Asn Pro
            370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
            435                 440

<210> SEQ ID NO 50
<211> LENGTH: 452
<212> TYPE: PRT
<213> ORGANISM: Artificial Sequence
<220> FEATURE:
<223> OTHER INFORMATION: Synthetic polypeptide

<400> SEQUENCE: 50

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160
```

Asp Phe Tyr Ile Pro Lys Ala Thr Leu Lys Asp Ser Gly Ser Tyr Phe
            165                 170                 175

Cys Arg Gly Leu Val Gly Ser Lys Asn Val Ser Ser Glu Thr Val Asn
        180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
            245                 250                 255

Cys Asp Ile Tyr Ile Trp Ala Pro Leu Ala Gly Thr Cys Gly Val Leu
        260                 265                 270

Leu Leu Ser Leu Val Ile Thr Leu Tyr Cys Gln Leu Gly Leu His Ile
            275                 280                 285

Trp Gln Leu Arg Ser Gln Cys Met Trp Pro Arg Glu Thr Gln Leu Leu
        290                 295                 300

Leu Glu Val Pro Pro Ser Thr Glu Asp Ala Arg Ser Cys Gln Phe Pro
305                 310                 315                 320

Glu Glu Glu Arg Gly Glu Arg Ser Ala Glu Glu Lys Gly Arg Leu Gly
            325                 330                 335

Asp Leu Trp Val Arg Val Lys Phe Ser Arg Ser Ala Asp Ala Pro Ala
        340                 345                 350

Tyr Gln Gln Gly Gln Asn Gln Leu Tyr Asn Glu Leu Asn Leu Gly Arg
            355                 360                 365

Arg Glu Glu Tyr Asp Val Leu Asp Lys Arg Arg Gly Arg Asp Pro Glu
        370                 375                 380

Met Gly Gly Lys Pro Arg Arg Lys Asn Pro Gln Glu Gly Leu Tyr Asn
385                 390                 395                 400

Glu Leu Gln Lys Asp Lys Met Ala Glu Ala Tyr Ser Glu Ile Gly Met
            405                 410                 415

Lys Gly Glu Arg Arg Arg Gly Lys Gly His Asp Gly Leu Tyr Gln Gly
        420                 425                 430

Leu Ser Thr Ala Thr Lys Asp Thr Tyr Asp Ala Leu His Met Gln Ala
            435                 440                 445

Leu Pro Pro Arg
    450

<210> SEQ ID NO 51
<211> LENGTH: 454
<212> TYPE: PRT
<213> ORGANISM: Artificial Sequence
<220> FEATURE:
<223> OTHER INFORMATION: Synthetic polypeptide

<400> SEQUENCE: 51

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

```
Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Cys Val Lys Arg Arg Lys
        275                 280                 285

Pro Arg Gly Asp Val Val Lys Val Ile Val Ser Val Gln Arg Lys Arg
290                 295                 300

Gln Glu Ala Glu Gly Glu Ala Thr Val Ile Glu Ala Leu Gln Ala Pro
305                 310                 315                 320

Pro Asp Val Thr Thr Val Ala Val Glu Glu Thr Ile Pro Ser Phe Thr
                325                 330                 335

Gly Arg Ser Pro Asn His Arg Val Lys Phe Ser Arg Ser Ala Asp Ala
            340                 345                 350

Pro Ala Tyr Gln Gln Gly Gln Asn Gln Leu Tyr Asn Glu Leu Asn Leu
        355                 360                 365

Gly Arg Arg Glu Glu Tyr Asp Val Leu Asp Lys Arg Arg Gly Arg Asp
370                 375                 380

Pro Glu Met Gly Gly Lys Pro Arg Arg Lys Asn Pro Gln Glu Gly Leu
385                 390                 395                 400

Tyr Asn Glu Leu Gln Lys Asp Lys Met Ala Glu Ala Tyr Ser Glu Ile
                405                 410                 415

Gly Met Lys Gly Glu Arg Arg Arg Gly Lys Gly His Asp Gly Leu Tyr
            420                 425                 430

Gln Gly Leu Ser Thr Ala Thr Lys Asp Thr Tyr Asp Ala Leu His Met
        435                 440                 445

Gln Ala Leu Pro Pro Arg
    450

<210> SEQ ID NO 52
<211> LENGTH: 442
<212> TYPE: PRT
```

<213> ORGANISM: Artificial Sequence
<220> FEATURE:
<223> OTHER INFORMATION: Synthetic polypeptide

<400> SEQUENCE: 52

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Lys Tyr Phe Phe Lys
        275                 280                 285

Lys Glu Val Gln Gln Leu Ser Val Ser Phe Ser Ser Leu Gln Ile Lys
290                 295                 300

Ala Leu Gln Asn Ala Val Glu Lys Glu Val Gln Ala Glu Asp Asn Ile
305                 310                 315                 320

Tyr Ile Glu Asn Ser Leu Tyr Ala Thr Asp Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
        355                 360                 365

Arg Gly Arg Asp Pro Glu Met Gly Gly Lys Pro Arg Arg Lys Asn Pro
370                 375                 380

Gln Glu Gly Leu Tyr Asn Glu Leu Gln Lys Asp Lys Met Ala Glu Ala
```

```
              385                 390                 395                 400
Tyr Ser Glu Ile Gly Met Lys Gly Glu Arg Arg Gly Lys Gly His
                    405                 410                 415
Asp Gly Leu Tyr Gln Gly Leu Ser Thr Ala Thr Lys Asp Thr Tyr Asp
                420                 425                 430
Ala Leu His Met Gln Ala Leu Pro Pro Arg
            435                 440

<210> SEQ ID NO 53
<211> LENGTH: 453
<212> TYPE: PRT
<213> ORGANISM: Artificial Sequence
<220> FEATURE:
<223> OTHER INFORMATION: Synthetic polypeptide

<400> SEQUENCE: 53

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Tyr Lys Val Gly Phe Phe
        275                 280                 285

Lys Arg Asn Leu Lys Glu Lys Met Glu Ala Gly Arg Gly Val Pro Asn
    290                 295                 300

Gly Ile Pro Ala Glu Asp Ser Glu Gln Leu Ala Ser Gly Gln Glu Ala
```

```
            305                 310                 315                 320
    Gly Asp Pro Gly Cys Leu Lys Pro Leu His Glu Lys Asp Ser Glu Ser
                        325                 330                 335

Gly Gly Gly Lys Asp Arg Val Lys Phe Ser Arg Ser Ala Asp Ala Pro
                        340                 345                 350

Ala Tyr Gln Gln Gly Gln Asn Gln Leu Tyr Asn Glu Leu Asn Leu Gly
                        355                 360                 365

Arg Arg Glu Glu Tyr Asp Val Leu Asp Lys Arg Gly Arg Asp Pro
            370                 375                 380

Glu Met Gly Gly Lys Pro Arg Arg Lys Asn Pro Gln Glu Gly Leu Tyr
    385                 390                 395                 400

Asn Glu Leu Gln Lys Asp Lys Met Ala Glu Ala Tyr Ser Glu Ile Gly
                        405                 410                 415

Met Lys Gly Glu Arg Arg Arg Gly Lys Gly His Asp Gly Leu Tyr Gln
                        420                 425                 430

Gly Leu Ser Thr Ala Thr Lys Asp Thr Tyr Asp Ala Leu His Met Gln
                        435                 440                 445

Ala Leu Pro Pro Arg
                450

<210> SEQ ID NO 54
<211> LENGTH: 510
<212> TYPE: PRT
<213> ORGANISM: Artificial Sequence
<220> FEATURE:
<223> OTHER INFORMATION: Synthetic polypeptide

<400> SEQUENCE: 54

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
            195                 200                 205

Pro Pro Gly Tyr Gln Thr Thr Thr Pro Ala Pro Arg Pro Pro Thr Pro
```

```
                210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
                260                 265                 270

Leu Leu Ser Leu Val Ile Thr Leu Tyr Cys Lys Arg Lys Lys Gln Arg
                275                 280                 285

Ser Arg Arg Asn Asp Glu Glu Leu Glu Thr Arg Ala His Arg Val Ala
                290                 295                 300

Thr Glu Glu Arg Gly Arg Lys Pro His Gln Ile Pro Ala Ser Thr Pro
305                 310                 315                 320

Gln Asn Pro Ala Thr Ser Gln His Pro Pro Pro Pro Gly His Arg
                325                 330                 335

Ser Gln Ala Pro Ser His Arg Pro Pro Pro Gly His Arg Val Gln
                340                 345                 350

His Gln Pro Gln Lys Arg Pro Ala Pro Ser Gly Thr Gln Val His
                355                 360                 365

Gln Gln Lys Gly Pro Pro Leu Pro Arg Pro Arg Val Gln Pro Lys Pro
                370                 375                 380

Pro His Gly Ala Ala Glu Asn Ser Leu Ser Pro Ser Ser Asn Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
                420                 425                 430

Leu Asp Lys Arg Arg Gly Arg Asp Pro Glu Met Gly Gly Lys Pro Arg
                435                 440                 445

Arg Lys Asn Pro Gln Glu Gly Leu Tyr Asn Glu Leu Gln Lys Asp Lys
                450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg
                500                 505                 510

<210> SEQ ID NO 55
<211> LENGTH: 365
<212> TYPE: PRT
<213> ORGANISM: Artificial Sequence
<220> FEATURE:
<223> OTHER INFORMATION: Synthetic polypeptide

<400> SEQUENCE: 55

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
                35                  40                  45

Thr Leu Lys Cys Gln Gly Ala Tyr Ser Pro Glu Asp Asn Ser Thr Gln
                50                  55                  60

Trp Phe His Asn Glu Ser Leu Ile Ser Ser Gln Ala Ser Ser Tyr Phe
```

```
            65                  70                  75                  80
Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
            130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
                195                 200                 205

Pro Pro Gly Tyr Gln Thr Thr Thr Pro Ala Pro Arg Pro Pro Thr Pro
            210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Pro Gln Leu Cys Tyr Ile Leu Asp Ala Ile Leu Phe Leu Tyr
                260                 265                 270

Gly Ile Val Leu Thr Leu Leu Tyr Cys Arg Leu Lys Ile Gln Val Arg
                275                 280                 285

Lys Ala Ala Ile Thr Ser Tyr Glu Lys Ser Asp Gly Val Tyr Thr Gly
            290                 295                 300

Leu Ser Thr Arg Asn Gln Glu Thr Tyr Glu Thr Leu Lys His Glu Lys
305                 310                 315                 320

Pro Pro Gln Lys Arg Gly Arg Lys Lys Leu Leu Tyr Ile Phe Lys Gln
                325                 330                 335

Pro Phe Met Arg Pro Val Gln Thr Thr Gln Glu Glu Asp Gly Cys Ser
                340                 345                 350

Cys Arg Phe Pro Glu Glu Glu Glu Gly Gly Cys Glu Leu
                355                 360                 365

<210> SEQ ID NO 56
<211> LENGTH: 366
<212> TYPE: PRT
<213> ORGANISM: Artificial Sequence
<220> FEATURE:
<223> OTHER INFORMATION: Synthetic polypeptide

<400> SEQUENCE: 56

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
```

```
                65                  70                  75                  80
    Ile Asp Ala Ala Thr Val Asp Asp Ser Gly Glu Tyr Arg Cys Gln Thr
                        85                  90                  95

Asn Leu Ser Thr Leu Ser Asp Pro Val Gln Leu Glu Val His Ile Gly
                100                 105                 110

Trp Leu Leu Gln Ala Pro Arg Trp Val Phe Lys Glu Glu Asp Pro
                115                 120                 125

Ile His Leu Arg Cys His Ser Trp Lys Asn Thr Ala Leu His Lys Val
                130                 135                 140

Thr Tyr Leu Gln Asn Gly Lys Gly Arg Lys Tyr Phe His His Asn Ser
    145                 150                 155                 160

Asp Phe Tyr Ile Pro Lys Ala Thr Leu Lys Asp Ser Gly Ser Tyr Phe
                    165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
                195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
    225                 230                 235                 240

Arg Pro Ala Ala Gly Gly Ala Val His Thr Arg Gly Leu Asp Phe Ala
                    245                 250                 255

Cys Asp Ile Tyr Ile Trp Ala Pro Leu Ala Gly Thr Cys Gly Val Leu
                260                 265                 270

Leu Leu Ser Leu Val Ile Thr Leu Tyr Cys Lys Arg Gly Arg Lys Lys
                275                 280                 285

Leu Leu Tyr Ile Phe Lys Gln Pro Phe Met Arg Pro Val Gln Thr Thr
                290                 295                 300

Gln Glu Glu Asp Gly Cys Ser Cys Arg Phe Pro Glu Glu Glu Glu Gly
    305                 310                 315                 320

Gly Cys Glu Leu Arg Leu Lys Ile Gln Val Arg Lys Ala Ala Ile Thr
                    325                 330                 335

Ser Tyr Glu Lys Ser Asp Gly Val Tyr Thr Gly Leu Ser Thr Arg Asn
                340                 345                 350

Gln Glu Tyr Glu Thr Leu Lys His Glu Lys Pro Pro Gln
                355                 360                 365

<210> SEQ ID NO 57
<211> LENGTH: 432
<212> TYPE: PRT
<213> ORGANISM: Artificial Sequence
<220> FEATURE:
<223> OTHER INFORMATION: Synthetic polypeptide

<400> SEQUENCE: 57

Met Ala Leu Pro Val Thr Ala Leu Leu Leu Pro Leu Ala Leu Leu Leu
    1               5                   10                  15

His Ala Ala Arg Pro Gly Met Arg Thr Glu Asp Leu Pro Lys Ala Val
                    20                  25                  30

Val Phe Leu Glu Pro Gln Trp Tyr Arg Val Leu Glu Lys Asp Ser Val
                35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
```

```
                65                  70                  75                  80
Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
        130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Glu Val Met Tyr Pro Pro Pro Tyr Leu Asp
210                 215                 220

Asn Glu Lys Ser Asn Gly Thr Ile Ile His Val Lys Gly Lys His Leu
225                 230                 235                 240

Cys Pro Ser Pro Leu Phe Pro Gly Pro Ser Lys Pro Phe Trp Val Leu
                245                 250                 255

Val Val Val Gly Gly Val Leu Ala Cys Tyr Ser Leu Leu Val Thr Val
            260                 265                 270

Ala Phe Ile Ile Phe Trp Val Arg Ser Lys Arg Ser Arg Leu Leu His
        275                 280                 285

Ser Asp Tyr Met Asn Met Thr Pro Arg Arg Pro Gly Pro Thr Arg Lys
290                 295                 300

His Tyr Gln Pro Tyr Ala Pro Pro Arg Asp Phe Ala Ala Tyr Arg Ser
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
        355                 360                 365

Pro Arg Arg Lys Asn Pro Gln Glu Gly Leu Tyr Asn Glu Leu Gln Lys
370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430

<210> SEQ ID NO 58
<211> LENGTH: 390
<212> TYPE: PRT
<213> ORGANISM: Artificial Sequence
<220> FEATURE:
<223> OTHER INFORMATION: Synthetic polypeptide

<400> SEQUENCE: 58

Met Ala Leu Pro Val Thr Ala Leu Leu Leu Pro Leu Ala Leu Leu Leu
```

```
1               5                   10                  15
His Ala Ala Arg Pro Gly Met Arg Thr Glu Asp Leu Pro Lys Ala Val
                20                  25                  30
Val Phe Leu Glu Pro Gln Trp Tyr Arg Val Leu Glu Lys Asp Ser Val
                35                  40                  45
Thr Leu Lys Cys Gln Gly Ala Tyr Ser Pro Glu Asp Asn Ser Thr Gln
                50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
                100                 105                 110
Trp Leu Leu Leu Gln Ala Pro Arg Trp Val Phe Lys Glu Glu Asp Pro
                115                 120                 125
Ile His Leu Arg Cys His Ser Trp Lys Asn Thr Ala Leu His Lys Val
                130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
                180                 185                 190
Ile Thr Ile Thr Gln Gly Leu Ala Val Ser Thr Ile Ser Ser Phe Phe
                195                 200                 205
Pro Pro Gly Tyr Gln Ile Tyr Ile Trp Ala Pro Leu Ala Gly Thr Cys
                210                 215                 220
Gly Val Leu Leu Leu Ser Leu Val Ile Thr Leu Tyr Cys Arg Ser Lys
225                 230                 235                 240
Arg Ser Arg Leu Leu His Ser Asp Tyr Met Asn Met Thr Pro Arg Arg
                245                 250                 255
Pro Gly Pro Thr Arg Lys His Tyr Gln Pro Tyr Ala Pro Pro Arg Asp
                260                 265                 270
Phe Ala Ala Tyr Arg Ser Arg Val Lys Phe Ser Arg Ser Ala Asp Ala
                275                 280                 285
Pro Ala Tyr Gln Gln Gly Gln Asn Gln Leu Tyr Asn Glu Leu Asn Leu
                290                 295                 300
Gly Arg Arg Glu Glu Tyr Asp Val Leu Asp Lys Arg Gly Arg Asp
305                 310                 315                 320
Pro Glu Met Gly Gly Lys Pro Arg Arg Lys Asn Pro Gln Glu Gly Leu
                325                 330                 335
Tyr Asn Glu Leu Gln Lys Asp Lys Met Ala Glu Ala Tyr Ser Glu Ile
                340                 345                 350
Gly Met Lys Gly Glu Arg Arg Arg Gly Lys Gly His Asp Gly Leu Tyr
                355                 360                 365
Gln Gly Leu Ser Thr Ala Thr Lys Asp Thr Tyr Asp Ala Leu His Met
                370                 375                 380
Gln Ala Leu Pro Pro Arg
385                 390

<210> SEQ ID NO 59
<211> LENGTH: 483
<212> TYPE: PRT
<213> ORGANISM: Artificial Sequence
```

```
<220> FEATURE:
<223> OTHER INFORMATION: Synthetic polypeptide

<400> SEQUENCE: 59

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Leu Leu His Ser Asp Tyr Met Asn Met Thr Pro Arg Arg Pro Gly Pro
290                 295                 300

Thr Arg Lys His Tyr Gln Pro Tyr Ala Pro Pro Arg Asp Phe Ala Ala
305                 310                 315                 320

Tyr Arg Ser Gln Arg Arg Lys Tyr Arg Ser Asn Lys Gly Glu Ser Pro
                325                 330                 335

Val Glu Pro Ala Glu Pro Cys His Tyr Ser Cys Pro Arg Glu Glu Glu
            340                 345                 350

Gly Ser Thr Ile Pro Ile Gln Glu Asp Tyr Arg Lys Pro Glu Pro Ala
        355                 360                 365

Cys Ser Pro Arg Val Lys Phe Ser Arg Ser Ala Asp Ala Pro Ala Tyr
370                 375                 380

Gln Gln Gly Gln Asn Gln Leu Tyr Asn Glu Leu Asn Leu Gly Arg Arg
385                 390                 395                 400
```

```
Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
            435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 60
<211> LENGTH: 472
<212> TYPE: PRT
<213> ORGANISM: Artificial Sequence
<220> FEATURE:
<223> OTHER INFORMATION: Synthetic polypeptide

<400> SEQUENCE: 60

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270
```

```
Leu Leu Ser Leu Val Ile Thr Leu Tyr Cys Arg Ser Lys Arg Ser Arg
            275                 280                 285

Leu Leu His Ser Asp Tyr Met Asn Met Thr Pro Arg Arg Pro Gly Pro
        290                 295                 300

Thr Arg Lys His Tyr Gln Pro Tyr Ala Pro Pro Arg Asp Phe Ala Ala
305                 310                 315                 320

Tyr Arg Ser Arg Arg Asp Gln Arg Leu Pro Pro Asp Ala His Lys Pro
                325                 330                 335

Pro Gly Gly Gly Ser Phe Arg Thr Pro Ile Gln Glu Glu Gln Ala Asp
            340                 345                 350

Ala His Ser Thr Leu Ala Lys Ile Arg Val Lys Phe Ser Arg Ser Ala
        355                 360                 365

Asp Ala Pro Ala Tyr Gln Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
450                 455                 460

His Met Gln Ala Leu Pro Pro Arg
465                 470

<210> SEQ ID NO 61
<211> LENGTH: 477
<212> TYPE: PRT
<213> ORGANISM: Artificial Sequence
<220> FEATURE:
<223> OTHER INFORMATION: Synthetic polypeptide

<400> SEQUENCE: 61

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160
```

```
Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Ser Lys Arg Ser Arg Leu Leu His Ser Asp Tyr
                325                 330                 335

Met Asn Met Thr Pro Arg Arg Pro Gly Pro Thr Arg Lys His Tyr Gln
            340                 345                 350

Pro Tyr Ala Pro Pro Arg Asp Phe Ala Ala Tyr Arg Ser Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg
465                 470                 475

<210> SEQ ID NO 62
<211> LENGTH: 474
<212> TYPE: PRT
<213> ORGANISM: Artificial Sequence
<220> FEATURE:
<223> OTHER INFORMATION: Synthetic polypeptide

<400> SEQUENCE: 62

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45
```

```
Thr Leu Lys Cys Gln Gly Ala Tyr Ser Pro Glu Asp Asn Ser Thr Gln
 50                  55                  60

Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Glu Val Met Tyr Pro Pro Pro Tyr Leu Asp
    210                 215                 220

Asn Glu Lys Ser Asn Gly Thr Ile Ile His Val Lys Gly Lys His Leu
225                 230                 235                 240

Cys Pro Ser Pro Leu Phe Pro Gly Pro Ser Lys Pro Phe Trp Val Leu
                245                 250                 255

Val Val Val Gly Gly Val Leu Ala Cys Tyr Ser Leu Leu Val Thr Val
            260                 265                 270

Ala Phe Ile Ile Phe Trp Val Arg Ser Lys Arg Ser Arg Leu Leu His
        275                 280                 285

Ser Asp Tyr Met Asn Met Thr Pro Arg Arg Pro Gly Pro Thr Arg Lys
290                 295                 300

His Tyr Gln Pro Tyr Ala Pro Pro Arg Asp Phe Ala Ala Tyr Arg Ser
305                 310                 315                 320

Lys Arg Gly Arg Lys Lys Leu Leu Tyr Ile Phe Lys Gln Pro Phe Met
                325                 330                 335

Arg Pro Val Gln Thr Thr Gln Glu Glu Asp Gly Cys Ser Cys Arg Phe
            340                 345                 350

Pro Glu Glu Glu Glu Gly Gly Cys Glu Leu Arg Val Lys Phe Ser Arg
        355                 360                 365

Ser Ala Asp Ala Pro Ala Tyr Gln Gln Gly Gln Asn Gln Leu Tyr Asn
    370                 375                 380

Glu Leu Asn Leu Gly Arg Arg Glu Glu Tyr Asp Val Leu Asp Lys Arg
385                 390                 395                 400

Arg Gly Arg Asp Pro Glu Met Gly Gly Lys Pro Arg Arg Lys Asn Pro
                405                 410                 415

Gln Glu Gly Leu Tyr Asn Glu Leu Gln Lys Asp Lys Met Ala Glu Ala
            420                 425                 430

Tyr Ser Glu Ile Gly Met Lys Gly Glu Arg Arg Arg Gly Lys Gly His
        435                 440                 445

Asp Gly Leu Tyr Gln Gly Leu Ser Thr Ala Thr Lys Asp Thr Tyr Asp
    450                 455                 460

Ala Leu His Met Gln Ala Leu Pro Pro Arg
```

```
                    465                 470
```

<210> SEQ ID NO 63
<211> LENGTH: 433
<212> TYPE: PRT
<213> ORGANISM: Artificial Sequence
<220> FEATURE:
<223> OTHER INFORMATION: Synthetic polypeptide

<400> SEQUENCE: 63

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Glu Val Met Tyr Pro Pro Tyr Leu Asp
    210                 215                 220

Asn Glu Lys Ser Asn Gly Thr Ile Ile His Val Lys Gly Lys His Leu
225                 230                 235                 240

Cys Pro Ser Pro Leu Phe Pro Gly Pro Ser Lys Pro Phe Trp Val Leu
                245                 250                 255

Val Val Val Gly Gly Val Leu Ala Cys Tyr Ser Leu Leu Val Thr Val
            260                 265                 270

Ala Phe Ile Ile Phe Trp Val Lys Arg Gly Arg Lys Lys Leu Leu Tyr
        275                 280                 285

Ile Phe Lys Gln Pro Phe Met Arg Pro Val Gln Thr Thr Gln Glu Glu
    290                 295                 300

Asp Gly Cys Ser Cys Arg Phe Pro Glu Glu Glu Glu Gly Gly Cys Glu
305                 310                 315                 320

Leu Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
```

```
                355                 360                 365
Lys Pro Arg Arg Lys Asn Pro Gln Glu Gly Leu Tyr Asn Glu Leu Gln
370                 375                 380
Lys Asp Lys Met Ala Glu Ala Tyr Ser Glu Ile Gly Met Lys Gly Glu
385                 390                 395                 400
Arg Arg Arg Gly Lys Gly His Asp Gly Leu Tyr Gln Gly Leu Ser Thr
                405                 410                 415
Ala Thr Lys Asp Thr Tyr Asp Ala Leu His Met Gln Ala Leu Pro Pro
            420                 425                 430
Arg

<210> SEQ ID NO 64
<211> LENGTH: 442
<212> TYPE: PRT
<213> ORGANISM: Artificial Sequence
<220> FEATURE:
<223> OTHER INFORMATION: Synthetic polypeptide

<400> SEQUENCE: 64

Met Ala Leu Pro Val Thr Ala Leu Leu Leu Pro Leu Ala Leu Leu Leu
1               5                   10                  15
His Ala Ala Arg Pro Gly Met Arg Thr Glu Asp Leu Pro Lys Ala Val
            20                  25                  30
Val Phe Leu Glu Pro Gln Trp Tyr Arg Val Leu Glu Lys Asp Ser Val
        35                  40                  45
Thr Leu Lys Cys Gln Gly Ala Tyr Ser Pro Glu Asp Asn Ser Thr Gln
    50                  55                  60
Trp Phe His Asn Glu Ser Leu Ile Ser Ser Gln Ala Ser Ser Tyr Phe
65                  70                  75                  80
Ile Asp Ala Ala Thr Val Asp Asp Ser Gly Glu Tyr Arg Cys Gln Thr
                85                  90                  95
Asn Leu Ser Thr Leu Ser Asp Pro Val Gln Leu Glu Val His Ile Gly
            100                 105                 110
Trp Leu Leu Leu Gln Ala Pro Arg Trp Val Phe Lys Glu Glu Asp Pro
        115                 120                 125
Ile His Leu Arg Cys His Ser Trp Lys Asn Thr Ala Leu His Lys Val
    130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
            180                 185                 190
Ile Thr Ile Thr Gln Gly Leu Ala Val Ser Thr Ile Ser Ser Phe Phe
        195                 200                 205
Pro Pro Gly Tyr Gln Thr Thr Thr Pro Ala Pro Arg Pro Pro Thr Pro
    210                 215                 220
Ala Pro Thr Ile Ala Ser Gln Pro Leu Ser Leu Arg Pro Glu Ala Cys
225                 230                 235                 240
Arg Pro Ala Ala Gly Gly Ala Val His Thr Arg Gly Leu Asp Phe Ala
                245                 250                 255
Cys Asp Ile Tyr Ile Trp Ala Pro Leu Ala Gly Thr Cys Gly Val Leu
            260                 265                 270
Leu Leu Ser Leu Val Ile Thr Leu Tyr Cys Gln Arg Arg Lys Tyr Arg
        275                 280                 285
```

```
Ser Asn Lys Gly Glu Ser Pro Val Glu Pro Ala Glu Pro Cys His Tyr
        290                 295                 300

Ser Cys Pro Arg Glu Glu Gly Ser Thr Ile Pro Ile Gln Glu Asp
305                 310                 315                 320

Tyr Arg Lys Pro Glu Pro Ala Cys Ser Pro Arg Val Lys Phe Ser Arg
                325                 330                 335

Ser Ala Asp Ala Pro Ala Tyr Gln Gln Gly Gln Asn Gln Leu Tyr Asn
            340                 345                 350

Glu Leu Asn Leu Gly Arg Arg Glu Glu Tyr Asp Val Leu Asp Lys Arg
        355                 360                 365

Arg Gly Arg Asp Pro Glu Met Gly Gly Lys Pro Arg Arg Lys Asn Pro
370                 375                 380

Gln Glu Gly Leu Tyr Asn Glu Leu Gln Lys Asp Lys Met Ala Glu Ala
385                 390                 395                 400

Tyr Ser Glu Ile Gly Met Lys Gly Glu Arg Arg Arg Gly Lys Gly His
                405                 410                 415

Asp Gly Leu Tyr Gln Gly Leu Ser Thr Ala Thr Lys Asp Thr Tyr Asp
            420                 425                 430

Ala Leu His Met Gln Ala Leu Pro Pro Arg
            435                 440

<210> SEQ ID NO 65
<211> LENGTH: 435
<212> TYPE: PRT
<213> ORGANISM: Artificial Sequence
<220> FEATURE:
<223> OTHER INFORMATION: Synthetic polypeptide

<400> SEQUENCE: 65

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205
```

```
Pro Pro Gly Tyr Gln Thr Thr Thr Pro Ala Pro Arg Pro Pro Thr Pro
        210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
                260                 265                 270

Leu Leu Ser Leu Val Ile Thr Leu Tyr Cys Arg Ser Lys Arg Ser Arg
        275                 280                 285

Leu Leu His Ser Asp Tyr Met Asn Met Thr Pro Arg Arg Pro Gly Pro
        290                 295                 300

Thr Arg Lys His Tyr Gln Pro Tyr Ala Pro Pro Arg Asp Phe Ala Ala
305                 310                 315                 320

Tyr Arg Ser Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
                340                 345                 350

Glu Glu Tyr Asp Val Leu Asp Lys Arg Gly Arg Asp Pro Glu Met
        355                 360                 365

Gly Gly Lys Pro Arg Arg Lys Asn Pro Gln Glu Gly Leu Tyr Asn Glu
370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
                420                 425                 430

Pro Pro Arg
        435

<210> SEQ ID NO 66
<211> LENGTH: 428
<212> TYPE: PRT
<213> ORGANISM: Artificial Sequence
<220> FEATURE:
<223> OTHER INFORMATION: Synthetic polypeptide

<400> SEQUENCE: 66

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125
```

```
Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Lys Lys Tyr Ser Ser
        275                 280                 285

Ser Val His Asp Pro Asn Gly Glu Tyr Met Phe Met Arg Ala Val Asn
290                 295                 300

Thr Ala Lys Lys Ser Arg Leu Thr Asp Val Thr Leu Arg Val Lys Phe
305                 310                 315                 320

Ser Arg Ser Ala Asp Ala Pro Ala Tyr Gln Gln Gly Gln Asn Gln Leu
                325                 330                 335

Tyr Asn Glu Leu Asn Leu Gly Arg Arg Glu Glu Tyr Asp Val Leu Asp
            340                 345                 350

Lys Arg Arg Gly Arg Asp Pro Glu Met Gly Gly Lys Pro Arg Arg Lys
        355                 360                 365

Asn Pro Gln Glu Gly Leu Tyr Asn Glu Leu Gln Lys Asp Lys Met Ala
370                 375                 380

Glu Ala Tyr Ser Glu Ile Gly Met Lys Gly Glu Arg Arg Arg Gly Lys
385                 390                 395                 400

Gly His Asp Gly Leu Tyr Gln Gly Leu Ser Thr Ala Thr Lys Asp Thr
                405                 410                 415

Tyr Asp Ala Leu His Met Gln Ala Leu Pro Pro Arg
            420                 425

<210> SEQ ID NO 67
<211> LENGTH: 431
<212> TYPE: PRT
<213> ORGANISM: Artificial Sequence
<220> FEATURE:
<223> OTHER INFORMATION: Synthetic polypeptide

<400> SEQUENCE: 67

Met Ala Leu Pro Val Thr Ala Leu Leu Leu Pro Leu Ala Leu Leu Leu
1               5                   10                  15

His Ala Ala Arg Pro Gly Met Thr Glu Asp Leu Pro Lys Ala Val
            20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60
```

-continued

```
Trp Phe His Asn Glu Ser Leu Ile Ser Ser Gln Ala Ser Ser Tyr Phe
 65                  70                  75                  80

Ile Asp Ala Ala Thr Val Asp Asp Ser Gly Glu Tyr Arg Cys Gln Thr
                 85                  90                  95

Asn Leu Ser Thr Leu Ser Asp Pro Val Gln Leu Glu Val His Ile Gly
            100                 105                 110

Trp Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Arg Asp Gln Arg Leu
        275                 280                 285

Pro Pro Asp Ala His Lys Pro Pro Gly Gly Gly Ser Phe Arg Thr Pro
290                 295                 300

Ile Gln Glu Glu Gln Ala Asp Ala His Ser Thr Leu Ala Lys Ile Arg
305                 310                 315                 320

Val Lys Phe Ser Arg Ser Ala Asp Ala Pro Ala Tyr Gln Gln Gly Gln
                325                 330                 335

Asn Gln Leu Tyr Asn Glu Leu Asn Leu Gly Arg Arg Glu Glu Tyr Asp
            340                 345                 350

Val Leu Asp Lys Arg Arg Gly Arg Asp Pro Glu Met Gly Gly Lys Pro
        355                 360                 365

Arg Arg Lys Asn Pro Gln Glu Gly Leu Tyr Asn Glu Leu Gln Lys Asp
370                 375                 380

Lys Met Ala Glu Ala Tyr Ser Glu Ile Gly Met Lys Gly Glu Arg Arg
385                 390                 395                 400

Arg Gly Lys Gly His Asp Gly Leu Tyr Gln Gly Leu Ser Thr Ala Thr
                405                 410                 415

Lys Asp Thr Tyr Asp Ala Leu His Met Gln Ala Leu Pro Pro Arg
            420                 425                 430
```

<210> SEQ ID NO 68
<211> LENGTH: 469
<212> TYPE: PRT
<213> ORGANISM: Artificial Sequence
<220> FEATURE:
<223> OTHER INFORMATION: Synthetic polypeptide

<400> SEQUENCE: 68

```
Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
        50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Arg Ser Lys Arg Ser Arg
        275                 280                 285

Leu Leu His Ser Asp Tyr Met Asn Met Thr Pro Arg Arg Pro Gly Pro
290                 295                 300

Thr Arg Lys His Tyr Gln Pro Tyr Ala Pro Pro Arg Asp Phe Ala Ala
305                 310                 315                 320

Tyr Arg Ser Lys Lys Lys Tyr Ser Ser Ser Val His Asp Pro Asn Gly
                325                 330                 335

Glu Tyr Met Phe Met Arg Ala Val Asn Thr Ala Lys Lys Ser Arg Leu
            340                 345                 350

Thr Asp Val Thr Leu Arg Val Lys Phe Ser Arg Ser Ala Asp Ala Pro
        355                 360                 365

Ala Tyr Gln Gln Gly Gln Asn Gln Leu Tyr Asn Glu Leu Asn Leu Gly
370                 375                 380

Arg Arg Glu Glu Tyr Asp Val Leu Asp Lys Arg Arg Gly Arg Asp Pro
385                 390                 395                 400

Glu Met Gly Gly Lys Pro Arg Arg Lys Asn Pro Gln Glu Gly Leu Tyr
                405                 410                 415
```

-continued

```
Asn Glu Leu Gln Lys Asp Lys Met Ala Glu Ala Tyr Ser Glu Ile Gly
            420                 425                 430

Met Lys Gly Glu Arg Arg Gly Lys Gly His Asp Gly Leu Tyr Gln
        435                 440                 445

Gly Leu Ser Thr Ala Thr Lys Asp Thr Tyr Asp Ala Leu His Met Gln
    450                 455                 460

Ala Leu Pro Pro Arg
465

<210> SEQ ID NO 69
<211> LENGTH: 391
<212> TYPE: PRT
<213> ORGANISM: Artificial Sequence
<220> FEATURE:
<223> OTHER INFORMATION: Synthetic polypeptide

<400> SEQUENCE: 69

Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Tyr Ile Trp Ala Pro Leu Ala Gly Thr Cys
    210                 215                 220

Gly Val Leu Leu Leu Ser Leu Val Ile Thr Leu Tyr Cys Lys Arg Gly
225                 230                 235                 240

Arg Lys Lys Leu Leu Tyr Ile Phe Lys Gln Pro Phe Met Arg Pro Val
                245                 250                 255

Gln Thr Thr Gln Glu Glu Asp Gly Cys Ser Cys Arg Phe Pro Glu Glu
            260                 265                 270

Glu Glu Gly Gly Cys Glu Leu Arg Val Lys Phe Ser Arg Ser Ala Asp
        275                 280                 285

Ala Pro Ala Tyr Gln Gln Gly Gln Asn Gln Leu Tyr Asn Glu Leu Asn
    290                 295                 300
```

```
Leu Gly Arg Arg Glu Glu Tyr Asp Val Leu Asp Lys Arg Arg Gly Arg
305                 310                 315                 320

Asp Pro Glu Met Gly Gly Lys Pro Arg Arg Lys Asn Pro Gln Glu Gly
                325                 330                 335

Leu Tyr Asn Glu Leu Gln Lys Asp Lys Met Ala Glu Ala Tyr Ser Glu
                340                 345                 350

Ile Gly Met Lys Gly Glu Arg Arg Gly Lys Gly His Asp Gly Leu
            355                 360                 365

Tyr Gln Gly Leu Ser Thr Ala Thr Lys Asp Thr Tyr Asp Ala Leu His
370                 375                 380

Met Gln Ala Leu Pro Pro Arg
385                 390

<210> SEQ ID NO 70
<211> LENGTH: 397
<212> TYPE: PRT
<213> ORGANISM: Artificial Sequence
<220> FEATURE:
<223> OTHER INFORMATION: Synthetic polypeptide

<400> SEQUENCE: 70

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Tyr Ile Trp Ala Pro Leu Ala Gly Thr Cys
    210                 215                 220

Gly Val Leu Leu Leu Ser Leu Val Ile Thr Leu Tyr Cys Gln Arg Arg
225                 230                 235                 240

Lys Tyr Arg Ser Asn Lys Gly Glu Ser Pro Val Glu Pro Ala Glu Pro
                245                 250                 255

Cys His Tyr Ser Cys Pro Arg Glu Glu Glu Gly Ser Thr Ile Pro Ile
            260                 265                 270
```

```
Gln Glu Asp Tyr Arg Lys Pro Glu Pro Ala Cys Ser Pro Arg Val Lys
            275                 280                 285

Phe Ser Arg Ser Ala Asp Ala Pro Ala Tyr Gln Gln Gly Gln Asn Gln
    290                 295                 300

Leu Tyr Asn Glu Leu Asn Leu Gly Arg Arg Glu Glu Tyr Asp Val Leu
305                 310                 315                 320

Asp Lys Arg Arg Gly Arg Asp Pro Glu Met Gly Gly Lys Pro Arg Arg
                325                 330                 335

Lys Asn Pro Gln Glu Gly Leu Tyr Asn Glu Leu Gln Lys Asp Lys Met
                340                 345                 350

Ala Glu Ala Tyr Ser Glu Ile Gly Met Lys Gly Glu Arg Arg Arg Gly
            355                 360                 365

Lys Gly His Asp Gly Leu Tyr Gln Gly Leu Ser Thr Ala Thr Lys Asp
            370                 375                 380

Thr Tyr Asp Ala Leu His Met Gln Ala Leu Pro Pro Arg
385                 390                 395

<210> SEQ ID NO 71
<211> LENGTH: 383
<212> TYPE: PRT
<213> ORGANISM: Artificial Sequence
<220> FEATURE:
<223> OTHER INFORMATION: Synthetic polypeptide

<400> SEQUENCE: 71

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Tyr Ile Trp Ala Pro Leu Ala Gly Thr Cys
    210                 215                 220

Gly Val Leu Leu Leu Ser Leu Val Ile Thr Leu Tyr Cys Lys Lys Lys
225                 230                 235                 240
```

```
Tyr Ser Ser Ser Val His Asp Pro Asn Gly Glu Tyr Met Phe Met Arg
                245                 250                 255

Ala Val Asn Thr Ala Lys Lys Ser Arg Leu Thr Asp Val Thr Leu Arg
            260                 265                 270

Val Lys Phe Ser Arg Ser Ala Asp Ala Pro Ala Tyr Gln Gln Gly Gln
        275                 280                 285

Asn Gln Leu Tyr Asn Glu Leu Asn Leu Gly Arg Arg Glu Glu Tyr Asp
    290                 295                 300

Val Leu Asp Lys Arg Arg Gly Arg Asp Pro Glu Met Gly Gly Lys Pro
305                 310                 315                 320

Arg Arg Lys Asn Pro Gln Glu Gly Leu Tyr Asn Glu Leu Gln Lys Asp
                325                 330                 335

Lys Met Ala Glu Ala Tyr Ser Glu Ile Gly Met Lys Gly Glu Arg Arg
            340                 345                 350

Arg Gly Lys Gly His Asp Gly Leu Tyr Gln Gly Leu Ser Thr Ala Thr
        355                 360                 365

Lys Asp Thr Tyr Asp Ala Leu His Met Gln Ala Leu Pro Pro Arg
    370                 375                 380

<210> SEQ ID NO 72
<211> LENGTH: 386
<212> TYPE: PRT
<213> ORGANISM: Artificial Sequence
<220> FEATURE:
<223> OTHER INFORMATION: Synthetic polypeptide

<400> SEQUENCE: 72

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Tyr Ile Trp Ala Pro Leu Ala Gly Thr Cys
    210                 215                 220
```

-continued

```
Gly Val Leu Leu Leu Ser Leu Val Ile Thr Leu Tyr Cys Arg Arg Asp
225                 230                 235                 240

Gln Arg Leu Pro Pro Asp Ala His Lys Pro Pro Gly Gly Gly Ser Phe
            245                 250                 255

Arg Thr Pro Ile Gln Glu Glu Gln Ala Asp Ala His Ser Thr Leu Ala
        260                 265                 270

Lys Ile Arg Val Lys Phe Ser Arg Ser Ala Asp Ala Pro Ala Tyr Gln
    275                 280                 285

Gln Gly Gln Asn Gln Leu Tyr Asn Glu Leu Asn Leu Gly Arg Arg Glu
290                 295                 300

Glu Tyr Asp Val Leu Asp Lys Arg Arg Gly Arg Asp Pro Glu Met Gly
305                 310                 315                 320

Gly Lys Pro Arg Arg Lys Asn Pro Gln Glu Gly Leu Tyr Asn Glu Leu
            325                 330                 335

Gln Lys Asp Lys Met Ala Glu Ala Tyr Ser Glu Ile Gly Met Lys Gly
        340                 345                 350

Glu Arg Arg Arg Gly Lys Gly His Asp Gly Leu Tyr Gln Gly Leu Ser
    355                 360                 365

Thr Ala Thr Lys Asp Thr Tyr Asp Ala Leu His Met Gln Ala Leu Pro
370                 375                 380

Pro Arg
385

<210> SEQ ID NO 73
<211> LENGTH: 395
<212> TYPE: PRT
<213> ORGANISM: Artificial Sequence
<220> FEATURE:
<223> OTHER INFORMATION: Synthetic polypeptide

<400> SEQUENCE: 73

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190
```

```
Ile Thr Ile Thr Gln Gly Leu Ala Val Ser Thr Ile Ser Ser Phe Phe
            195                 200                 205

Pro Pro Gly Tyr Gln Phe Ala Cys Asp Ile Tyr Ile Trp Ala Pro Leu
        210                 215                 220

Ala Gly Thr Cys Gly Val Leu Leu Ser Leu Val Ile Thr Leu Tyr
225                 230                 235                 240

Cys Lys Arg Gly Arg Lys Leu Leu Tyr Ile Phe Lys Gln Pro Phe
                245                 250                 255

Met Arg Pro Val Gln Thr Thr Gln Glu Asp Gly Cys Ser Cys Arg
                260                 265                 270

Phe Pro Glu Glu Glu Glu Gly Gly Cys Glu Leu Arg Val Lys Phe Ser
        275                 280                 285

Arg Ser Ala Asp Ala Pro Ala Tyr Gln Gln Gly Gln Asn Gln Leu Tyr
    290                 295                 300

Asn Glu Leu Asn Leu Gly Arg Arg Glu Glu Tyr Asp Val Leu Asp Lys
305                 310                 315                 320

Arg Arg Gly Arg Asp Pro Glu Met Gly Gly Lys Pro Arg Arg Lys Asn
                325                 330                 335

Pro Gln Glu Gly Leu Tyr Asn Glu Leu Gln Lys Asp Lys Met Ala Glu
                340                 345                 350

Ala Tyr Ser Glu Ile Gly Met Lys Gly Glu Arg Arg Arg Gly Lys Gly
            355                 360                 365

His Asp Gly Leu Tyr Gln Gly Leu Ser Thr Ala Thr Lys Asp Thr Tyr
        370                 375                 380

Asp Ala Leu His Met Gln Ala Leu Pro Pro Arg
385                 390                 395

<210> SEQ ID NO 74
<211> LENGTH: 394
<212> TYPE: PRT
<213> ORGANISM: Artificial Sequence
<220> FEATURE:
<223> OTHER INFORMATION: Synthetic polypeptide

<400> SEQUENCE: 74

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160
```

Asp Phe Tyr Ile Pro Lys Ala Thr Leu Lys Asp Ser Gly Ser Tyr Phe
            165                 170                 175

Cys Arg Gly Leu Val Gly Ser Lys Asn Val Ser Ser Glu Thr Val Asn
        180                 185                 190

Ile Thr Ile Thr Gln Gly Leu Ala Val Ser Thr Ile Ser Ser Phe Phe
    195                 200                 205

Pro Pro Gly Tyr Gln Phe Ala Cys Asp Ile Tyr Ile Trp Ala Pro Leu
210                 215                 220

Ala Gly Thr Cys Gly Val Leu Leu Leu Ser Leu Val Ile Thr Leu Tyr
225                 230                 235                 240

Cys Arg Ser Lys Arg Ser Arg Leu Leu His Ser Asp Tyr Met Asn Met
                245                 250                 255

Thr Pro Arg Arg Pro Gly Pro Thr Arg Lys His Tyr Gln Pro Tyr Ala
            260                 265                 270

Pro Pro Arg Asp Phe Ala Ala Tyr Arg Ser Arg Val Lys Phe Ser Arg
        275                 280                 285

Ser Ala Asp Ala Pro Ala Tyr Gln Gln Gly Gln Asn Gln Leu Tyr Asn
    290                 295                 300

Glu Leu Asn Leu Gly Arg Arg Glu Glu Tyr Asp Val Leu Asp Lys Arg
305                 310                 315                 320

Arg Gly Arg Asp Pro Glu Met Gly Gly Lys Pro Arg Arg Lys Asn Pro
                325                 330                 335

Gln Glu Gly Leu Tyr Asn Glu Leu Gln Lys Asp Lys Met Ala Glu Ala
            340                 345                 350

Tyr Ser Glu Ile Gly Met Lys Gly Glu Arg Arg Arg Gly Lys Gly His
        355                 360                 365

Asp Gly Leu Tyr Gln Gly Leu Ser Thr Ala Thr Lys Asp Thr Tyr Asp
    370                 375                 380

Ala Leu His Met Gln Ala Leu Pro Pro Arg
385                 390

<210> SEQ ID NO 75
<211> LENGTH: 438
<212> TYPE: PRT
<213> ORGANISM: Artificial Sequence
<220> FEATURE:
<223> OTHER INFORMATION: Synthetic polypeptide

<400> SEQUENCE: 75

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

```
Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
                180                 185                 190

Ile Thr Ile Thr Gln Gly Leu Ala Val Ser Thr Ile Ser Ser Phe Phe
                195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Phe Trp Val Leu Val Val Gly Gly Val Leu Ala Cys Tyr
                260                 265                 270

Ser Leu Leu Val Thr Val Ala Phe Ile Ile Phe Trp Val Arg Ser Lys
    275                 280                 285

Arg Ser Arg Leu Leu His Ser Asp Tyr Met Asn Met Thr Pro Arg Arg
    290                 295                 300

Pro Gly Pro Thr Arg Lys His Tyr Gln Pro Tyr Ala Pro Pro Arg Asp
305                 310                 315                 320

Phe Ala Ala Tyr Arg Ser Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
                340                 345                 350

Gly Arg Arg Glu Glu Tyr Asp Val Leu Asp Lys Arg Gly Arg Asp
    355                 360                 365

Pro Glu Met Gly Gly Lys Pro Arg Arg Lys Asn Pro Gln Glu Gly Leu
370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
                420                 425                 430

Gln Ala Leu Pro Pro Arg
                435

<210> SEQ ID NO 76
<211> LENGTH: 419
<212> TYPE: PRT
<213> ORGANISM: Artificial Sequence
<220> FEATURE:
<223> OTHER INFORMATION: Synthetic polypeptide

<400> SEQUENCE: 76

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45
```

```
Thr Leu Lys Cys Gln Gly Ala Tyr Ser Pro Glu Asp Asn Ser Thr Gln
 50                  55                  60
Trp Phe His Asn Glu Ser Leu Ile Ser Ser Gln Ala Ser Ser Tyr Phe
 65                  70                  75                  80
Ile Asp Ala Ala Thr Val Asp Asp Ser Gly Glu Tyr Arg Cys Gln Thr
                 85                  90                  95
Asn Leu Ser Thr Leu Ser Asp Pro Val Gln Leu Glu Val His Ile Gly
                100                 105                 110
Trp Leu Leu Leu Gln Ala Pro Arg Trp Val Phe Lys Glu Glu Asp Pro
                115                 120                 125
Ile His Leu Arg Cys His Ser Trp Lys Asn Thr Ala Leu His Lys Val
            130                 135                 140
Thr Tyr Leu Gln Asn Gly Lys Gly Arg Lys Tyr Phe His His Asn Ser
145                 150                 155                 160
Asp Phe Tyr Ile Pro Lys Ala Thr Leu Lys Asp Ser Gly Ser Tyr Phe
                165                 170                 175
Cys Arg Gly Leu Val Gly Ser Lys Asn Val Ser Ser Glu Thr Val Asn
                180                 185                 190
Ile Thr Ile Thr Gln Gly Leu Ala Val Ser Thr Ile Ser Ser Phe Phe
            195                 200                 205
Pro Pro Gly Tyr Gln Lys Ser Asn Gly Thr Ile Ile His Val Lys Gly
210                 215                 220
Lys His Leu Cys Pro Ser Pro Leu Phe Pro Gly Pro Ser Lys Pro Phe
225                 230                 235                 240
Trp Val Leu Val Val Val Gly Gly Val Leu Ala Cys Tyr Ser Leu Leu
                245                 250                 255
Val Thr Val Ala Phe Ile Ile Phe Trp Val Arg Ser Lys Arg Ser Arg
                260                 265                 270
Leu Leu His Ser Asp Tyr Met Asn Met Thr Pro Arg Arg Pro Gly Pro
            275                 280                 285
Thr Arg Lys His Tyr Gln Pro Tyr Ala Pro Pro Arg Asp Phe Ala Ala
                290                 295                 300
Tyr Arg Ser Arg Val Lys Phe Ser Arg Ser Ala Asp Ala Pro Ala Tyr
305                 310                 315                 320
Gln Gln Gly Gln Asn Gln Leu Tyr Asn Glu Leu Asn Leu Gly Arg Arg
                325                 330                 335
Glu Glu Tyr Asp Val Leu Asp Lys Arg Arg Gly Arg Asp Pro Glu Met
                340                 345                 350
Gly Gly Lys Pro Arg Arg Lys Asn Pro Gln Glu Gly Leu Tyr Asn Glu
            355                 360                 365
Leu Gln Lys Asp Lys Met Ala Glu Ala Tyr Ser Glu Ile Gly Met Lys
370                 375                 380
Gly Glu Arg Arg Arg Gly Lys Gly His Asp Gly Leu Tyr Gln Gly Leu
385                 390                 395                 400
Ser Thr Ala Thr Lys Asp Thr Tyr Asp Ala Leu His Met Gln Ala Leu
                405                 410                 415
Pro Pro Arg

<210> SEQ ID NO 77
<211> LENGTH: 409
<212> TYPE: PRT
<213> ORGANISM: Artificial Sequence
<220> FEATURE:
<223> OTHER INFORMATION: Synthetic polypeptide
```

```
<400> SEQUENCE: 77

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Gly Lys His Leu Cys Pro Ser Pro Leu Phe Pro
210                 215                 220

Gly Pro Ser Lys Pro Phe Trp Val Leu Val Val Gly Gly Val Leu
225                 230                 235                 240

Ala Cys Tyr Ser Leu Leu Val Thr Val Ala Phe Ile Ile Phe Trp Val
                245                 250                 255

Arg Ser Lys Arg Ser Arg Leu Leu His Ser Asp Tyr Met Asn Met Thr
            260                 265                 270

Pro Arg Arg Pro Gly Pro Thr Arg Lys His Tyr Gln Pro Tyr Ala Pro
        275                 280                 285

Pro Arg Asp Phe Ala Ala Tyr Arg Ser Arg Val Lys Phe Ser Arg Ser
290                 295                 300

Ala Asp Ala Pro Ala Tyr Gln Gln Gly Gln Asn Gln Leu Tyr Asn Glu
305                 310                 315                 320

Leu Asn Leu Gly Arg Arg Glu Glu Tyr Asp Val Leu Asp Lys Arg Arg
                325                 330                 335

Gly Arg Asp Pro Glu Met Gly Gly Lys Pro Arg Arg Lys Asn Pro Gln
            340                 345                 350

Glu Gly Leu Tyr Asn Glu Leu Gln Lys Asp Lys Met Ala Glu Ala Tyr
        355                 360                 365

Ser Glu Ile Gly Met Lys Gly Glu Arg Arg Arg Gly Lys Gly His Asp
370                 375                 380

Gly Leu Tyr Gln Gly Leu Ser Thr Ala Thr Lys Asp Thr Tyr Asp Ala
385                 390                 395                 400

Leu His Met Gln Ala Leu Pro Pro Arg
                405
```

<210> SEQ ID NO 78
<211> LENGTH: 393
<212> TYPE: PRT
<213> ORGANISM: Artificial Sequence
<220> FEATURE:
<223> OTHER INFORMATION: Synthetic polypeptide

<400> SEQUENCE: 78

```
Met Ala Leu Pro Val Thr Ala Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
                100                 105                 110

Trp Leu Leu Leu Gln Ala Pro Arg Trp Val Phe Lys Glu Glu Asp Pro
            115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
    195                 200                 205

Pro Pro Gly Tyr Gln Phe Trp Val Leu Val Val Gly Gly Val Leu
210                 215                 220

Ala Cys Tyr Ser Leu Leu Val Thr Val Ala Phe Ile Ile Phe Trp Val
225                 230                 235                 240

Arg Ser Lys Arg Ser Arg Leu Leu His Ser Asp Tyr Met Asn Met Thr
                245                 250                 255

Pro Arg Arg Pro Gly Pro Thr Arg Lys His Tyr Gln Pro Tyr Ala Pro
            260                 265                 270

Pro Arg Asp Phe Ala Ala Tyr Arg Ser Arg Val Lys Phe Ser Arg Ser
        275                 280                 285

Ala Asp Ala Pro Ala Tyr Gln Gln Gly Gln Asn Gln Leu Tyr Asn Glu
    290                 295                 300

Leu Asn Leu Gly Arg Arg Glu Glu Tyr Asp Val Leu Asp Lys Arg Arg
305                 310                 315                 320

Gly Arg Asp Pro Glu Met Gly Gly Lys Pro Arg Arg Lys Asn Pro Gln
                325                 330                 335

Glu Gly Leu Tyr Asn Glu Leu Gln Lys Asp Lys Met Ala Glu Ala Tyr
            340                 345                 350

Ser Glu Ile Gly Met Lys Gly Glu Arg Arg Arg Gly Lys Gly His Asp
        355                 360                 365
```

```
Gly Leu Tyr Gln Gly Leu Ser Thr Ala Thr Lys Asp Thr Tyr Asp Ala
        370                 375                 380

Leu His Met Gln Ala Leu Pro Pro Arg
385                 390

<210> SEQ ID NO 79
<211> LENGTH: 436
<212> TYPE: PRT
<213> ORGANISM: Artificial Sequence
<220> FEATURE:
<223> OTHER INFORMATION: Synthetic polypeptide

<400> SEQUENCE: 79

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
                20                  25                  30

Val Phe Leu Glu Pro Gln Trp Tyr Arg Val Leu Glu Lys Asp Ser Val
            35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Thr Thr Thr Pro Ala Pro Arg Pro Pro Thr Pro
    210                 215                 220

Ala Pro Thr Ile Ala Ser Gln Pro Leu Ser Leu Arg Pro Glu Ala Cys
225                 230                 235                 240

Arg Pro Ala Ala Gly Gly Ala Val His Thr Arg Gly Leu Asp Phe Ala
                245                 250                 255

Cys Asp Ile Tyr Ile Trp Ala Pro Leu Ala Gly Thr Cys Gly Val Leu
            260                 265                 270

Leu Leu Ser Leu Val Ile Thr Leu Tyr Cys Lys Arg Gly Arg Lys Lys
        275                 280                 285

Leu Leu Tyr Ile Phe Lys Gln Pro Phe Met Arg Pro Val Gln Thr Thr
    290                 295                 300

Gln Glu Glu Asp Gly Cys Ser Cys Arg Phe Pro Glu Glu Glu Glu Gly
305                 310                 315                 320

Gly Cys Glu Leu Arg Val Lys Phe Ser Arg Ser Ala Asp Ala Pro Ala
                325                 330                 335
```

```
Tyr Gln Gln Gly Gln Asn Gln Leu Tyr Asn Glu Leu Asn Leu Gly Arg
            340                 345                 350

Arg Glu Glu Tyr Asp Val Leu Asp Lys Arg Arg Gly Arg Asp Pro Glu
            355                 360                 365

Met Gly Gly Lys Pro Arg Arg Lys Asn Pro Gln Glu Gly Leu Tyr Asn
370                 375                 380

Glu Leu Gln Lys Asp Lys Met Ala Glu Ala Tyr Ser Glu Ile Gly Met
385                 390                 395                 400

Lys Gly Glu Arg Arg Arg Gly Lys Gly His Asp Gly Leu Tyr Gln Gly
                405                 410                 415

Leu Ser Thr Ala Thr Lys Asp Thr Tyr Asp Ala Leu His Met Gln Ala
            420                 425                 430

Leu Pro Pro Arg
            435

<210> SEQ ID NO 80
<211> LENGTH: 429
<212> TYPE: PRT
<213> ORGANISM: Artificial Sequence
<220> FEATURE:
<223> OTHER INFORMATION: Synthetic polypeptide

<400> SEQUENCE: 80

Met Ala Leu Pro Val Thr Ala Leu Leu Leu Pro Leu Ala Leu Leu Leu
1               5                   10                  15

His Ala Ala Arg Pro Gly Met Arg Thr Glu Asp Leu Pro Lys Ala Val
            20                  25                  30

Val Phe Leu Glu Pro Gln Trp Tyr Arg Val Leu Glu Lys Asp Ser Val
        35                  40                  45

Thr Leu Lys Cys Gln Gly Ala Tyr Ser Pro Glu Asp Asn Ser Thr Gln
    50                  55                  60

Trp Phe His Asn Glu Ser Leu Ile Ser Ser Gln Ala Ser Ser Tyr Phe
65                  70                  75                  80

Ile Asp Ala Ala Thr Val Asp Asp Ser Gly Glu Tyr Arg Cys Gln Thr
                85                  90                  95

Asn Leu Ser Thr Leu Ser Asp Pro Val Gln Leu Glu Val His Ile Gly
            100                 105                 110

Trp Leu Leu Leu Gln Ala Pro Arg Trp Val Phe Lys Glu Glu Asp Pro
        115                 120                 125

Ile His Leu Arg Cys His Ser Trp Lys Asn Thr Ala Leu His Lys Val
    130                 135                 140

Thr Tyr Leu Gln Asn Gly Lys Gly Arg Lys Tyr Phe His His Asn Ser
145                 150                 155                 160

Asp Phe Tyr Ile Pro Lys Ala Thr Leu Lys Asp Ser Gly Ser Tyr Phe
                165                 170                 175

Cys Arg Gly Leu Val Gly Ser Lys Asn Val Ser Ser Glu Thr Val Asn
            180                 185                 190

Ile Thr Ile Thr Gln Gly Leu Ala Val Ser Thr Ile Ser Ser Phe Phe
        195                 200                 205

Pro Pro Gly Tyr Gln Ile Glu Val Met Tyr Pro Pro Tyr Leu Asp
    210                 215                 220

Asn Glu Lys Ser Asn Gly Thr Ile Ile His Val Lys Gly Lys His Leu
225                 230                 235                 240

Cys Pro Ser Pro Leu Phe Pro Gly Pro Ser Lys Pro Ile Tyr Ile Trp
                245                 250                 255
```

```
Ala Pro Leu Ala Gly Thr Cys Gly Val Leu Leu Ser Leu Val Ile
            260                 265                 270

Thr Leu Tyr Cys Arg Ser Lys Arg Ser Arg Leu Leu His Ser Asp Tyr
        275                 280                 285

Met Asn Met Thr Pro Arg Arg Pro Gly Pro Thr Arg Lys His Tyr Gln
    290                 295                 300

Pro Tyr Ala Pro Pro Arg Asp Phe Ala Ala Tyr Arg Ser Arg Val Lys
305                 310                 315                 320

Phe Ser Arg Ser Ala Asp Ala Pro Ala Tyr Gln Gln Gly Gln Asn Gln
                325                 330                 335

Leu Tyr Asn Glu Leu Asn Leu Gly Arg Arg Glu Glu Tyr Asp Val Leu
            340                 345                 350

Asp Lys Arg Arg Gly Arg Asp Pro Glu Met Gly Gly Lys Pro Arg Arg
            355                 360                 365

Lys Asn Pro Gln Glu Gly Leu Tyr Asn Glu Leu Gln Lys Asp Lys Met
        370                 375                 380

Ala Glu Ala Tyr Ser Glu Ile Gly Met Lys Gly Glu Arg Arg Arg Gly
385                 390                 395                 400

Lys Gly His Asp Gly Leu Tyr Gln Gly Leu Ser Thr Ala Thr Lys Asp
                405                 410                 415

Thr Tyr Asp Ala Leu His Met Gln Ala Leu Pro Pro Arg
            420                 425

<210> SEQ ID NO 81
<211> LENGTH: 414
<212> TYPE: PRT
<213> ORGANISM: Artificial Sequence
<220> FEATURE:
<223> OTHER INFORMATION: Synthetic polypeptide

<400> SEQUENCE: 81

Met Ser Lys Lys Ile Ser Gly Gly Ser Val Val Glu Met Gln Gly Asp
1               5                   10                  15

Glu Met Thr Arg Ile Ile Trp Glu Leu Ile Lys Glu Lys Leu Ile Phe
            20                  25                  30

Pro Tyr Val Glu Leu Asp Leu His Ser Tyr Asp Leu Gly Ile Glu Asn
        35                  40                  45

Arg Asp Ala Thr Asn Asp Gln Val Thr Lys Asp Ala Ala Glu Ala Ile
    50                  55                  60

Lys Lys His Asn Val Gly Val Lys Cys Ala Thr Ile Thr Pro Asp Glu
65                  70                  75                  80

Lys Arg Val Glu Glu Phe Lys Leu Lys Gln Met Trp Lys Ser Pro Asn
            85                  90                  95

Gly Thr Ile Arg Asn Ile Leu Gly Gly Thr Val Phe Arg Glu Ala Ile
        100                 105                 110

Ile Cys Lys Asn Ile Pro Arg Leu Val Ser Gly Trp Val Lys Pro Ile
    115                 120                 125

Ile Ile Gly Arg His Ala Tyr Gly Asp Gln Tyr Arg Ala Thr Asp Phe
130                 135                 140

Val Val Pro Gly Pro Gly Lys Val Glu Ile Thr Tyr Thr Pro Ser Asp
145                 150                 155                 160

Gly Thr Gln Lys Val Thr Tyr Leu Val His Asn Phe Glu Glu Gly Gly
            165                 170                 175

Gly Val Ala Met Gly Met Tyr Asn Gln Asp Lys Ser Ile Glu Asp Phe
        180                 185                 190
```

```
Ala His Ser Ser Phe Gln Met Ala Leu Ser Lys Gly Trp Pro Leu Tyr
        195                 200                 205

Leu Ser Thr Lys Asn Thr Ile Leu Lys Lys Tyr Asp Gly Arg Phe Lys
    210                 215                 220

Asp Ile Phe Gln Glu Ile Tyr Asp Lys Tyr Lys Ser Gln Phe Glu
225                 230                 235                 240

Ala Gln Lys Ile Trp Tyr Glu His Arg Leu Ile Asp Asp Met Val Ala
                245                 250                 255

Gln Ala Met Lys Ser Glu Gly Gly Phe Ile Trp Ala Cys Lys Asn Tyr
            260                 265                 270

Asp Gly Asp Val Gln Ser Asp Ser Val Ala Gln Gly Tyr Gly Ser Leu
        275                 280                 285

Gly Met Met Thr Ser Val Leu Val Cys Pro Asp Gly Lys Thr Val Glu
    290                 295                 300

Ala Glu Ala Ala His Gly Thr Val Thr Arg His Tyr Arg Met Tyr Gln
305                 310                 315                 320

Lys Gly Gln Glu Thr Ser Thr Asn Pro Ile Ala Ser Ile Phe Ala Trp
                325                 330                 335

Thr Arg Gly Leu Ala His Arg Ala Lys Leu Asp Asn Asn Lys Glu Leu
            340                 345                 350

Ala Phe Phe Ala Asn Ala Leu Glu Glu Val Ser Ile Glu Thr Ile Glu
        355                 360                 365

Ala Gly Phe Met Thr Lys Asp Leu Ala Ala Cys Ile Lys Gly Leu Pro
    370                 375                 380

Asn Val Gln Arg Ser Asp Tyr Leu Asn Thr Phe Glu Phe Met Asp Lys
385                 390                 395                 400

Leu Gly Glu Asn Leu Lys Ile Lys Leu Ala Gln Ala Lys Leu
                405                 410

<210> SEQ ID NO 82
<211> LENGTH: 452
<212> TYPE: PRT
<213> ORGANISM: Artificial Sequence
<220> FEATURE:
<223> OTHER INFORMATION: Synthetic polypeptide

<400> SEQUENCE: 82

Met Ala Gly Tyr Leu Arg Val Val Arg Ser Leu Cys Arg Ala Ser Gly
1               5                   10                  15

Ser Arg Pro Ala Trp Ala Pro Ala Ala Leu Thr Ala Pro Thr Ser Gln
            20                  25                  30

Glu Gln Pro Arg Arg His Tyr Ala Asp Lys Arg Ile Lys Val Ala Lys
        35                  40                  45

Pro Val Val Glu Met Asp Gly Asp Glu Met Thr Arg Ile Ile Trp Gln
    50                  55                  60

Phe Ile Lys Glu Lys Leu Ile Leu Pro His Val Asp Ile Gln Leu Lys
65                  70                  75                  80

Tyr Phe Asp Leu Gly Leu Pro Asn Arg Asp Gln Thr Asp Asp Gln Val
                85                  90                  95

Thr Ile Asp Ser Ala Leu Ala Thr Gln Lys Tyr Ser Val Ala Val Lys
            100                 105                 110

Cys Ala Thr Ile Thr Pro Asp Glu Ala Arg Val Glu Glu Phe Lys Leu
        115                 120                 125

Lys Lys Met Trp Lys Ser Pro Asn Gly Thr Ile Arg Asn Ile Leu Gly
    130                 135                 140
```

Gly Thr Val Phe Arg Glu Pro Ile Ile Cys Lys Asn Ile Pro Arg Leu
145                 150                 155                 160

Val Pro Gly Trp Thr Lys Pro Ile Thr Ile Gly Arg His Ala His Gly
            165                 170                 175

Asp Gln Tyr Lys Ala Thr Asp Phe Val Ala Asp Arg Ala Gly Thr Phe
        180                 185                 190

Lys Met Val Phe Thr Pro Lys Asp Gly Ser Gly Val Lys Glu Trp Glu
    195                 200                 205

Val Tyr Asn Phe Pro Ala Gly Val Gly Met Gly Met Tyr Asn Thr
210                 215                 220

Asp Glu Ser Ile Ser Gly Phe Ala His Ser Cys Phe Gln Tyr Ala Ile
225                 230                 235                 240

Gln Lys Lys Trp Pro Leu Tyr Met Ser Thr Lys Asn Thr Ile Leu Lys
            245                 250                 255

Ala Tyr Asp Gly Arg Phe Lys Asp Ile Phe Gln Glu Ile Phe Asp Lys
        260                 265                 270

His Tyr Lys Thr Asp Phe Asp Lys Asn Lys Ile Trp Tyr Glu His Arg
    275                 280                 285

Leu Ile Asp Asp Met Val Ala Gln Val Leu Lys Ser Ser Gly Gly Phe
290                 295                 300

Val Trp Ala Cys Lys Asn Tyr Asp Gly Asp Val Gln Ser Asp Ile Leu
305                 310                 315                 320

Ala Gln Gly Phe Gly Ser Leu Gly Leu Met Thr Ser Val Leu Val Cys
            325                 330                 335

Pro Asp Gly Lys Thr Ile Glu Ala Glu Ala Ala His Gly Thr Val Thr
        340                 345                 350

Arg His Tyr Arg Glu His Gln Lys Gly Arg Pro Thr Ser Thr Asn Pro
    355                 360                 365

Ile Ala Ser Ile Phe Ala Trp Thr Arg Gly Leu Glu His Arg Gly Lys
370                 375                 380

Leu Asp Gly Asn Gln Asp Leu Ile Arg Phe Ala Gln Met Leu Glu Lys
385                 390                 395                 400

Val Cys Val Glu Thr Val Glu Ser Gly Ala Met Thr Lys Asp Leu Ala
            405                 410                 415

Gly Cys Ile His Gly Leu Ser Asn Val Lys Leu Asn Glu His Phe Leu
        420                 425                 430

Asn Thr Thr Asp Phe Leu Asp Thr Ile Lys Ser Asn Leu Asp Arg Ala
    435                 440                 445

Leu Gly Arg Gln
    450

<210> SEQ ID NO 83
<211> LENGTH: 334
<212> TYPE: PRT
<213> ORGANISM: Artificial Sequence
<220> FEATURE:
<223> OTHER INFORMATION: Synthetic polypeptide

<400> SEQUENCE: 83

Met Ser Glu Pro Ile Arg Val Leu Val Thr Gly Ala Ala Gly Gln Ile
1               5                   10                  15

Ala Tyr Ser Leu Leu Tyr Ser Ile Gly Asn Gly Ser Val Phe Gly Lys
            20                  25                  30

Asp Gln Pro Ile Ile Leu Val Leu Leu Asp Ile Thr Pro Met Met Gly
        35                  40                  45

Val Leu Asp Gly Val Leu Met Glu Leu Gln Asp Cys Ala Leu Pro Leu
 50                  55                  60

Leu Lys Asp Val Ile Ala Thr Asp Lys Glu Asp Val Ala Phe Lys Asp
 65                  70                  75                  80

Leu Asp Val Ala Ile Leu Val Gly Ser Met Pro Arg Arg Glu Gly Met
                 85                  90                  95

Glu Arg Lys Asp Leu Leu Lys Ala Asn Val Lys Ile Phe Lys Ser Gln
             100                 105                 110

Gly Ala Ala Leu Asp Lys Tyr Ala Lys Lys Ser Val Lys Val Ile Val
         115                 120                 125

Val Gly Asn Pro Ala Asn Thr Asn Cys Leu Thr Ala Ser Lys Ser Ala
130                 135                 140

Pro Ser Ile Pro Lys Glu Asn Phe Ser Cys Leu Thr Arg Leu Asp His
145                 150                 155                 160

Asn Arg Ala Lys Ala Gln Ile Ala Leu Lys Leu Gly Val Thr Ala Asn
                165                 170                 175

Asp Val Lys Asn Val Ile Ile Trp Gly Asn His Ser Ser Thr Gln Tyr
            180                 185                 190

Pro Asp Val Asn His Ala Lys Val Lys Leu Gln Gly Lys Glu Val Gly
        195                 200                 205

Val Tyr Glu Ala Leu Lys Asp Asp Ser Trp Leu Lys Gly Glu Phe Val
210                 215                 220

Thr Thr Val Gln Gln Arg Gly Ala Ala Val Ile Lys Ala Arg Lys Leu
225                 230                 235                 240

Ser Ser Ala Met Ser Ala Ala Lys Ala Ile Cys Asp His Val Arg Asp
                245                 250                 255

Ile Trp Phe Gly Thr Pro Glu Gly Glu Phe Val Ser Met Gly Val Ile
            260                 265                 270

Ser Asp Gly Asn Ser Tyr Gly Val Pro Asp Asp Leu Leu Tyr Ser Phe
        275                 280                 285

Pro Val Val Ile Lys Asn Lys Thr Trp Lys Phe Val Glu Gly Leu Pro
290                 295                 300

Ile Asn Asp Phe Ser Arg Glu Lys Met Asp Leu Thr Ala Lys Glu Leu
305                 310                 315                 320

Thr Glu Glu Lys Glu Ser Ala Phe Glu Phe Leu Ser Ser Ala
                325                 330

<210> SEQ ID NO 84
<211> LENGTH: 338
<212> TYPE: PRT
<213> ORGANISM: Artificial Sequence
<220> FEATURE:
<223> OTHER INFORMATION: Synthetic polypeptide

<400> SEQUENCE: 84

Met Leu Ser Ala Leu Ala Arg Pro Ala Ser Ala Ala Leu Arg Arg Ser
1               5                   10                  15

Phe Ser Thr Ser Ala Gln Asn Asn Ala Lys Val Ala Val Leu Gly Ala
                20                  25                  30

Ser Gly Gly Ile Gly Gln Pro Leu Ser Leu Leu Leu Lys Asn Ser Pro
            35                  40                  45

Leu Val Ser Arg Leu Thr Leu Tyr Asp Ile Ala His Thr Pro Gly Val
        50                  55                  60

Ala Ala Asp Leu Ser His Ile Glu Thr Lys Ala Ala Val Lys Gly Tyr
65                  70                  75                  80

Leu Gly Pro Glu Gln Leu Pro Asp Cys Leu Lys Gly Cys Asp Val Val
                    85                  90                  95

Val Ile Pro Ala Gly Val Pro Arg Lys Pro Gly Met Thr Arg Asp Asp
                100                 105                 110

Leu Phe Asn Thr Asn Ala Thr Ile Val Ala Thr Leu Thr Ala Ala Cys
                115                 120                 125

Ala Gln His Cys Pro Glu Ala Met Ile Cys Val Ile Ala Asn Pro Val
            130                 135                 140

Asn Ser Thr Ile Pro Ile Thr Ala Glu Val Phe Lys Lys His Gly Val
145                 150                 155                 160

Tyr Asn Pro Asn Lys Ile Phe Gly Val Thr Thr Leu Asp Ile Val Arg
                165                 170                 175

Ala Asn Thr Phe Val Ala Glu Leu Lys Gly Leu Asp Pro Ala Arg Val
                180                 185                 190

Asn Val Pro Val Ile Gly Gly His Ala Gly Lys Thr Ile Ile Pro Leu
                195                 200                 205

Ile Ser Gln Cys Thr Pro Lys Val Asp Phe Pro Gln Asp Gln Leu Thr
210                 215                 220

Ala Leu Thr Gly Arg Ile Gln Glu Ala Gly Thr Glu Val Val Lys Ala
225                 230                 235                 240

Lys Ala Gly Ala Gly Ser Ala Thr Leu Ser Met Ala Tyr Ala Gly Ala
                245                 250                 255

Arg Phe Val Phe Ser Leu Val Asp Ala Met Asn Gly Lys Glu Gly Val
                260                 265                 270

Val Glu Cys Ser Phe Val Lys Ser Gln Glu Thr Glu Cys Thr Tyr Phe
                275                 280                 285

Ser Thr Pro Leu Leu Leu Gly Lys Lys Gly Ile Glu Lys Asn Leu Gly
                290                 295                 300

Ile Gly Lys Val Ser Ser Phe Glu Glu Lys Met Ile Ser Asp Ala Ile
305                 310                 315                 320

Pro Glu Leu Lys Ala Ser Ile Lys Lys Gly Glu Asp Phe Val Lys Thr
                325                 330                 335

Leu Lys

<210> SEQ ID NO 85
<211> LENGTH: 533
<212> TYPE: PRT
<213> ORGANISM: Artificial Sequence
<220> FEATURE:
<223> OTHER INFORMATION: Synthetic polypeptide

<400> SEQUENCE: 85

Met Ala Phe Ala Asn Leu Arg Lys Val Leu Ile Ser Asp Ser Leu Asp
1               5                   10                  15

Pro Cys Cys Arg Lys Ile Leu Gln Asp Gly Gly Leu Gln Val Val Glu
                20                  25                  30

Lys Gln Asn Leu Ser Lys Glu Glu Leu Ile Ala Glu Leu Gln Asp Cys
            35                  40                  45

Glu Gly Leu Ile Val Arg Ser Ala Thr Lys Val Thr Ala Asp Val Ile
        50                  55                  60

Asn Ala Ala Glu Lys Leu Gln Val Val Gly Arg Ala Gly Thr Gly Val
65                  70                  75                  80

Asp Asn Val Asp Leu Glu Ala Ala Thr Arg Lys Gly Ile Leu Val Met
                85                  90                  95

```
Asn Thr Pro Asn Gly Asn Ser Leu Ser Ala Ala Glu Leu Thr Cys Gly
            100                 105                 110

Met Ile Met Cys Leu Ala Arg Gln Ile Pro Gln Ala Thr Ala Ser Met
        115                 120                 125

Lys Asp Gly Lys Trp Glu Arg Lys Lys Phe Met Gly Thr Glu Leu Asn
130                 135                 140

Gly Lys Thr Leu Gly Ile Leu Gly Leu Gly Arg Ile Gly Arg Glu Val
145                 150                 155                 160

Ala Thr Arg Met Gln Ser Phe Gly Met Lys Thr Ile Gly Tyr Asp Pro
                165                 170                 175

Ile Ile Ser Pro Glu Val Ser Ala Ser Phe Gly Val Gln Gln Leu Pro
            180                 185                 190

Leu Glu Glu Ile Trp Pro Leu Cys Asp Phe Ile Thr Val His Thr Pro
        195                 200                 205

Leu Leu Pro Ser Thr Thr Gly Leu Leu Asn Asp Asn Thr Phe Ala Gln
210                 215                 220

Cys Lys Lys Gly Val Arg Val Val Asn Cys Ala Arg Gly Gly Ile Val
225                 230                 235                 240

Asp Glu Gly Ala Leu Leu Arg Ala Leu Gln Ser Gly Gln Cys Ala Gly
                245                 250                 255

Ala Ala Leu Asp Val Phe Thr Glu Glu Pro Pro Arg Asp Arg Ala Leu
            260                 265                 270

Val Asp His Glu Asn Val Ile Ser Cys Pro His Leu Gly Ala Ser Thr
        275                 280                 285

Lys Glu Ala Gln Ser Arg Cys Gly Glu Glu Ile Ala Val Gln Phe Val
290                 295                 300

Asp Met Val Lys Gly Lys Ser Leu Thr Gly Val Val Asn Ala Gln Ala
305                 310                 315                 320

Leu Thr Ser Ala Phe Ser Pro His Thr Lys Pro Trp Ile Gly Leu Ala
                325                 330                 335

Glu Ala Leu Gly Thr Leu Met Arg Ala Trp Ala Gly Ser Pro Lys Gly
            340                 345                 350

Thr Ile Gln Val Ile Thr Gln Gly Thr Ser Leu Lys Asn Ala Gly Asn
        355                 360                 365

Cys Leu Ser Pro Ala Val Ile Val Gly Leu Leu Lys Glu Ala Ser Lys
370                 375                 380

Gln Ala Asp Val Asn Leu Val Asn Ala Lys Leu Leu Val Lys Glu Ala
385                 390                 395                 400

Gly Leu Asn Val Thr Thr Ser His Ser Pro Ala Ala Pro Gly Glu Gln
                405                 410                 415

Gly Phe Gly Glu Cys Leu Leu Ala Val Ala Leu Ala Gly Ala Pro Tyr
            420                 425                 430

Gln Ala Val Gly Leu Val Gln Gly Thr Thr Pro Val Leu Gln Gly Leu
        435                 440                 445

Asn Gly Ala Val Phe Arg Pro Glu Val Pro Leu Arg Arg Asp Leu Pro
450                 455                 460

Leu Leu Leu Phe Arg Thr Gln Thr Ser Asp Pro Ala Met Leu Pro Thr
465                 470                 475                 480

Met Ile Gly Leu Leu Ala Glu Ala Gly Val Arg Leu Leu Ser Tyr Gln
                485                 490                 495

Thr Ser Leu Val Ser Asp Gly Glu Thr Trp His Val Met Gly Ile Ser
            500                 505                 510

Ser Leu Leu Pro Ser Leu Glu Ala Trp Lys Gln His Val Thr Glu Ala
```

-continued

```
               515                 520                 525

Phe Gln Phe His Phe
    530

<210> SEQ ID NO 86
<211> LENGTH: 622
<212> TYPE: PRT
<213> ORGANISM: Artificial Sequence
<220> FEATURE:
<223> OTHER INFORMATION: Synthetic polypeptide

<400> SEQUENCE: 86

Met Pro Pro Gln Leu Gln Asn Gly Leu Asn Leu Ser Ala Lys Val Val
1               5                   10                  15

Gln Gly Ser Leu Asp Ser Leu Pro Gln Ala Val Arg Glu Phe Leu Glu
            20                  25                  30

Asn Asn Ala Glu Leu Cys Gln Pro Asp His Ile His Ile Cys Asp Gly
        35                  40                  45

Ser Glu Glu Asn Gly Arg Leu Leu Gly Gln Met Glu Glu Glu Gly
    50                  55                  60

Ile Leu Arg Arg Leu Lys Lys Tyr Asp Asn Cys Trp Leu Ala Leu Thr
65                  70                  75                  80

Asp Pro Arg Asp Val Ala Arg Ile Glu Ser Lys Thr Val Ile Val Thr
                85                  90                  95

Gln Glu Gln Arg Asp Thr Val Pro Ile Pro Lys Thr Gly Leu Ser Gln
            100                 105                 110

Leu Gly Arg Trp Met Ser Glu Glu Asp Phe Glu Lys Ala Phe Asn Ala
        115                 120                 125

Arg Phe Pro Gly Cys Met Lys Gly Arg Thr Met Tyr Val Ile Pro Phe
    130                 135                 140

Ser Met Gly Pro Leu Gly Ser Pro Leu Ser Lys Ile Gly Ile Glu Leu
145                 150                 155                 160

Thr Asp Ser Pro Tyr Val Val Ala Ser Met Arg Ile Met Thr Arg Met
                165                 170                 175

Gly Thr Pro Val Leu Glu Ala Val Gly Asp Gly Glu Phe Val Lys Cys
            180                 185                 190

Leu His Ser Val Gly Cys Pro Leu Pro Leu Gln Lys Pro Leu Val Asn
        195                 200                 205

Asn Trp Pro Cys Asn Pro Glu Leu Thr Leu Ile Ala His Leu Pro Asp
    210                 215                 220

Arg Arg Glu Ile Ile Ser Phe Gly Ser Gly Tyr Gly Gly Asn Ser Leu
225                 230                 235                 240

Leu Gly Lys Lys Cys Phe Ala Leu Arg Met Ala Ser Arg Leu Ala Lys
                245                 250                 255

Glu Glu Gly Trp Leu Ala Glu His Met Leu Ile Leu Gly Ile Thr Asn
            260                 265                 270

Pro Glu Gly Glu Lys Lys Tyr Leu Ala Ala Phe Pro Ser Ala Cys
        275                 280                 285

Gly Lys Thr Asn Leu Ala Met Met Asn Pro Ser Leu Pro Gly Trp Lys
    290                 295                 300

Val Glu Cys Val Gly Asp Asp Ile Ala Trp Met Lys Phe Asp Ala Gln
305                 310                 315                 320

Gly His Leu Arg Ala Ile Asn Pro Glu Asn Gly Phe Phe Gly Val Ala
                325                 330                 335

Pro Gly Thr Ser Val Lys Thr Asn Pro Asn Ala Ile Lys Thr Ile Gln
```

```
            340                 345                 350
Lys Asn Thr Ile Phe Thr Asn Val Ala Glu Thr Ser Asp Gly Gly Val
            355                 360                 365
Tyr Trp Glu Gly Ile Asp Glu Pro Leu Ala Ser Gly Val Thr Ile Thr
            370                 375                 380
Ser Trp Lys Asn Lys Glu Trp Ser Ser Glu Asp Gly Glu Pro Cys Ala
385                 390                 395                 400
His Pro Asn Ser Arg Phe Cys Thr Pro Ala Ser Gln Cys Pro Ile Ile
            405                 410                 415
Asp Ala Ala Trp Glu Ser Pro Glu Gly Val Pro Ile Glu Gly Ile Ile
            420                 425                 430
Phe Gly Gly Arg Arg Pro Ala Gly Val Pro Leu Val Tyr Glu Ala Leu
            435                 440                 445
Ser Trp Gln His Gly Val Phe Val Gly Ala Ala Met Arg Ser Glu Ala
            450                 455                 460
Thr Ala Ala Ala Glu His Lys Gly Lys Ile Ile Met His Asp Pro Phe
465                 470                 475                 480
Ala Met Arg Pro Phe Phe Gly Tyr Asn Phe Gly Lys Tyr Leu Ala His
            485                 490                 495
Trp Leu Ser Met Ala Gln His Pro Ala Ala Lys Leu Pro Lys Ile Phe
            500                 505                 510
His Val Asn Trp Phe Arg Lys Asp Lys Glu Gly Lys Phe Leu Trp Pro
            515                 520                 525
Gly Phe Gly Glu Asn Ser Arg Val Leu Glu Trp Met Phe Asn Arg Ile
            530                 535                 540
Asp Gly Lys Ala Ser Thr Lys Leu Thr Pro Ile Gly Tyr Ile Pro Lys
545                 550                 555                 560
Glu Asp Ala Leu Asn Leu Lys Gly Leu Gly His Ile Asn Met Met Glu
            565                 570                 575
Leu Phe Ser Ile Ser Lys Glu Phe Trp Glu Lys Glu Val Glu Asp Ile
            580                 585                 590
Glu Lys Tyr Leu Glu Asp Gln Val Asn Ala Asp Leu Pro Cys Glu Ile
            595                 600                 605
Glu Arg Glu Ile Leu Ala Leu Lys Gln Arg Ile Ser Gln Met
            610                 615                 620

<210> SEQ ID NO 87
<211> LENGTH: 413
<212> TYPE: PRT
<213> ORGANISM: Artificial Sequence
<220> FEATURE:
<223> OTHER INFORMATION: Synthetic polypeptide

<400> SEQUENCE: 87

Met Ala Pro Pro Ser Val Phe Ala Glu Val Pro Gln Ala Gln Pro Val
1                   5                   10                  15
Leu Val Phe Lys Leu Thr Ala Asp Phe Arg Glu Asp Pro Asp Pro Arg
            20                  25                  30
Lys Val Asn Leu Gly Val Gly Ala Tyr Arg Thr Asp Asp Cys His Pro
            35                  40                  45
Trp Val Leu Pro Val Val Lys Lys Val Glu Gln Lys Ile Ala Asn Asp
            50                  55                  60
Asn Ser Leu Asn His Glu Tyr Leu Pro Ile Leu Gly Leu Ala Glu Phe
65                  70                  75                  80
Arg Ser Cys Ala Ser Arg Leu Ala Leu Gly Asp Asp Ser Pro Ala Leu
```

```
                    85                  90                  95
Lys Glu Lys Arg Val Gly Val Gln Ser Leu Gly Thr Gly Ala
                100                 105                 110

Leu Arg Ile Gly Ala Asp Phe Leu Ala Arg Trp Tyr Asn Gly Thr Asn
                115                 120                 125

Asn Lys Asn Thr Pro Val Tyr Val Ser Ser Pro Thr Trp Glu Asn His
130                 135                 140

Asn Ala Val Phe Ser Ala Ala Gly Phe Lys Asp Ile Arg Ser Tyr Arg
145                 150                 155                 160

Tyr Trp Asp Ala Glu Lys Arg Gly Leu Asp Leu Gln Gly Phe Leu Asn
                165                 170                 175

Asp Leu Glu Asn Ala Pro Glu Phe Ser Ile Val Val Leu His Ala Cys
                180                 185                 190

Ala His Asn Pro Thr Gly Ile Asp Pro Thr Pro Glu Gln Trp Lys Gln
                195                 200                 205

Ile Ala Ser Val Met Lys His Arg Phe Leu Phe Pro Phe Asp Ser
210                 215                 220

Ala Tyr Gln Gly Phe Ala Ser Gly Asn Leu Glu Arg Asp Ala Trp Ala
225                 230                 235                 240

Ile Arg Tyr Phe Val Ser Glu Gly Phe Glu Phe Cys Ala Gln Ser
                245                 250                 255

Phe Ser Lys Asn Phe Gly Leu Tyr Asn Glu Arg Val Gly Asn Leu Thr
                260                 265                 270

Val Val Gly Lys Glu Pro Glu Ser Ile Leu Gln Val Leu Ser Gln Met
                275                 280                 285

Glu Lys Ile Val Arg Ile Thr Trp Ser Asn Pro Pro Ala Gln Gly Ala
290                 295                 300

Arg Ile Val Ala Ser Thr Leu Ser Asn Pro Glu Leu Phe Glu Glu Trp
305                 310                 315                 320

Thr Gly Asn Val Lys Thr Met Ala Asp Arg Ile Leu Thr Met Arg Ser
                325                 330                 335

Glu Leu Arg Ala Arg Leu Glu Ala Leu Lys Thr Pro Gly Thr Trp Asn
                340                 345                 350

His Ile Thr Asp Gln Ile Gly Met Phe Ser Phe Thr Gly Leu Asn Pro
                355                 360                 365

Lys Gln Val Glu Tyr Leu Val Asn Glu Lys His Ile Tyr Leu Leu Pro
                370                 375                 380

Ser Gly Arg Ile Asn Val Ser Gly Leu Thr Thr Lys Asn Leu Asp Tyr
385                 390                 395                 400

Val Ala Thr Ser Ile His Glu Ala Val Thr Lys Ile Gln
                405                 410

<210> SEQ ID NO 88
<211> LENGTH: 430
<212> TYPE: PRT
<213> ORGANISM: Artificial Sequence
<220> FEATURE:
<223> OTHER INFORMATION: Synthetic polypeptide

<400> SEQUENCE: 88

Met Ala Leu Leu His Ser Gly Arg Val Leu Pro Gly Ile Ala Ala Ala
1               5                   10                  15

Phe His Pro Gly Leu Ala Ala Ala Ser Ala Arg Ala Ser Ser Trp
                20                  25                  30

Trp Thr His Val Glu Met Gly Pro Pro Asp Pro Ile Leu Gly Val Thr
```

35                  40                  45
Glu Ala Phe Lys Arg Asp Thr Asn Ser Lys Lys Met Asn Leu Gly Val
 50                  55                  60
Gly Ala Tyr Arg Asp Asp Asn Gly Lys Pro Tyr Val Leu Pro Ser Val
 65                  70                  75                  80
Arg Lys Ala Glu Ala Gln Ile Ala Ala Lys Asn Leu Asp Lys Glu Tyr
                 85                  90                  95
Leu Pro Ile Gly Gly Leu Ala Glu Phe Cys Lys Ala Ser Ala Glu Leu
                100                 105                 110
Ala Leu Gly Glu Asn Ser Glu Val Leu Lys Ser Gly Arg Phe Val Thr
            115                 120                 125
Val Gln Thr Ile Ser Gly Thr Gly Ala Leu Arg Ile Gly Ala Ser Phe
        130                 135                 140
Leu Gln Arg Phe Phe Lys Phe Ser Arg Asp Val Phe Leu Pro Lys Pro
145                 150                 155                 160
Thr Trp Gly Asn His Thr Pro Ile Phe Arg Asp Ala Gly Met Gln Leu
                165                 170                 175
Gln Gly Tyr Arg Tyr Tyr Asp Pro Lys Thr Cys Gly Phe Asp Phe Thr
                180                 185                 190
Gly Ala Val Glu Asp Ile Ser Lys Ile Pro Glu Gln Ser Val Leu Leu
            195                 200                 205
Leu His Ala Cys Ala His Asn Pro Thr Gly Val Asp Pro Arg Pro Glu
        210                 215                 220
Gln Trp Lys Glu Ile Ala Thr Val Val Lys Lys Arg Asn Leu Phe Ala
225                 230                 235                 240
Phe Phe Asp Met Ala Tyr Gln Gly Phe Ala Ser Gly Asp Gly Asp Lys
                245                 250                 255
Asp Ala Trp Ala Val Arg His Phe Ile Glu Gln Gly Ile Asn Val Cys
                260                 265                 270
Leu Cys Gln Ser Tyr Ala Lys Asn Met Gly Leu Tyr Gly Glu Arg Val
            275                 280                 285
Gly Ala Phe Thr Met Val Cys Lys Asp Ala Asp Glu Ala Lys Arg Val
        290                 295                 300
Glu Ser Gln Leu Lys Ile Leu Ile Arg Pro Met Tyr Ser Asn Pro Pro
305                 310                 315                 320
Leu Asn Gly Ala Arg Ile Ala Ala Ala Ile Leu Asn Thr Pro Asp Leu
                325                 330                 335
Arg Lys Gln Trp Leu Gln Glu Val Lys Val Met Ala Asp Arg Ile Ile
                340                 345                 350
Gly Met Arg Thr Gln Leu Val Ser Asn Leu Lys Lys Glu Gly Ser Thr
            355                 360                 365
His Asn Trp Gln His Ile Thr Asp Gln Ile Gly Met Phe Cys Phe Thr
        370                 375                 380
Gly Leu Lys Pro Glu Gln Val Glu Arg Leu Ile Lys Glu Phe Ser Ile
385                 390                 395                 400
Tyr Met Thr Lys Asp Gly Arg Ile Ser Val Ala Gly Val Thr Ser Ser
                405                 410                 415
Asn Val Gly Tyr Leu Ala His Ala Ile His Gln Val Thr Lys
            420                 425                 430

<210> SEQ ID NO 89
<211> LENGTH: 496
<212> TYPE: PRT
<213> ORGANISM: Artificial Sequence
<220> FEATURE:
<223> OTHER INFORMATION: Synthetic polypeptide

<400> SEQUENCE: 89

```
Met Ala Ser Ser Thr Gly Asp Arg Ser Gln Ala Val Arg His Gly Leu
1               5                   10                  15

Arg Ala Lys Val Leu Thr Leu Asp Gly Met Asn Pro Arg Val Arg Arg
            20                  25                  30

Val Glu Tyr Ala Val Arg Gly Pro Ile Val Gln Arg Ala Leu Glu Leu
        35                  40                  45

Glu Gln Glu Leu Arg Gln Gly Val Lys Lys Pro Phe Thr Glu Val Ile
    50                  55                  60

Arg Ala Asn Ile Gly Asp Ala Gln Ala Met Gly Gln Arg Pro Ile Thr
65                  70                  75                  80

Phe Leu Arg Gln Val Leu Ala Leu Cys Val Asn Pro Asp Leu Leu Ser
                85                  90                  95

Ser Pro Asn Phe Pro Asp Asp Ala Lys Lys Arg Ala Glu Arg Ile Leu
            100                 105                 110

Gln Ala Cys Gly Gly His Ser Leu Gly Ala Tyr Ser Val Ser Ser Gly
        115                 120                 125

Ile Gln Leu Ile Arg Glu Asp Val Ala Arg Tyr Ile Glu Arg Arg Asp
    130                 135                 140

Gly Gly Ile Pro Ala Asp Pro Asn Asn Val Phe Leu Ser Thr Gly Ala
145                 150                 155                 160

Ser Asp Ala Ile Val Thr Val Leu Lys Leu Leu Val Ala Gly Glu Gly
                165                 170                 175

His Thr Arg Thr Gly Val Leu Ile Pro Ile Pro Gln Tyr Pro Leu Tyr
            180                 185                 190

Ser Ala Thr Leu Ala Glu Leu Gly Ala Val Gln Val Asp Tyr Tyr Leu
        195                 200                 205

Asp Glu Glu Arg Ala Trp Ala Leu Asp Val Ala Glu Leu His Arg Ala
    210                 215                 220

Leu Gly Gln Ala Arg Asp His Cys Arg Pro Arg Ala Leu Cys Val Ile
225                 230                 235                 240

Asn Pro Gly Asn Pro Thr Gly Gln Val Gln Thr Arg Glu Cys Ile Glu
                245                 250                 255

Ala Val Ile Arg Phe Ala Phe Glu Glu Arg Leu Phe Leu Leu Ala Asp
            260                 265                 270

Glu Val Tyr Gln Asp Asn Val Tyr Ala Ala Gly Ser Gln Phe His Ser
        275                 280                 285

Phe Lys Lys Val Leu Met Glu Met Gly Pro Pro Tyr Ala Gly Gln Gln
    290                 295                 300

Glu Leu Ala Ser Phe His Ser Thr Ser Lys Gly Tyr Met Gly Glu Cys
305                 310                 315                 320

Gly Phe Arg Gly Gly Tyr Val Glu Val Val Asn Met Asp Ala Ala Val
                325                 330                 335

Gln Gln Gln Met Leu Lys Leu Met Ser Val Arg Leu Cys Pro Pro Val
            340                 345                 350

Pro Gly Gln Ala Leu Leu Asp Leu Val Val Ser Pro Pro Ala Pro Thr
        355                 360                 365

Asp Pro Ser Phe Ala Gln Phe Gln Ala Glu Lys Gln Ala Val Leu Ala
    370                 375                 380

Glu Leu Ala Ala Lys Ala Lys Leu Thr Glu Gln Val Phe Asn Glu Ala
385                 390                 395                 400
```

Pro Gly Ile Ser Cys Asn Pro Val Gln Gly Ala Met Tyr Ser Phe Pro
            405                 410                 415

Arg Val Gln Leu Pro Pro Arg Ala Val Glu Arg Ala Gln Glu Leu Gly
        420                 425                 430

Leu Ala Pro Asp Met Phe Phe Cys Leu Arg Leu Leu Glu Glu Thr Gly
        435                 440                 445

Ile Cys Val Val Pro Gly Ser Gly Phe Gly Gln Arg Glu Gly Thr Tyr
    450                 455                 460

His Phe Arg Met Thr Ile Leu Pro Pro Leu Glu Lys Leu Arg Leu Leu
465                 470                 475                 480

Leu Glu Lys Leu Ser Arg Phe His Ala Lys Phe Thr Leu Glu Tyr Ser
                485                 490                 495

<210> SEQ ID NO 90
<211> LENGTH: 669
<212> TYPE: PRT
<213> ORGANISM: Artificial Sequence
<220> FEATURE:
<223> OTHER INFORMATION: Synthetic polypeptide

<400> SEQUENCE: 90

Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Gly Trp Pro
    50                  55                  60

Ala Glu Pro Leu Ala Arg Gly Leu Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
            275                 280                 285

Lys Pro Leu Lys Tyr Ala Ile Ala Val Asn Asp Leu Gly Thr Glu Tyr
290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
355                 360                 365

Glu Tyr Val Gly Phe Ser Asn Ala Thr Phe Gln Ser Glu Arg Glu Ser
370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
530                 535                 540

Glu Gly Gly Asp Gln Arg Val Lys Ser Val Ile Asn Leu Leu Phe Ala
545                 550                 555                 560

Ala Tyr Thr Gly Asp Val Ser Ala Leu Arg Arg Phe Ala Leu Ser Ala
                565                 570                 575

Met Asp Met Glu Gln Arg Asp Tyr Asp Ser Arg Thr Ala Leu His Val
            580                 585                 590

Ala Ala Ala Glu Gly His Val Glu Val Val Lys Phe Leu Leu Glu Ala
        595                 600                 605

Cys Lys Val Asn Pro Phe Pro Lys Asp Arg Trp Asn Asn Thr Pro Met
610                 615                 620

Asp Glu Ala Leu His Phe Gly His His Asp Val Phe Lys Ile Leu Gln
625                 630                 635                 640

Glu Tyr Gln Val Gln Tyr Thr Pro Gln Gly Asp Ser Asp Asn Gly Lys
                645                 650                 655

Glu Asn Gln Thr Val His Lys Asn Leu Asp Gly Leu Leu
            660                 665

<210> SEQ ID NO 91
<211> LENGTH: 370

```
<212> TYPE: PRT
<213> ORGANISM: Artificial Sequence
<220> FEATURE:
<223> OTHER INFORMATION: Synthetic polypeptide

<400> SEQUENCE: 91

Met Asp Ala Pro Arg Gln Val Val Asn Phe Gly Pro Gly Pro Ala Lys
1               5                   10                  15

Leu Pro His Ser Val Leu Glu Ile Gln Lys Glu Leu Leu Asp Tyr
                20                  25                  30

Lys Gly Val Gly Ile Ser Val Leu Glu Met Ser His Arg Ser Ser Asp
            35                  40                  45

Phe Ala Lys Ile Ile Asn Asn Thr Glu Asn Leu Val Arg Glu Leu Leu
    50                  55                  60

Ala Val Pro Asp Asn Tyr Lys Val Ile Phe Leu Gln Gly Gly Gly Cys
65                  70                  75                  80

Gly Gln Phe Ser Ala Val Pro Leu Asn Leu Ile Gly Leu Lys Ala Gly
                85                  90                  95

Arg Cys Ala Asp Tyr Val Val Thr Gly Ala Trp Ser Ala Lys Ala Ala
                100                 105                 110

Glu Glu Ala Lys Lys Phe Gly Thr Ile Asn Ile Val His Pro Lys Leu
                115                 120                 125

Gly Ser Tyr Thr Lys Ile Pro Asp Pro Ser Thr Trp Asn Leu Asn Pro
130                 135                 140

Asp Ala Ser Tyr Val Tyr Tyr Cys Ala Asn Glu Thr Val His Gly Val
145                 150                 155                 160

Glu Phe Asp Phe Ile Pro Asp Val Lys Gly Ala Val Leu Val Cys Asp
                165                 170                 175

Met Ser Ser Asn Phe Leu Ser Lys Pro Val Asp Val Ser Lys Phe Gly
                180                 185                 190

Val Ile Phe Ala Gly Ala Gln Lys Asn Val Gly Ser Ala Gly Val Thr
            195                 200                 205

Val Val Ile Val Arg Asp Asp Leu Leu Gly Phe Ala Leu Arg Glu Cys
210                 215                 220

Pro Ser Val Leu Glu Tyr Lys Val Gln Ala Gly Asn Ser Ser Leu Tyr
225                 230                 235                 240

Asn Thr Pro Pro Cys Phe Ser Ile Tyr Val Met Gly Leu Val Leu Glu
                245                 250                 255

Trp Ile Lys Asn Asn Gly Gly Ala Ala Ala Met Glu Lys Leu Ser Ser
                260                 265                 270

Ile Lys Ser Gln Thr Ile Tyr Glu Ile Ile Asp Asn Ser Gln Gly Phe
            275                 280                 285

Tyr Val Cys Pro Val Glu Pro Gln Asn Arg Ser Lys Met Asn Ile Pro
290                 295                 300

Phe Arg Ile Gly Asn Ala Lys Gly Asp Asp Ala Leu Glu Lys Arg Phe
305                 310                 315                 320

Leu Asp Lys Ala Leu Glu Leu Asn Met Leu Ser Leu Lys Gly His Arg
                325                 330                 335

Ser Val Gly Gly Ile Arg Ala Ser Leu Tyr Asn Ala Val Thr Ile Glu
                340                 345                 350

Asp Val Gln Lys Leu Ala Ala Phe Met Lys Lys Phe Leu Glu Met His
                355                 360                 365

Gln Leu
    370
```

```
<210> SEQ ID NO 92
<211> LENGTH: 391
<212> TYPE: PRT
<213> ORGANISM: Artificial Sequence
<220> FEATURE:
<223> OTHER INFORMATION: Synthetic polypeptide

<400> SEQUENCE: 92

Met Thr Tyr Lys Cys Ala Val Val Asp Val Pro Phe Gly Gly Ala Lys
1               5                   10                  15

Ala Gly Val Lys Ile Asn Pro Lys Asn Tyr Thr Asp Asn Glu Leu Glu
            20                  25                  30

Lys Ile Thr Arg Arg Phe Thr Met Glu Leu Ala Lys Lys Gly Phe Ile
        35                  40                  45

Gly Pro Gly Ile Asp Val Pro Ala Pro Asp Met Ser Thr Gly Glu Arg
    50                  55                  60

Glu Met Ser Trp Ile Ala Asp Thr Tyr Ala Ser Thr Ile Gly His Tyr
65                  70                  75                  80

Asp Ile Asn Ala His Ala Cys Val Thr Gly Lys Pro Ile Ser Gln Gly
                85                  90                  95

Gly Ile His Gly Arg Ile Ser Ala Thr Gly Arg Gly Val Phe His Gly
            100                 105                 110

Ile Glu Asn Phe Ile Asn Glu Ala Ser Tyr Met Ser Ile Leu Gly Met
        115                 120                 125

Thr Pro Gly Phe Gly Asp Lys Thr Phe Val Val Gln Gly Phe Gly Asn
130                 135                 140

Val Gly Leu His Ser Met Arg Tyr Leu His Arg Phe Gly Ala Lys Cys
145                 150                 155                 160

Ile Ala Val Gly Glu Ser Asp Gly Ser Ile Trp Asn Pro Asp Gly Ile
                165                 170                 175

Asp Pro Lys Glu Leu Glu Asp Phe Lys Leu Gln His Gly Ser Ile Leu
            180                 185                 190

Gly Phe Pro Lys Ala Lys Pro Tyr Glu Gly Ser Ile Leu Glu Ala Asp
        195                 200                 205

Cys Asp Ile Leu Ile Pro Ala Ala Ser Glu Lys Gln Leu Thr Lys Ser
    210                 215                 220

Asn Ala Pro Arg Val Lys Ala Lys Ile Ile Ala Glu Gly Ala Asn Gly
225                 230                 235                 240

Pro Thr Thr Pro Glu Ala Asp Lys Ile Phe Leu Glu Arg Asn Ile Met
                245                 250                 255

Val Ile Pro Asp Leu Tyr Leu Asn Ala Gly Gly Val Thr Val Ser Tyr
            260                 265                 270

Phe Glu Trp Leu Lys Asn Leu Asn His Val Ser Tyr Gly Arg Leu Thr
        275                 280                 285

Phe Lys Tyr Glu Arg Asp Ser Asn Tyr His Leu Leu Met Ser Val Gln
    290                 295                 300

Glu Ser Leu Glu Arg Lys Phe Gly Lys His Gly Gly Thr Ile Pro Ile
305                 310                 315                 320

Val Pro Thr Ala Glu Phe Gln Asp Arg Ile Ser Gly Ala Ser Glu Lys
                325                 330                 335

Asp Ile Val His Ser Gly Leu Ala Tyr Thr Met Glu Arg Ser Ala Arg
            340                 345                 350

Gln Ile Met Arg Thr Ala Met Lys Tyr Asn Leu Gly Leu Asp Leu Arg
        355                 360                 365
```

Thr Ala Ala Tyr Val Asn Ala Ile Glu Lys Val Phe Lys Val Tyr Asn
370                 375                 380

Glu Ala Gly Val Thr Phe Thr
385                 390

<210> SEQ ID NO 93
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 93

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
                100                 105                 110

Ala Pro Arg Trp Val Phe Lys Glu Glu Asp Pro Ile His Leu Arg Cys
            115                 120                 125

His Ser Trp Lys Asn Thr Ala Leu His Lys Val Thr Tyr Leu Gln Asn
        130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
                180                 185                 190

Gly Leu Ala Val Ser Thr Ile Ser Ser Phe Phe Pro Pro Gly Tyr Gln
            195                 200                 205

Val Ser Phe Cys Leu Val Met Val Leu Leu Phe Ala Val Asp Thr Gly
        210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 94
<211> LENGTH: 254
<212> TYPE: PRT
<213> ORGANISM: Artificial Sequence
<220> FEATURE:
<223> OTHER INFORMATION: Synthetic polypeptide

<400> SEQUENCE: 94

Met Trp Gln Leu Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

```
Gln Trp Tyr Arg Val Leu Glu Lys Asp Ser Val Thr Leu Lys Cys Gln
         35                  40                  45
Gly Ala Tyr Ser Pro Glu Asp Asn Ser Thr Gln Trp Phe His Asn Glu
     50                  55                  60
Ser Leu Ile Ser Ser Gln Ala Ser Ser Tyr Phe Ile Asp Ala Ala Thr
 65                  70                  75                  80
Val Asp Asp Ser Gly Glu Tyr Arg Cys Gln Thr Asn Leu Ser Thr Leu
                 85                  90                  95
Ser Asp Pro Val Gln Leu Glu Val His Ile Gly Trp Leu Leu Leu Gln
             100                 105                 110
Ala Pro Arg Trp Val Phe Lys Glu Glu Asp Pro Ile His Leu Arg Cys
         115                 120                 125
His Ser Trp Lys Asn Thr Ala Leu His Lys Val Thr Tyr Leu Gln Asn
     130                 135                 140
Gly Lys Gly Arg Lys Tyr Phe His His Asn Ser Asp Phe Tyr Ile Pro
145                 150                 155                 160
Lys Ala Thr Leu Lys Asp Ser Gly Ser Tyr Phe Cys Arg Gly Leu Val
                165                 170                 175
Gly Ser Lys Asn Val Ser Ser Glu Thr Val Asn Ile Thr Ile Thr Gln
            180                 185                 190
Gly Leu Ala Val Ser Thr Ile Ser Ser Phe Phe Pro Pro Gly Tyr Gln
        195                 200                 205
Val Ser Phe Cys Leu Val Met Val Leu Leu Phe Ala Val Asp Thr Gly
    210                 215                 220
Leu Tyr Phe Ser Val Lys Thr Asn Ile Arg Ser Ser Thr Arg Asp Trp
225                 230                 235                 240
Lys Asp His Lys Phe Lys Trp Arg Lys Asp Pro Gln Asp Lys
                245                 250
```

<210> SEQ ID NO 95
<211> LENGTH: 300
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (16)..(300)
<223> OTHER INFORMATION: these amino acids may be absent

<400> SEQUENCE: 95

```
Gly Gly Gly Gly Ser Gly Gly Gly Ser Gly Gly Gly Gly Ser Gly Gly
 1               5                  10                  15
Gly Gly Gly Ser Gly Gly Gly Ser Gly Gly Gly Ser Gly Gly
            20                  25                  30
Gly Gly Ser Gly Gly Gly Ser Gly Gly Gly Ser Gly Gly Gly
         35                  40                  45
Gly Ser Gly Gly Gly Ser Gly Gly Gly Ser Gly Gly Gly Gly
     50                  55                  60
Ser Gly Gly Gly Ser Gly Gly Gly Ser Gly Gly Gly Gly Ser
 65                  70                  75                  80
Gly Gly Gly Gly Ser Gly Gly Gly Ser Gly Gly Gly Gly Ser Gly
                 85                  90                  95
Gly Gly Gly Ser Gly Gly Gly Ser Gly Gly Gly Ser Gly Gly
             100                 105                 110
Gly Gly Ser Gly Gly Gly Gly Ser Gly Gly Gly Gly Ser Gly Gly Gly
```

```
                    115                 120                 125
Gly Ser Gly Gly Gly Ser Gly Gly Gly Ser Gly Gly Gly Gly
        130                 135                 140
Ser Gly Gly Gly Gly Ser Gly Gly Gly Ser Gly Gly Gly Ser
145                 150                 155                 160
Gly Gly Gly Gly Ser Gly Gly Gly Ser Gly Gly Gly Ser Gly
                165                 170                 175
Gly Gly Gly Ser Gly Gly Gly Ser Gly Gly Gly Ser Gly Gly
            180                 185                 190
Gly Gly Ser Gly Gly Gly Ser Gly Gly Gly Ser Gly Gly Gly
        195                 200                 205
Gly Ser Gly Gly Gly Ser Gly Gly Gly Ser Gly Gly Gly Gly
    210                 215                 220
Ser Gly Gly Gly Ser Gly Gly Gly Ser Gly Gly Gly Gly Ser
225                 230                 235                 240
Gly Gly Gly Gly Ser Gly Gly Gly Ser Gly Gly Gly Ser Gly
                245                 250                 255
Gly Gly Gly Ser Gly Gly Gly Ser Gly Gly Gly Ser Gly Gly
            260                 265                 270
Gly Gly Ser Gly Gly Gly Ser Gly Gly Gly Ser Gly Gly Gly
        275                 280                 285
Gly Ser Gly Gly Gly Ser Gly Gly Gly Gly Ser
    290                 295                 300

<210> SEQ ID NO 96
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 96

Gly Gly Gly Gly Ser Gly Gly Gly Gly Ser Gly Gly Gly Gly Ser
1               5                   10                  15

<210> SEQ ID NO 97
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 97

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 98
<211> LENGTH: 45
<212> TYPE: PRT
<213> ORGANISM: Artificial Sequence
<220> FEATURE:
<223> OTHER INFORMATION: Synthetic polypeptide

<400> SEQUENCE: 98

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30
```

```
Gly Gly Ser Gly Gly Gly Ser Gly Gly Gly Gly Ser
        35                  40                  45

<210> SEQ ID NO 99
<211> LENGTH: 60
<212> TYPE: PRT
<213> ORGANISM: Artificial Sequence
<220> FEATURE:
<223> OTHER INFORMATION: Synthetic polypeptide

<400> SEQUENCE: 99

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Gly Ser Gly Gly
            20                  25                  30

Gly Gly Ser Gly Gly Gly Gly Ser Gly Gly Gly Ser Gly Gly Gly
        35                  40                  45

Gly Ser Gly Gly Gly Gly Ser Gly Gly Gly Ser
    50                  55                  60

<210> SEQ ID NO 100
<211> LENGTH: 75
<212> TYPE: PRT
<213> ORGANISM: Artificial Sequence
<220> FEATURE:
<223> OTHER INFORMATION: Synthetic polypeptide

<400> SEQUENCE: 100

Gly Gly Gly Gly Ser Gly Gly Gly Gly Ser Gly Gly Gly Ser Gly
1               5                   10                  15

Gly Gly Gly Ser Gly Gly Gly Ser Gly Gly Gly Gly Ser Gly Gly
            20                  25                  30

Gly Gly Ser Gly Gly Gly Gly Ser Gly Gly Gly Ser Gly Gly Gly
        35                  40                  45

Gly Ser Gly Gly Gly Gly Ser Gly Gly Gly Ser Gly Gly Gly Gly
    50                  55                  60

Ser Gly Gly Gly Gly Ser Gly Gly Gly Ser
65                  70                  75

<210> SEQ ID NO 101
<211> LENGTH: 150
<212> TYPE: PRT
<213> ORGANISM: Artificial Sequence
<220> FEATURE:
<223> OTHER INFORMATION: Synthetic polypeptide

<400> SEQUENCE: 101

Gly Gly Gly Gly Ser Gly Gly Gly Gly Ser Gly Gly Gly Ser Gly
1               5                   10                  15

Gly Gly Gly Ser Gly Gly Gly Ser Gly Gly Gly Gly Ser Gly Gly
            20                  25                  30

Gly Gly Ser Gly Gly Gly Gly Ser Gly Gly Gly Gly Ser Gly Gly
        35                  40                  45

Gly Ser Gly Gly Gly Ser Gly Gly Gly Gly Ser Gly Gly Gly Gly
    50                  55                  60

Ser Gly Gly Gly Gly Ser Gly Gly Gly Ser Gly Gly Gly Gly Ser
65                  70                  75                  80

Gly Gly Gly Gly Ser Gly Gly Gly Gly Ser Gly Gly Gly Ser Gly
                85                  90                  95
```

```
Gly Gly Gly Ser Gly Gly Gly Ser Gly Gly Gly Ser Gly Gly
            100                 105                 110

Gly Gly Ser Gly Gly Gly Ser Gly Gly Gly Ser Gly Gly Gly
        115                 120                 125

Gly Ser Gly Gly Gly Ser Gly Gly Gly Ser Gly Gly Gly
    130                 135                 140

Ser Gly Gly Gly Gly Ser
145                 150

<210> SEQ ID NO 102
<211> LENGTH: 225
<212> TYPE: PRT
<213> ORGANISM: Artificial Sequence
<220> FEATURE:
<223> OTHER INFORMATION: Synthetic polypeptide

<400> SEQUENCE: 102

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser Gly Gly Gly
        35                  40                  45

Gly Ser Gly Gly Gly Ser Gly Gly Gly Ser Gly Gly Gly Gly
    50                  55                  60

Ser Gly Gly Gly Gly Ser Gly Gly Gly Ser Gly Gly Gly Ser
65                  70                  75                  80

Gly Gly Gly Gly Ser Gly Gly Gly Ser Gly Gly Gly Ser Gly
            85                  90                  95

Gly Gly Gly Ser Gly Gly Gly Ser Gly Gly Gly Ser Gly Gly
            100                 105                 110

Gly Gly Ser Gly Gly Gly Ser Gly Gly Gly Ser Gly Gly Gly
        115                 120                 125

Gly Ser Gly Gly Gly Ser Gly Gly Gly Ser Gly Gly Gly Gly
    130                 135                 140

Ser Gly Gly Gly Ser Gly Gly Gly Ser Gly Gly Gly Gly Ser
145                 150                 155                 160

Gly Gly Gly Gly Ser Gly Gly Gly Ser Gly Gly Gly Ser Gly
            165                 170                 175

Gly Gly Gly Ser Gly Gly Gly Ser Gly Gly Gly Ser Gly Gly
            180                 185                 190

Gly Gly Ser Gly Gly Gly Ser Gly Gly Gly Ser Gly Gly Gly
        195                 200                 205

Gly Ser Gly Gly Gly Ser Gly Gly Gly Ser Gly Gly Gly Gly
    210                 215                 220

Ser
225

<210> SEQ ID NO 103
<211> LENGTH: 300
<212> TYPE: PRT
<213> ORGANISM: Artificial Sequence
<220> FEATURE:
<223> OTHER INFORMATION: Synthetic polypeptide

<400> SEQUENCE: 103

Gly Gly Gly Gly Ser Gly Gly Gly Gly Ser Gly Gly Gly Ser Gly
1               5                   10                  15
```

Gly Gly Gly Ser Gly Gly Gly Ser Gly Gly Gly Ser Gly Gly
                20                  25                  30
Gly Gly Ser Gly Gly Gly Ser Gly Gly Gly Ser Gly Gly Gly
            35                  40                  45
Gly Ser Gly Gly Gly Ser Gly Gly Gly Ser Gly Gly Gly Gly
        50                  55                  60
Ser Gly Gly Gly Ser Gly Gly Gly Ser Gly Gly Gly Gly Ser
65                  70                  75                  80
Gly Gly Gly Gly Ser Gly Gly Gly Ser Gly Gly Gly Ser Gly
                85                  90                  95
Gly Gly Gly Ser Gly Gly Gly Ser Gly Gly Gly Ser Gly Gly
            100                 105                 110
Gly Gly Ser Gly Gly Gly Ser Gly Gly Gly Ser Gly Gly Gly
        115                 120                 125
Gly Ser Gly Gly Gly Ser Gly Gly Gly Ser Gly Gly Gly Gly
    130                 135                 140
Ser Gly Gly Gly Ser Gly Gly Gly Ser Gly Gly Gly Gly Ser
145                 150                 155                 160
Gly Gly Gly Gly Ser Gly Gly Gly Ser Gly Gly Gly Ser Gly
                165                 170                 175
Gly Gly Gly Ser Gly Gly Gly Ser Gly Gly Gly Ser Gly Gly
            180                 185                 190
Gly Gly Ser Gly Gly Gly Ser Gly Gly Gly Ser Gly Gly Gly
        195                 200                 205
Gly Ser Gly Gly Gly Ser Gly Gly Gly Ser Gly Gly Gly Gly
    210                 215                 220
Ser Gly Gly Gly Ser Gly Gly Gly Ser Gly Gly Gly Gly Ser
225                 230                 235                 240
Gly Gly Gly Gly Ser Gly Gly Gly Ser Gly Gly Gly Ser Gly
                245                 250                 255
Gly Gly Gly Ser Gly Gly Gly Ser Gly Gly Gly Ser Gly Gly
            260                 265                 270
Gly Gly Ser Gly Gly Gly Ser Gly Gly Gly Ser Gly Gly Gly
        275                 280                 285
Gly Ser Gly Gly Gly Ser Gly Gly Gly Ser
    290                 295                 300

<210> SEQ ID NO 104
<211> LENGTH: 487
<212> TYPE: PRT
<213> ORGANISM: Artificial Sequence
<220> FEATURE:
<223> OTHER INFORMATION: Synthetic polypeptide

<400> SEQUENCE: 104

Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Val His Ser Asn Arg Asn Thr Tyr Leu His Trp Tyr Leu Gln
    50                  55                  60

Lys Pro Gly Gln Ser Pro Gln Leu Leu Ile Tyr Lys Val Ser Asn Arg
65                  70                  75                  80

```
Phe Ser Gly Val Pro Asp Arg Phe Ser Gly Ser Gly Thr Asp
                85                  90                  95

Phe Thr Leu Lys Ile Ser Arg Val Glu Ala Glu Asp Val Gly Val Tyr
                100                 105                 110

Tyr Cys Ser Gln Asn Thr His Val Pro Pro Thr Phe Gly Gln Gly Thr
            115                 120                 125

Lys Leu Glu Ile Lys Arg Gly Gly Gly Ser Gly Gly Gly Gly Ser
    130                 135                 140

Gly Gly Gly Gly Ser Gln Val Gln Leu Val Gln Ser Gly Ala Glu Val
145                 150                 155                 160

Lys Lys Pro Gly Ala Ser Val Lys Val Ser Cys Lys Ala Ser Gly Tyr
                165                 170                 175

Thr Phe Thr Asp Tyr Glu Met His Trp Val Arg Gln Ala Pro Gly Gln
            180                 185                 190

Gly Leu Glu Trp Met Gly Ala Leu Asp Pro Lys Thr Gly Asp Thr Ala
        195                 200                 205

Tyr Ser Gln Lys Phe Lys Gly Arg Val Thr Leu Thr Ala Asp Lys Ser
    210                 215                 220

Thr Ser Thr Ala Tyr Met Glu Leu Ser Ser Leu Thr Ser Glu Asp Thr
225                 230                 235                 240

Ala Val Tyr Tyr Cys Thr Arg Phe Tyr Ser Tyr Thr Tyr Trp Gly Gln
                245                 250                 255

Gly Thr Leu Val Thr Val Ser Ser Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 105
<211> LENGTH: 483
<212> TYPE: PRT
<213> ORGANISM: Artificial Sequence
<220> FEATURE:
<223> OTHER INFORMATION: Synthetic polypeptide

<400> SEQUENCE: 105

```
Met Ala Leu Pro Val Thr Ala Leu Leu Leu Pro Leu Ala Leu Leu Leu
1               5                   10                  15

His Ala Ala Arg Pro Asp Val Val Met Thr Gln Ser Pro Leu Ser Leu
            20                  25                  30

Pro Val Thr Pro Gly Glu Pro Ala Ser Ile Ser Cys Arg Ser Ser Gln
        35                  40                  45

Ser Leu Val His Ser Asn Arg Asn Thr Tyr Leu His Trp Tyr Leu Gln
    50                  55                  60

Lys Pro Gly Gln Ser Pro Gln Leu Leu Ile Tyr Lys Val Ser Asn Arg
65                  70                  75                  80

Phe Ser Gly Val Pro Asp Arg Phe Ser Gly Ser Gly Ser Gly Thr Asp
                85                  90                  95

Phe Thr Leu Lys Ile Ser Arg Val Glu Ala Glu Asp Val Gly Val Tyr
            100                 105                 110

Tyr Cys Ser Gln Asn Thr His Val Pro Pro Thr Phe Gly Gln Gly Thr
        115                 120                 125

Lys Leu Glu Ile Lys Arg Gly Gly Gly Ser Gly Gly Gly Gly Ser
    130                 135                 140

Gly Gly Gly Gly Ser Gln Val Gln Leu Val Gln Ser Gly Ala Glu Val
145                 150                 155                 160

Lys Lys Pro Gly Ala Ser Val Lys Val Ser Cys Lys Ala Ser Gly Tyr
                165                 170                 175

Thr Phe Thr Asp Tyr Glu Met His Trp Val Arg Gln Ala Pro Gly Gln
            180                 185                 190

Gly Leu Glu Trp Met Gly Ala Leu Asp Pro Lys Thr Gly Asp Thr Ala
        195                 200                 205

Tyr Ser Gln Lys Phe Lys Gly Arg Val Thr Leu Thr Ala Asp Lys Ser
    210                 215                 220

Thr Ser Thr Ala Tyr Met Glu Leu Ser Ser Leu Thr Ser Glu Asp Thr
225                 230                 235                 240

Ala Val Tyr Tyr Cys Thr Arg Phe Tyr Ser Tyr Thr Tyr Trp Gly Gln
                245                 250                 255

Gly Thr Leu Val Thr Val Ser Ser Ile Glu Val Met Tyr Pro Pro Pro
            260                 265                 270

Tyr Leu Asp Asn Glu Lys Ser Asn Gly Thr Ile Ile His Val Lys Gly
        275                 280                 285

Lys His Leu Cys Pro Ser Pro Leu Phe Pro Gly Pro Ser Lys Pro Phe
    290                 295                 300

Trp Val Leu Val Val Val Gly Gly Val Leu Ala Cys Tyr Ser Leu Leu
305                 310                 315                 320

Val Thr Val Ala Phe Ile Ile Phe Trp Val Arg Ser Lys Arg Ser Arg
                325                 330                 335

Leu Leu His Ser Asp Tyr Met Asn Met Thr Pro Arg Arg Pro Gly Pro
            340                 345                 350

Thr Arg Lys His Tyr Gln Pro Tyr Ala Pro Pro Arg Asp Phe Ala Ala
        355                 360                 365
```

```
Tyr Arg Ser Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
            405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg

<210> SEQ ID NO 106
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 106

Ala Thr Asn Phe Ser Leu Leu Lys Gln Ala Gly Asp Val Glu Glu Asn
1               5                   10                  15

Pro Gly Pro

<210> SEQ ID NO 107
<211> LENGTH: 18
<212> TYPE: PRT
<213> ORGANISM: Artificial Sequence
<220> FEATURE:
<223> OTHER INFORMATION: Synthetic polypeptide

<400> SEQUENCE: 107

Ala Thr Asn Phe Ser Leu Leu Lys Gln Ala Gly Asp Val Glu Glu Asn
1               5                   10                  15

Pro Gly
```

CHIMERIC ANTIGEN RECEPTOR POLYPEPTIDES IN COMBINATION WITH TRANS METABOLISM MOLECULES MODULATING KREBS CYCLE AND THERAPEUTIC USES THEREOF

CROSS REFERENCE TO RELATED APPLICATIONS

This application is a United States National Phase Application under 35 U.S.C. § 371 of International Application No. PCT/US2019/046550, filed Aug. 14, 2019, which claims the benefit of the filing dates of U.S. Provisional Application No. 62/718,491, filed Aug. 14, 2018, and U.S. Provisional Application No. 62/718,579, filed Aug. 14, 2018. The entire contents of each of the prior applications are incorporated by reference herein.

SEQUENCE LISTING

The application contains a Sequence Listing that has been filed electronically in the form of a text file, created Jan. 14, 2021, and named "112309-0024-Sequence-Listing.txt" (379,152 bytes), the contents of which are incorporated by reference herein in their entirety.

BACKGROUND OF DISCLOSURE

Cancer immunotherapy, including cell-based therapy, is used to provoke immune responses attacking tumor cells while sparing normal tissues. It is a promising option for treating various types of cancer because of its potential to evade genetic and cellular mechanisms of drug resistance, and to target tumor cells while sparing normal tissues.

Cell-based therapy may involve cytotoxic T cells having reactivity skewed toward cancer cells. Eshhar et al., *Proc. Natl. Acad. Sci. U.S.A;* 1993; 90(2):720-724; Geiger et al., *J Immunol.* 1999; 162(10):5931-5939; Brentjens et al., *Nat. Med.* 2003; 9(3):279-286; Cooper et al., *Blood.* 2003; 101 (4):1637-1644; and Imai et al., *Leukemia.* 2004; 18:676-684. One approach is to express a chimeric receptor having an antigen-binding domain fused to one or more T cell activation signaling domains. Binding of a cancer antigen via the antigen-binding domain results in T cell activation and triggers cytotoxicity. Recent results of clinical trials with infusions of chimeric receptor-expressing autologous T lymphocytes provided compelling evidence of their clinical potential. Pule et al., *Nat. Med.* 2008; 14(11):1264-1270; Porter et al., *N Engl J Med;* 2011; 25; 365(8):725-733; Brentjens et al., *Blood.* 2011; 118(18):4817-4828; Till et al., *Blood.* 2012; 119(17):3940-3950; Kochenderfer et al., *Blood.* 2012; 119(12):2709-2720; and Brentjens et al., *Sci Transl Med.* 2013; 5(177):177ra138.

Another approach is to express an antibody-coupled T cell Receptor (ACTR) protein in a hematopoietic cell (e.g., a hematopoietic stem cell, an immune cell, such as an NK cell or a T cell), the ACTR protein containing an extracellular Fc-binding domain. When the ACTR-expressing hematopoietic cells (e.g., ACTR-expressing T cells, also called "ACTR T cells") are administered to a subject together with an anti-cancer antibody, they may enhance toxicity against cancer cells targeted by the antibody via their binding to the Fc domain of the antibody. Kudo et al., *Cancer Research* (2014) 74:93-103.

Cell-based immune therapies, while promising, have faced challenges caused by specific characteristics of the tumor microenvironment (TME), which is cellular environment created via the interaction between malignant tumor cells and non-transformed cells. It is therefore of great importance to develop strategies to improve efficacy of cell-based immune therapies in light of the TME.

SUMMARY OF DISCLOSURE

The present disclosure is based on the development of strategies to modulate the Krebs cycle in hematopoietic cells such as immune cells, including those that express a chimeric receptor polypeptide, such as an antibody-coupled T-cells receptor (ACTR) polypeptide or a chimeric antigen receptor (CAR) polypeptide, for use in cell-based immune therapy. Modulation of the Krebs cycle may be achieved by expressing (e.g., over-expressing) in hematopoietic cells (e.g., hematopoietic stem cells (HSCs) or immune cells such as T cells or natural killer cells) one or more Krebs cycle modulating polypeptides such as those described herein. Such genetically engineered immune cells are expected to have modulated (e.g., enhanced) Krebs cycle reactions, for example, in a low glucose environment, a low-amino acid environment, a low pH environment, and/or a hypoxic environment (e.g., in a tumor microenvironment). Such genetically engineered immune cells may also have modulated epigenetic states (e.g., acetylation states) and/or modulated levels of immunosuppressive metabolites (e.g., kynurenine). As such, hematopoieic cells such as HSCs or immune cells that co-express one or more Krebs cycle modulating polypeptides and a chimeric receptor polypeptide would exhibit superior bioactivities (e.g., under tumor microenvironment such as low glucose, low amino acid, low pH, and/or hypoxic conditions, optionally in the presence of a therapeutic antibody), for example, cell proliferation, activation (e.g., increased cytokine production, e.g., IL-2 or IFNγ production), cytotoxicity, and/or in vivo anti-tumor activity.

Accordingly, provided herein are modified (e.g., genetically modified) hematopoietic cells (e.g., hematopoietic stem cells, immune cells such as T cells or natural killer cells) that have a modulated Krebs cycle relative to a native immune cell of the same type, particularly, for example, in low glucose, low amino acid, low pH, and/or hypoxic conditions. The modified immune cells may express or overly express a Krebs cycle modulating polypeptide.

In some embodiments, the Krebs cycle modulating polypeptide may be an enzyme that catalyzes a reaction of the Krebs cycle. Examples include, but are not limited to, isocitrate dehydrogenase (IDH) such as IDH1 or IDH2, malate dehydrogenase (MDH) such as MDH1 or MDH2, or phosphoglycerate dehydrogenase (PHGDH). In other embodiments, the Krebs cycle modulating polypeptide is an enzyme that uses a Krebs cycle metabolite as a substrate. Examples include, but are not limited to, a glutamic-oxaloacetic transaminase (GOT) such as GOT1 or GOT2 (also known as aspartate transaminase or aspartate aminotransferase) or phosphoenolpyruvate carboxykinase 1 (PCK1). In yet other embodiments, the Krebs cycle modulating polypeptide is an enzyme that converts a precursor to a Krebs cycle metabolite. Examples include, but are not limited to, a phosphoserine aminotransferase (PSAT1), a glutamate dehydrogenase (GDH1), a glutamic-pyruvate transaminase 1 (GPT1), or a glutaminase (GLS).

The modified immune cells may further express a chimeric receptor polypeptide, which may comprise (a) an extracellular target binding domain; (b) a transmembrane domain; and (c) a cytoplasmic signaling domain (e.g., a cytoplasmic domain that comprises an immunoreceptor tyrosine-based activation motif (ITAM)). In some embodiments, the chimeric receptor polypeptide is an antibody-coupled T cell receptor (ACTR), which comprises an extracellular Fc-binding domain (a). In other embodiments, the chimeric receptor is a chimeric antigen receptor (CAR), which comprises an extracellular antigen binding domain (a). In some examples, (c) is located at the C-terminus of the chimeric receptor polypeptide. In some instances, the chimeric polypeptide may further comprise at least one co-stimulatory signaling domain. In other instances, the chimeric receptor polypeptide may be free of co-stimulatory signaling domains.

Any of the chimeric receptor polypeptides described herein (e.g., an ACTR polypeptide or a CAR polypeptide) may further comprise a hinge domain, which is located at the C-terminus of (a) and the N-terminus of (b). In other examples, the chimeric receptor polypeptide may be free of any hinge domain. In yet other examples, the chimeric receptor polypeptide, for example, an ACTR polypeptide, may be free of a hinge domain from any non-CD16A receptor. Alternatively or in addition, the chimeric receptor polypeptide further comprises a signal peptide at its N-terminus.

In some embodiments, the chimeric receptor polypeptide disclosed herein may be an ACTR polypeptide comprising an Fc binding domain (a). In some examples, the Fc binding domain of (a) can be an extracellular ligand-binding domain of an Fc-receptor, for example, an extracellular ligand-binding domain of an Fc-gamma receptor, an Fc-alpha receptor, or an Fc-epsilon receptor. In particular examples, the Fc binding domain is an extracellular ligand-binding domain of CD16A (e.g., F158 CD16A or V158 CD16A), CD32A, or CD64A. In other examples, the Fc binding domain of (a) can be an antibody fragment that binds the Fc portion of an immunoglobulin. For example, the antibody fragment can be a single chain variable fragment (ScFv), a single domain antibody, (e.g., a nanobody). Additionally, the Fc binding domain of (a) can be a naturally-occurring protein that binds the Fc portion of an immunoglobulin or an Fc-binding fragment thereof. For example, the Fc binding domain can be Protein A or Protein G, or an Fc-binding fragment thereof. In further examples, the Fc binding domain of (a) can be a synthetic polypeptide that binds the Fc portion of an immunoglobulin. Examples include, but are not limited to, a Kunitz peptide, a SMIP, an avimer, an affibody, a DARPin, or an anticalin.

In some embodiments, the chimeric receptor polypeptide disclosed herein can be a CAR polypeptide comprising an extracellular antigen binding domain (a). In some examples, the extracellular antigen binding domain of (a) is a single chain antibody fragment that binds to a tumor antigen, a pathogenic antigen, or an immune cell specific to an autoantigen. In certain examples, the tumor antigen is associated with a hematologic tumor. Examples include, but are not limited to, CD19, CD20, CD22, Kappa-chain, CD30, CD123, CD33, LeY, CD138, CD5, BCMA, CD7, CD40, and IL-1RAP. In certain examples, the tumor antigen is associated with a solid tumor. Examples include, but are not limited to, GD2, GPC3, FOLR (e.g., FOLR1 or FOLR2), HER2, EphA2, EFGRVIII, IL13RA2, VEGFR2, ROR1, NKG2D, EpCAM, CEA, Mesothelin, MUC1, CLDN18.2, CD171, CD133, PSCA, cMET, EGFR, PSMA, FAP, CD70, MUC16, L1-CAM, B7H3, and CAIX. In certain examples, the pathogenic antigen is a bacterial antigen, a viral antigen, or a fungal antigen, for example, those described herein.

In some embodiments, the transmembrane domain of (b) in any of the chimeric receptor polypeptide (e.g., ACTR or CAR polypeptide) can be of a single-pass membrane protein, e.g., CD8α, CD8β, 4-1BB, CD28, CD34, CD4, FcεRIγ, CD16A, OX40, CD3ζ, CD3ε, CD3γ, CD3δ, TCRα, CD32, CD64, VEGFR2, FAS, and FGFR2B. Alternatively, the transmembrane domain of (b) can be a non-naturally occurring hydrophobic protein segment.

In some embodiments, the at least one co-stimulatory signaling domain of the chimeric receptor polypeptides described herein (e.g., ACTR or CAR polypeptides), if applicable, can be of a co-stimulatory molecule, which can be 4-1BB, CD28, $CD28_{LL\_GG}$ variant, OX40, ICOS, CD27, GITR, ICOS, HVEM, TIM1, LFA1, and CD2. In some examples, the at least one co-stimulatory signaling domains is a CD28 co-stimulatory signaling domain or a 4-1BB co-stimulatory signaling domain. In some instances, the ACTR polypeptide may comprise two co-stimulatory signaling domains. In some instances, one of the co-stimulatory signaling domains is a CD28 co-stimulatory signaling domain; and the other co-stimulatory domain can be a 4-1BB co-stimulatory signaling domain, an OX40 co-stimulatory signaling domain, a CD27 co-stimulatory signaling domain, or an ICOS co-stimulatory signaling domain. Specific examples include, but are not limited to, CD28 and 4-1BB; or $CD28_{LL\_GG}$ variant and 4-1BB. Alternatively, any of the chimeric receptor polypeptide may be free of any co-stimulatory signaling domain.

In some embodiments, the cytoplasmic signaling domain of (c) in any of the chimeric receptor polypeptides described herein (e.g., ACTR or CAR polypeptides) can be a cytoplasmic domain of CD3ζ or FcεR1γ.

In some embodiments, the hinge domain of any of the chimeric polypeptides described herein (e.g., ACTR or CAR polypeptides), when applicable, can be of CD28, CD16A, CD8α, or IgG. In other examples, the hinge domain is a non-naturally occurring peptide. For example, the non-naturally occurring peptide may be an extended recombinant polypeptide (XTEN) or a $(Gly_4Ser)_n$ polypeptide, in which n is an integer of 3-12, inclusive. In some examples, the hinge domain is a short segment, which may contain up to 60 amino acid residues.

In specific examples, an ACTR polypeptide as described herein may comprise (i) a CD28 co-stimulatory domain; and (ii) a CD28 transmembrane domain, a CD28 hinge domain, or a combination thereof. For example, the ACTR polypeptide comprises components (a)-(e) as shown in Table 3. In particular examples, the ACTR polypeptide comprises the amino acid sequence selected from SEQ ID NOs: 1-80.

In specific examples, a CAR polypeptide described herein may comprise (i) a CD28 co-stimulatory domain or a 4-1BB co-stimulatory domain; and (ii) a CD28 transmembrane domain, a CD28 hinge domain, or a combination thereof. In further specific examples, a CAR polypeptide described herein may comprise (i) a CD28 co-stimulatory domain or a 4-1BB co-stimulatory domain, (ii) a CD8 transmembrane domain, a CD8 hinge domain, or a combination thereof. For example, the CAR polypeptide may comprise an amino acid sequence selected from SEQ ID NOs: 104 and 105.

The hematopoietic cells described herein, expressing the Krebs cycle modulating polypeptide and optionally the chimeric receptor polypeptide, may be a hematopoietic stem cell or a progeny thereof. In some embodiments, the hematopoietic cells can be immune cells such as natural killer cell, monocyte/macrophage, neutrophil, eosinophil, or T cell. The immune cells can be derived from peripheral blood mononuclear cells (PBMC), hematopoietic stem cells (HSCs), or induced pluripotent stem cells (iPSCs). In some examples, the immune cell is a T cell, in which the expression of an endogenous T cell receptor, an endogenous major histocompatibility complex, an endogenous beta-2-microglobulin, or a combination thereof has been inhibited or eliminated.

Any of the hematopoietic cells (e.g., HSCs or immune cells) described herein may comprise a nucleic acid or a nucleic acid set, which collectively comprises: (a) a first nucleotide sequence encoding the Krebs cycle modulating polypeptide; and optionally (b) a second nucleotide sequence encoding the chimeric antigen receptor (CAR) polypeptide. The nucleic acid or the nucleic acid set is an RNA molecule or a set of RNA molecules. In some instances, the immune cell comprises the nucleic acid, which comprises both the first nucleotide sequence and the second nucleotide sequence. In some embodiments, the coding sequence of the Krebs cycle modulating polypeptide is upstream of that of the CAR polypeptide. In some embodiments, the coding sequence of the CAR polypeptide is upstream of that of the Krebs cycle modulating polypeptide. Such a nucleic acid may further comprise a third nucleotide sequence located between the first nucleotide sequence and the second nucleotide sequence, wherein the third nucleotide sequence encodes a ribosomal skipping site (e.g., a P2A peptide), an internal ribosome entry site (IRES), or a second promoter.

In some examples, the nucleic acid or the nucleic acid set is comprised within a vector or a set of vectors, which can be an expression vector or a set of expression vectors (e.g., viral vectors such as lentiviral vectors or retroviral vectors). A nucleic acid set or a vector set refers to a group of two or more nucleic acid molecules or two or more vectors, each encoding one of the polypeptides of interest (i.e., the Krebs cycle modulating polypeptide and the CAR polypeptide). Any of the nucleic acids described herein is also within the scope of the present disclosure.

In another aspect, the present disclosure provides a pharmaceutical composition, comprising any of the immune cells described herein and a pharmaceutically acceptable carrier.

Moreover, provided herein is a method for inhibiting cells expressing a target antigen (e.g., reducing the number of such cells, blocking cell proliferation, and/or suppressing cell activity) in a subject, the method comprising administering to a subject in need thereof a population of the immune cells described herein, which may co-express the Krebs cycle modulating polypeptide and the CAR polypeptide. The subject (e.g., a human patient such as a human patient suffering from a cancer) may have been treated or is being treated with an anti-cancer therapy (e.g., an anti-cancer agent). In some examples, at least some of the cells expressing the target antigen are located in a low-glucose environment, a low-amino acid (e.g., low glutamine) environment, a low-pH environment, and/or a hypoxic environment, for example a tumor microenvironment.

In some examples, the immune cells are autologous. In other examples, the immune cells are allogeneic. In any of the methods described herein, the immune cells can be activated, expanded, or both ex vivo. In some instances, the immune cells comprise T cells, which are activated in the presence of one or more of anti-CD3 antibody, anti-CD28 antibody, IL-2, phytohemoagglutinin, and an engineered artificial stimulatory cell or particle.

In other instances, the immune cells comprise natural killer cells, which are activated in the presence of one or more of 4-1BB ligand, anti-4-1BB antibody, IL-15, anti-IL-15 receptor antibody, IL-2, IL-12, IL-21 and K562 cells, an engineered artificial stimulatory cell or particle.

In some examples, the subject to be treated by the methods described herein may be a human patient suffering from a cancer, for example, carcinoma, lymphoma, sarcoma, blastoma, and leukemia. Additional exemplary target cancer includes, but are not limited to, a cancer of B-cell origin, breast cancer, gastric cancer, neuroblastoma, osteosarcoma, lung cancer, skin cancer, prostate cancer, colon cancer, renal cell carcinoma, ovarian cancer, rhabdomyosarcoma, leukemia, mesothelioma, pancreatic cancer, head and neck cancer, retinoblastoma, glioma, glioblastoma, liver cancer, and thyroid cancer. Exemplary cancers of B-cell origin is selected from the group consisting of B-lineage acute lymphoblastic leukemia, B-cell chronic lymphocytic leukemia, and B-cell non-Hodgkin's lymphoma.

Also within the scope of the present disclosure are uses of the genetically engineered immune cells described herein, which co-express a Krebs cycle modulating polypeptide and a CAR polypeptide for treating a target disease or disorder such as cancer or an infectious disorder, and uses thereof for manufacturing a medicament for the intended medical treatment.

The details of one or more embodiments of the disclosure are set forth in the description below. Other features or advantages of the present disclosure will be apparent from the detailed description of several embodiments and also from the appended claims.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 2A: 1.25 mM glucose. FIG. 2B: 10 mM glucose. Proliferation of CAR-T cells co-expressing GOT1 is enhanced relative to cells expressing CAR-T alone at both 1.25 mM and 10 mM glucose.

FIG. 3A and FIG. 3B are diagrams that show proliferation of T cells expressing a GPC3-targeting CAR (SEQ ID NO: 104) or co-expressing the GPC3-targeting CAR and GOT2 (SEQ ID NO: 88) in the presence of GPC3-expressing JHH7 target cells. FIG. 3A: 1.25 mM glucose. FIG. 3B: 10 mM glucose. Proliferation of CAR-T cells co-expressing GOT2 is enhanced relative to cells expressing CAR-T alone at both 1.25 mM and 10 mM glucose.

FIG. 7 is a chart showing peripheral blood counts of T cells from mice bearing Hep3B xenograft tumors treated with T cells expressing a GPC3-targeting CAR and T cells co-expressing the GPC3-targeting CAR (SEQ ID NO: 104) and GOT2 (SEQ ID NO: to 88).

FIG. 8A: Western blot demonstrating increased expression of GOT2 in T cells co-expressing anti-GPC3 CAR (SEQ ID NO: 104) and GOT2 (SEQ ID NO: 88) relative to T cells expressing CAR alone. T cells were activated with Hep3B GPC3-expressing tumor cells for 4 days. Blots were stained with anti-human GOT2 antibody or anti-human GAPDH for loading control, respectively.

FIG. 8B: T cells co-expressing anti-GPC3 CAR and GOT2 show increased aspartate aminotransferase (AST) enzyme activity relative to T cells expressing CAR alone. T cells were activated with Hep3B GPC3-expressing tumor cells for 8 days and aspartate aminotransferase enzyme activity was measured using a commercially available Aspartate Aminotransferase Activity Assay (Abcam).

FIG. 9A: CAR T cells were activated with Hep3B GPC3-expressing tumor cells for 6 days. Proliferation was assessed by flow cytometry using intracellular cell trace violet dilution as a measure of cell division for CD3+ T cells; FIG. 9B: ACTR T cells were activated with HepG2 GPC3-expressing tumor cells plus anti-GPC3 antibody (GC33, 1 µg/ml) for 3 days. Proliferation was assessed by flow cytometry cell counts of CD3+ T cells. Results are expressed for GOT2 co-expressing constructs relative to parental construct.

FIG. 10A: GPC3-CAR (SEQ ID NO: 104). FIG. 10B: ACTR (SEQ ID NO: 1). FIG. 10C: ACTR (SEQ ID NO: 57). T cells were activated for 24 hrs with GPC3-expressing HepG2 cells with the addition of anti-GPC3 antibody to ACTR co-cultures, IL-17A was measured in supernatants using an MSD assay. Enhanced IL-17A production relative to T cells expressing CAR or ACTR alone was observed for constructs co-expressing GOT2, independent of construct type (CAR or ACTR) and primary costimulatory domain (4-1BB or CD28).

FIGS. 11A-11C are diagrams that show T cells co-expressing GOT2 (SEQ ID NO: 88) and anti-GPC3 CAR (SEQ ID NO: 104) or ACTR (SEQ ID NO: 1 and SEQ ID NO: 57) show enhanced CD4+ polyfunctionality relative to T cells expressing CAR or ACTR alone. FIG. 11A: GPC3-CAR (SEQ ID NO: 104). FIG. 11B: ACTR (SEQ ID NO: 1). FIG. 11C: ACTR (SEQ ID NO: 57). T cells were incubated at 37° C., 5% $CO_2$ for 6 hr with GPC3-expressing HepG2 cells, with the additions of anti-GPC3 antibody in ACTR co-cultures, in the presence of protein transport inhibitors Brefeldin A and Monensin. Cells were fixed and intracellular staining for IFNγ, IL-2, TNFα, and IL-17A was evaluated by flow cytometry. A higher frequency of CD4+ T cells producing greater than one, two, or three cytokines simultaneously was observed for T cells co-expressing GOT2 and ACTR or CAR relative to cells expressing CAR or ACTR alone, independent of chimeric receptor type (CAR or ACTR) and primary costimulatory domain (4-1BB or CD28).

FIG. 12A: GPC3-CAR (SEQ ID NO: 104). FIG. 12B: ACTR (SEQ ID NO: 1). FIG. 12C: ACTR (SEQ ID NO: 57). CAR (SEQ ID NO: 104) T cells generated from 11 healthy donors and ACTR T cells generated from 2 healthy donors (4-1BB primary costimulation domain, SEQ ID NO: 1; CD28 primary costimulation domain, SEQ ID NO: 57) were stained for a panel of surface markers and analyzed by flow cytometry for naïve-like phenotypic markers. Cells were gated on CD8+/CAR+(CAR) or CD8+/CD16+(ACTR+). The subset of these populations staining positive for markers CD27, CD45RO and CD62L and staining negative for CD45RA was enriched in T cells co-expressing GOT2 and ACTR or CAR relative to cells expressing CAR or ACTR alone, independent of chimeric receptor type (CAR or ACTR) and primary costimulatory domain (4-1BB or CD28).

FIGS. 17A-17C are diagrams that show T cells co-expressing GOT2 (SEQ ID NO: 88) and anti-GPC3 CAR (SEQ ID NO: 104) demonstrated enhanced activation in tumor relative to T cells expressing CAR alone. FIG. 17A: CD69. FIG. 17B: CD25. FIG. 17C: ICOS. T cells co-expressing CAR and GOT2 demonstrated increased expression of activation markers relative to T cells expressing CAR alone.

FIG. 18A: CD4+ T cell subset. FIG. 18B: CD8+ T cell subset.

FIGS. 19A-19D are diagrams that show CARs co-expressing GOT2 resist exhaustion in GPC3-expressing tumor; activation of CARs is specific to tumor vs. antigen-negative spleen. FIG. 19A: day 6, CD4+ T cell subset. FIG. 19B: day 6, CD8+ T cell subset. FIG. 19C: day 13, CD4+ T cell subset. FIG. 19D: day 13, CD8+ T cell subset.

FIG. 20A: IL-17A. FIG. 20B: IFNγ.

DETAILED DESCRIPTION OF DISCLOSURE

Figure 1:
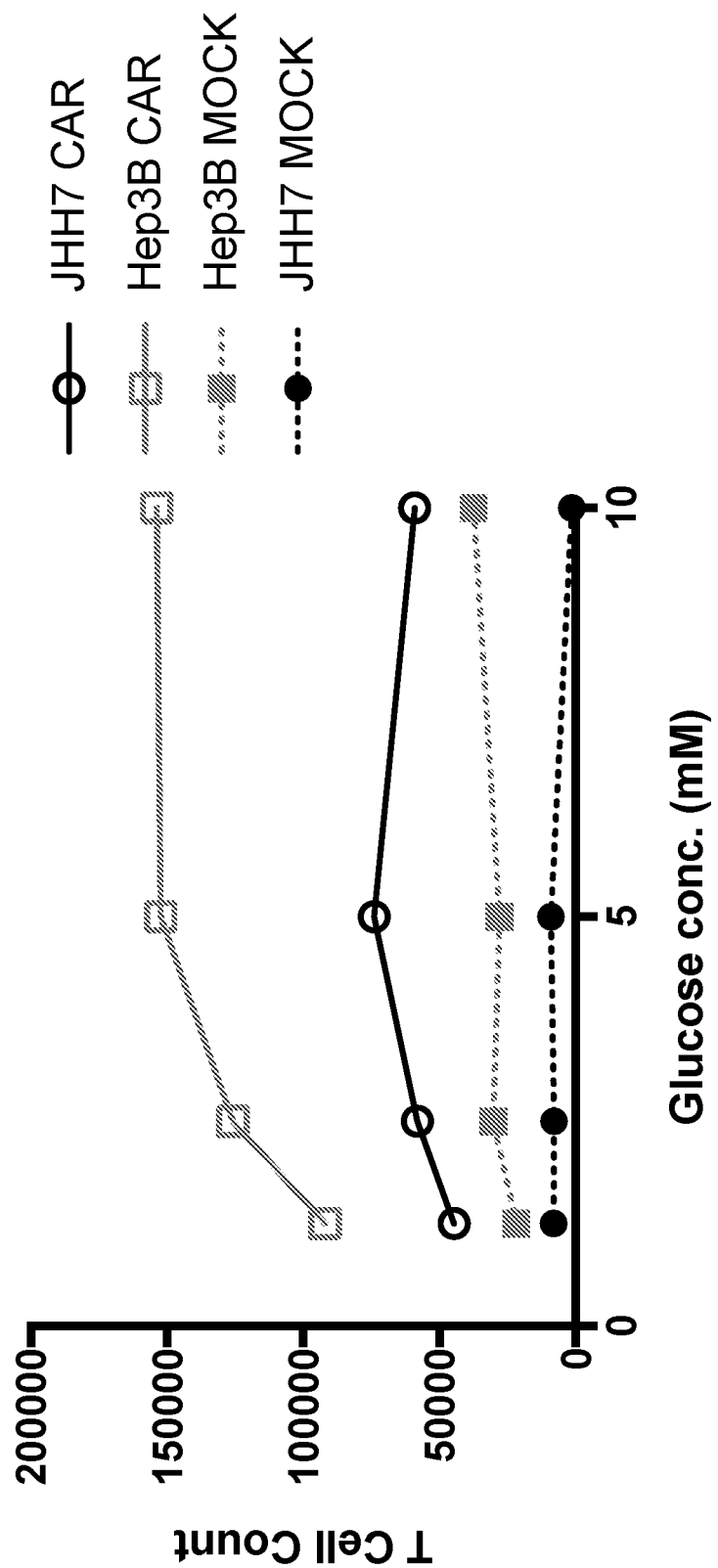
FIG. 1 is a diagram showing proliferation of T cells expressing a GPC3-targeting CAR (SEQ ID NO: 104) or "mock" untransduced T cells in the presence of GPC3-expressing JHH7 or Hep3B target cells and varying concentrations of glucose. Proliferation of CAR-T cells varies as a function of glucose concentration.
Figure 2A:
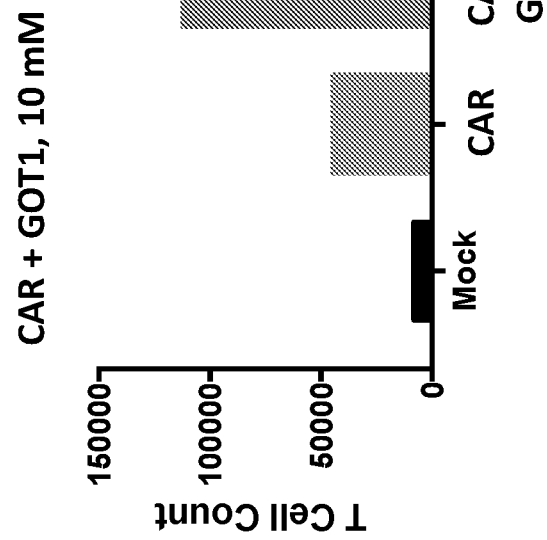
FIG. 2A and FIG. 2B are diagrams that show proliferation of T cells expressing a GPC3-targeting CAR (SEQ ID NO: 104) or co-expressing the GPC3-targeting CAR and GOT1 (SEQ ID NO: 87) in the presence of GPC3-expressing JHH7 target cells.
Figure 2B:
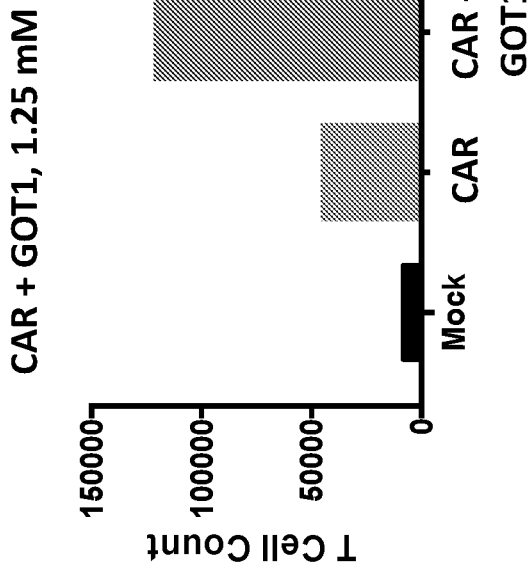

Tumor microenvironments have specific characteristics, such as low glucose, low amino acid, low pH, and/or hypoxic conditions, some of which may constrain the activity of effector immune cells such as effector T cells. The present disclosure is based, at least in part, on the development of various approaches for enhancing effector immune cell activities in tumor microenvironments via modulating (e.g., enhancing) Krebs cycle reactions by the effector immune cells, thereby enhancing their growth and bioactivity. The Krebs cycle can be modulated by various factors, including the expression level of Krebs cycle enzymes (e.g., naturally occurring enzymes or functional equivalents thereof), the activation status of such enzymes, the expression level and activity of enzymes that uses Krebs cycle metabolites as substrates, and/or the expression level and activity of enzymes that converts precursors to Krebs cycle metabolites.

The studies disclosed herein demonstrate, unexpectedly, that co-expression of a Krebs cycle modulating polypeptide such as GOT1 or GOT2 and a chimeric receptor polypeptide such as a CAR (e.g., having a 4-1BB co-stimulatory domain) or an ACTR (e.g., having a 4-1BB or CD28 co-stimulatory domain) in immune cells such as T cells exhibited superior features both in vitro and in vivo as relative to immune cells expressing only the CAR or the ACTR. For example, co-expression of GOT1 or GOT2 with CAR or ACTR enhanced T cell proliferation/expansion and T cell function, particularly under solid tumor microenvironment conditions (e.g., hypoxia, low glucose condition, and presence of TME inhibitors). For example, co-expression of GOT2 contributed to resistance of long-term expression of inhibitory receptors (e.g., PD1) and maintained T cell function in the tumor microenvironment. Further, co-expression of GOT1 or GOT2 with CAR or ACTR enhanced anti-tumor effects.

Accordingly, the present disclosure provides modified (e.g., genetically engineered) hematopoietic cells (e.g., HSCs or immune cells) that possess elevated Krebs to cycle modulating activity. Modification of the Krebs cycle in immune cells can be achieved by any suitable approaches. For example, the modified immune cells may express one or more Krebs cycle modulating factors, which can be a molecule of any type that either is involved in the Krebs cycle directly (e.g., an enzyme catalyzing one or more reactions of the Krebs cycle) or modulates the Krebs cycle indirectly via affecting the expression level, activity, and/or degradation of one or more Krebs cycle enzymes. In some embodiments, the Krebs cycle modulating factor can be a Krebs cycle modulating polypeptide as those described herein that enhances Krebs cycle modulation in immune cells expressing such as relative to their native counterpart. In other embodiments, the Krebs cycle modulating factor can be a nucleic acid (e.g., microRNA, interfering RNA such as siRNA or shRNA, or antisense nucleic acid) that regulates expression of one or more enzymes catalyzing one or more reactions of the Krebs cycle. In further embodiments, the Krebs cycle modulating factor may be a transcriptional factor that regulates expressing of one or more Krebs cycle enzymes.

Such a genetically engineered immune cell may further express a chimeric receptor polypeptide, e.g., an antibody-coupled T cell receptor (ACTR) polypeptide or a chimeric antigen receptor (CAR) polypeptide. Also provided herein are uses of the genetically engineered immune cells, optionally in combination with an Fc-containing agent when needed (e.g., when the immune cells express an ACTR polypeptide), for improving immune cell proliferation, and/or an inhibiting or decreasing in target cells (e.g., target cancer cells) in a subject (e.g., a human cancer patient), e.g., via ADCC. The present disclosure also provides pharmaceutical compositions and kits comprising the described genetically engineered immune cells.

The genetically engineered immune cells described herein, expressing (e.g., over-expressing) a Krebs cycle modulating polypeptide, may confer at least the following advantages. The expression of the Krebs cycle modulating polypeptide would enhance the metabolic activity of a T cell. As such, the genetically engineered immune cells may proliferate better, produce more cytokines, exhibit greater anti-tumor cytotoxicity, exhibit less immunosuppressive metabolites, and/or exhibit greater T cell survival in a tumor environment (e.g., low-glucose, low amino acid, low pH, and/or hypoxic environment relative to immune cells that do not express (or do not over-express) the Krebs cycle modulating polypeptide, leading to enhanced cytokine production, survival rate, cytotoxicity, and/or anti-tumor activity.

I. Krebs Cycle Modulating Polypeptides

As used herein, a Krebs cycle modulating polypeptide refers to any polypeptide that modulates the Krebs cycle, which links various metabolic pathways such as the metabolic pathways for processing glucose, amino acids and/or fatty acids. The Krebs cycle, also known as the citric acid cycle and tricarboxylic acid (TCA) cycle, is a metabolic pathway which begins with adding acetyl-CoA generated in glycolysis to oxaloacetate, forming citrate. Such a polypeptide may regulate one or more reversible enzymatic reactions in the Krebs cycle in favor of one direction relative to the other so as to regulate the metabolites generated therefrom. An increased input to the Krebs cycle from one metabolic source may redirect upstream metabolites of another pathway. For example, a Krebs cycle modulating polypeptide may redirect alanine into the glycolytic pathway, increase α-keto-glutarate (aKG) for TCA and/or serine synthesis pathway via, e.g., PSAT1, facilitate the TCA cycle in mitochondria and/or the cytoplasm; move glucose out of the TCA cycle to produce serine via PSAT1 or PSPH.

Additionally, a Krebs cycle modulating polypeptide may increase Krebs cycle activity in the mitochondria and/or the cytoplasm. A Krebs cycle modulating polypeptide may also transform inhibitory metabolites such as lactate into pyruvate to promote Krebs cycle activity. Any such Krebs cycle modulating polypeptide, which may be of any suitable species (e.g., mammalian such as human), may be contemplated for use with the compositions and methods described herein.

Alternatively, the Krebs cycle metabolite polypeptide may be a molecule that is mutated to mimic an activated Krebs cycle modulating polypeptide (e.g., a phosphorylation mimic) or mutated to impact its intracellular trafficking (e.g., traffic to mitochondria) such that the activity of the Krebs cycle is modulated. Alternatively, expression of an endogenous Krebs cycle polypeptide may be modulated, for example, by expressing a transcription factor or a microRNA, or by modulating the polypeptide's stability or degradation, for example, by modulating factors that mediate its degradation, for example an E3 ligase that is part of the ubiquitin/proteasome pathway. Additionally, the trafficking of an endogenous Krebs cycle polypeptide may be modulated, for example, by expressing a polypeptide that increases its trafficking to a desired subcellular compartment, for example, mitochondria. Further, a Krebs cycle modulating polypeptide may be a polypeptide that enzymatically converts substrates, found in high levels in the tumor microenvironment, that inhibit or limit the activity of immune cells, to molecules that no longer have inhibitory effects thus improving immune cell function.

Krebs cycle modulating polypeptides may be polypeptides having the enzymatic activity to catalyze a reaction in the Krebs cycle, for example, naturally-occurring enzymes that catalyze a Krebs cycle reaction, or functional variants/homologs thereof that catalyze the same Krebs cycle reaction. Examples include, but are not limited to, isocitrate dehydrogenase (IDH, including IDH1 or IDH2), malate dehydrogenase (MDH, including MDH1 or MDH2), or phosphoglycerate dehydrogenase (PHGDH).

Isocitrate dehydrogenase (IDH) refers to any polypeptide (enzyme) that catalyzes the oxidative decarboxylation of isocitrate, leading to production of α-ketoglutarate and $CO_2$. Malate dehydrogenase (MDH) refers to any polypeptide (enzyme) that catalyzes the oxidation of malate to oxaloacetate using the reduction of $NAD^+$ to NADH. Phosphoglycerate dehydrogenase (PHGDH) refers to any polypeptide (enzyme) that catalyzes the reactions to convert 3-phospho-D-glycerate to 3-phosphonooxypyruvate and to convert 2-hydrozyglutarate to 2-oxoglutarate, using the reduction of $NAD^+$ to NADH. Amino acid sequences of exemplary IDH, MDH, and PHGDH are provided below:

IDH1
(SEQ ID NO: 81)
MSKKISGGSVVEMQGDEMTRIIWELIKEKLIFPYVELDLHSYDLGIENRDA

TNDQVTKDAAEAIKKHNVGVKCATITPDEKRVEEFKLKQMWKSPNGTIRNI

LGGTVFREAIICKNIPRLVSGWVKPIIIGRHAYGDQYRATDFVVPGPGKVE

ITYTPSDGTQKVTYLVHNFEEGGGVAMGMYNQDKSIEDFAHSSFQMALSKG

WPLYLSTKNTILKKYDGRFKDIFQEIYDKQYKSQFEAQKIWYEHRLIDDMV

AQAMKSEGGFIWACKNYDGDVQSDSVAQGYGSLGMMTSVLVCPDGKTVEAE

AAHGTVTRHYRMYQKGQETSTNPIASIFAWTRGLAHRAKLDNNKELAFFAN

ALEEVSIETIEAGFMTKDLAACIKGLPNVQRSDYLNTFEFMDKLGENLKIK

LAQAKL

IDH2
(SEQ ID NO: 82)
MAGYLRVVRSLCRASGSRPAWAPAALTAPTSQEQPRRHYADKRIKVAKPVV

EMDGDEMTRIIWQFIKEKLILPHVDIQLKYFDLGLPNRDQTDDQVTIDSAL

ATQKYSVAVKCATITPDEARVEEFKLKKMWKSPNGTIRNILGGTVFREPII

CKNIPRLVPGWTKPITIGRHAHGDQYKATDFVADRAGTFKMVFTPKDGSGV

KEWEVYNFPAGGVGMGMYNTDESISGFAHSCFQYAIQKKWPLYMSTKNTIL

KAYDGRFKDIFQEIFDKHYKTDFDKNKIWYEHRLIDDMVAQVLKSSGGFVW

ACKNYDGDVQSDILAQGFGSLGLMTSVLVCPDGKTIEAEAAHGTVTRHYRE

HQKGRPTSTNPIASIFAWTRGLEHRGKLDGNQDLIRFAQMLEKVCVETVES

GAMTKDLAGCIHGLSNVKLNEHFLNTTDFLDTIKSNLDRALGRQ

MDH1
(SEQ ID NO: 83)
MSEPIRVLVTGAAGQIAYSLLYSIGNGSVFGKDQPIILVLLDITPMMGVLD

GVLMELQDCALPLLKDVIATDKEDVAFKDLDVAILVGSMPRREGMERKDLL

KANVKIFKSQGAALDKYAKKSVKVIVVGNPANTNCLTASKSAPSIPKENFS

CLTRLDHNRAKAQIALKLGVTANDVKNVIIWGNHSSTQYPDVNHAKVKLQG

KEVGVYEALKDDSWLKGEFVTTVQQRGAAVIKARKLSSAMSAAKAICDHVR

DIWFGTPEGEFVSMGVISDGNSYGVPDDLLYSFPVVIKNKTWKFVEGLPIN

DFSREKMDLTAKELTEEKESAFEFLSSA

MDH2
(SEQ ID NO: 84)
MLSALARPASAALRRSFSTSAQNNAKVAVLGASGGIGQPLSLLLKNSPLVS

RLTLYDIAHTPGVAADLSHIETKAAVKGYLGPEQLPDCLKGCDVVVIPAGV

PRKPGMTRDDLFNTNATIVATLTAACAQHCPEAMICVIANPVNSTIPITAE

VFKKHGVYNPNKIFGVTTLDIVRANTFVAELKGLDPARVNVPVIGGHAGKT

IIPLISQCTPKVDFPQDQLTALTGRIQEAGTEVVKAKAGAGSATLSMAYAG

ARFVFSLVDAMNGKEGVVECSFVKSQETECTYFSTPLLLGKKGIEKNLGIG

KVSSFEEKMISDAIPELKASIKKGEDFVKTLK

PHGDH
(SEQ ID NO: 85)
MAFANLRKVLISDSLDPCCRKILQDGGLQVVEKQNLSKEELIAELQDCEGL

IVRSATKVTADVINAAEKLQVVGRAGTGVDNVDLEAATRKGILVMNTPNGN

SLSAAELTCGMIMCLARQIPQATASMKDGKWERKKFMGTELNGKTLGILGL

GRIGREVATRMQSFGMKTIGYDPIISPEVSASFGVQQLPLEEIWPLCDFIT

VHTPLLPSTTGLLNDNTFAQCKKGVRVVNCARGGIVDEGALLRALQSGQCA

GAALDVFTEEPPRDRALVDHENVISCPHLGASTKEAQSRCGEEIAVQFVDM

VKGKSLTGVVNAQALTSAFSPHTKPWIGLAEALGTLMRAWAGSPKGTIQVI

TQGTSLKNAGNCLSPAVIVGLLKEASKQADVNLVNAKLLVKEAGLNVTTSH

-continued
SPAAPGEQGFGECLLAVALAGAPYQAVGLVQGTTPVLQGLNGAVFRPEVPL

RRDLPLLLFRTQTSDPAMLPTMIGLLAEAGVRLLSYQTSLVSDGETWHVMG

ISSLLPSLEAWKQHVTEAFQFHF

Krebs cycle modulating polypeptides may also be polypeptides that uses a Krebs cycle metabolite as a substrate, for example, a glutamic-oxaloacetic transaminase (GOT, including GOT1 and GOT2) or phosphoenolpyruvate carboxykinase 1 (PCK1). Glutamic-oxaloacetic transaminase (GOT), also known as aspartate aminotransferase (AST), refers to any pyridoxal phosphate (PLP)-dependent enzyme that catalyzes the reversible reaction to transfer an α-amino group between aspartate and glutamate. In some instances, GOT exists in cytoplasmic and inner-membrane mitochondrial forms, GOT1 and GOT2, respectively. GOT is also known as. Various PLP-depending enzymes, in addition to GOT1 and GOT2, may also be Krebs cycle modulating polypeptides, for example, aminotransferase, tryptophan synthase, alanine racemase, D-amino acid aminotransferase, and glycogen phophorylase. All of these enzymes are within the scope of the present disclosure. Phosphoenolpyruvate carboxykinase 1 (PCK1) refers to any polypeptide (enzyme) that converts oxaloacetate into phosphoenolpyruvate and carbon dioxide. Amino acid sequences of exemplary GOT and PCK1 are provided below:

PCK1
(SEQ ID NO: 86)
MPPQLQNGLNLSAKVVQGSLDSLPQAVREFLENNAELCQPDHIHICDGSEE

ENGRLLGQMEEEGILRRLKKYDNCWLALTDPRDVARIESKTVIVTQEQRDT

VPIPKTGLSQLGRWMSEEDFEKAFNARFPGCMKGRTMYVIPFSMGPLGSPL

SKIGIELTDSPYVVASMRIMTRMGTPVLEAVGDGEFVKCLHSVGCPLPLQK

PLVNNWPCNPELTLIAHLPDRREIISFGSGYGGNSLLGKKCFALRMASRLA

KEEGWLAEHMLILGITNPEGEKKYLAAAFPSACGKTNLAMMNPSLPGWKVE

CVGDDIAWMKFDAQGHLRAINPENGFFGVAPGTSVKTNPNAIKTIQKNTIF

TNVAETSDGGVYWEGIDEPLASGVTITSWKNKEWSSEDGEPCAHPNSRFCT

PASQCPIIDAAWESPEGVPIEGIIFGGRRPAGVPLVYEALSWQHGVFVGAA

MRSEATAAAEHKGKIIMHDPFAMRPFFGYNFGKYLAHWLSMAQHPAAKLPK

IFHVNWFRKDKEGKFLWPGFGENSRVLEWMFNRIDGKASTKLTPIGYIPKE

DALNLKGLGHINMMELFSISKEFWEKEVEDIEKYLEDQVNADLPCEIEREI

LALKQRISQM

GOT1
(SEQ ID NO: 87)
MAPPSVFAEVPQAQPVLVFKLTADFREDPDPRKVNLGVGAYRTDDCHPWVL

PVVKKVEQKIANDNSLNHEYLPILGLAEFRSCASRLALGDDSPALKEKRVG

GVQSLGGTGALRIGADFLARWYNGTNNKNTPVYVSSPTWENHNAVFSAAGF

KDIRSYRYWDAEKRGLDLQGFLNDLENAPEFSIVVLHACAHNPTGIDPTPE

QWKQIASVMKHRFLPFFFDSAYQGFASGNLERDAWAIRYFVSEGFEFFCAQ

SFSKNFGLYNERVGNLTVVGKEPESILQVLSQMEKIVRITWSNPPAQGARI

-continued
VASTLSNPELFEEWTGNVKTMADRILTMRSELRARLEALKTPGTWNHITDQ

IGMFSFTGLNPKQVEYLVNEKHIYLLPSGRINVSGLTTKNLDYVATSIHEA

VTKIQ

GOT2
(SEQ ID NO: 88)
MALLHSGRVLPGIAAAFHPGLAAAASARASSWWTHVEMGPPDPILGVTEAF

KRDTNSKKMNLGVGAYRDDNGKPYVLPSVRKAEAQIAAKNLDKEYLPIGGL

AEFCKASAELALGENSEVLKSGRFVTVQTISGTGALRIGASFLQRFFKFSR

DVFLPKPTWGNHTPIFRDAGMQLQGYRYYDPKTCGFDFTGAVEDISKIPEQ

SVLLLHACAHNPTGVDPRPEQWKEIATVVKKRNLFAFFDMAYQGFASGDGD

KDAWAVRHFIEQGINVCLCQSYAKNMGLYGERVGAFTMVCKDADEAKRVES

QLKILIRPMYSNPPLNGARIAAAILNTPDLRKQWLQEVKVMADRIIGMRTQ

LVSNLKKEGSTHNWQHITDQIGMFCFTGLKPEQVERLIKEFSIYMTKDGRI

SVAGVTSSNVGYLAHAIHQVTK

In addition, a Krebs cycle modulating polypeptide may be an enzyme that converts a precursor to a Krebs cycle metabolite, for example, phosphoserine aminotransferase (PSAT1), glutamate dehydrogenase (GDH1; also known as GLUD1), glutamate-pyruvate transaminase 1 (GPT1), or glutaminase (GLS). Phosphoserine aminotransferase (PSAT1) refers to any polypeptide (enzyme) that catalyzes the reversible conversion of 3-phosphohydroxypyruvate to phosphoserine and of 3-hydroxy-2-oxo-4-phosphonooxybutanoate to phosphohydroxythreonine. PSAT1 makes 2-oxoglutarate and 0-phospho-L-serine. Glutamate dehydrogenase (GDH1) refers to any polypeptide (enzyme) that converts glutamate to α-ketoglutarate, and vice versa. GDH1 coverts glutamate to 2-oxoglutarate (alpha-ketoglutarate). Glutamate-pyruvate transaminase 1 (GPT1) refers to any polypeptide (enzyme) that catalyzes reversible transamination between alanine and 2-oxoglutarate to form pyruvate and glutamate. Glutaminase (GLS) refers to any polypeptide (enzyme) that generates glutamate from glutamine. Amino acid sequences of exemplary PSAT1, GDH1, GPT1, and GLS are provided below:

GPT1
(SEQ ID NO: 89)
MASSTGDRSQAVRHGLRAKVLTLDGMNPRVRRVEYAVRGPIVQRALELEQE

LRQGVKKPFTEVIRANIGDAQAMGQRPITFLRQVLALCVNPDLLSSPNFPD

DAKKRAERILQACGGHSLGAYSVSSGIQLIREDVARYIERRDGGIPADPNN

VFLSTGASDAIVTVLKLLVAGEGHTRTGVLIPIPQYPLYSATLAELGAVQV

DYYLDEERAWALDVAELHRALGQARDHCRPRALCVINPGNPTGQVQTRECI

EAVIRFAFEERLFLLADEVYQDNVYAAGSQFHSFKKVLMEMGPPYAGQQEL

ASFHSTSKGYMGECGFRGGYVEVVNMDAAVQQQMLKLMSVRLCPPVPGQAL

LDLVVSPPAPTDPSFAQFQAEKQAVLAELAAKAKLTEQVFNEAPGISCNPV

-continued

```
QGAMYSFPRVQLPPRAVERAQELGLAPDMFFCLRLLEETGICVVPGSGFGQ

REGTYHFRMTILPPLEKLRLLLEKLSRFHAKFTLEYS
```

GLS (SEQ ID NO: 90)
```
MMRLRGSGMLRDLLLRSPAGVSATLRRAQPLVTLCRRPRGGGRPAAGPAAA

ARLHPWWGGGGWPAEPLARGLSSSPSEILQELGKGSTHPQPGVSPPAAPAA

PGPKDGPGETDAFGNSEGKELVASGENKIKQGLLPSLEDLLFYTIAEGQEK

IPVHKFITALKSTGLRTSDPRLKECMDMLRLTLQTTSDGVMLDKDLFKKCV

QSNIVLLTQAFRRKFVIPDFMSFTSHIDELYESAKKQSGGKVADYIPQLAK

FSPDLWGVSVCTVDGQRHSTGDTKVPFCLQSCVKPLKYAIAVNDLGTEYVH

RYVGKEPSGLRFNKLFLNEDDKPHNPMVNAGAIVVTSLIKQGVNNAEKFDY

VMQFLNKMAGNEYVGFSNATFQSERESGDRNFAIGYYLKEKKCFPEGTDMV

GILDFYFQLCSIEVTCESASVMAATLANGGFCPITGERVLSPEAVRNTLSL

MHSCGMYDFSGQFAFHVGLPAKSGVAGGILLVVPNVMGMMCWSPPLDKMGN

SVKGIHFCHDLVSLCNFHNYDNLRHFAKKLDPRREGGDQRVKSVINLLFAA

YTGDVSALRRFALSAMDMEQRDYDSRTALHVAAAEGHVEVVKFLLEACKVN

PFPKDRWNNTPMDEALHFGHHDVFKILQEYQVQYTPQGDSDNGKENQTVHK

NLDGLL
```

PSAT1

(SEQ ID NO: 91)
```
MDAPRQVVNFGPGPAKLPHSVLLEIQKELLDYKGVGISVLEMSHRSSDFAK

IINNTENLVRELLAVPDNYKVIFLQGGGCGQFSAVPLNLIGLKAGRCADYV

VTGAWSAKAAEEAKKFGTINIVHPKLGSYTKIPDPSTWNLNPDASYVYYCA

NETVHGVEFDFIPDVKGAVLVCDMSSNFLSKPVDVSKFGVIFAGAQKNVGS

AGVTVVIVRDDLLGFALRECPSVLEYKVQAGNSSLYNTPPCFSIYVMGLVL

EWIKNNGGAAAMEKLSSIKSQTIYEIIDNSQGFYVCPVEPQNRSKMNIPFR

IGNAKGDDALEKRFLDKALELNMLSLKGHRSVGGIRASLYNAVTIEDVQKL

AAFMKKFLEMHQL
```

GDH1

(SEQ ID NO: 92)
```
MTYKCAVVDVPFGGAKAGVKINPKNYTDNELEKITRRFTMELAKKGFIGPG

IDVPAPDMSTGEREMSWIADTYASTIGHYDINAHACVTGKPISQGGIHGRI

SATGRGVFHGIENFINEASYMSILGMTPGFGDKTFVVQGFGNVGLHSMRYL

HRFGAKCIAVGESDGSIWNPDGIDPKELEDFKLQHGSILGFPKAKPYEGSI

LEADCDILIPAASEKQLTKSNAPRVKAKIIAEGANGPTTPEADKIFLERNI

MVIPDLYLNAGGVTVSYFEWLKNLNHVSYGRLTFKYERDSNYHLLMSVQES

LERKFGKHGGTIPIVPTAEFQDRISGASEKDIVHSGLAYTMERSARQIMRT

AMKYNLGLDLRTAAYVNAIEKVFKVYNEAGVTFT
```

The Krebs cycle modulating polypeptide may be a naturally-occurring polypeptide from a suitable species, for example, a mammalian Krebs cycle modulating polypeptide such as those derived from human or a non-human primate. Such naturally-occurring polypeptides are known in the art and can be obtained, for example, using any of the above-noted amino acid sequences as a query to search a publicly available gene database, for example GenBank. The Krebs cycle modulating polypeptide for use in the instant disclosure may share a sequence identity of at least 85% (e.g., 90%, 95%, 97%, 98%, 99%, or above) as any of the exemplary proteins noted above.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

In some embodiments, the Krebs cycle modulating polypeptide may be conjugated to a subcellular compartment-localization signaling peptide (e.g., mitochondria-localization signaling peptide) for trafficking the polypeptide to a desired subcellular compartment. For example, a GOT2 polypeptide may comprise a mitochondria-localization signaling peptide such that it can be trafficked to mitochondria in a host immune cell.

Alternatively, the Krebs cycle modulating polypeptide may be a functional variant of a native counterpart. Such a functional variant may contain one or more mutations outside the functional domain(s) of the native counterpart. Functional domains of a native Krebs cycle modulating polypeptide may be known in the art or can be predicted based on its amino acid sequence. Mutations outside the functional domain(s) would not be expected to substantially affect the biological activity of the protein. In some instances, the functional variant may exhibit increased Krebs cycle modulation as relative to the native counterpart. Alternatively, the functional variant may exhibit decreased Krebs cycle modulation as relative to the native counterpart.

A functional variant of a Krebs cycle modulating polypeptide may be a functional variant of a wild-type polypeptide, which may comprise one or more mutations as relative to the native counterpart and retain substantially the same biological activity as the native counterpart. In some embodiments, the functional variant of the Krebs cycle modulating polypeptide comprises at least one, at least two, at least three, at least four, at least five, at least six, or more mutations as relative to the native counterpart.

For example, a functional variant of GOT may comprise at least one, at least two, at least three, at least four, at least five, at least six, or more mutations as relative to the native counterpart. In some embodiments, a functional variant of GOT comprises a mutation of a lysine residue at position 159 (e.g., K159Q) in SEQ ID NO: 88. In some embodiments, a functional variant of GOT comprises a mutation of a lysine residue at position 185 (e.g., K185Q) in SEQ ID NO: 88. In some embodiments, a functional variant of GOT comprises a mutation of a lysine residue at position 404 (e.g., K404Q) in SEQ ID NO: 88. In some embodiments, a functional variant of GOT comprises a mutation of a lysine residue at position 159 (e.g., K159Q) and position 185 (e.g., K185Q) in SEQ ID NO: 88. In some embodiments, a functional variant of GOT comprises a mutation of a lysine residue at position 185 (e.g., K185Q) and position 404 (e.g., K404Q) in SEQ ID NO: 88. In some embodiments, a functional variant of GOT comprises a mutation of a lysine residue at position 159 (e.g., K159Q) and position 404 (e.g., K404Q) in SEQ ID NO: 88. In some embodiments, a functional variant of GOT comprises a mutation of a lysine residue at position 159 (e.g., K159Q), position 185 (e.g., K185Q), and position 404 (e.g., K404Q) in SEQ ID NO: 88. See also Yang et al., *The EMBO Journal* (2015) 34: 1100-1125, the relevant disclosures of which are incorporated by reference herein for the purpose and subject matter reference herein.

In some embodiments, the functional variant of the Krebs cycle modulating polypeptide may exhibit one or more biological properties (e.g., modification status, catalytic activity, cellular location and/or binding partners) that may be altered as relative to the native counterpart. Non-limiting examples of a functional variant of a Krebs cycle modulating polypeptide include a functional variant of an enzyme that catalyzes a reaction in the Krebs cycle (e.g., a functional variant of IDH, MDH, or PHGDH), a functional variant of an enzyme that uses a Krebs cycle metabolite as a substrate (e.g., a functional variant of GOT or PCK1), and a functional variant of an enzyme that converts a precursor to a Krebs cycle metabolite (e.g., a functional variant of PSAT1, GDH1, GPT1, or GLS).

Alternatively or in addition, the functional variant may contain a conservative mutation(s) at one or more positions in the native counterpart (e.g., up to 20 positions, up to 15 positions, up to 10 positions, up to 5, 4, 3, 2, 1 position(s)). As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references which compile such methods, e.g., Molecular Cloning: A Laboratory Manual, J. Sambrook, et al., eds., Second Edition, Cold Spring Harbor Laboratory Press, Cold Spring Harbor, New York, 1989, or Current Protocols in Molecular Biology, F. M. Ausubel, et al., eds., John Wiley & Sons, Inc., New York. Conservative substitutions of amino acids include substitutions made amongst amino acids within the following groups: (a) M, I, L, V; (b) F, Y, W; (c) K, R, H; (d) A, G; (e) S, T; (0 Q, N; and (g) E, D.

II. Chimeric Receptor Polypeptides

As used herein, a chimeric receptor polypeptide refers to a non-naturally occurring molecule that can be expressed on the surface of a host cell. A chimeric receptor polypeptide comprises an extracellular target binding domain that can target an antigen of interest (e.g., an antigen associated with a disease such as cancer or an antigen associated with a pathogen; see discussions herein). An extracellular target binding domain may bind to an antigen of interest directly (e.g., an extracellular antigen binding domain in a CAR polypeptide as disclosed herein). Alternatively, an extracellular target binding domain may bind to the antigen of interest via an intermediate, for example, an Fc-containing agent such as an antibody. A chimeric receptor polypeptide may further comprise a transmembrane domain, a hinge domain, a cytoplasmic signaling domain, one or more co-stimulatory domains, a cytoplasmic signaling domain, or a combination thereof. In some instances, the chimeric receptor polypeptide may be free of co-stimulatory domains. The chimeric receptor polypeptides are configured such that, when expressed on a host cell, the extracellular target binding domain is located extracellularly for binding to a target antigen, directly or indirectly. The optional co-stimulatory signaling domain may be located in the cytoplasm for triggering activation and/or effector signaling.

In some embodiments, chimeric receptor polypeptides described herein may further comprise a hinge domain, which may be located at the C-terminus of the extracellular target binding domain and the N-terminus of the transmembrane domain. The hinge may be of any suitable length. In other embodiments, the chimeric receptor polypeptide described herein may have no hinge domain at all. In yet other embodiments, the chimeric receptor polypeptide described herein may have a shortened hinge domain (e.g., including up to 25 amino acid residues).

In some embodiments, a chimeric receptor polypeptide as described herein may comprise, from N-terminus to C-terminus, the extracellular target binding domain, the transmembrane domain, and the cytoplasmic signaling domain. In some embodiments, a chimeric receptor polypeptide as described herein comprises, from N-terminus to C-terminus, the extracellular target binding domain, the transmembrane domain, at least one co-stimulatory signaling domain, and the cytoplasmic signaling domain. In other embodiments, a chimeric receptor polypeptide as described herein comprises, from N-terminus to C-terminus, the extracellular target binding domain, the transmembrane domain, the cytoplasmic signaling domains, and at least one co-stimulatory signaling domain.

In some embodiments, the chimeric receptor polypeptide can be an antibody-coupled T cell receptor (ACTR) polypeptide. As used herein, an ACTR polypeptide (a.k.a., an ACTR construct) refers to a non-naturally occurring molecule that can be expressed on the surface of a host cell and comprises an extracellular domain with binding affinity and specificity for the Fc portion of an immunoglobulin ("Fc binder" or "Fc binding domain"), a transmembrane domain, and a cytoplasmic signaling domain. In some embodiments, the ACTR polypeptides described herein may further include at least one co-stimulatory signaling domain.

In other embodiments, the chimeric receptor polypeptide disclosed herein may be a chimeric antigen receptor (CAR) polypeptide. As used herein, a CAR polypeptide (a.k.a., a CAR construct) refers to a non-naturally occurring molecule that can be expressed on the surface of a host cell and comprises an extracellular antigen binding domain, a transmembrane domain, and a cytoplasmic signaling domain. The CAR polypeptides described herein may further include at least one co-stimulatory signaling domain.

The extracellular antigen binding domain may be any peptide or polypeptide that specifically binds to a target antigen, including naturally occurring antigens that are associated with a medical condition (e.g., a disease), or an antigenic moiety conjugated to a therapeutic agent that targets a disease-associated antigen.

In some embodiments, the CAR polypeptides described herein may further include at least one co-stimulatory signaling domain. The CAR polypeptides are configured such that, when expressed on a host cell, the extracellular antigen-binding domain is located extracellularly for binding to a target molecule and the cytoplasmic signaling domain. The optional co-stimulatory signaling domain may be located in the cytoplasm for triggering activation and/or effector signaling.

As used herein, the phrase "a protein X transmembrane domain" (e.g., a CD8 transmembrane domain) refers to any portion of a given protein, i.e., transmembrane-spanning protein X, that is thermodynamically stable in a membrane.

As used herein, the phrase "a protein X cytoplasmic signaling domain," for example, a CD3ζ cytoplasmic signaling domain, refers to any portion of a protein (protein X) that interacts with the interior of a cell or organelle and is capable of relaying a primary signal as known in the art, which lead to immune cell proliferation and/or activation. The cytoplasmic signaling domain as described herein differs from a co-stimulatory signaling domain, which relays a secondary signal for fully activating immune cells.

As used herein, the phrase "a protein X co-stimulatory signaling domain," e.g., a CD28 co-stimulatory signaling domain, refers to the portion of a given co-stimulatory protein (protein X, such as CD28, 4-1BB, OX40, CD27, or ICOS) that can transduce co-stimulatory signals (secondary signals) into immune cells (such as T cells), leading to fully activation of the immune cells.

A. Extracellular Target Binding Domain

The chimeric receptor polypeptides disclosed herein comprise an extracellular domain that targets an antigen of interest (e.g., those described herein) via either direct binding or indirectly binding (through an intermediate such as an antibody). The chimeric receptor polypeptides may be ACTR polypeptides that comprise an Fc binding domain. Alternatively, the chimeric receptor polypeptides may be CAR polypeptides that comprise an extracellular antigen binding domain.

Fc Binding Domains

The ACTR polypeptides described herein comprise an extracellular domain that is an Fc binding domain, i.e., capable of binding to the Fc portion of an immunoglobulin (e.g., IgG, IgA, IgM, or IgE) of a suitable mammal (e.g., human, mouse, rat, goat, sheep, or monkey). Suitable Fc binding domains may be derived from naturally occurring proteins such as mammalian Fc receptors or certain bacterial proteins (e.g., protein A, protein G). Additionally, Fc binding domains may be synthetic polypeptides engineered specifically to bind the Fc portion of any of the antibodies described herein with high affinity and specificity. For example, such an Fc binding domain can be an antibody or an antigen-binding fragment thereof that specifically binds the Fc portion of an immunoglobulin. Examples include, but are not limited to, a single-chain variable fragment (scFv), a domain antibody, or single domain antibodies (e.g., nanobodies). Alternatively, an Fc binding domain can be a synthetic peptide that specifically binds the Fc portion, such as a Kunitz domain, a small modular immunopharmaceutical (SMIP), an adnectin, an avimer, an affibody, a DARPin, or an anticalin, which may be identified by screening a peptide combinatory library for binding activities to Fc.

In some embodiments, the Fc binding domain is an extracellular ligand-binding domain of a mammalian Fc receptor. As used herein, an "Fc receptor" is a cell surface bound receptor that is expressed on the surface of many immune cells (including B cells, dendritic cells, natural killer (NK) cells, macrophage, neutrophils, mast cells, and eosinophils) and exhibits binding specificity to the Fc domain of an antibody. Fc receptors are typically comprised of at least two immunoglobulin (Ig)-like domains with binding specificity to an Fc (fragment crystallizable) portion of an antibody. In some instances, binding of an Fc receptor to an Fc portion of the antibody may trigger antibody dependent cell-mediated cytotoxicity (ADCC) effects. The Fc receptor used for constructing an ACTR polypeptide as described herein may be a naturally-occurring polymorphism variant (e.g., the CD16 V158 variant), which may have increased or decreased affinity to Fc as compared to a wild-type counterpart. Alternatively, the Fc receptor may be a functional variant of a wild-type counterpart, which carry one or more mutations (e.g., up to 10 amino acid residue substitutions including 1, 2, 3, 4, 5, 6, 7, 8, 9, or 10 mutations) that alter the binding affinity to the Fc portion of an Ig molecule. In some instances, the mutation may alter the glycosylation pattern of the Fc receptor and thus the binding affinity to Fc.

The table below lists a number of exemplary polymorphisms in Fc receptor extracellular domains (see, e.g., Kim et al., *J. Mol. Evol.* 53:1-9, 2001) which may be used in any of the methods or constructs described herein:

TABLE 1

Exemplary Polymorphisms in Fc Receptors

| Amino Acid Number | 19 | 48 | 65 | 89 | 105 | 130 | 134 | 141 | 142 | 158 |
|---|---|---|---|---|---|---|---|---|---|---|
| FCR10 | R | S | D | I | D | G | F | Y | T | V |
| P08637 | R | S | D | I | D | G | F | Y | I | F |
| S76824 | R | S | D | I | D | G | F | Y | I | V |
| J04162 | R | N | D | V | D | D | F | H | I | V |
| M31936 | S | S | N | I | D | D | F | H | I | V |
| M24854 | S | S | N | I | E | D | S | H | I | V |
| X07934 | R | S | N | I | D | D | F | H | I | V |
| X14356 (FcγRII) | N | N | N | S | E | S | S | S | I | I |
| M31932 (FcγRI) | S | T | N | R | E | A | F | T | I | G |
| X06948 (FcαεI) | R | S | E | S | Q | S | E | S | I | V |

Fc receptors are classified based on the isotype of the antibody to which it is able to bind. For example, Fc-gamma receptors (FcγR) generally bind to IgG antibodies, such as one or more subtype thereof (i.e., IgG1, IgG2, IgG3, IgG4); Fc-alpha receptors (FcαR) generally bind to IgA antibodies; and Fc-epsilon receptors (FcεR) generally bind to IgE antibodies. In some embodiments, the Fc receptor is an Fc-gamma receptor, an Fc-alpha receptor, or an Fc-epsilon receptor. Examples of Fc-gamma receptors include, without limitation, CD64A, CD64B, CD64C, CD32A, CD32B, CD16A, and CD16B. An example of an Fc-alpha receptor is FcαR1/CD89. Examples of Fc-epsilon receptors include, without limitation, FcεRI and FcεRII/CD23. The table below lists exemplary Fc receptors for use in constructing the ACTR polypeptides described herein and their binding activity to corresponding Fc domains:

TABLE 2

Exemplary Fc Receptors

| Receptor name | Principal antibody ligand | Affinity for ligand |
|---|---|---|
| FcγRI (CD64) | IgG1 and IgG3 | High (Kd ~$10^{-9}$M) |
| FcγRIIA (CD32) | IgG | Low (Kd >$10^{-7}$M) |
| FcγRIIB1 (CD32) | IgG | Low (Kd >$10^{-7}$M) |
| FcγRIIB2 (CD32) | IgG | Low (Kd >$10^{-7}$M) |
| FcγRIIIA (CD16a) | IgG | Low (Kd >$10^{-6}$M) |
| FcγRIIIB (CD16b) | IgG | Low (Kd >$10^{-6}$M) |
| FcεRI | IgE | High (Kd ~$10^{-10}$M) |
| FcεRII (CD23) | IgE | Low (Kd >$10^{-7}$M) |
| FcαRI (CD89) | IgA | Low (Kd >$10^{-6}$M) |
| Fcα/μR | IgA and IgM | High for IgM, Mid for IgA |
| FcRn | IgG | |

Selection of the ligand binding domain of an Fc receptor for use in the ACTR polypeptides described herein will be apparent to one of skill in the art. For example, it may depend on factors such as the isotype of the antibody to which binding of the Fc receptor is desired and the desired affinity of the binding interaction.

The extracellular antigen binding domain of any of the CAR polypeptides In some examples, the Fc binding domain is the extracellular ligand-binding domain of CD16, which may incorporate a naturally occurring polymorphism that may modulate affinity for Fc. In some examples, the Fc binding domain is the extracellular ligand-binding domain of CD16 incorporating a polymorphism at position 158 (e.g., valine or phenylalanine). In some embodiments, the Fc binding domain is produced under conditions that alter its glycosylation state and its affinity for Fc.

The amino acid sequences of human CD16A F158 and CD16A V158 variants are provided below with the F158 and V158 residue highlighted in bold/face and underlined (signal peptide italicized):

```
CD16A F158 (SEQ ID NO: 93):
MWQLLLPTALLLLVSAGMRTEDLPKAVVFLEPQWYRVLEKDSVTLKCQGAY

SPEDNSTQWFHNESLISSQASSYFIDAATVDDSGEYRCQTNLSTLSDPVQL

EVHIGWLLLQAPRWVFKEEDPIHLRCHSWKNTALHKVTYLQNGKGRKYFHH

NSDFYIPKATLKDSGSYFCRGLFGSKNVSSETVNITITQGLAVSTISSFFP

PGYQVSFCLVMVLLFAVDTGLYFSVKTNIRSSTRDWKDHKFKWRKDPQDK

CD16A V158 (SEQ ID NO: 94):
MWQLLLPTALLLLVSAGMRTEDLPKAVVFLEPQWYRVLEKDSVTLKCQGAY

SPEDNSTQWFHNESLISSQASSYFIDAATVDDSGEYRCQTNLSTLSDPVQL

EVHIGWLLLQAPRWVFKEEDPIHLRCHSWKNTALHKVTYLQNGKGRKYFHH

NSDFYIPKATLKDSGSYFCRGLVGSKNVSSETVNITITQGLAVSTISSFFP

PGYQVSFCLVMVLLFAVDTGLYFSVKTNIRSSTRDWKDHKFKWRKDPQDK
```

In some embodiments, the Fc binding domain is the extracellular ligand-binding domain of CD16 incorporating modifications that render the ACTR polypeptide specific for a subset of IgG antibodies. For example, mutations that increase or decrease the affinity for an IgG subtype (e.g., IgG1) may be incorporated.

Any of the Fc binding domains described herein may have a suitable binding affinity for the Fc portion of a therapeutic antibody. As used herein, "binding affinity" refers to the apparent association constant or $K_A$. The $K_A$ is the reciprocal of the dissociation constant, $K_D$. The extracellular ligand-binding domain of an Fc receptor domain of the ACTR polypeptides described herein may have a binding affinity $K_d$ of at least $10^{-5}$, $10^{-6}$, $10^{-7}$, $10^{-8}$, $10^{-9}$, $10^{-10}$ M or lower for the Fc portion of antibody. In some embodiments, the Fc binding domain has a high binding affinity for an antibody, isotype(s) of antibodies, or subtype(s) thereof, as compared to the binding affinity of the Fc binding domain to another antibody, isotype(s) of antibodies, or subtypes(s) thereof. In some embodiments, the extracellular ligand-binding domain of an Fc receptor has specificity for an antibody, isotype(s) of antibodies, or subtype(s) thereof, as compared to binding of the extracellular ligand-binding domain of an Fc receptor to another antibody, isotype(s) of antibodies, or subtypes(s) thereof.

Other Fc binding domains as known in the art may also be used in the ACTR constructs described herein including, for example, those described in WO2015058018A1 and PCT Application No.: PCT/US2018/015999, the relevant disclosures of each of which are incorporated by reference for the purpose and subject matter referenced herein.

Extracellular Antigen Binding Domains

The CAR polypeptides described herein comprise an extracellular antigen binding domain, which re-directs the specificity of immune cells expressing the CAR polypeptide. As used herein, "an extracellular antigen binding domain" refers to a peptide or polypeptide having binding specificity to a target antigen of interest, which can be a naturally occurring antigen associated with a medical condition (e.g., a disease), or an antigenic moiety conjugated to a therapeutic agent that targets a disease-associated antigen. The extracellular antigen binding domain as described herein does not comprise an extracellular domain of an Fc receptor, and may not bind to the Fc portion of an immunoglobulin. An extracellular domain that does not bind to an Fc fragment means that the binding activity between the two is not detectable using a conventional assay or only background or biologically insignificant binding activity is detected using the conventional assay.

In some instances, the extracellular antigen binding domain of any CAR polypeptides described herein is a peptide or polypeptide capable of binding to a cell surface antigen (e.g., a tumor antigen), or an antigen (or a fragment thereof) that is complex with a major histocompatibility complex and be presented on the cell surface of an antigen-presenting cell. Such an extracellular antigen binding domain may be a single-chain antibody fragment (scFv), which may be derived from an antibody that binds the target cell surface antigen with a high binding affinity. Table 1 below lists exemplary cell-surface target antigens and exemplary antibodies binding to such.

TABLE 3

Exemplary Cell Surface Target Antigen and Exemplary Antibodies Binding to Such

| Exemplary Target Antigens | Exemplary Antibodies | Exemplary Target Antigens | Exemplary Antibodies and Fc-fusion Agents |
|---|---|---|---|
| CD137 (4-1BB) | utomilumab | CD74 | milatuzumab |
| Trophoblast glycoprotein (5T4) | naptumomab estafenatox | HLA-DR | IMMU-114 |
| Adenosine A2a receptor (A2aR) | anti-A2aR mAbs | Hsp70 | mi-TUMEXtx |
| Alk-1 protein kinase (ACVRL1) | ascrinvacumab | Hsp 90 | ZSG-102 |
| ADAM-10 (ADAM10) | 8C7 | ICAM-1 | BI-505 |
| TACE (ADAM17) | MEDI-3622 | Inducible T-cell co-stimulator (ICOS) | GSK-3359609 |
| ADAM-28 (ADAM28) | GFC-201 | Immunoglobulin kappa (Ig kappa) | KappaMab |
| CD156; Immunoglobulin G1; Immunoglobulin G2 (ADAM8) | MAB-1031 | Immunoglobulin antigen (Ig lambda) | LambdaMab |

TABLE 3-continued

Exemplary Cell Surface Target Antigen and Exemplary Antibodies Binding to Such

| Exemplary Target Antigens | Exemplary Antibodies | Exemplary Target Antigens | Exemplary Antibodies and Fc-fusion Agents |
|---|---|---|---|
| ADAM-9 (ADAM9) | AEX-6003 | IL-6 receptor (IL-6R) | tocilizumab |
| Anterior gradient protein 2 homolog (AGR2) | agtuzumab | IL-7 receptor (IL-7R) | anti-IL7R mAbs |
| Anaplastic lymphoma kinase (ALK) | KTN-0125 | IL-13 receptor alpha 1 subunit (IL13RA1) | ASLAN-004 |
| Angiopoietin ligand-2 (Ang-2); Vascular endothelial growth factor-A (VEGF-A) | vanucizumab | IL-13 receptor alpha 2 subunit (IL13RA2) | anti-IL13RA2 mAbs |
| Lactadherin (Anti-idiotype) | TriAb (11D10) | IL-1 receptor accessory protein (IL1RAP) | CAN-04 |
| Tumor necrosis factor ligand 13 (APRIL) | BION-1301 | IL-2 receptor beta (IL2R beta) | Mikbetal |
| Aspartate beta-hydroxylase (ASPH) | PAN-622 | Immunoglobulin like domain receptor 2 (ILDR2) | BAY-1905254 |
| Axl tyrosine kinase (AXL) | BA-3011 | Integrin alpha-X/beta-1 (Integrin a10b1) | anti-Integrin a10b1 mAbs |
| CD276 antigen (B7-H3) | BVD m276; hu8H9 | Integrin alpha-3/beta-1 (Integrin a3b1) | BCMab-1 |
| V-set domain-containing T-cell activation inhibitor 1 (VTCN1; also B7-H4) | FPA-150 | Integrin alpha-6/beta-4 (Integrin a6b4) | 90Y-ITGA6B4 |
| B-cell activating factor; (BAFF; also TNFSF13B and CD257) | blisibimod | Integrin alpha-9 (Integrin a9) | GND-001 |
| B-cell activating factor receptor; (BAFF-R; also TNFSF13C and CD268) | VAY736 | CD49b (Integrin alpha 2) | Vatelizumab |
| BAG molecular chaperone regulator 3 (BAG3) | anti-BAG3 mAbs | CD49c (Integrin alpha 3) | anti-CD49c mAbs |
| Basigin (BSG; CD147) | cHAb18 | CD49d; (Integrin alpha 4) | anti-CD49d mAbs |
| B-cell maturation antigen (BCMA; also TNFRSF17) | SEA-BCMA | CD51 | abituzumab |
| ADP ribosyl cyclase-2 (BST1) | OX-001 | CD29 (integrin beta 1) | OS-2966 |
| B and T lymphocyte attenuator (BTLA) | 40E4 | CD61 (Integrin beta 3) | anti-CD61 mAbs |
| Complement C5a receptor (C5aR) | neutrazumab | Jagged-1 | anti-Jagged-1 mAbs |
| CACNA2D1 calcium channel subunit (CACNA2D1) | anti-CACNA2D1 mAbs | Kidney-associated antigen 1 (KAAG1) | AB-3A4 |
| Carbonic anhydrase-IX (CAIX) | G250 | Potassium channel subfamily K member 9 (KCNK9) | Y-4 |
| Calreticulin (CALR) | Anti-CALR mAbs | KIR2DL1/2L3 | lirilumab |
| Caveolin 1 (CAV1) | anti-CAV1 mAbs | tyrosine-protein kinase kit (KIT) | CDX-0158 |
| Carbonic anhydrase-XII (CAXII) | 177Lu-6A10-Fab; anti-CAXII mAbs | L1CAM | anti-L1CAM mAbs |
| CCR2 chemokine receptor (CCR2) | plozalizumab | Death receptor 5 (DR5) | APOMAB |
| CCR3 chemokine receptor (CCR3) | anti-CCR3 mAbs | CD223 (LAG3) | relatlimab |
| CCR4 chemokine receptor (CCR4) | mogamulizumab | Lewis Y | hu3S193; MB311 |
| CCR5 chemokine receptor (CCR5) | PRO 140; CCR5mAb004 | Zinc transporter SLC39A6 | SGN-LIV1 (LIV1) |
| CCR7 chemokine receptor (CCR7) | anti-CCR7 mAbs | Lysyl oxidase-like protein 2 (LOXL2) | AB-0023 |
| CCR9 chemokine receptor (CCR9) | anti-CCR9 mAbs | Leucine rich repeat-containing protein 15 (LRRC15) | ABBV-085 |
| Interleukin-3 receptor alpha (IL3RA; CD123) | CSL362; KHK2823 | Leucine rich repeat-containing protein 32 (LRRC32) | ARGX-115 |
| Aminopeptidase N (CD13) | MI-130110 | Lymphocyte antigen 75 (LY75) | MEN-1309 |

TABLE 3-continued

Exemplary Cell Surface Target Antigen and Exemplary Antibodies Binding to Such

| Exemplary Target Antigens | Exemplary Antibodies | Exemplary Target Antigens | Exemplary Antibodies and Fc-fusion Agents |
|---|---|---|---|
| Prominin 1 (CD133) | anti-CD133 mAbs | Ly6/PLAUR domain-containing protein 3 (LYPD3) | BAY-1129980 |
| Syndecan-1 (CD138) | indatuximab ravtansine | Melanoma associated antigen (MAGE peptide presented in MHC) | LxC-002 |
| CD160 | ELB-021 | Matriptase (ST14) | anti-ST14 mAbs |
| Activated leukocyte cell adhesion molecule (CD166) | CX-2009 | MICA/B | IPH4301 |
| B-lymphocyte antigen CD19 | MOR208 | MIF/HLA-A2 (MIF peptide presented in MHC) | RL21A |
| B-lymphocyte antigen CD20 | rituximab; obinituzumab; ocaratuzumab | Anti-mullerian hormone II (MHR2) | GM-102 |
| Membrane glycoprotein OX2 CD200 | samalizumab | MMPl/HLA (MMP1 peptide presented in MHC1) | Anti-MMPl/HLA mAbs |
| CD22 | epratuzumab | Metalloprotease-9 (MMP9) | andecaliximab |
| Immunoglobulin epsilon Fc receptor II (CD23) | lumiliximab | Mesothelin (MSLN) | MORAb-009 |
| Signal transducer CD24 | anti-CD24 mAbs | Mucin 1 (MUC1) | PankoMab-GEX |
| IL-2 receptor alpha subunit CD25 | 90Y-daclizumab | Mucin 13 (MUC13) | anti-MUC13 mAbs |
| CD27 | varilumab | Endomucin (MUC14) | anti-MUC14 mAbs |
| CD28 | theralizumab | Mucin 16 (MUC16) | sofituzumab |
| CD3 | Muromonab-CD3 (OKT3) | Cell surface glycoprotein MUC18 (CD146) | AA98 |
| CD30 | brentuximab vedotin | Mucin 5AC (MUC5AC) | ensituximab |
| Immunoglobulin gamma Fc receptor IIB (CD32B) | BI-1206 | N-glycolyl GM3 (NeuGcGM3) | 99mTc-labeled 14F7 |
| CD33 | lintuzumab | Sodium-dependent phosphate transport protein 2B (SLC34A2) | XMT-1536 |
| CD37 | ollertuzumab | Nucleolin (NCL) | anti-nucleolin mAbs |
| ADP ribosyl cyclase-1 (CD38) | daratumumab | Nectin-4 | enfortumab vedotin |
| CD39 | OREG-103 | Neurofibromin (NF1) | anti-neurofibromin mAbs |
| CD4 | IT-1208 | NGcGM3 ganglioside | racotumomab |
| CD40 | lucatumumab | NKG2A | monalizumab |
| CD43 | leukotuximab | non-POU domain-containing octamer-binding protein (NONO) | PAT-LM1 |
| CD44 | RG7356 | Notch-1 | brontictuzumab |
| CD45 | 131I-BC8 | CD73 | oleclumab |
| Membrane cofactor protein (CD46) | AugmAb | Netrin-1 (NTN1) | NP-137 |
| CD47 | Hu5F9-G4 | OX-40 | PF-04518600 |
| CD52 | alemtuzumab | P2X purinoceptor 7 (P2RX7) | BIL-010t |
| CD55 | PAT-SC1 | FGF receptor (pan FGFR) | MM-161 |
| Neural cell adhesion molecule 1; (CD56) | IMGN-901 | Integrin (Pan integrin) | NOD201 |
| T-cell differentiation antigen CD6 | itolizumab | P-cadherin, also cadherin-3 (CDH3) | PCA-062 |
| CD70 | SGN-70 | Programmed cell death protein 1 (PD-1) | pembrolizumab |
| CD79b | polatuzumab vedotin | Programmed cell death ligand 1 (PD-L1) | avelumab; Euchloe H12 |
| CD8 | anti-CD8 mAbs | Programmed cell death ligand 2 (PD-L2) | rHIgMl2B7 |
| CD80 | galiximab | PDGF receptor alpha (PDGFRA) | olaratumumab |
| CD98 | IGN-523 | Placenta specific protein 1 (PLAC1) | anti-PLAC1 mAbs |
| CD99 | NV-103 | PR1/HLA (PR1 peptide in MHC) | anti-PR1/HLA mAbs |

TABLE 3-continued

Exemplary Cell Surface Target Antigen and Exemplary Antibodies Binding to Such

| Exemplary Target Antigens | Exemplary Antibodies | Exemplary Target Antigens | Exemplary Antibodies and Fc-fusion Agents |
|---|---|---|---|
| Cadherin-1 (CDH1) | anti-CDH1 mAbs | Prolactin receptor PRLR | ABBV-176 |
| Cadherin-17 (CDH17) | anti-CDH17 mAbs | Phosphatidylserine | anti-phosphatidylserine mAbs |
| Cadherin 19 (CDH19) | anti-CDH19 mAbs | Prostate stem cell antigen (PSCA) | anti-PSCA mAbs |
| Cadherin-6 (CDH6) | HKT-288 | Glutamate carboxypeptidase II (PSMA) | ATL-101 |
| CD66a (CEACAM1) | CM-24 | Parathyroid hormone-related protein (PTH-rP) | CAL |
| CD66e (CEACAM5) | IMMU-130 | Tyrosine-protein kinase-like 7 (PTK7) | cofetuzumab pelidotin |
| CD66c; CD66e (CEACAM5/6) | NEO-201 | Protein tyrosine phosphatase IVA3 (PTP4A3) | PRL3-zumab |
| Claudin 18 (Claudin 18.2) | IMAB362 | Poliovirus receptor related immunoglobulin domain containing (PVRIG) | COM-701 |
| Claudin 6 | IMAB027 | Receptor activator of nuclear factor kappa-B ligand (RANKL) | denosumab |
| SLAM family member 7 (CS1) | elotuzumab | Recepteur d'origine nantais (RON) | anti-RON mAbs |
| colony stimulating factor-1 receptor (CSF1R) | cabiralizumab | Tyrosine-protein kinase transmembrane receptor ROR1 (ROR1); also NTRKR1 | cirmtuzumab |
| Cytotoxic T-lymphocyte protein-4 (CTLA4) | ipilumumab | Tyrosine-protein kinase transmembrane receptor ROR2 (ROR2); also NTRKR2 | BA-3021 |
| Coxsackievirus and adenovirus receptor (CXADR) | anti-CXADR mAbs | R-spondin-3 (RSPO3) | rosmantuzumab |
| CXCR2 chemokine receptor | anti-CXCR2 mAbs | Sphingosine-1-phosphate receptor 3 (S1PR3) | EDD7H9 |
| CXCR3 chemokine receptor | anti-CXCR3 mAbs | Surface Antigen In Leukemia (SAIL) | IGN-786 |
| CXCR4 chemokine receptor | ulocuplumab | Semaphorin-4D (SEMA4D) | VX-15 |
| CXCR5 chemokine receptor | STI-B030X | carbohydrate antigen 19-9 (CA 19-9) | MVT-1075 |
| CXCR7 chemokine receptor | anti-CXCR7 mAbs | Sialyl Thomsen nouveau antigen (STn) | anti-STn mAbs |
| DCLK1 | anti-DCLK1 mAbs | Sialic acid-binding Ig-like lectin 8 (Siglec-8) | AK-002 |
| Dickkopf-related protein 1 (DKK1) | BHQ-880 | Sialic acid-binding Ig-like lectin 9 (Siglec-9) | anti-Siglec-9 mAbs |
| DLK1 | ADCT-701 | Signal Regulatory Protein Alpha (SIRPA) | OSE-172 |
| Delta-like protein ligand 3 (DLL3) | SC16LD6.5 | CD48; also SLAM family member 2 (SLAMF2) | SGN-CD48A |
| Delta-like protein ligand 4 (DLL4); VEGF (VEGF) | navicixizumab | CD352; SLAM family member 6 (SLAMF6) | SGN-CD352A |
| Dipeptidyl peptidase-4 (DPP4), (also CD26) | YSCMA | Neutral amino acid transporter B0 (SLC1A5) | KM-8094 |
| Death receptor-3 (DR3) | PTX-35 | Somatostatin 2 receptor (SSTR2) | XmAb-18087 |
| TRAIL-1 receptor (DR4) | HuYON007 MultYbody | Stabilin 1 (STAB1) | FP-1305 |
| TRAIL-1 receptor; TRAIL-2 receptor (DR4/DR5) | DR4/DR5 Surrobody | Metalloreductase (STEAP1) | 89Zr-DFO-MSTP2109A |
| TRAIL-2 receptor (DR5) | DS-8273 | Survivin | anti-suivivin mAbs |

TABLE 3-continued

Exemplary Cell Surface Target Antigen and Exemplary Antibodies Binding to Such

| Exemplary Target Antigens | Exemplary Antibodies | Exemplary Target Antigens | Exemplary Antibodies and Fc-fusion Agents |
|---|---|---|---|
| EGF-like protein 6 (EGFL6) | anti-EGFL6 mAbs | TAG-72 | 90Y-IDEC-159 |
| Epidermal growth factor receptor (EGFR) | cetuximab; Sym004; nimotuzumab | T cell receptor (TCR) | anti-TCR mAbs |
| Epidermal growth factor receptor vIII (EGFRvIII) | ABT-806 | Endosialin (TEM1) | ontuxizumab |
| Epithelial membrane protein 2 (EMP2) | ONCR-201 | Anthrax toxin receptor 1 (ANTXR1); also TEM8 | anti-TEM8 mAbs |
| Endoglin | carotuximab | Tissue factor (TF) | MORAb-066 |
| Ectonucleotide pyrophosphatase/phosph odiesterase family member 3 (ENPP3) | AGS-16C3F | Transforming growth factor, beta receptor II TGF-beta type II (TGFBR2) | anti-TGFBR2 mAbs |
| Prostaglandin $E_2$ receptor 2 (PTGER2) | anti-PTGER2 mAbs | Thomsen-Friedenreich Antigen | JAA-F11 |
| Prostaglandin $E_2$ receptor 4 (PTGER4) | anti-PTGER4 mAbs | T cell immunoreceptor with Ig and ITIM domains (TIGIT) | BMS-986207 |
| EpCAM | oportuzumab monatox | Hepatitis A virus cellular receptor 1 (HAVCR1); also TIM-1 | CDX-014 |
| Ephrin type-A receptor 2 (EphA2) | MEDI-547 | Hepatitis A virus cellular receptor 2 (HAVCR2); also TIM-3 | MBG453 |
| Ephrin type-A receptor 3 (EphA3) | KB004 | Toll-like receptor 2 (TLR-2) | OPN-305 |
| Fibroblast activation protein (FAP) | F19 | Toll-like receptor 4 (TLR-4) | anti-TLR4 mAbs |
| CD95 (FAS) | asunercept | Transmembrane 4 L6 family member 1 (TM4SF1) | anti-TM4SF1 mAbs |
| Fc receptor like protein 5 (FCRL5) | RG-6160 | Tumor necrosis factor receptor 2 (TNFR2) | anti-TNFR2 mAbs |
| FGF receptor 1 (FGFR1) | FP-1039 | CD71 | anti-CD71 mAbs |
| FGF receptor 2b (FGFR2b) | FPA-144 | Triggering receptor expressed on myeloid cells 1 (TREM1) | anti-TREM1 mAbs |
| FGF receptor 3 (FGFR3) | B-701 | Tumor-associated calcium signal transducer 2 (Trop-2) | DS-1062 |
| fms-like tyrosine kinase 3 (FLT3) | Flysyn | TWEAK Receptor (TWEAKR) | MRT-101 |
| Folate receptor alpha (FOLR1) | farletuzumab; IMGN853; KHK2805 | Tyrosine-protein kinase receptor TYRO3 (TYRO3) | ELB-031 |
| Folate receptor beta (FOLR2) | anti-FOLR beta mAbs | Urokinase receptor (uPAR) | MNPR-101 |
| Frizzled-1; Frizzled-2; Frizzled-5; Frizzled-7; Frizzled-8; (FZD1,2,5,7,8) | vantictumab | VEGF-2 (VEGFR2) | ramucirumab |
| Follistatin-like protein 1 (FSTL1) | anti-FSTL1 mAbs | Vimentin | pritumumab |
| Fucosyl-GM1 | BMS-986012 | V-domain Ig suppressor of T cell activation (VISTA) | JNJ-61610588 |
| Frizzled-10 (FZD10) | OTSA-101 | Integrin alpha-4/beta-1 | natalizumab |
| GCSF-R (Also, CD114 and CSFR3) | CSL324 | Immunoglobulin iota chain (VPREB1) | anti-VPREB1 mAbs |
| Galectin 3 binding protein (LGAL S3) | MP-1959 | Wilms tumor protein (WT1/HLA); peptide presented in MHC | ESK1 WT1 |
| Guanylate cyclase 2C (GUCY2C) | TAK-164 | Glypican-3 (GPC3) | codrituzumab |
| GD2 | dinutuximab | Transmembrane glycoprotein NMB (GPNMB) | CDX-011 |

TABLE 3-continued

Exemplary Cell Surface Target Antigen and Exemplary Antibodies Binding to Such

| Exemplary Target Antigens | Exemplary Antibodies | Exemplary Target Antigens | Exemplary Antibodies and Fc-fusion Agents |
|---|---|---|---|
| GD3 | PF-06688992 | Leucine-rich repeat-containing G-protein coupled receptor 5 (LGR5) | BNC-101 |
| glucocorticoid-induced TNFR-related protein (GITR) | BMS-986156 | G-protein coupled receptor family C group 5 member D (GPRC5D) | JNJ-64407564 |
| glucocorticoid-induced TNFR-related protein ligand (GITRL) | EU-102 | Ferritin | Ferritarg P |
| premelanocyte protein (PMEL) | anti-PMEL mAbs | Erbb2 tyrosine kinase (HER2) | trastuzumab; pertuzumab; margetuximab |
| Cell surface A33 antigen (GPA33) | Anti-GPA33 mAbs | Erbb3 tyrosine kinase (HER3) | patritumab |
| Glypican-1 (GPC1) | MIL-38 | Globo H | OBI-888 |

The extracellular antigen binding domain may comprise an antigen binding fragment (e.g., a scFv) derived from any of the antibodies listed in Table 1 depending upon the target antigen of interest.

In other embodiments, the extracellular antigen binding domain of any of the CAR polypeptides described herein may be specific to a pathogenic antigen, such as a bacterial antigen, a viral antigen, or a fungal antigen. Some examples are provided below: influenza virus neuraminidase, hemagglutinin, or M2 protein, human respiratory syncytial virus (RSV) F glycoprotein or G glycoprotein, herpes simplex virus glycoprotein gB, gC, gD, or gE, *Chlamydia* MOMP or PorB protein, Dengue virus core protein, matrix protein, or glycoprotein E, measles virus hemagglutinin, herpes simplex virus type 2 glycoprotein gB, poliovirus I VP1, envelope glycoproteins of HIV 1, hepatitis B core antigen or surface antigen, diptheria toxin, *Streptococcus* 24M epitope, Gonococcal pilin, pseudorabies virus g50 (gpD), pseudorabies virus II (gpB), pseudorabies virus III (gpC), pseudorabies virus glycoprotein H, pseudorabies virus glycoprotein E, transmissible gastroenteritis glycoprotein 195, transmissible gastroenteritis matrix protein, or human hepatitis C virus glycoprotein E1 or E2.

In addition, the extracellular antigen binding domain of the CAR polypeptide described herein may be specific to a tag conjugated to a therapeutic agent, which targets an antigen associated with a disease or disorder (e.g., a tumor antigen or a pathogenic antigen as described herein). In some instances, the tag conjugated to the therapeutic agent can be antigenic and the extracellular antigen binding domain of the CAR polypeptide can be an antigen-binding fragment (e.g., scFv) of an antibody having high binding affinity and/or specificity to the antigenic tag. Exemplary antigenic tags include, but are not limited to, biotin, avidin, a fluorescent molecule (e.g., GFP, YRP, luciferase, or RFP), Myc, Flag, His (e.g., poly His such as 6xHis), HA (hemeagglutinin), GST, MBP (maltose binding protein), KLH (keyhole limpet hemocyanins), trx, T7, HSV, VSV (e.g., VSV-G), Glu-Glu, V5, e-tag, S-tag, KT3, E2, Au1, Au5, and/or thioredoxin.

In other instances, the tag conjugated to the therapeutic agent is a member of a ligand-receptor pair and the extracellular antigen binding domain comprises the other member of the ligand-receptor pair or a fragment thereof that binds the tag. For example, the tag conjugated to the therapeutic agent can be biotin and the extracellular antigen binding domain of the CAR polypeptide can comprise a biotin-binding fragment of avidin. See, e.g., Urbanska et al., 2012, Lohmueller et al., 2018. Other examples include anti-Tag CAR, in which the extracellular antigen binding domain is a scFv fragment specific to a protein tag, such as FITC (Tamada et al., 2012, Kim et al., 2015; Cao et al., 2016; and Ma et al., 2016), PNE (Rodgers et al., 2016), La-SS-B (Cartellieri et al., 2016), Biotin (Lohmullular et al., 2017), and Leucine-Zipper (Cho et al., 2018). Selection of the antigen binding domain for use in the CAR polypeptides described herein will be apparent to one of skill in the art. For example, it may depend on factors such as the type of target antigen and the desired affinity of the binding interaction.

The extracellular antigen binding domain of any of the CAR polypeptides described herein may have suitable binding affinity for a target antigen (e.g., any one of the targets described herein) or antigenic epitopes thereof. As used herein, "binding affinity" refers to the apparent association constant or $K_A$. The $K_A$ is the reciprocal of the dissociation constant ($K_D$). The extracellular antigen binding domain for use in the CAR polypeptides described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an extracellular antigen binding domain for a first antigen relative to a second antigen can be indicated by a higher $K_A$ (or a smaller numerical value $K_D$) for binding the first antigen than the $K_A$ (or numerical value $K_D$) for binding the second antigen. In such cases, the extracellular antigen binding domain has specificity for the first antigen (e.g., a first protein in a first conformation or mimic thereof) relative to the second antigen (e.g., the same first protein in a second conformation or mimic thereof or a second protein). Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

[Bound]=[Free]/(Kd+[Free])

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

B. Transmembrane Domain

The transmembrane domain of the chimeric receptor polypeptides (e.g., ACTR polypeptides or CAR polypeptides) described herein can be in any form known in the art. As used herein, a "transmembrane domain" refers to any protein structure that is thermodynamically stable in a cell membrane, preferably a eukaryotic cell membrane. A transmembrane domain compatible for use in the chimeric receptor polypeptides used herein may be obtained from a naturally occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 2, 3, 4, 5, 6, 7 or more times).

Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the chimeric receptor polypeptide described herein is derived from a Type I single-pass membrane protein. Single-pass membrane proteins include, but are not limited to, CD8α, CD8β, 4-1BB/CD137, CD27, CD28, CD34, CD4, FcεRIγ, CD16, OX40/CD134, CD3, CD3E, CD3γ, CD3δ, TCRα, TCRβ, TCRζ, CD32, CD64, CD64, CD45, CD5, CD9, CD22, CD37, CD80, CD86, CD40, CD40L/CD154, VEGFR2, FAS, and FGFR2B. In some embodiments, the transmembrane domain is from a membrane protein selected from the following: CD8α, CD8β3, 4-1BB/CD137, CD28, CD34, CD4, FcεRIγ, CD16, OX40/CD134, CD3ζ, CD3ε, CD3γ, CD3δ, TCRα, CD32, CD64, VEGFR2, FAS, and FGFR2B. In some examples, the transmembrane domain is of CD8 (e.g., the transmembrane domain is of CD8α). In some examples, the transmembrane domain is of 4-1BB/CD137. In other examples, the transmembrane domain is of CD28. In some cases, the chimeric receptor polypeptide described herein may be free of a hinge domain from any non-CD16A receptor. In some instances, such a chimeric receptor polypeptide may be free of any hinge domain. Alternatively or in addition, such a chimeric receptor polypeptide may comprise two or more co-stimulatory regions as described herein. In other examples, the transmembrane domain is of CD34. In yet other examples, the transmembrane domain is not derived from human CD8α. In some embodiments, the transmembrane domain of the chimeric receptor polypeptide is a single-pass alpha helix.

Transmembrane domains from multi-pass membrane proteins may also be compatible for use in the chimeric receptor polypeptides described herein. Multi-pass membrane proteins may comprise a complex alpha helical structure (e.g., at least 2, 3, 4, 5, 6, 7 or more alpha helices) or a beta sheet structure. Preferably, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side. Either one or multiple helix passes from a multi-pass membrane protein can be used for constructing the chimeric receptor polypeptide described herein.

Transmembrane domains for use in the chimeric receptor polypeptides described herein can also comprise at least a portion of a synthetic, non-naturally occurring protein segment. In some embodiments, the transmembrane domain is a synthetic, non-naturally occurring alpha helix or beta sheet. In some embodiments, the protein segment is at least approximately 20 amino acids, e.g., at least 18, 19, 20, 21, 22, 23, 24, 25, 26, 27, 28, 29, 30, or more amino acids. Examples of synthetic transmembrane domains are known in the art, for example in U.S. Pat. No. 7,052,906 B1 and PCT Publication No. WO 2000/032776 A2, the relevant disclosures of each of which are incorporated by reference herein.

In some embodiments, the amino acid sequence of the transmembrane domain does not comprise cysteine residues. In some embodiments, the amino acid sequence of the transmembrane domain comprises one cysteine residue. In some embodiments, the amino acid sequence of the transmembrane domain comprises two cysteine residues. In some embodiments, the amino acid sequence of the transmembrane domain comprises more than two cysteine residues (e.g., 3, 4, 5, or more).

The transmembrane domain may comprise a transmembrane region and a cytoplasmic region located at the C-terminal side of the transmembrane domain. The cytoplasmic region of the transmembrane domain may comprise three or more amino acids and, in some embodiments, helps to orient the transmembrane domain in the lipid bilayer. In some embodiments, one or more cysteine residues are present in the transmembrane region of the transmembrane domain. In some embodiments, one or more cysteine residues are present in the cytoplasmic region of the transmembrane domain. In some embodiments, the cytoplasmic region of the transmembrane domain comprises positively charged amino acids. In some embodiments, the cytoplasmic region of the transmembrane domain comprises the amino acids arginine, serine, and lysine.

In some embodiments, the transmembrane region of the transmembrane domain comprises hydrophobic amino acid residues. In some embodiments, the transmembrane region comprises mostly hydrophobic amino acid residues, such as alanine, leucine, isoleucine, methionine, phenylalanine, tryptophan, or valine. In some embodiments, the transmembrane region is hydrophobic. In some embodiments, the transmembrane region comprises a poly-leucine-alanine sequence.

The hydropathy, hydrophobic or hydrophilic characteristics of a protein or protein segment, can be assessed by any method known in the art including, for example, the Kyte and Doolittle hydropathy analysis.

C. Co-Stimulatory Signaling Domains

Many immune cells require co-stimulation, in addition to stimulation of an antigen-specific signal, to promote cell proliferation, differentiation and survival, as well as to activate effector functions of the cell. In some embodiments, the chimeric receptor polypeptides, such as ACTR or CAR polypeptides, described herein comprise at least one co-stimulatory signaling domain. In certain embodiments, the chimeric receptor polypeptides may contain a CD28 co-stimulatory signaling domain or a 4-1BB (CD137) co-stimulatory signaling domain. The term "co-stimulatory signaling domain," as used herein, refers to at to least a fragment of a co-stimulatory signaling protein that mediates signal transduction within a cell to induce an immune response such as an effector function (a secondary signal). As known in the art, activation of immune cells such as T cells often requires two signals: (1) the antigen specific signal (primary signal) triggered by the engagement of T cell receptor (TCR) and antigenic peptide/MHC complexes presented by antigen presenting cells, which typically is driven by CD3ζ as a component of the TCR complex; and (ii) a co-stimulatory signal (secondary signal) triggered by the interaction between a co-stimulatory receptor and its ligand. A co-stimulatory receptor transduces a co-stimulatory signal (secondary signal) as an addition to the TCR-triggered signaling and modulates responses mediated by immune cells, such as T cells, NK cells, macrophages, neutrophils, or eosinophils.

Activation of a co-stimulatory signaling domain in a host cell (e.g., an immune cell) may induce the cell to increase or decrease the production and secretion of cytokines, phagocytic properties, proliferation, differentiation, survival, and/or cytotoxicity. The co-stimulatory signaling domain of any co-stimulatory molecule may be compatible for use in the chimeric receptor polypeptides described herein. The type(s) of co-stimulatory signaling domain is selected based on factors such as the type of the immune cells in which the chimeric receptor polypeptides would be expressed (e.g., T cells, NK cells, macrophages, neutrophils, or eosinophils) and the desired immune effector function (e.g. ADCC). Examples of co-stimulatory signaling domains for use in the chimeric receptor polypeptides may be the cytoplasmic signaling domain of co-stimulatory proteins, including, without limitation, members of the B7/CD28 family (e.g., B7-1/CD80, B7-2/CD86, B7-H1/PD-L1, B7-H2, B7-H3, B7-H4, B7-H6, B7-H7, BTLA/CD272, CD28, CTLA-4, Gi24/VISTA/B7-H5, ICOS/CD278, PD-1, PD-L2/B7-DC, and PDCD6); members of the TNF superfamily (e.g., 4-1BB/TNFRSF9/CD137, 4-1BB Ligand/TNFSF9, BAFF/BLyS/TNFSF13B, BAFF R/TNFRSF13C, CD27/TNFRSF7, CD27 Ligand/TNFSF7, CD30/TNFRSF8, CD30 Ligand/TNFSF8, CD40/TNFRSF5, CD40/TNFSF5, CD40 Ligand/TNFSF5, DR3/TNFRSF25, GITR/TNFRSF18, GITR Ligand/TNFSF18, HVEM/TNFRSF14, LIGHT/TNFSF14, Lymphotoxin-alpha/TNF-beta, OX40/TNFRSF4, OX40 Ligand/TNFSF4, RELT/TNFRSF19L, TACI/TNFRSF13B, TL1A/TNFSF15, TNF-alpha, and TNF RIFTNFRSF1B); members of the SLAM family (e.g., 2B4/CD244/SLAMF4, BLAME/SLAMF8, CD2, CD2F-10/SLAMF9, CD48/SLAMF2, CD58/LFA-3, CD84/SLAMF5, CD229/SLAMF3, CRACC/SLAMF7, NTB-A/SLAMF6, and SLAM/CD150); and any other co-stimulatory molecules, such as CD2, CD7, CD53, CD82/Kai-1, CD90/Thy1, CD96, CD160, CD200, CD300α/LMIR1, HLA Class I, HLA-DR, Ikaros, Integrin alpha 4/CD49d, Integrin alpha 4 beta 1, Integrin alpha 4 beta 7/LPAM-1, LAG-3, TCL1A, TCL1B, CRTAM, DAP12, Dectin-1/CLEC7A, DPPIV/CD26, EphB6, TIM-1/KIM-1/HAVCR, TIM-4, TSLP, TSLP R, lymphocyte function associated antigen-1 (LFA-1), and NKG2C. In some embodiments, the co-stimulatory signaling domain is of 4-1BB, CD28, OX40, ICOS, CD27, GITR, HVEM, TIM1, LFA1 (CD11α) or CD2, or any variant thereof.

Also within the scope of the present disclosure are variants of any of the co-stimulatory signaling domains described herein, such that the co-stimulatory signaling domain is capable of modulating the immune response of the immune cell. In some embodiments, the co-stimulatory signaling domains comprises up to 10 amino acid residue mutations (e.g., 1, 2, 3, 4, 5, or 8) such as amino acid substitutions, deletions, or additions as compared to a wild-type counterpart. Such co-stimulatory signaling domains comprising one or more amino acid variations (e.g., amino acid substitutions, deletions, or additions) may be referred to as variants.

Mutation of amino acid residues of the co-stimulatory signaling domain may result in an increase in signaling transduction and enhanced stimulation of immune responses relative to co-stimulatory signaling domains that do not comprise the mutation. Mutation of amino acid residues of the co-stimulatory signaling domain may result in a decrease in signaling transduction and reduced stimulation of immune responses relative to co-stimulatory signaling domains that do not comprise the mutation. For example, mutation of residues 186 and 187 of the native CD28 amino acid sequence may result in an increase in co-stimulatory activity and induction of immune responses by the co-stimulatory domain of the chimeric receptor polypeptide. In some embodiments, the mutations are substitution of a lysine at each of positions 186 and 187 with a glycine residue of the CD28 co-stimulatory domain, referred to as a $CD28_{LL \to GG}$ variant. Additional mutations that can be made in co-stimulatory signaling domains that may enhance or reduce co-stimulatory activity of the domain will be evident to one of ordinary skill in the art. In some embodiments, the co-stimulatory signaling domain is of 4-1BB, CD28, OX40, or $CD28_{LL \to GG}$ variant.

In some embodiments, the chimeric receptor polypeptides may contain a single co-stimulatory domain such as, for example, a CD27 co-stimulatory domain, a CD28 co-stimulatory domain, a 4-1BB co-stimulatory domain, an ICOS co-stimulatory domain, or an OX40 co-stimulatory domain.

In some embodiments, the chimeric receptor polypeptides may comprise more than one co-stimulatory signaling domain (e.g., 2, 3, or more). In some embodiments, the chimeric receptor polypeptide comprises two or more of the same co-stimulatory signaling domains, for example, two copies of the co-stimulatory signaling domain of CD28. In some embodiments, the chimeric receptor polypeptide comprises two or more co-stimulatory signaling domains from different co-stimulatory proteins, such as any two or more co-stimulatory proteins described herein. Selection of the type(s) of co-stimulatory signaling domains may be based on factors such as the type of host cells to be used with the chimeric receptor polypeptides (e.g., T cells or NK cells) and the desired immune effector function. In some embodiments, the chimeric receptor polypeptide comprises two co-stimulatory signaling domains, for example, two copies of the co-stimulatory signaling domain of CD28. In some embodiments, the chimeric receptor polypeptide may comprise two or more co-stimulatory signaling domains from different co-stimulatory receptors, such as any two or more co-stimulatory receptors described herein, for example, CD28 and 4-1BB, CD28 and CD27, CD28 and ICOS, $CD28_{LL \to GG}$ variant and 4-1BB, CD28 and OX40, or $CD28_{LL \to GG}$ variant and OX40. In some embodiments, the two co-stimulatory signaling domains are CD28 and 4-1BB. In some embodiments, the two co-stimulatory signaling domains are $CD28_{LL} \to G_G$ variant and 4-1BB. In some embodiments, the two co-stimulatory signaling domains are CD28 and OX40. In some embodiments, the two co-stimulatory signaling domains are $CD28_{LL \to GG}$ variant and OX40. In some embodiments, the chimeric receptor polypeptides described herein may contain a combination of a CD28 and ICOSL. In some embodiments, the chimeric receptor polypeptide described herein may contain a combination of CD28 and CD27. In certain embodiments, the 4-1BB co-stimulatory domain is located N-terminal to the CD28 or $CD28_{LL \to GG}$ variant co-stimulatory signaling domain.

In some embodiments, the chimeric receptor polypeptides described herein do not comprise a co-stimulatory signaling domain.

D. Cytoplasmic Signaling Domain

Any cytoplasmic signaling domain can be used to create the chimeric receptor polypeptides described herein (e.g., ACTR polypeptides or CAR polypeptides). Such a cytoplasmic domain may be any signaling domain involved in triggering cell signaling (primary signaling) that leads to immune cell proliferation and/or activation. The cytoplasmic signaling domain as described herein is not a co-stimulatory signaling domain, which, as known in the art, relays a co-stimulatory or secondary signal for fully activating immune cells.

The cytoplasmic domain described herein may comprise an immunoreceptor tyrosine-based activation motif (ITAM) domain (e.g., at least one ITAM domain, at least two ITAM domains, or at least three ITAM domains) or may be ITAM free. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif $YxxL/Ix_{(6-8)}YxxL/I$. ITAMs within signaling molecules are important for signal transduction within the cell, which is mediated at least in part by phosphorylation of tyrosine residues in the ITAM following activation of the signaling molecule. ITAMs may also function as docking sites for other proteins involved in signaling pathways.

In some examples, the cytoplasmic signaling domain is of CD3ζ or FcεR1γ. In other examples, cytoplasmic signaling domain is not derived from human CD3. In yet other examples, the cytoplasmic signaling domain is not derived from an Fc receptor, when the extracellular Fc-binding domain of the same chimeric receptor polypeptide is derived from CD16A.

In one specific embodiment, several signaling domains can be fused together for additive or synergistic effect. Non-limiting examples of useful additional signaling domains include part or all of one or more of TCR Zeta chain, CD28, OX40/CD134, 4-1BB/CD137, FcεR1γ, ICOS/CD278, IL2R-beta/CD122, IL-2R-gamma/CD132, and CD40.

In other embodiments, the cytoplasmic signaling domain described herein is free of the ITAM motif. Examples include, but are not limited to, the cytoplasmic signaling domain of Jak/STAT, Toll-interleukin receptor (TIR), and tyrosine kinase.

E. Hinge Domain

In some embodiments, the chimeric receptor polypeptides such as ACTR polypeptides or CAR polypeptides described herein further comprise a hinge domain that is located between the extracellular ligand-binding domain and the transmembrane domain. A hinge domain is an amino acid segment that is generally found between two domains of a protein and may allow for flexibility of the protein and movement of one or both of the domains relative to one another. Any amino acid sequence that provides such flexibility and movement of the extracellular ligand-binding domain relative to the transmembrane domain of the chimeric receptor polypeptide can be used.

Hinge domains of any protein known in the art to comprise a hinge domain are compatible for use in the chimeric receptor polypeptides described herein. In some embodiments, the hinge domain is at least a portion of a hinge domain of a naturally occurring protein and confers flexibility to the chimeric receptor polypeptide. In some embodiments, the hinge domain is of CD8. In some embodiments, the hinge domain is a portion of the hinge domain of CD8, e.g., a fragment containing at least 15 (e.g., 20, 25, 30, 35, or 40) consecutive amino acids of the hinge domain of CD8. In some embodiments, the hinge domain is of CD28. In some embodiments, the hinge domain is a portion of the hinge domain of CD28, e.g., a fragment containing at least 15 (e.g., 20, 25, 30, 35, or 40) consecutive amino acids of the hinge domain of CD28. The hinge domain and/or the transmembrane domain may be linked to additional amino acids (e.g., 15 aa, 10-aa, 8-aa, 6-aa, or 4-aa) at the N-terminal portion, at the C-terminal portion, or both. Examples can be found, e.g., in Ying et al., Nature Medicine, 25(6): 947-953 (2019).

In some embodiments, the hinge domain is of CD16A receptor, for example, the whole hinge domain of a CD16A receptor or a portion thereof, which may consists of up to 40 consecutive amino acid residues of the CD16A receptor (e.g., 20, 25, 30, 35, or 40). Such a chimeric receptor polypeptide (e.g., an ACTR polypeptide) may contain no hinge domain from a different receptor (a non-CD16A receptor).

Hinge domains of antibodies, such as an IgG, IgA, IgM, IgE, or IgD antibodies, are also compatible for use in the chimeric receptor polypeptides described herein. In some embodiments, the hinge domain is the hinge domain that joins the constant domains CH1 and CH2 of an antibody. In some embodiments, the hinge domain is of an antibody and comprises the hinge domain of the antibody and one or more constant regions of the antibody. In some embodiments, the hinge domain comprises the hinge domain of an antibody and the CH3 constant region of the antibody. In some embodiments, the hinge domain comprises the hinge domain of an antibody and the CH2 and CH3 constant regions of the antibody. In some embodiments, the antibody is an IgG, IgA, IgM, IgE, or IgD antibody. In some embodiments, the antibody is an IgG antibody. In some embodiments, the antibody is an IgG1, IgG2, IgG3, or IgG4 antibody. In some embodiments, the hinge region comprises the hinge region and the CH2 and CH3 constant regions of an IgG1 antibody. In some embodiments, the hinge region comprises the hinge region and the CH3 constant region of an IgG1 antibody.

Non-naturally occurring peptides may also be used as hinge domains for the chimeric receptor polypeptides described herein. In some embodiments, the hinge domain between the C-terminus of the extracellular target-binding domain and the N-terminus of the transmembrane domain is a peptide linker, such as a $(Gly_xSer)_n$ linker, wherein x and n, independently can be an integer between 3 and 12, including 3, 4, 5, 6, 7, 8, 9, 10, 11, 12, or more. In some embodiments, the hinge domain is $(Gly_4Ser)_{12}$ (SEQ ID NO:95), wherein n can be an integer between 3 and 60, including 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60. In certain embodiments, n can be an integer greater than 60. In some embodiments, the hinge domain is $(Gly_4Ser)_3$ (SEQ ID NO: 96). In some embodiments, the hinge domain is $(Gly_4Ser)_6$ (SEQ ID NO: 97). In some embodiments, the hinge domain is $(Gly_4Ser)_9$ (SEQ ID NO: 98). In some embodiments, the hinge domain is $(Gly_4Ser)_{12}$ (SEQ ID NO: 99). In some embodiments, the hinge domain is $(Gly_4Ser)_{15}$ (SEQ ID NO: 100). In some embodiments, the hinge domain is $(Gly_4Ser)_{30}$ (SEQ ID NO: 101). In some embodiments, the hinge domain is $(Gly_4Ser)_{45}$ (SEQ ID NO: 102). In some embodiments, the hinge domain is $(Gly_4Ser)_{60}$ (SEQ ID NO: 103).

In other embodiments, the hinge domain is an extended recombinant polypeptide (XTEN), which is an unstructured polypeptide consisting of hydrophilic residues of varying lengths (e.g., 10-80 amino acid residues). Amino acid sequences of XTEN peptides will be evident to one of skill in the art and can be found, for example, in U.S. Pat. No. 8,673,860, the relevant disclosures of which are incorporated by reference herein. In some embodiments, the hinge domain is an XTEN peptide and comprises 60 amino acids. In some embodiments, the hinge domain is an XTEN peptide and comprises 30 amino acids. In some embodiments, the hinge domain is an XTEN peptide and comprises 45 amino acids. In some embodiments, the hinge domain is an XTEN peptide and comprises 15 amino acids.

Any of the hinge domains used for making the chimeric receptor polypeptide as described herein may contain up to 250 amino acid residues. In some instances, the chimeric receptor polypeptide may contain a relatively long hinge domain, for example, containing 150-250 amino acid residues (e.g., 150-180 amino acid residues, 180-200 amino acid residues, or 200-250 amino acid residues). In other instances, the chimeric receptor polypeptide may contain a medium sized hinge domain, which may contain 60-150 amino acid residues (e.g., 60-80, 80-100, 100-120, or 120-150 amino acid residues). Alternatively, to the chimeric receptor polypeptide may contain a short hinge domain, which may contain less than 60 amino acid residues (e.g., 1-30 amino acids or 31-60 amino acids). In some embodiments, a chimeric receptor polypeptide (e.g., an ACTR polypeptide) described herein contains no hinge domain or no hinge domain from a non-CD16A receptor.

F. Signal Peptide

In some embodiments, the chimeric receptor polypeptide (e.g., ACTR polypeptide or CAR polypeptide) may also comprise a signal peptide (also known as a signal sequence) at the N-terminus of the polypeptide. In general, signal sequences are peptide sequences that target a polypeptide to the desired site in a cell. In some embodiments, the signal sequence targets the chimeric receptor polypeptide to the secretory pathway of the cell and will allow for integration and anchoring of the chimeric receptor polypeptide into the lipid bilayer. Signal sequences including signal sequences of naturally occurring proteins or synthetic, non-naturally occurring signal sequences that are compatible for use in the chimeric receptor polypeptides described herein will be evident to one of skill in the art. In some embodiments, the signal sequence from CD8α. In some embodiments, the signal sequence is from CD28. In other embodiments, the signal sequence is from the murine kappa chain. In yet other embodiments, the signal sequence is from CD16.

G. Examples of ACTR Polypeptides

Exemplary ACTR constructs for use with the methods and compositions described herein may be found, for example, in the instant description and figures or may be found in PCT Patent Publication No.: WO2016040441A1, WO2017/161333, and PCT Application No.: PCT/US2018/015999, each of which is incorporated by reference herein for this purpose. The ACTR polypeptides described herein may comprise a CD16A extracellular domain with binding affinity and specificity for the Fc portion of an IgG molecule, a transmembrane domain, and a CD3ζ cytoplasmic signaling domain. In some embodiments, the ACTR polypeptides may further include one or more co-stimulatory signaling domains, one of which may be a CD28 co-stimulatory signaling domain or a 4-1BB co-stimulatory signaling domain. The ACTR polypeptides are configured such that, when expressed on a host cell, the extracellular ligand-binding domain is located extracellularly for binding to a target molecule and the CD3ζ cytoplasmic signaling domain. The co-stimulatory signaling domain may be located in the cytoplasm for triggering activation and/or effector signaling.

In some embodiments, an ACTR polypeptide as described herein may comprise, from N-terminus to C-terminus, the Fc binding domain such as a CD16A extracellular domain, the transmembrane domain, the optional one or more co-stimulatory domains (e.g., a CD28 co-stimulatory domain, a 4-1BB co-stimulatory signaling domain, an OX40 co-stimulatory signaling domain, a CD27 co-stimulatory signaling domain, or an ICOS co-stimulatory signaling domain), and the CD3ζ cytoplasmic signaling domain.

Alternatively or in addition, the ACTR polypeptides described herein may contain two or more co-stimulatory signaling domains, which may link to each other or be separated by the cytoplasmic signaling domain. The extracellular Fc binder, transmembrane domain, optional co-stimulatory signaling domain(s), and cytoplasmic signaling domain in an ACTR polypeptide may be linked to each other directly, or via a peptide linker. In some embodiments, any of the ACTR polypeptides described herein may comprise a signal sequence at the N-terminus.

Table 4 provides exemplary ACTR polypeptides described herein. These exemplary constructs have, from N-terminus to C-terminus in order, the signal sequence, the Fc binding domain (e.g., an extracellular domain of an Fc receptor), the hinge domain, and the transmembrane, while the positions of the optional co-stimulatory domain and the cytoplasmic signaling domain can be switched.

TABLE 4

Exemplary Components of ACTR polypeptides.

| Exemplary AA Sequence (SEQ ID NO) | Signal Sequence | Extracellular domain of Fc receptor | Hinge domain | Trans-membrane domain | Co-stimulatory domain | Cytoplasmic Signaling domain |
|---|---|---|---|---|---|---|
| 1 | CD8α | CD16A-V158 | CD8α | CD8α | 4-1BB (CD137) | CD3ζ |
| 2 | CD8α | CD16A-V158 | CD8α | 4-1BB (CD137) | 4-1BB (CD137) | CD3ζ |
| 3 | CD8α | CD16A-V158 | CD8α | CD28 | 4-1BB (CD137) | CD3ζ |
| 4 | CD8α | CD16A-V158 | CD8α | CD34 | 4-1BB (CD137) | CD3ζ |
| 5 | CD8α | CD16A-V158 | CD8α | Designed hydrophobic ™ domain | 4-1BB (CD137) | CD3ζ |
| 6 | CD8α | CD32A | CD8α | CD8α | 4-1BB (CD137) | CD3ζ |
| 7 | CD8α | CD16A-V158 | CD8α | CD8α | CD28 | CD3ζ |
| 8 | CD8α | CD16A-V158 | CD8α | CD8α | OX40 (CD134) | CD3ζ |
| 9 | CD8α | CD16A-V158 | CD8α | CD8α | CD28 + 4-1BB | CD3ζ |
| 10 | CD8α | CD16A-V158 | None | CD8α | 4-1BB (CD137) | CD3ζ |
| 11 | CD8α | CD16A-V158 | XTEN | CD8α | 4-1BB (CD137) | CD3ζ |
| 12 | CD8α | CD16A-V158 | CD8α | CD8α | CD28 LL to GG mutant | CD3ζ |
| 13 | CD8α | CD16A-V158 | CD8α | CD8α | CD28 LL to GG mutant + 4-1BB | CD3ζ |
| 14 | CD8α | CD16A-V158 | CD8α | CD4 | 4-1BB (CD137) | CD3ζ |
| 15 | CD8α | CD16A-V158 | CD8α | CD4 | CD28 LL to GG mutant + 4-1BB | CD3ζ |
| 16 | CD8α | CD16A-V158 | CD8α | FcεRIγ | 4-1BB (CD137) | CD3ζ |
| 17 | CD8a | CD16A-V158 | CD8a | Designed hydrophobic ™ domain, predicted dimerization | 4-1BB (CD137) | CD3ζ |
| 18 | CD8α | CD16A-V158 | CD8α | CD8β | 4-1BB (CD137) | CD3ζ |
| 19 | CD8α | CD16A-V158 | CD8α | C16α | 4-1BB (CD137) | CD3ζ |
| 20 | CD8α | CD16A-V158 | CD8α | OX40 (CD134) | 4-1BB (CD137) | CD3ζ |
| 21 | CD8α | CD16A-V158 | CD8α | CD3ζ | 4-1BB (CD137) | CD3ζ |
| 22 | CD8α | CD16A-V158 | CD8α | CD3ε | 4-1BB (CD137) | CD3ζ |
| 23 | CD8α | CD16A-V158 | CD8α | CD3γ | 4-1BB (CD137) | CD3ζ |
| 24 | CD8α | CD16A-V158 | CD8α | CD3δ | 4-1BB (CD137) | CD3ζ |
| 25 | CD8α | CD16A-V158 | CD8α | TCR-α | 4-1BB (CD137) | CD3ζ |
| 26 | CD8α | CD16A-V158 | CD8α | CD32 | 4-1BB (CD137) | CD3ζ |
| 27 | CD8α | CD16A-V158 | CD8α | CD64 | 4-1BB (CD137) | CD3ζ |
| 28 | CD8α | CD16A-V158 | CD8α | VEGFR2 | 4-1BB (CD137) | CD3ζ |
| 29 | CD8α | CD16A-V158 | CD8α | FAS | 4-1BB (CD137) | CD3ζ |
| 30 | CD8α | CD16A-V158 | CD8α | FGFR2B | 4-1BB (CD137) | CD3ζ |
| 31 | CD8α | CD16A-F158 | CD8α | CD8α | 4-1BB (CD137) | CD3ζ |
| 32 | CD8α | CD64A | CD8α | CD8α | 4-1BB (CD137) | CD3ζ |

TABLE 4-continued

Exemplary Components of ACTR polypeptides.

| Exemplary AA Sequence (SEQ ID NO) | Signal Sequence | Extracellular domain of Fc receptor | Hinge domain | Trans-membrane domain | Co-stimulatory domain | Cytoplasmic Signaling domain |
|---|---|---|---|---|---|---|
| 33 | CD8α | CD16A-V158 | IgG1 (hinge-CH2—CH3) | CD8α | 4-1BB (CD137) | CD3ζ |
| 34 | CD8α | CD16A-V158 | IgG1 (hinge-CH3) | CD8α | 4-1BB (CD137) | CD3ζ |
| 35 | CD8α | CD16A-V158 | IgG1 (hinge) | CD8α | 4-1BB (CD137) | CD3ζ |
| 36 | CD8α | CD16A-V158 | CD8-alpha fragment 1 (30 amino acids) | CD8α | 4-1BB (CD137) | CD3ζ |
| 37 | CD8α | CD16A-V158 | CD8-alpha fragment 2 (15 amino acids) | CD8α | 4-1BB (CD137) | CD3ζ |
| 38 | CD8α | CD16A-V158 | (Gly4Ser) × 3 (60 amino acids) | CD8α | 4-1BB (CD137) | CD3ζ |
| 39 | CD8α | CD16A-V158 | (Gly4Ser) × 6 (45 amino acids) | CD8α | 4-1BB (CD137) | CD3ζ |
| 40 | CD8α | CD16A-V158 | (Gly4Ser) × 9 (30 amino acids) | CD8α | 4-1BB (CD137) | CD3ζ |
| 41 | CD8α | CD16A-V158 | (Gly4Ser) × 12 (15 amino acids) | CD8α | 4-1BB (CD137) | CD3ζ |
| 42 | CD8α | CD16A-V158 | XTEN (60 amino acids) | CD8α | 4-1BB (CD137) | CD3ζ |
| 43 | CD8α | CD16A-V158 | XTEN (30 amino acids) | CD8α | 4-1BB (CD137) | CD3ζ |
| 44 | CD8α | CD16A-V158 | XTEN (15 amino acids) | CD8α | 4-1BB (CD137) | CD3ζ |
| 45 | CD28 | CD16A-V158 | CD8α | CD8α | 4-1BB (CD137) | CD3ζ |
| 46 | Murine kappa chain | CD16A-V158 | CD8α | CD8α | 4-1BB (CD137) | CD3ζ |
| 47 | CD16 | CD16A-V158 | CD8α | CD8α | 4-1BB (CD137) | CD3ζ |
| 48 | CD8α | CD16A-V158 | CD8α | CD8α | ICOS | CD3ζ |
| 49 | CD8α | CD16A-V158 | CD8α | CD8α | CD27 | CD3ζ |
| 50 | CD8α | CD16A-V158 | CD8α | CD8α | GITR | CD3ζ |
| 51 | CD8α | CD16A-V158 | CD8α | CD8α | HVEM | CD3ζ |
| 52 | CD8α | CD16A-V158 | CD8α | CD8α | TIM1 | CD3ζ |
| 53 | CD8α | CD16A-V158 | CD8α | CD8α | LFA1 (CD11a) | CD3ζ |
| 54 | CD8α | CD16A-V158 | CD8α | CD8α | CD2 | CD3ζ |
| 55 | CD8α | CD16A-V158 | CD8α | FcεR1γ | 4-1BB (CD137) | FcεR1γ |
| 56 | CD8α | CD16A-V158 | CD8α | CD8α | 4-1BB (CD137) | FcεR1γ |
| 57 | CD8α | CD16A-V158 | CD28 (e.g., 39aa) | CD28 | CD28 | CD3ζ |
| 58 | CD8α | CD16A-V158 | none | CD8 | CD28 | CD3ζ |
| 59 | CD8α | CD16A-V158 | CD8 | CD8 | CD28 + CD27 | CD3ζ |
| 60 | CD8α | CD16A-V158 | CD8 | CD8 | CD28 + OX40 | CD3ζ |
| 61 | CD8α | CD16A-V158 | CD8 | CD8 | 4-1BB + CD28 | CD3ζ |
| 62 | CD8α | CD16A-V158 | CD28 | CD28 | CD28 + 4-1BB | CD3ζ |
| 63 | CD8α | CD16A-V158 | CD28 | CD28 | 4-1BB | CD3ζ |
| 64 | CD8α | CD16A-V158 | CD8 | CD8 | CD27 | CD3ζ |
| 65 | CD8α | CD16A-V158 | CD8 | CD8 | CD28 | CD3ζ |
| 66 | CD8α | CD16A-V158 | CD8 | CD8 | ICOS | CD3ζ |
| 67 | CD8α | CD16A-V158 | CD8 | CD8 | OX40 | CD3ζ |
| 68 | CD8α | CD16A-V158 | CD8 | CD8 | CD28 and ICOS | CD3ζ |

TABLE 4-continued

Exemplary Components of ACTR polypeptides.

| Exemplary AA Sequence (SEQ ID NO) | Signal Sequence | Extracellular domain of Fc receptor | Hinge domain | Trans-membrane domain | Co-stimulatory domain | Cytoplasmic Signaling domain |
|---|---|---|---|---|---|---|
| 69 | CD8α | CD16A-V158 | none | CD8 | 4-1BB | CD3ζ |
| 70 | CD8α | CD16A-V158 | none | CD8 | CD27 | CD3ζ |
| 71 | CD8α | CD16A-V158 | none | CD8 | ICOS | CD3ζ |
| 72 | CD8α | CD16A-V158 | none | CD8 | OX40 | CD3ζ |
| 73 | CD8α | CD16A-V158 | none | CD8 + 4aa | 4-1BB | CD3ζ |
| 74 | CD8α | CD16A-V158 | none | CD8 + 4aa | CD28 | CD3ζ |
| 75 | CD8α | CD16A-V158 | CD8 | CD28 | CD28 | CD3ζ |
| 76 | CD8α | CD16A-V158 | CD28 (26aa) | CD28 | CD28 | CD3ζ |
| 77 | CD8α | CD16A-V158 | CD28 (16aa) | CD28 | CD28 | CD3ζ |
| 78 | CD8α | CD16A-V158 | none | CD28 | CD28 | CD3ζ |
| 79 | CD8α | CD16A-V158 | CD8 | CD8 | 41BB | CD3ζ |
| 80 | CD8α | CD16A-V158 | CD28 (39aa) | CD8 | CD28 | CD3ζ |

Amino acid sequences of the example ACTR polypeptides are provided below (signal sequence italicized).

SEQ ID NO: 1:
*MALPVTALLLPLALLLHAARP*GMRTEDLPKAVVFLEPQWYRVLEKDSVTLKCQGAYSPEDNSTQWFHNESLISSQ

ASSYFIDAATVDDSGEYRCQTNLSTLSDPVQLEVHIGWLLLQAPRWVFKEEDPIHLRCHSWKNTALHKVTYLQNG

KGRKYFHHNSDFYIPKATLKDSGSYFCRGLVGSKNVSSETVNITITQGLAVSTISSFFPPGYQTTTPAPRPPTPA

PTIASQPLSLRPEACRPAAGGAVHTRGLDFACDIYIWAPLAGTCGVLLLSLVITLYCKRGRKKLLYIFKQPFMRP

VQTTQEEDGCSCRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR

SEQ ID NO: 2:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIISFFLALTSTALLFLLFFLTLRFSVVKRG

KRGRKKLLYIFKQPFMRPVQTTQEEDGCSCRFPEEEEGGCELRVKFSRSADAPAYQQGQNQLYNELNLGRRE

EYDVLDKRRGRDPEMGGKPRRKNPQEGLYNELQKDKMAEAYSEIGMKGERRRGKGHDGLYQGLSTATKDTYD

ALHMQALPPR

SEQ ID NO: 3:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDFWVLVVVGGVLACYSLLVTVAFIIFWVRSK

KRGRKKLLYIFKQPFMRPVQTTQEEDGCSCRFPEEEEGGCELRVKFSRSADAPAYQQGQNQLYNELNLGRRE

EYDVLDKRRGRDPEMGGKPRRKNPQEGLYNELQKDKMAEAYSEIGMKGERRRGKGHDGLYQGLSTATKDTYD

ALHMQALPPR

SEQ ID NO: 4:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDLIALVTSGALLAVLGITGYFLMNRKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 5:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDLLAALLALLAALLALLAALLARSKKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 6:
MALPVTALLLPLALLLHAARPQAAAPPKAVLKLEPPWINVLQEDSVTLTCQGARSPESDSIQWFHNGNLIPT

HTQPSYRFKANNNDSGEYTCQTGQTSLSDPVHLTVLSEWLVLQTPHLEFQEGETIMLRCHSWKDKPLVKVTF

FQNGKSQKFSHLDPTFSIPQANHSHSGDYHCTGNIGYTLFSSKPVTITVQVPSMGSSSPMGTTTPAPRPPTP

APTIASQPLSLRPEACRPAAGGAVHTRGLDFACDIYIWAPLAGTCGVLLLSLVITLYCKRGRKKLLYIFKQP

FMRPVQTTQEEDGCSCRFPEEEEGGCELRVKFSRSADAPAYQQGQNQLYNELNLGRREEYDVLDKRRGRDPE

MGGKPRRKNPQEGLYNELQKDKMAEAYSEIGMKGERRRGKGHDGLYQGLSTATKDTYDALHMQALPPR

SEQ ID NO: 7:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCRSKRSR

LLHSDYMNMTPRRPGPTRKHYQPYAPPRDFAAYRSRVKFSRSADAPAYQQGQNQLYNELNLGRREEYDVLDK

RRGRDPEMGGKPRRKNPQEGLYNELQKDKMAEAYSEIGMKGERRRGKGHDGLYQGLSTATKDTYDALHMQAL

PPR

SEQ ID NO: 8:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCALYLLR

RDQRLPPDAHKPPGGGSFRTPIQEEQADAHSTLAKIRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 9:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCRSKRSR

LLHSDYMNMTPRRPGPTRKHYQPYAPPRDFAAYRSKRGRKKLLYIFKQPFMRPVQTTQEEDGCSCRFPEEEE

GGCELRVKFSRSADAPAYQQGQNQLYNELNLGRREEYDVLDKRRGRDPEMGGKPRRKNPQEGLYNELQKDKM

AEAYSEIGMKGERRRGKGHDGLYQGLSTATKDTYDALHMQALPPR

SEQ ID NO: 10:
MALPVTALLLPLALLLHAARPGMRTEDLPKAVVFLEPQWYRVLEKDSVTLKCQGAYSPEDNSTQWFHNESLI
SSYQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQIYI
WAPLAGTCGVLLLSLVITLYCKRGRKKLLYIFKQPFMRPVQTTQEEDGCSCRFPEEEEGGCELRVKFSRSAD
APAYQQGQNQLYNELNLGRREEYDVLDKRRGRDPEMGGKPRRKNPQEGLYNELQKDKMAEAYSEIGMKGERR
RGKGHDGLYQGLSTATKDTYDALHMQALPPR

SEQ ID NO: 11:
MALPVTALLLPLALLLHAARPGMRTEDLPKAVVFLEPQWYRVLEKDSVTLKCQGAYSPEDNSTQWFHNESLI
SSYQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQGGS
PAGSPTSTEEGTSESATPESGPGTSTEPSEGSAPGSPAGSPTIYIWAPLAGTCGVLLLSLVITLYCKRGRKK
LLYIFKQPFMRPVQTTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQA
LPPR

SEQ ID NO: 12:
MALPVTALLLPLALLLHAARPGMRTEDLPKAVVFLEPQWYRVLEKDSVTLKCQGAYSPEDNSTQWFHNESLI
SSYQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCRSKRSR
GGHSDYMNMTPRRPGPTRKHYQPYAPPRDFAAYRSRVKFSRSADAPAYQQGQNQLYNELNLGRREEYDVLDK
RRGRDPEMGGKPRRKNPQEGLYNELQKDKMAEAYSEIGMKGERRRGKGHDGLYQGLSTATKDTYDALHMQAL
PPR

SEQ ID NO: 13:
MALPVTALLLPLALLLHAARPGMRTEDLPKAVVFLEPQWYRVLEKDSVTLKCQGAYSPEDNSTQWFHNESLI
SSYQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCRSKRSR
GGHSDYMNMTPRRPGPTRKHYQPYAPPRDFAAYRSKRGRKKLLYIFKQPFMRPVQTTQEEDGCSCRFPEEEE
GGCELRVKFSRSADAPAYQQGQNQLYNELNLGRREEYDVLDKRRGRDPEMGGKPRRKNPQEGLYNELQKDKM
AEAYSEIGMKGERRRGKGHDGLYQGLSTATKDTYDALHMQALPPR

SEQ ID NO: 14:
MALPVTALLLPLALLLHAARPGMRTEDLPKAVVFLEPQWYRVLEKDSVTLKCQGAYSPEDNSTQWFHNESLI
SSYQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDMALIVLGGVAGLLLFIGLGIFFCVRKRGRK
KLLYIFKQPFMRPVQTTQEEDGCSCRFPEEEEGGCELRVKFSRSADAPAYQQGQNQLYNELNLGRREEYDVL
DKRRGRDPEMGGKPRRKNPQEGLYNELQKDKMAEAYSEIGMKGERRRGKGHDGLYQGLSTATKDTYDALHMQ
ALPPR

SEQ ID NO: 15:
MALPVTALLLPLALLLHAARPGMRTEDLPKAVVFLEPQWYRVLEKDSVTLKCQGAYSPEDNSTQWFHNESLI
SSYQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT

-continued

PAPRPPTPAPTIASQPLSLRPEACRPAAGGAVHTRGLDFACDMALIVLGGVAGLLLFIGLGIFFCVRRSKRS

RGGHSDYMNMTPRRPGPTRKHYQPYAPPRDFAAYRSRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 16:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDLCYILDAILFLYGIVLTLLYCRLKKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 17:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDLLLILLGVLAGVLATLAALLARSKKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 18:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDITLGLLVAGVLVLLVSLGVAIHLCKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 19:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDVSFCLVMVLLFAVDTGLYFSVKTNKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 20:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDVAAILGLGLVLGLLGPLAILLALYKRGRKK

-continued

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 21:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDLCYLLDGIIFIYGVILTALFLRVKKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 22:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDVMSVATIVIVDICITGGLLLLVYYWSKNRK

RGRKKLLYIFKQPFMRPVQTTQEEDGCSCRFPEEEEGGCELRVKFSRSADAPAYQQGQNQLYNELNLGRREE

YDVLDKRRGRDPEMGGKPRRKNPQEGLYNELQKDKMAEAYSEIGMKGERRRGKGHDGLYQGLSTATKDTYDA

LHMQALPPR

SEQ ID NO: 23:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDGFLFAEIVSIFVLAVGVYFIAGQDKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 24:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDGIIVTDVIATLLLALGVFCFAGHETKRGRK

KLLYIFKQPFMRPVQTTQEEDGCSCRFPEEEEGGCELRVKFSRSADAPAYQQGQNQLYNELNLGRREEYDVL

DKRRGRDPEMGGKPRRKNPQEGLYNELQKDKMAEAYSEIGMKGERRRGKGHDGLYQGLSTATKDTYDALHMQ

ALPPR

SEQ ID NO: 25:
MALPVTALLLPLALLLHAARPGMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDVIGFRILLLKVAGFNLLMTLRLWKRGRKKL

LYIFKQPFMRPVQTTQEEDGCSCRFPEEEEGGCELRVKFSRSADAPAYQQGQNQLYNELNLGRREEYDVLDK

RRGRDPEMGGKPRRKNPQEGLYNELQKDKMAEAYSEIGMKGERRRGKGHDGLYQGLSTATKDTYDALHMQAL

PPR

-continued

SEQ ID NO: 26:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIIVAVVIATAVAAIVAAVVALIYCRKKRGR
KKLLYIFKQPFMRPVQTTQEEDGCSCRFPEEEEGGCELRVKFSRSADAPAYQQGQNQLYNELNLGRREEYDV
LDKRRGRDPEMGGKPRRKNPQEGLYNELQKDKMAEAYSEIGMKGERRRGKGHDGLYQGLSTATKDTYDALHM
QALPPR

SEQ ID NO: 27:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDVLFYLAVGIMFLVNTVLWVTIRKEKRGRKK
LLYIFKQPFMRPVQTTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQA
LPPR

SEQ ID NO: 28:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIIILVGTAVIAMFFWLLLVIILRTKRGRKK
LLYIFKQPFMRPVQTTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQA
LPPR

SEQ ID NO: 29:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDLGWLCLLLLPIPLIVWVKRKKRGRKKLLYI
FKQPFMRPVQTTQEEDGCSCRFPEEEEGGCELRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTATKDTYDALHMQALPPR

SEQ ID NO: 30:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIAIYCIGVFLIACMVVTVILCRMKKRGRKK
LLYIFKQPFMRPVQTTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQA
LPPR

SEQ ID NO: 31:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLFGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCKRGRKK

-continued

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 32:
*MALPVTALLLPLALLLHAARP*QVDTTKAVITLQPPWVSVFQEETVTLHCEVLHLPGSSSTQWFLNGTATQTS

TPSYRITSASVNDSGEYRCQRGLSGRSDPIQLEIHRGWLLLQVSSRVFTEGEPLALRCHAWKDKLVYNVLYY

RNGKAFKFFHWNSNLTILKTNISHNGTYHCSGMGKHRYTSAGISVTVKELFPAPVLNASVTSPLLEGNLVTL

SCETKLLLQRPGLQLYFSFYMGSKTLRGRNTSSEYQILTARREDSGLYWCEAATEDGNVLKRSPELELQVLG

LQLPTPVWFHIYIWAPLAGTCGVLLLSLVITLYCKRGRKKLLYIFKQPFMRPVQTTQEEDGCSCRFPEEEEG

GCELRVKFSRSADAPAYQQGQNQLYNELNLGRREEYDVLDKRRGRDPEMGGKPRRKNPQEGLYNELQKDKMA

EAYSEIGMKGERRRGKGHDGLYQGLSTATKDTYDALHMQALPPR

SEQ ID NO: 33:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQEPK

SCDKTHTCPPCPAPELLGGPSVFLFPPKPKDTLMISRTPEVTCVVVDVSHEDPEVKFNWYVDGVEVHNAKTK

PREEQYNSTYRVVSVLTVLHQDWLNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLTVDKSRWQQGNVFSCSVMHEALHN

HYTQKSISISPGKIYIWAPLAGTCGVLLLSLVITLYCKRGRKKLLYIFKQPFMRPVQTTQEEDGCSCRFPEE

EEGGCELRVKFSRSADAPAYQQGQNQLYNELNLGRREEYDVLDKRRGRDPEMGGKPRRKNPQEGLYNELQKD

KMAEAYSEIGMKGERRRGKGHDGLYQGLSTATKDTYDALHMQALPPR

SEQ ID NO: 34:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQEPK

SCDKTHTCPGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKIYIWAPLAGTCGVLLLSLVITLYCKRGR

KKLLYIFKQPFMRPVQTTQEEDGCSCRFPEEEEGGCELRVKFSRSADAPAYQQGQNQLYNELNLGRREEYDV

LDKRRGRDPEMGGKPRRKNPQEGLYNELQKDKMAEAYSEIGMKGERRRGKGHDGLYQGLSTATKDTYDALHM

QALPPR

SEQ ID NO: 35:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQEPK

SCDKTHTCPIYIWAPLAGTCGVLLLSLVITLYCKRGRKKLLYIFKQPFMRPVQTTQEEDGCSCRFPEEEEGG

CELRVKFSRSADAPAYQQGQNQLYNELNLGRREEYDVLDKRRGRDPEMGGKPRRKNPQEGLYNELQKDKMAE

AYSEIGMKGERRRGKGHDGLYQGLSTATKDTYDALHMQALPPR

SEQ ID NO: 36:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

-continued

PAPRPPTPAPTIASQPLSLRPEAFACDIYIWAPLAGTCGVLLLSLVITLYCKRGRKKLLYIFKQPFMRPVQT

TQEEDGCSCRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR

SEQ ID NO: 37:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPFACDIYIWAPLAGTCGVLLLSLVITLYCKRGRKKLLYIFKQPFMRPVQTTQEEDGCSCRFPEEE

EGGCELRVKFSRSADAPAYQQGQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR

SEQ ID NO: 38:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQGGG

GSGGGGSGGGGSIYIWAPLAGTCGVLLLSLVITLYCKRGRKKLLYIFKQPFMRPVQTTQEEDGCSCRFPEEE

EGGCELRVKFSRSADAPAYQQGQNQLYNELNLGRREEYDVLDKRRGRDPEMGGKPRRKNPQEGLYNELQKDK

MAEAYSEIGMKGERRRGKGHDGLYQGLSTATKDTYDALHMQALPPR

SEQ ID NO: 39:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQGGG

GSGGGGSGGGGSGGGGSGGGGSGGGGSIYIWAPLAGTCGVLLLSLVITLYCKRGRKKLLYIFKQPFMRPVQT

TQEEDGCSCRFPEEEEGGCELRVKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTYDALHMQALPPR

SEQ ID NO: 40:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQGGG

GSGGGGSGGGGSGGGGSGGGGSGGGGSGGGGSGGGGSGGGGSIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 41:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQGGG

GSGGGGSGGGGSGGGGSGGGGSGGGGSGGGGSGGGGSGGGGSGGGGSGGGGSIYIWAPLAGTCGVLL

LSLVITLYCKRGRKKLLYIFKQPFMRPVQTTQEEDGCSCRFPEEEEGGCELRVKFSRSADAPAYQQGQNQLY

NELNLGRREEYDVLDKRRGRDPEMGGKPRRKNPQEGLYNELQKDKMAEAYSEIGMKGERRRGKGHDGLYQGL

STATKDTYDALHMQALPPR

SEQ ID NO: 42:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQGGS

-continued

PAGSPTSTEEGTSESATPESGPGTSTEPSEGSAPGSPAGSPTSTEEGTSTEPSEGSAIYIWAPLAGTCGVLL
LSLVITLYCKRGRKKLLYIFKQPFMRPVQTTQEEDGCSCRFPEEEEGGCELRVKFSRSADAPAYQQGQNQLY
NELNLGRREEYDVLDKRRGRDPEMGGKPRRKNPQEGLYNELQKDKMAEAYSEIGMKGERRRGKGHDGLYQGL
STATKDTYDALHMQALPPR

SEQ ID NO: 43:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQGGS
PAGSPTSTEEGTSESATPESGPGTSTEIYIWAPLAGTCGVLLLSLVITLYCKRGRKKLLYIFKQPFMRPVQT
TQEEDGCSCRFPEEEEGGCELRVKFSRSADAPAYQQGQNQLYNELNLGRREEYDVLDKRRGRDPEMGGKPRR
KNPQEGLYNELQKDKMAEAYSEIGMKGERRRGKGHDGLYQGLSTATKDTYDALHMQALPPR

SEQ ID NO: 44:
MALPVTALLLPLALLLHAARPGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQGGS
PAGSPTSTEEGTIYIWAPLAGTCGVLLLSLVITLYCKRGRKKLLYIFKQPFMRPVQTTQEEDGCSCRFPEEE
EGGCELRVKFSRSADAPAYQQGQNQLYNELNLGRREEYDVLDKRRGRDPEMGGKPRRKNPQEGLYNELQKDK
MAEAYSEIGMKGERRRGKGHDGLYQGLSTATKDTYDALHMQALPPR

SEQ ID NO: 45:
MLRLLLALNLFPSIQVTGGMRTEDLPKAVVFLEPQWYRVLEKDSVTLKCQGAYSPEDNSTQWFHNESLISSQ
ASSYFIDAATVDDSGEYRCQTNLSTLSDPVQLEVHIGWLLLQAPRWVFKEEDPIHLRCHSWKNTALHKVTYL
QNGKGRKYFHHNSDFYIPKATLKDSGSYFCRGLVGSKNVSSETVNITITQGLAVSTISSFFPPGYQTTTPAP
RPPTPAPTIASQPLSLRPEACRPAAGGAVHTRGLDFACDIYIWAPLAGTCGVLLLSLVITLYCKRGRKKLLY
IFKQPFMRPVQTTQEEDGCSCRFPEEEEGGCELRVKFSRSADAPAYQQGQNQLYNELNLGRREEYDVLDKRR
GRDPEMGGKPRRKNPQEGLYNELQKDKMAEAYSEIGMKGERRRGKGHDGLYQGLSTATKDTYDALHMQALPP
R

SEQ ID NO: 46:
METDTLLLWVLLLWVPGSTGDGMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCKRGRKK
LLYIFKQPFMRPVQTTQEEDGCSCRFPEEEEGGCELRVKFSRSADAPAYQQGQNQLYNELNLGRREEYDVLD
KRRGRDPEMGGKPRRKNPQEGLYNELQKDKMAEAYSEIGMKGERRRGKGHDGLYQGLSTATKDTYDALHMQA
LPPR

SEQ ID NO: 47:
MWQLLLPTALLLLVSAGMRTEDLPKAVVFLEPQWYRVLEKDSVTLKCQGAYSPEDNSTQWFHNESLISSQAS
SYFIDAATVDDSGEYRCQTNLSTLSDPVQLEVHIGWLLLQAPRWVFKEEDPIHLRCHSWKNTALHKVTYLQN
GKGRKYFHHNSDFYIPKATLKDSGSYFCRGLVGSKNVSSETVNITITQGLAVSTISSFFPPGYQTTTPAPRP
PTPAPTIASQPLSLRPEACRPAAGGAVHTRGLDFACDIYIWAPLAGTCGVLLLSLVITLYCKRGRKKLLYIF
KQPFMRPVQTTQEEDGCSCRFPEEEEGGCELRVKFSRSADAPAYQQGQNQLYNELNLGRREEYDVLDKRRGR
DPEMGGKPRRKNPQEGLYNELQKDKMAEAYSEIGMKGERRRGKGHDGLYQGLSTATKDTYDALHMQALPPR

SEQ ID NO: 48:
*MALPVTALLLPLALLLHAARP*GMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCCWLTKK
KYSSSVHDPNGEYMFMRAVNTAKKSRLTDVTLRVKFSRSADAPAYQQGQNQLYNELNLGRREEYDVLDKRRG
RDPEMGGKPRRKNPQEGLYNELQKDKMAEAYSEIGMKGERRRGKGHDGLYQGLSTATKDTYDALHMQALPPR

SEQ ID NO: 49:
*MALPVTALLLPLALLLHAARP*GMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCQRRKYR
SNKGESPVEPAEPCRYSCPREEEGSTIPIQEDYRKPEPACSPRVKFSRSADAPAYQQGQNQLYNELNLGRRE
EYDVLDKRRGRDPEMGGKPRRKNPQEGLYNELQKDKMAEAYSEIGMKGERRRGKGHDGLYQGLSTATKDTYD
ALHMQALPPR

SEQ ID NO: 50:
*MALPVTALLLPLALLLHAARP*GMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCQLGLHI
WQLRSQCMWPRETQLLLEVPPSTEDARSCQFPEEERGERSAEEKGRLGDLWVRVKFSRSADAPAYQQGQNQL
YNELNLGRREEYDVLDKRRGRDPEMGGKPRRKNPQEGLYNELQKDKMAEAYSEIGMKGERRRGKGHDGLYQG
LSTATKDTYDALHMQALPPR

SEQ ID NO: 51:
*MALPVTALLLPLALLLHAARP*GMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCCVKRRK
PRGDVVKVIVSVQRKRQEAEGEATVIEALQAPPDVTTVAVEETIPSFTGRSPNHRVKFSRSADAPAYQQGQN
QLYNELNLGRREEYDVLDKRRGRDPEMGGKPRRKNPQEGLYNELQKDKMAEAYSEIGMKGERRRGKGHDGLY
QGLSTATKDTYDALHMQALPPR

SEQ ID NO: 52:
*MALPVTALLLPLALLLHAARP*GMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCKKYFFK
KEVQQLSVSFSSLQIKALQNAVEKEVQAEDNIYIENSLYATDRVKFSRSADAPAYQQGQNQLYNELNLGRRE
EYDVLDKRRGRDPEMGGKPRRKNPQEGLYNELQKDKMAEAYSEIGMKGERRRGKGHDGLYQGLSTATKDTYD
ALHMQALPPR

SEQ ID NO: 53:
*MALPVTALLLPLALLLHAARP*GMRTEDLPKAVVFLEPQWYRVLEKDSVTLKCQGAYSPEDNSTQWFHNESLI
SSQASSYFIDAATVDDSGEYRCQTNLSTLSDPVQLEVHIGWLLLQAPRWVFKEEDPIHLRCHSWKNTALHKV
TYLQNGKGRKYFHHNSDFYIPKATLKDSGSYFCRGLVGSKNVSSETVNITITQGLAVSTISSFFPPGYQTTT
PAPRPPTPAPTIASQPLSLRPEACRPAAGGAVHTRGLDFACDIYIWAPLAGTCGVLLLSLVITLYCYKVGFF

KRNLKEKMEAGRGVPNGIPAEDSEQLASGQEAGDPGCLKPLHEKDSESGGGKDRVKFSRSADAPAYQQGQNQ

LYNELNLGRREEYDVLDKRRGRDPEMGGKPRRKNPQEGLYNELQKDKMAEAYSEIGMKGERRRGKGHDGLYQ

GLSTATKDTYDALHMQALPPR

SEQ ID NO: 54:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCKRKKQR

SRRNDEELETRAHRVATEERGRKPHQIPASTPQNPATSQHPPPPPGHRSQAPSHRPPPPGHRVQHQPQKRPP

APSGTQVHQQKGPPLPRPRVQPKPPHGAAENSLSPSSNRVKFSRSADAPAYQQGQNQLYNELNLGRREEYDV

LDKRRGRDPEMGGKPRRKNPQEGLYNELQKDKMAEAYSEIGMKGERRRGKGHDGLYQGLSTATKDTYDALHM

QALPPR

SEQ ID NO: 55:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDPQLCYILDAILFLYGIVLTLLYCRLKIQVR

KAAITSYEKSDGVYTGLSTRNQETYETLKHEKPPQKRGRKKLLYIFKQPFMRPVQTTQEEDGCSCRFPEEEE

GGCEL

SEQ ID NO: 56:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCKRGRKK

LLYIFKQPFMRPVQTTQEEDGCSCRFPEEEEGGCELRLKIQVRKAAITSYEKSDGVYTGLSTRNQETYETLK

HEKPPQ

SEQ ID NO: 57:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIEV

MYPPPYLDNEKSNGTIIHVKGKHLCPSPLFPGPSKPFWVLVVVGGVLACYSLLVTVAFIIFWVRSKRSLLH

SDYMNMTPRRPGPTRKHYQPYAPPRDFAAYRSRVKFSRSADAPAYQQGQNQLYNELNLGRREEYDVLDKRRG

RDPEMGGKPRRKNPQEGLYNELQKDKMAEAYSEIGMKGERRRGKGHDGLYQGLSTATKDTYDALHMQALPPR

SEQ ID NO: 58:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIYI

WAPLAGTCGVLLLSLVITLYCRSKRSRLLHSDYMNMTPRRPGPTRKHYQPYAPPRDFAAYRSRVKFSRSADA

PAYQQGQNQLYNELNLGRREEYDVLDKRRGRDPEMGGKPRRKNPQEGLYNELQKDKMAEAYSEIGMKGERRR

GKGHDGLYQGLSTATKDTYDALHMQALPPR

SEQ ID NO: 59:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

-continued

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCRSKRSR

LLHSDYMNMTPRRPGPTRKHYQPYAPPRDFAAYRSQRRKYRSNKGESPVEPAEPCHYSCPREEEGSTIPIQE

DYRKPEPACSPRVKFSRSADAPAYQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALPPR

SEQ ID NO: 60:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCRSKRSR

LLHSDYMNMTPRRPGPTRKHYQPYAPPRDFAAYRSRRDQRLPPDAHKPPGGGSFRTPIQEEQADAHSTLAKI

RVKFSRSADAPAYQQGQNQLYNELNLGRREEYDVLDKRRGRDPEMGGKPRRKNPQEGLYNELQKDKMAEAYS

EIGMKGERRRGKGHDGLYQGLSTATKDTYDALHMQALPPR

SEQ ID NO: 61:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCKRGRKK

LLYIFKQPFMRPVQTTQEEDGCSCRFPEEEEGGCELRSKRSRLLHSDYMNMTPRRPGPTRKHYQPYAPPRDF

AAYRSRVKFSRSADAPAYQQGQNQLYNELNLGRREEYDVLDKRRGRDPEMGGKPRRKNPQEGLYNELQKDKM

AEAYSEIGMKGERRRGKGHDGLYQGLSTATKDTYDALHMQALPPR

SEQ ID NO: 62:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIEV

MYPPPYLDNEKSNGTIIHVKGKHLCPSPLFPGPSKPFWVLVVVGGVLACYSLLVTVAFIIFWVRSKRSRLLH

SDYMNMTPRRPGPTRKHYQPYAPPRDFAAYRSKRGRKKLLYIFKQPFMRPVQTTQEEDGCSCRFPEEEEGGC

ELRVKFSRSADAPAYQQGQNQLYNELNLGRREEYDVLDKRRGRDPEMGGKPRRKNPQEGLYNELQKDKMAEA

YSEIGMKGERRRGKGHDGLYQGLSTATKDTYDALHMQALPPR

SEQ ID NO: 63:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIEV

MYPPPYLDNEKSNGTIIHVKGKHLCPSPLFPGPSKPFWVLVVVGGVLACYSLLVTVAFIIFWVKRGRKKLLY

IFKQPFMRPVQTTQEEDGCSCRFPEEEEGGCELRVKFSRSADAPAYQQGQNQLYNELNLGRREEYDVLDKRR

GRDPEMGGKPRRKNPQEGLYNELQKDKMAEAYSEIGMKGERRRGKGHDGLYQGLSTATKDTYDALHMQALPP

R

SEQ ID NO: 64:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCQRRKYR

SNKGESPVEPAEPCHYSCPREEEGSTIPIQEDYRKPEPACSPRVKFSRSADAPAYQQGQNQLYNELNLGRRE

-continued

EYDVLDKRRGRDPEMGGKPRRKNPQEGLYNELQKDKMAEAYSEIGMKGERRRGKGHDGLYQGLSTATKDTYD

ALHMQALPPR

SEQ ID NO: 65:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCRSKRSR

LLHSDYMNMTPRRPGPTRKHYQPYAPPRDFAAYRSRVKFSRSADAPAYQQGQNQLYNELNLGRREEYDVLDK

RRGRDPEMGGKPRRKNPQEGLYNELQKDKMAEAYSEIGMKGERRRGKGHDGLYQGLSTATKDTYDALHMQAL

PPR

SEQ ID NO: 66:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCKKKYSS

SVHDPNGEYMFMRAVNTAKKSRLTDVTLRVKFSRSADAPAYQQGQNQLYNELNLGRREEYDVLDKRRGRDPE

MGGKPRRKNPQEGLYNELQKDKMAEAYSEIGMKGERRRGKGHDGLYQGLSTATKDTYDALHMQALPPR

SEQ ID NO: 67:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCRRDQRL

PPDAHKPPGGGSFRTPIQEEQADAHSTLAKIRVKFSRSADAPAYQQGQNQLYNELNLGRREEYDVLDKRRGR

DPEMGGKPRRKNPQEGLYNELQKDKMAEAYSEIGMKGERRRGKGHDGLYQGLSTATKDTYDALHMQALPPR

SEQ ID NO: 68:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCRSKRSR

LLHSDYMNMTPRRPGPTRKHYQPYAPPRDFAAYRSKKKYSSSVHDPNGEYMFMRAVNTAKKSRLTDVTLRVK

FSRSADAPAYQQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR

SEQ ID NO: 69:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIYI

WAPLAGTCGVLLLSLVITLYCKRGRKKLLYIFKQPFMRPVQTTQEEDGCSCRFPEEEEGGCELRVKFSRSAD

APAYQQGQNQLYNELNLGRREEYDVLDKRRGRDPEMGGKPRRKNPQEGLYNELQKDKMAEAYSEIGMKGERR

RGKGHDGLYQGLSTATKDTYDALHMQALPPR

SEQ ID NO: 70:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIYI

WAPLAGTCGVLLLSLVITLYCQRRKYRSNKGESPVEPAEPCHYSCPREEEGSTIPIQEDYRKPEPACSPRVK

FSRSADAPAYQQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR

SEQ ID NO: 71:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIYI

WAPLAGTCGVLLLSLVITLYCKKKYSSSVHDPNGEYMFMRAVNTAKKSRLTDVTLRVKFSRSADAPAYQQGQ

NQLYNELNLGRREEYDVLDKRRGRDPEMGGKPRRKNPQEGLYNELQKDKMAEAYSEIGMKGERRRGKGHDGL

YQGLSTATKDTYDALHMQALPPR

SEQ ID NO: 72:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQIYI

WAPLAGTCGVLLLSLVITLYCRRDQRLPPDAHKPPGGGSFRTPIQEEQADAHSTLAKIRVKFSRSADAPAYQ

QGQNQLYNELNLGRREEYDVLDKRRGRDPEMGGKPRRKNPQEGLYNELQKDKMAEAYSEIGMKGERRRGKGH

DGLYQGLSTATKDTYDALHMQALPPR

SEQ ID NO: 73:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQFAC

DIYIWAPLAGTCGVLLLSLVITLYCKRGRKKLLYIFKQPFMRPVQTTQEEDGCSCRFPEEEEGGCELRVKFS

RSADAPAYQQGQNQLYNELNLGRREEYDVLDKRRGRDPEMGGKPRRKNPQEGLYNELQKDKMAEAYSEIGMK

GERRRGKGHDGLYQGLSTATKDTYDALHMQALPPR

SEQ ID NO: 74:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQFAC

DIYIWAPLAGTCGVLLLSLVITLYCRSKRSRLLHSDYMNMTPRRPGPTRKHYQPYAPPRDFAAYRSRVKFSR

SADAPAYQQGQNQLYNELNLGRREEYDVLDKRRGRDPEMGGKPRRKNPQEGLYNELQKDKMAEAYSEIGMKG

ERRRGKGHDGLYQGLSTATKDTYDALHMQALPPR

SEQ ID NO: 75:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDFWVLVVVGGVLACYSLLVTVAFIIFWVRSK

RSRLLHSDYMNMTPRRPGPTRKHYQPYAPPRDFAAYRSRVKFSRSADAPAYQQGQNQLYNELNLGRREEYDV

LDKRRGRDPEMGGKPRRKNPQEGLYNELQKDKMAEAYSEIGMKGERRRGKGHDGLYQGLSTATKDTYDALHM

QALPPR

SEQ ID NO: 76:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQKSN

GTIIHVKGKHLCPSPLFPGPSKPFWVLVVVGGVLACYSLLVTVAFIIFWVRSKRSRLLHSDYMNMTPRRPGP

TRKHYQPYAPPRDFAAYRSRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR

SEQ ID NO: 77:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQGKH

LCPSPLFPGPSKPFWVLVVVGGVLACYSLLVTVAFIIFWVRSKRSRLLHSDYMNMTPRRPGPTRKHYQPYAP

PRDFAAYRSRVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

SEQ ID NO: 78:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQFWV

LVVVGGVLACYSLLVTVAFIIFWVRSKRSRLLHSDYMNMTPRRPGPTRKHYQPYAPPRDFAAYRSRVKFSRS

ADAPAYQQGQNQLYNELNLGRREEYDVLDKRRGRDPEMGGKPRRKNPQEGLYNELQKDKMAEAYSEIGMKGE

RRRGKGHDGLYQGLSTATKDTYDALHMQALPPR

SEQ ID NO: 79:
*MALPVTALLLPLALLLHAARP*GMRTEDLPKAVVFLEPQWYRVLEKDSVTLKCQGAYSPEDNSTQWFHNESLI

SSQASSYFIDAATVDDSGEYRCQTNLSTLSDPVQLEVHIGWLLLQAPRWVFKEEDPIHLRCHSWKNTALHKV

TYLQNGKGRKYFHHNSDFYIPKATLKDSGSYFCRGLVGSKNVSSETVNITITQGLAVSTISSFFPPGYQTTT

PAPRPPTPAPTIASQPLSLRPEACRPAAGGAVHTRGLDFACDIYIWAPLAGTCGVLLLSLVITLYCKRGRKK

LLYIFKQPFMRPVQTTQEEDGCSCRFPEEEEGGCELRVKFSRSADAPAYQQGQNQLYNELNLGRREEYDVLD

KRRGRDPEMGGKPRRKNPQEGLYNELQKDKMAEAYSEIGMKGERRRGKGHDGLYQGLSTATKDTYDALHMQA

LPPR

SEQ ID NO: 80:
*MALPVTALLLPLALLLHAARP*GMRTEDLPKAVVFLEPQWYRVLEKDSVTLKCQGAYSPEDNSTQWFHNESLISSQ

ASSYFIDAATVDDSGEYRCQTNLSTLSDPVQLEVHIGWLLLQAPRWVFKEEDPIHLRCHSWKNTALHKVTYLQNG

KGRKYFHHNSDFYIPKATLKDSGSYFCRGLVGSKNVSSETVNITITQGLAVSTISSFFPPGYQIEVMYPPPYLDN

EKSNGTIIHVKGKHLCPSPLFPGPSKPIYIWAPLAGTCGVLLLSLVITLYCRSKRSRLLHSDYMNMTPRRPGPTR

KHYQPYAPPRDFAAYRSRVKFSRSADAPAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQALPPR

H. Examples of CAR Polypeptides

Exemplary CAR polypeptides for use with the methods and compositions described herein may be found, for example, in the instant description and figures or as those known in the art. The CAR polypeptides described herein may comprise an extracellular domain comprising a single-chain antibody fragment (scFv) with binding affinity and specificity for an antigen of interest (e.g., those listed in Table 3 above), a transmembrane domain, and a CD3ζ cytoplasmic signaling domain. In some embodiments, the CAR polypeptides may further include one or more co-stimulatory signaling domains, one of which may be a CD28 co-stimulatory signaling domain or a 4-1BB co-stimulatory signaling domain. The CAR polypeptides are configured such that, when expressed on a host cell, the extracellular antigen-binding domain is located extracellularly for binding to a target molecule and the CD3ζ cytoplasmic signaling domain. The co-stimulatory signaling domain may be located in the cytoplasm for triggering activation and/or effector signaling.

In some embodiments, a CAR polypeptide as described herein may comprise, from N-terminus to C-terminus, the extracellular antigen binding domain, the transmembrane domain, the optional one or more co-stimulatory domains (e.g., a CD28 co-stimulatory domain, a 4-1BB co-stimulatory signaling domain, an OX40 co-stimulatory signaling domain, a CD27 co-stimulatory signaling domain, or an ICOS co-stimulatory signaling domain), and the CD3ζ cytoplasmic signaling domain.

Alternatively or in addition, the CAR polypeptides described herein may contain two or more co-stimulatory signaling domains, which may link to each other or be separated by the cytoplasmic signaling domain. The extracellular antigen binding domain, transmembrane domain, optional co-stimulatory signaling domain(s), and cytoplasmic signaling domain in a CAR polypeptide may be linked to each other directly, or via a peptide linker. In some embodiments, any of the CAR polypeptides described herein may comprise a signal sequence at the N-terminus.

Table 5 provides exemplary CAR polypeptides described herein. These exemplary constructs have, from N-terminus to C-terminus in order, the signal sequence, the antigen binding domain (e.g., a scFv fragment targeting an antigen such as a tumor antigen or a pathogenic antigen), the hinge domain, and the transmembrane, while the positions of the optional co-stimulatory domain and the cytoplasmic signaling domain can be switched.

TABLE 5

Exemplary Components of CAR polypeptides.

| Signal Sequence | Extracellular domain (antigen binding) | Hinge domain | Transmembrane domain | Co-stimulatory domain | Cytoplasmic Signaling domain |
|---|---|---|---|---|---|
| CD8α | scFv (e.g., anti-GPC3 scFv) | CD8 | CD8 | 4-1BB | CD3ζ |
| CD8α | scFv (e.g., anti-GPC3 scFv) | CD28 | CD28 | CD28 | CD3ζ |

Amino acid sequences of the example CAR polypeptides are provided below (signal sequence italicized).

```
SEQ ID NO: 104:
MALPVTALLLPLALLLHAARPDVVMTQSPLSLPVTPGEPASISCRSSQSLV

HSNRNTYLHWYLQKPGQSPQLLIYKVSNRFSGVPDRFSGSGSGTDFTLKIS

RVEAEDVGVYYCSQNTHVPPTFGQGTKLEIKRGGGGSGGGGSGGGGSQVQL

VQSGAEVKKPGASVKVSCKASGYTFTDYEMHWVRQAPGQGLEWMGALDPKT

GDTAYSQKFKGRVTLTADKSTSTAYMELSSLTSEDTAVYYCTRFYSYTYWG

QGTLVTVSSTTTPAPRPPTPAPTIASQPLSLRPEACRPAAGGAVHTRGLDF

ACDIYIWAPLAGTCGVLLLSLVITLYCKRGRKKLLYIFKQPFMRPVQTTQE

EDGCSCRFPEEEEGGCELRVKFSRSADAPAYQQGQNQLYNELNLGRREEYD

VLDKRRGRDPEMGGKPRRKNPQEGLYNELQKDKMAEAYSEIGMKGERRRGK

GHDGLYQGLSTATKDTYDALHMQALPPR

SEQ ID NO: 105:
MALPVTALLLPLALLLHAARPDVVMTQSPLSLPVTPGEPASISCRSSQSLV

HSNRNTYLHWYLQKPGQSPQLLIYKVSNRFSGVPDRFSGSGSGTDFTLKIS

RVEAEDVGVYYCSQNTHVPPTFGQGTKLEIKRGGGGSGGGGSGGGGSQVQL

VQSGAEVKKPGASVKVSCKASGYTFTDYEMHWVRQAPGQGLEWMGALDPKT

GDTAYSQKFKGRVTLTADKSTSTAYMELSSLTSEDTAVYYCTRFYSYTYWG

QGTLVTVSSIEVMYPPPYLDNEKSNGTIIHVKGKHLCPSPLFPGPSKPFWV

LVVVGGVLACYSLLVTVAFIIFWVRSKRSRLLHSDYMNMTPRRPGPTRKHY

QPYAPPRDFAAYRSRVKFSRSADAPAYQQGQNQLYNELNLGRREEYDVLDK

RRGRDPEMGGKPRRKNPQEGLYNELQKDKMAEAYSEIGMKGERRRGKGHDG

LYQGLSTATKDTYDALHMQALPPR
```

III. Hematopoietic Cells Expressing Krebs Cycle Modulating Polypeptides and Optionally Chimeric Receptor Polypeptides Provided herein are genetically engineered host cells (e.g., hematopoietic cells such as HSCs and immune cells, e.g., T cells or NK cells) expressing one or more of the Krebs cycle modulating polypeptides as described herein. The genetically engineered host cells may further express a chimeric receptor polypeptide (e.g., ACTR-expressing cells, e.g., ACTR Tcells or CAR-expressing cells, e.g., CAR T cells) as also described herein. In some embodiments, the host cells are hematopoietic cells or a progeny thereof. In some embodiments, the hematopoietic cells can be hematopoietic stem cells. In other embodiments, the host cells are immune cells, such as T cells or NK cells. In some embodiments, the immune cells are T cells. In some embodiments, the immune cells are NK cells. In other embodiments, the immune cells can be established cell lines, for example, NK-92 cells.

In some embodiments, the genetically engineered hematopoietic cells such as HSCs or immune cells (e.g., T cells or NK cells) may co-express any of the CAR constructs such as those disclosed herein with any of the Krebs cycle modulating agents, such as a Krebs cycle modulating polypeptide (e.g., GOT1 or GOT2). In some embodiments, the CAR construct may comprise a co-stimulatory domain from 4-1BB or CD28 and the Krebs cycle modulating polypeptide is GOT1 or GOT2. The CAR construct may further comprise a hinge and transmembrane domain from CD8 or CD28.

In other embodiments, the genetically engineered hematopoietic cells such as HSCs or immune cells (e.g., T cells or NK cells) may co-express any of the ACTR constructs such as those disclosed herein with any of the Krebs cycle modulating agents, such as a Krebs cycle modulating polypeptide (e.g., GOT1 or GOT2). In some embodiments, the ACTR construct may comprise a co-stimulatory domain from 4-1 BB or CD28 and the Krebs cycle modulating polypeptide is GOT1 or GOT2. The ACTR constructs may further comprise a hinge and transmembrane domain from CD8 or CD28.

Alternatively, the genetically engineered host cells disclosed herein may not express any chimeric receptor polypeptides. In some embodiments, the genetically engineered immune cells, which may overly express one or more Krebs cycle modulating polypeptides as disclosed herein, may be derived from tumor-infiltrating lymphocytes (TILs). Overexpression of the Krebs cycle modulating polypeptides may enhance the anti-tumor activity or the TILs in tumor microenvironment. Alternatively or in addition, the genetically engineered immune cells may be T cells, which may further have genetically engineered T cell receptors. The TILs and/or genetically modified TCRs may target peptide-MHC complex, in which the peptide may be derived from a pathogen, a tumor antigen, or an auto-antigen. Some examples are provided in Table 6 below.

Any of the CAR constructs disclosed herein or an antibody to be co-used with ACTR T cells may also target any of the peptide in such peptide/MHC complex.

TABLE 6

Exemplary Peptide-MHC Targets

| Targets | Indications |
|---|---|
| NY-ESO-1 | Sarcoma, MM |
| MAGE-A10 | NSCLC, Bladder, HNSCC |
| MAGE-A4 | Sarcomas, others |
| PMEL | Melanoma |
| WT-1 | Ovarian |

TABLE 6-continued

Exemplary Peptide-MHC Targets

| Targets | Indications |
|---|---|
| AFP | HCC |
| HPV-16 E6 | Cervical |
| HPV-16 E7 | Cervical |

In some embodiments, the host cells are immune cells, such as T cells or NK cells. In some embodiments, the immune cells are T cells. For example, the T cells can be CD4+ helper cells or CD8+ cytotoxic cells, or a combination thereof. Alternatively or in addition, the T cells can be suppressive T cells such as $T_{reg}$ cells. In some embodiments, the immune cells are NK cells. In other embodiments, the immune cells can be established cell lines, for example, NK-92 cells. In some examples, the immune cells can be a mixture of different types of T cells and/or NK cells as known in the art. For example, the immune cells can be a population of immune cells isolated from a suitable donor (e.g., a human patient). See disclosures below.

In some instances, the Krebs cycle modulating polypeptide to be introduced into the host cells is identical to an endogenous protein of the host cell. Introducing additional copies of the coding sequences of the Krebs cycle modulating polypeptide into the host cell would enhance the expression level of the polypeptide (i.e., overly expressed) as relative to the native counterpart. In some instances, the Krebs cycle modulating polypeptide to be introduced into the host cells is heterologous to the host cell, i.e., does not exist or is not expressed in the host cell. Such a heterologous Krebs cycle modulating polypeptide may be a naturally-occurring protein not expressed in the host cell in nature (e.g., from a different species). Alternatively, the heterologous Krebs cycle modulating polypeptide may be a variant of a native protein, such as those described herein. In some examples, the exogenous (i.e., not native to the host cells) copy of the coding nucleic acid may exist extrachromosomally. In other examples, the exogenous copy of the coding sequence may be integrated into the chromosome of the host cell, and may be located at a site that is different from the native loci of the endogenous gene.

Such genetically engineered host cells have the capacity to have an enhanced rate of glycolysis and may, for example, have an enhanced capacity of taking glucose from the environment. Thus, these genetically engineered host cells may exhibit better growth and/or bioactivities under low glucose, low amino acid, low pH, and/or hypoxic conditions, for example in a tumor microenvironment. The genetically engineered cells, when expressing a chimeric receptor polypeptide as disclosed herein, can recognize and inhibit target cells, either directly (e.g., by CAR-expressing immune cells) or via an Fc-containing therapeutic agents such as an anti-tumor antibodies (e.g., by ACTR-expressing immune cells). Given their expected high proliferation rate, bioactivity, and/or survival rate in low glucose, low amino acid, low pH, and/or hypoxic environments (e.g., in a tumor microenvironment), the genetically engineered cells such as T cell and NK cells would be expected to have higher therapeutic efficacy relative to chimeric receptor polypeptide T cells that do not express or express a lower level or less active form of the Krebs cycle modulating polypeptide.

The population of immune cells can be obtained from any source, such as peripheral blood mononuclear cells (PBMCs), bone marrow, or tissues such as spleen, lymph node, thymus, stem cells, or tumor tissue. Alternatively, the immune cell population may be derived from stem cells, for example, hematopoietic stem cells and induced pluripotent stem cells (iPSCs). A source suitable for obtaining the type of host cells desired would be evident to one of skill in the art. In some embodiments, the population of immune cells is derived from PBMCs, which may be obtained from a patient (e.g., a human patient) who needs the treatment described herein. The type of host cells desired (e.g., T cells, NK cells, or T cells and NK cells) may be expanded within the population of cells obtained by co-incubating the cells with stimulatory molecules. As a non-limiting example, anti-CD3 and anti-CD28 antibodies may be used for expansion of T cells.

To construct the immune cells that express any of the Krebs cycle modulating polypeptides and optionally the chimeric receptor polypeptide described herein, expression vectors for stable or transient expression of the Krebs cycle modulating polypeptides and/or the chimeric receptor polypeptide may be created via conventional methods as described herein and introduced into immune host cells. For example, nucleic acids encoding the Krebs cycle modulating polypeptides and/or the chimeric receptor polypeptides may be cloned into one or two suitable expression vectors, such as a viral vector or a non-viral vector in operable linkage to a suitable promoter. In some instances, each of the coding sequences for the chimeric receptor polypeptide and the Krebs cycle modulating polypeptide are on two separate nucleic acid molecules and can be cloned into two separate vectors, which may be introduced into suitable host cells simultaneously or sequentially. Alternatively, the coding sequences for the chimeric receptor polypeptide and the Krebs cycle modulating polypeptide are on one nucleic acid molecule and can be cloned into one vector. The coding sequences of the chimeric receptor polypeptide and the Krebs cycle modulating polypeptide may be in operable linkage to two distinct promoters such that the expression of the two polypeptides is controlled by different promoters. Alternatively, the coding sequences of the chimeric receptor polypeptide and the Krebs cycle modulating polypeptide may be in operably linkage to one promoter such that the expression of the two polypeptides is controlled by a single promoter. Suitable sequences may be inserted between the coding sequences of the two polypeptides so that two separate polypeptides can be translated from a single mRNA molecule. Such sequences, for example, IRES or ribosomal skipping site, are well known in the art. Additional descriptions are provided below.

The nucleic acids and the vector(s) may be contacted, under suitable conditions, with a restriction enzyme to create complementary ends on each molecule that can pair with each other and be joined with a ligase. Alternatively, synthetic nucleic acid linkers can be ligated to the termini of the nucleic acid encoding the Krebs cycle modulating polypeptides and/or the chimeric receptor polypeptides. The synthetic linkers may contain nucleic acid sequences that correspond to a particular restriction site in the vector. The selection of expression vectors/plasmids/viral vectors would depend on the type of host cells for expression of the Krebs cycle modulating polypeptides and/or the chimeric receptor polypeptides, but should be suitable for integration and replication in eukaryotic cells.

A variety of promoters can be used for expression of the Krebs cycle modulating polypeptides and/or the chimeric receptor polypeptides described herein, including, without limitation, cytomegalovirus (CMV) intermediate early promoter, a viral LTR such as the Rous sarcoma virus LTR, HIV-LTR, HTLV-1 LTR, the simian virus 40 (SV40) early promoter, the human EF1-alpha promoter, or herpes simplex tk virus promoter. Additional promoters for expression of the Krebs cycle modulating polypeptides and/or the chimeric receptor polypeptides include any constitutively active promoter in an immune cell. Alternatively, any regulatable promoter may be used, such that its expression can be modulated within an immune cell.

Additionally, the vector may contain, for example, some or all of the following: a selectable marker gene, such as the neomycin gene or the kanamycin gene for selection of stable or transient transfectants in host cells; enhancer/promoter sequences from the immediate early gene of human CMV for high levels of transcription; intron sequences from the human EF1-alpha gene, transcription termination and RNA processing signals from SV40 for mRNA stability; SV40 polyomavirus origins of replication and ColE1 for proper episomal replication; internal ribosome binding sites (IRESes), versatile multiple cloning sites; T7 and SP6 RNA promoters for in vitro transcription of sense and antisense RNA; a "suicide switch" or "suicide gene" which when triggered causes cells carrying the vector to die (e.g., HSV thymidine kinase or an inducible caspase such as iCasp9), and reporter gene for assessing expression of the Krebs cycle modulating polypeptides and/or the chimeric receptor polypeptide.

In one specific embodiment, such vectors also include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine deaminase, purine nucleoside phosphorylase, nitroreductase, and caspases such as caspase 8.

Suitable vectors and methods for producing vectors containing transgenes are well known and available in the art. Examples of the preparation of vectors for expression of Krebs cycle modulating polypeptides and/or chimeric receptor polypeptides can be found, for example, in US2014/0106449, herein incorporated in its entirety by reference.

Any of the vectors comprising a nucleic acid sequence that encodes a Krebs cycle modulating polypeptide and/or a chimeric receptor polypeptide described herein is also within the scope of the present disclosure. Such a vector, or the sequence encoding a Krebs cycle modulating polypeptide and/or a chimeric receptor polypeptide contained therein, may be delivered into host cells such as host immune cells by any suitable method. Methods of delivering vectors to immune cells are well known in the art and may include DNA electroporation, RNA electroporation, transfection using reagents such as liposomes, or viral transduction (e.g., retroviral transduction such as lentiviral transduction).

In some embodiments, the vectors for expression of the Krebs cycle modulating polypeptides and/or the chimeric receptor polypeptides are delivered to host cells by viral transduction (e.g., retroviral transduction such as lentiviral or gamma-retroviral transduction). Exemplary viral methods for delivery include, but are not limited to, recombinant retroviruses (see, e.g., PCT Publication Nos. WO 90/07936; WO 94/03622; WO 93/25698; WO 93/25234; WO 93/11230; WO 93/10218; and WO 91/02805; U.S. Pat. Nos. 5,219,740 and 4,777,127; GB Patent No. 2,200,651; and EP Patent No. 0 345 242), alphavirus-based vectors, and adeno-associated virus (AAV) vectors (see, e.g., PCT Publication Nos. WO 94/12649, WO 93/03769; WO 93/19191; WO 94/28938; WO 95/11984; and WO 95/00655). In some embodiments, the vectors for expression of the Krebs cycle modulating polypeptides and/or the chimeric receptor polypeptides are retroviruses. In some embodiments, the vectors for expression of the Krebs cycle modulating polypeptides and/or the chimeric receptor polypeptides are lentiviruses.

Examples of references describing retroviral transduction include Anderson et al., U.S. Pat. No. 5,399,346; Mann et al., Cell 33:153 (1983); Temin et al., U.S. Pat. No. 4,650,764; Temin et al., U.S. Pat. No. 4,980,289; Markowitz et al., J. Virol. 62:1120 (1988); Temin et al., U.S. Pat. No. 5,124,263; International Patent Publication No. WO 95/07358, published Mar. 16, 1995, by Dougherty et al.; and Kuo et al., Blood 82:845 (1993). International Patent Publication No. WO 95/07358 describes high efficiency transduction of primary B lymphocytes. See also WO 2016/040441A1, which is incorporated by reference herein for the purpose and subject matter referenced herein.

In examples in which the vectors encoding Krebs cycle modulating polypeptides and/or chimeric receptor polypeptides are introduced to the host cells using a viral vector, viral particles that are capable of infecting the immune cells and carry the vector may be produced by any method known in the art and can be found, for example in PCT Application No. WO 1991/002805A2, WO 1998/009271 A1, and U.S. Pat. No. 6,194,191. The viral particles are harvested from the cell culture supernatant and may be isolated and/or purified prior to contacting the viral particles with the immune cells.

In some embodiments, RNA molecules encoding any of the Krebs cycle modulating polypeptides and/or the chimeric receptor polypeptides as described herein may be prepared by a conventional method (e.g., in vitro transcription) and then introduced into suitable host cells, e.g., those described herein, via known methods, e.g., Rabinovich et al., Human Gene Therapy 17:1027-1035.

In some instances, the nucleic acid encoding a Krebs cycle modulating polypeptide and the nucleic acid encoding a suitable chimeric receptor polypeptide may be cloned into separate expression vectors, which may be introduced into suitable host cells concurrently or sequentially. For example, an expression vector (or an RNA molecule) for expressing the Krebs cycle modulating polypeptide may be introduced into host cells first and transfected host cells expressing the Krebs cycle modulating polypeptide may be isolated and cultured in vitro. An expression vector (or an RNA molecule) for expressing a suitable chimeric receptor polypeptide can then introduced into the host cells that express the Krebs cycle modulating polypeptide and transfected cells expressing both polypeptides can be isolated. In another example, expression vectors (or RNA molecules) each for expressing the Krebs cycle modulating polypeptide and the chimeric receptor polypeptide can be introduced into host cells simultaneously and transfected host cells expressing both polypeptides can be isolated via routine methodology.

In other instances, the nucleic acid encoding the Krebs cycle modulating polypeptide and the nucleic acid encoding the chimeric receptor polypeptide may be cloned into the same expression vector. Polynucleotides (including vectors in which such polynucleotides are operably linked to at least one regulatory element) for expression of the chimeric receptor polypeptide and Krebs cycle modulating polypeptide are also within the scope of the present disclosure. Non-limiting examples of useful vectors of the disclosure include viral vectors such as, e.g., retroviral vectors including gamma retroviral vectors and lentiviral vectors, and adeno-associated virus vectors (AAV vectors).

In some instances, the nucleic acid(s) encoding the Krebs cycle modulating polypeptide and/or the chimeric receptor polypeptide may be delivered into host cells via transposon. In some instances, the encoding nucleic acid(s) may be delivered into host cells via gene editing, for example, by CRISPR, TALEN, zinc-finger nuclease (ZFN), or meganucleases.

In some instances, the nucleic acid described herein may comprise two coding sequences, one encoding a chimeric receptor polypeptide as described herein, and the other encoding a polypeptide capable of modulating the Krebs cycle (i.e., a Krebs cycle modulating polypeptide). The nucleic acid comprising the two coding sequences described herein may be configured such that the polypeptides encoded by the two coding sequences can be expressed as independent (and physically separate) polypeptides. To achieve this goal, the nucleic acid described herein may contain a third nucleotide sequence located between the first and second coding sequences. This third nucleotide sequence may, for example, encode a ribosomal skipping site. A ribosomal skipping site is a sequence that impairs normal peptide bond formation. This mechanism results in the translation of additional open reading frames from one messenger RNA. This third nucleotide sequence may, for example, encode a P2A, T2A, or F2A peptide (see, for example, Kim et al., PLoS One. 2011; 6(4):e18556). As a non-limiting example, an exemplary P2A peptide may have the amino acid sequence of ATNFSLLKQAGDVEENPGP SEQ ID NO.: 106.

In another embodiment, the third nucleotide sequence may encode an internal ribosome entry site (IRES). An IRES is an RNA element that allows translation initiation in an end-independent manner, also permitting the translation of additional open reading frames from one messenger RNA. Alternatively, the third nucleotide sequence may encode a second promoter controlling the expression of the second polypeptide. The third nucleotide sequence may also encode more than one ribosomal skipping sequence, IRES sequence, additional promoter sequence, or a combination thereof.

The nucleic acid may also include additional coding sequences (including, but not limited to, fourth and fifth coding sequences) and may be configured such that the polypeptides encoded by the additional coding sequences are expressed as further independent and physically separate polypeptides. To this end, the additional coding sequences may be separated from other coding sequences by one or more nucleotide sequences encoding one or more ribosomal skipping sequences, IRES sequences, or additional promoter sequences.

In some examples, the nucleic acid (e.g., an expression vector or an RNA molecule as described herein) may comprise coding sequences for both the Krebs cycle modulating polypeptide (e.g., those described herein) and a suitable chimeric receptor polypeptide, the two coding sequences, in any order, being separated by a third nucleotide sequence coding for a P2A peptide (e.g., ATNFSLLKQAGDVEENPGP; SEQ ID NO: 106). As a result, two separate polypeptides, the Krebs cycle modulating polypeptide and the chimeric receptor, can be produced from such a nucleic acid, wherein the P2A portion ATNFSLLKQAGDVEENPG (SEQ ID NO: 107) is linked to the upstream polypeptide (encoded by the upstream coding sequence) and residue P from the P2A peptide is linked to the downstream polypeptide (encoded by the downstream coding sequence). In some examples, the chimeric receptor polypeptide is the upstream one and the Krebs cycle modulating polypeptide is the downstream one. In other examples, the Krebs cycle modulating polypeptide is the upstream one and the chimeric receptor polypeptide is the downstream one.

In some examples, the nucleic acid (e.g., an expression vector or an RNA molecule as described herein) may comprise coding sequences for both the Krebs cycle modulating polypeptide (e.g., those described herein) and a suitable ACTR polypeptide, the two coding sequences, in any order, being separated by a third nucleotide sequence coding for a P2A peptide (e.g., ATNFSLLKQAGDVEENPGP; SEQ ID NO:106). As a result, two separate polypeptides, the Krebs cycle modulating polypeptide and the ACTR) can be produced from such a nucleic acid, wherein the P2A portion ATNFSLLKQAGDVEENPG (SEQ ID NO:107) is linked to the upstream polypeptide (encoded by the upstream coding sequence) and residue P from the P2A peptide is linked to the downstream polypeptide (encoded by the downstream coding sequence). In some examples, the ACTR polypeptide is the upstream one and the Krebs cycle modulating polypeptide is the downstream one. In other examples, the Krebs cycle modulating polypeptide is the upstream one and the ACTR polypeptide is the downstream one.

In some examples, the nucleic acid described above may further encode a linker (e.g., a GSG linker) between two segments of the encoded sequences, for example, between the upstream polypeptide and the P2A peptide.

In specific examples, the nucleic acid described herein is configured such that it expresses two separate polypeptides in the host cell to which the nucleic acid is transfected: (i) the first polypeptide that contains, from the N-terminus to the C-terminus, a suitable CAR (e.g., SEQ ID NO: 104 or SEQ ID NO: 105), a peptide linker (e.g., the GSG linker), and the ATNFSLLKQAGDVEENPG (SEQ ID NO:107) segment derived from the P2A peptide; and (ii) a second polypeptide that contains, from the N-terminus to the C-terminus, the P residue derived from the P2A peptide and the Krebs cycle modulating polypeptide (e.g., any of SEQ ID NOs: 81-92).

In specific examples, the nucleic acid described herein is configured such that it expresses two separate polypeptides in the host cell to which the nucleic acid is transfected: (i) the first polypeptide that contains, from the N-terminus to the C-terminus, a suitable ACTR (e.g., any of SEQ ID NOs:1-80 described herein, for example, SEQ ID NO:1 or SEQ ID NO: 57), a peptide linker (e.g., the GSG linker), and the ATNFSLLKQAGDVEENPG (SEQ ID NO:107) segment derived from the P2A peptide; and (ii) a second polypeptide that contains, from the N-terminus to the C-terminus, the P residue derived from the P2A peptide and the Krebs cycle modulating polypeptide (e.g., any of SEQ ID NOs: 81-92).

In some instances, additional polypeptides of interest may also be introduced into the host immune cells.

Following introduction into the host cells a vector encoding any of the Krebs cycle modulating polypeptides and/or the chimeric receptor polypeptides provided herein, or the nucleic acid encoding the chimeric receptor polypeptide and/or Krebs cycle modulating polypeptide (e.g., an RNA molecule), the cells may be cultured under conditions that allow for expression of the Krebs cycle modulating polypeptides and/or the chimeric receptor polypeptide. In examples in which the nucleic acid encoding the Krebs cycle modulating polypeptides and/or the chimeric receptor polypeptide is regulated by a regulatable promoter, the host cells may be cultured in conditions wherein the regulatable promoter is activated. In some embodiments, the promoter is an inducible promoter and the immune cells are cultured in the presence of the inducing molecule or in conditions in which the inducing molecule is produced. Determining whether the Krebs cycle modulating polypeptide and/or the chimeric receptor polypeptide is expressed will be evident to one of skill in the art and may be assessed by any known method, for example, detection of the Krebs cycle modulating polypeptide and/or the chimeric receptor polypeptide-encoding mRNA by quantitative reverse transcriptase PCR (qRT-PCR) or detection of the Krebs cycle modulating polypeptide and/or the chimeric receptor polypeptide protein by methods including Western blotting, fluorescence microscopy, and flow cytometry.

Alternatively, expression of the chimeric receptor polypeptide may take place in vivo after the immune cells are administered to a subject. As used herein, the term "subject" refers to any mammal such as a human, monkey, mouse, rabbit, or domestic mammal. For example, the subject may be a primate. In a preferred embodiment, the subject is human.

Alternatively, expression of a Krebs cycle modulating polypeptide and/or a chimeric receptor polypeptide in any of the immune cells disclosed herein can be achieved by introducing RNA molecules encoding the Krebs cycle modulating polypeptides and/or the chimeric receptor polypeptides. Such RNA molecules can be prepared by in vitro transcription or by chemical synthesis. The RNA molecules can then be introduced into suitable host cells such as immune cells (e.g., T cells, NK cells, or both T cells and NK cells) by, e.g., electroporation. For example, RNA molecules can be synthesized and introduced into host immune cells following the methods described in Rabinovich et al., Human Gene Therapy, 17:1027-1035 and WO 2013/040557.

In certain embodiments, a vector(s) or RNA molecule(s) comprising the Krebs cycle modulating polypeptide and/or the chimeric receptor polypeptide may be introduced to the host cells or immune cells in vivo. As a non-limiting example, this may be accomplished by administering a vector or RNA molecule encoding one or more Krebs cycle modulating polypeptides and/or one or more chimeric receptor polypeptides described herein directly to the subject (e.g., through intravenous administration), producing host cells comprising Krebs cycle modulating polypeptides and/or chimeric receptor polypeptides in vivo.

Methods for preparing host cells expressing any of the Krebs cycle modulating polypeptides and/or the chimeric receptor polypeptides described herein may also comprise activating the host cells ex vivo. Activating a host cell means stimulating a host cell into an activated state in which the cell may be able to perform effector functions. Methods of activating a host cell will depend on the type of host cell used for expression of the Krebs cycle modulating polypeptides and/or chimeric receptor polypeptides. For example, T cells may be activated ex vivo in the presence of one or more molecules including, but not limited to: an anti-CD3 antibody, an anti-CD28 antibody, IL-2, phytohemoagglutinin, engineered artificial stimulatory cells or particles, or a combination thereof. The engineered artificial stimulatory cells may be artificial antigen-presenting cells as known in the art. See, e.g., Neal et al., J. Immunol. Res. Ther. 2017, 2(1):68-79 and Turtle et al., Cancer J. 2010, 16(4):374-381, the relevant disclosures of each of which are hereby incorporated by reference for the purpose and subject matter referenced herein.

In other examples, NK cells may be activated ex vivo in the presence of one or more molecules such as a 4-1BB ligand, an anti-4-1BB antibody, IL-15, an anti-IL-15 receptor antibody, IL-2, IL12, IL-21, K562 cells, and/or engineered artificial stimulatory cells or particles. In some embodiments, the host cells expressing any of the Krebs cycle modulating polypeptides and/or the chimeric receptor polypeptides (ACTR-/CAR- and/or Krebs cycle modulating polypeptide-expressing cells) described herein are activated ex vivo prior to administration to a subject. Determining whether a host cell is activated will be evident to one of skill in the art and may include assessing expression of one or more cell surface markers associated with cell activation, expression or secretion of cytokines, and cell morphology.

Methods for preparing host cells expressing any of the Krebs cycle modulating polypeptides and/or the chimeric receptor polypeptides described herein may comprise expanding the host cells ex vivo. Expanding host cells may involve any method that results in an increase in the number of cells expressing Krebs cycle modulating polypeptides and/or chimeric receptor polypeptides, for example, allowing the host cells to proliferate or stimulating the host cells to proliferate. Methods for stimulating expansion of host cells will depend on the type of host cell used for expression of the Krebs cycle modulating polypeptides and/or the chimeric receptor polypeptides and will be evident to one of skill in the art. In some embodiments, the host cells expressing any of the Krebs cycle modulating polypeptides and/or the chimeric receptor polypeptides described herein are expanded ex vivo prior to administration to a subject.

In some embodiments, the host cells expressing the Krebs cycle modulating polypeptides and/or the chimeric receptor polypeptides are expanded and activated ex vivo prior to administration of the cells to the subject. Host cell activation and expansion may be used to allow integration of a viral vector into the genome and expression of the gene encoding a Krebs cycle modulating polypeptide and/or a chimeric receptor polypeptide as described herein. If mRNA electroporation is used, no activation and/or expansion may be required, although electroporation may be more effective when performed on activated cells. In some instances, a Krebs cycle modulating polypeptide and/or a chimeric receptor polypeptide is transiently expressed in a suitable host cell (e.g., for 3-5 days). Transient expression may be advantageous if there is a potential toxicity and should be helpful in initial phases of clinical testing for possible side effects.

Any of the host cells expressing the Krebs cycle modulating polypeptides and/or the chimeric receptor polypeptides may be mixed with a pharmaceutically acceptable carrier to form a pharmaceutical composition, which is also within the scope of the present disclosure.

The phrase "pharmaceutically acceptable", as used in connection with compositions of the present disclosure, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate, and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy $20^{th}$ Ed. (2000) Lippincott Williams and Wilkins, Ed. K. E. Hoover.

The pharmaceutical compositions of the disclosure may also contain one or more additional active compounds as necessary for the particular indication being treated, preferably those with complementary activities that do not adversely affect each other. Non-limiting examples of possible additional active compounds include, e.g., IL-2 as well as various agents known in the field and listed in the discussion of combination treatments, below.

IV. Immunotherapy Using the Genetically Engineered Hematopoietic Cells Described Herein The genetically-engineered hematopoietic cells (e.g., hematopoietic stem cells, immune cells, such as NK cells or T cells) disclosed herein may be used in immunotherapy against various disorders, for example, cancer, infectious diseases, and autoimmune diseases.

(a) Combined Immunotherapy of Genetically Engineered Hematopoietic Cells Expressing ACTR Polypeptides and Fc-Containing Therapeutic Agents The exemplary ACTR polypeptides of the present disclosure confer antibody-dependent cell cytotoxicity (ADCC) capacity to T lymphocytes and enhance ADCC in NK cells. When the receptor is engaged by an antibody bound to cells, it triggers T-cell activation, sustained proliferation and specific cytotoxicity against the bound cells.

The degree of affinity of CD16 for the Fc portion of Ig is a critical determinant of ADCC and thus to clinical responses to antibody immunotherapy. The CD16 with the V158 polymorphism which has a higher binding affinity for Ig and mediates superior ADCC relative to CD16 with the F158 polymorphism was selected as an example. Although the F158 receptor has lower potency than the V158 receptor in induction of T cell proliferation and ADCC, the F158 receptor may have lower in vivo toxicity than the V158 receptor making it useful in some clinical contexts.

The Krebs cycle modulating polypeptides to be co-expressed with an ACTR polypeptides in immune cells would facilitate cell-based immune therapy such as T-cell therapy or NK-cell therapy by allowing the cells to grow and/or function effectively in a low glucose, low amino acid, low pH, and/or hypoxic environment. Antibody-directed cytotoxicity could be stopped whenever required by simple withdrawal of antibody administration. Clinical safety can be further enhanced by using mRNA electroporation to express the Krebs cycle modulating polypeptides and/or the ACTR polypeptides transiently, to limit any potential autoimmune reactivity.

Thus, in one embodiment, the disclosure provides a method for enhancing efficacy of an antibody-based immunotherapy of a cancer in a subject in need thereof, which subject is being treated with an Fc-containing therapeutic agent such as a therapeutic antibody, which can bind to antigen-expressing cells. The Fc-containing therapeutic agent contains an Fc portion, for example, a human or humanized Fc portion, which can be recognized and bound by the Fc-binding portion (e.g., the extracellular domain of human CD16A) of the ACTR expressed on the engineered immune cells.

The methods described herein may comprise introducing into the subject a therapeutically effective amount an antibody and a therapeutically effective amount of the genetically engineered host cells such as hematopoietic cells, for example, immune cells (e.g., T lymphocytes or NK cells), which co-express a Krebs cycle modulating polypeptide and an ACTR polypeptide of the disclosure. The subject (e.g., a human patient such as a human cancer patient) has been treated or is being treating with an Fc-containing therapeutic agent specific to a target antigen. A target antigen may be any molecule that is associated with a disease or condition, including, but are not limited to, tumor antigens, pathogenic antigens (e.g., bacterial or viral), or antigens present on diseased cells, such as those described herein.

In the context of the present disclosure insofar as it relates to any of the disease conditions recited herein, the terms "treat", "treatment", and the like mean to relieve or alleviate at least one symptom associated with such condition, or to slow or reverse the progression of such condition. Within the meaning of the present disclosure, the term "treat" also denotes to arrest, delay the onset (i.e., the period prior to clinical manifestation of a disease) and/or reduce the risk of developing or worsening a disease. For example, in connection with cancer the term "treat" may mean eliminate or reduce a patient's tumor burden, or prevent, delay or inhibit metastasis, etc.

As used herein the term "therapeutically effective" applied to dose or amount refers to that quantity of a compound or pharmaceutical composition that is sufficient to result in a desired activity upon administration to a subject in need thereof. Note that when a combination of active ingredients is administered (e.g., a first pharmaceutical composition comprising an antibody, and a second pharmaceutical composition comprising a population of T lymphocytes or NK cells that express a Krebs cycle modulating polypeptide and/or an antibody-coupled T-cell receptor (ACTR) construct), the effective amount of the combination may or may not include amounts of each ingredient that would have been effective if administered individually. Within the context of the present disclosure, the term "therapeutically effective" refers to that quantity of a compound or pharmaceutical composition that is sufficient to delay the manifestation, arrest the progression, relieve or alleviate at least one symptom of a disorder treated by the methods of the present disclosure.

Host cells (e.g., hematopoietic cells, for example, immune cells such as T cells and NK cells) expressing Krebs cycle modulating polypeptides and ACTR polypeptides described herein are useful for enhancing ADCC in a subject and/or for enhancing the efficacy of an antibody-based immunotherapy and/or for enhancing growth and/or proliferation of immune cells in a low-glucose environment. In some embodiments, the subject is a mammal, such as a human, monkey, mouse, rabbit, or domestic mammal. In some embodiments, the subject is a human. In some embodiments, the subject is a human cancer patient. In some embodiments, the subject has been treated or is being treated with any of the therapeutic antibodies described herein.

To practice the method described herein, an effective amount of the host cells, for example, immune cells (e.g., NK cells and/or T lymphocytes) expressing any of the Krebs cycle modulating polypeptides and the ACTR polypeptides described herein and an effective amount of an antibody, or compositions thereof may be administered to a subject in need of the treatment via a suitable route, such as intravenous administration. As used herein, an effective amount refers to the amount of the respective agent (e.g., the NK cells and/or T lymphocytes expressing Krebs cycle modulating polypeptides, ACTR polypeptides, antibodies, or compositions thereof) that upon administration confers a therapeutic effect on the subject. Determination of whether an amount of the cells or compositions described herein achieved the therapeutic effect would be evident to one of skill in the art. Effective amounts vary, as recognized by those skilled in the art, depending on the particular condition being treated, the severity of the condition, the individual patient parameters including age, physical condition, size, gender, sex, and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human. In some embodiments, the subject in need of treatment is a human cancer patient. In some embodiments, the subject in need of treatment suffers from one or more pathogenic infections (e.g., viral, bacterial, and/or fungal infections).

The methods of the disclosure may be used for treatment of any cancer or any pathogen. Specific non-limiting examples of cancers which can be treated by the methods of the disclosure include, for example, lymphoma, breast cancer, gastric cancer, neuroblastoma, osteosarcoma, lung cancer, skin cancer, prostate cancer, colorectal cancer, renal cell carcinoma, ovarian cancer, rhabdomyosarcoma, leukemia, mesothelioma, pancreatic cancer, head and neck cancer, retinoblastoma, glioma, glioblastoma, thyroid cancer, hepatocellular cancer, esophageal cancer, and cervical cancer. In certain embodiments, the cancer may be a solid tumor.

The methods of this disclosure may also be used for treating infectious diseases, which may be caused by bacterial infection, viral infection, or fungus infection. In such instances, the genetically engineered immune cells can be co-used with an Fc-containing therapeutic agent (e.g., an antibody) that targets a pathogenic antigen (e.g., an antigen associated with the bacterium, virus, or fungus that causes the infection). Specific non-limiting examples of pathogenic antigens include, but are not limited to, bacterial, viral, and/or fungal antigens. Some examples are provided below: influenza virus neuraminidase, hemagglutinin, or M2 protein, human respiratory syncytial virus (RSV) F glycoprotein or G glycoprotein, herpes simplex virus glycoprotein gB, gC, gD, or gE, *Chlamydia* MOMP or PorB protein, Dengue virus core protein, matrix protein, or glycoprotein E, measles virus hemagglutinin, herpes simplex virus type 2 glycoprotein gB, poliovirus I VP1, envelope glycoproteins of HIV 1, hepatitis B core antigen or surface antigen, diptheria toxin, *Streptococcus* 24M epitope, Gonococcal pilin, pseudorabies virus g50 (gpD), pseudorabies virus II (gpB), pseudorabies virus III (gpC), pseudorabies virus glycoprotein H, pseudorabies virus glycoprotein E, transmissible gastroenteritis glycoprotein 195, transmissible gastroenteritis matrix protein, or human hepatitis C virus glycoprotein E1 or E2.

In some embodiments, the immune cells are administered to a subject in an amount effective in enhancing ADCC activity by least 20% and/or by at least 2-fold, e.g., enhancing ADCC by 50%, 80%, 100%, 2-fold, 5-fold, 10-fold, 20-fold, 50-fold, 100-fold, or more.

The immune cells are co-administered with an Fc-containing therapeutic agent such as a therapeutic antibody in order to target cells expressing the antigen to which the Fc-containing therapeutic agent binds. In some embodiments, more than one Fc-containing therapeutic agents, such as more than one antibodies can be co-used with the immune cells. Antibody-based immunotherapy may be used to treat, alleviate, or reduce the symptoms of any disease or disorder for which the immunotherapy is considered useful in a subject.

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof which comprise an Fc region, mutants thereof, fusion proteins comprising an antibody portion, humanized antibodies, chimeric antibodies, diabodies, single domain antibodies (e.g., nanobodies), linear antibodies, multispecific antibodies (e.g., bispecific antibodies) and any other modified configuration of the immunoglobulin molecule that comprises an antigen recognition site of the required specificity and an Fc region, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known. The antibody for use in the present disclosure contains an Fc region recognizable by the co-used ACTR- and/or Krebs cycle modulating enhancing polypeptide-expressing immune cells. The Fc region may be a human or humanized Fc region.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one example, the antibody used in the methods described herein is a humanized antibody. Humanized antibodies refer to forms of non-human (e.g. murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. The antibodies used herein may be glycosylated (e.g., fucosylated) or afucoslylated. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another example, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as a human. In some embodiments, amino acid modifications can be made in the variable region and/or the constant region.

The hematopoietic cells, for example, immune cells (e.g., T lymphocytes and/or NK cells) or HSCs expressing any of the Krebs cycle modulating polypeptides and/or the ACTR polypeptides disclosed herein may be administered to a subject who has been treated or is being treated with an Fc-containing antibody. For example, the immune cells may be administered to a human subject simultaneously with an antibody. Alternatively, the immune cells may be administered to a human subject during the course of an antibody-based immunotherapy. In some examples, the immune cells and an antibody can be administered to a human subject at least 4 hours apart, e.g., at least 12 hours apart, at least 1 day apart, at least 3 days apart, at least one week apart, at least two weeks apart, or at least one month apart.

In some embodiments, the antibodies described herein specifically bind to the corresponding target antigen or an epitope thereof. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to a target antigen or epitope if it binds with greater affinity, avidity, more readily, and/or with greater duration than it binds to other substances. For example, an antibody that specifically (or preferentially) binds to an antigen or an antigenic epitope therein is an antibody that binds this target antigen with greater affinity, avidity, more readily, and/or with greater duration than it binds to other antigens or other epitopes in the same antigen. It is also understood with this definition that, for example, an antibody that specifically binds to a first target antigen may or may not specifically or preferentially bind to to a second target antigen. As such, "specific binding" or "preferential binding" does not necessarily require (although it can include) exclusive binding. In some examples, an antibody that "specifically binds" to a target antigen or an epitope thereof may not bind to other antigens or other epitopes in the same antigen.

In some embodiments, an antibody as described herein has a suitable binding affinity for the target antigen (e.g., any one of the targets described herein) or antigenic epitopes thereof. The antibodies for use in the immune therapy methods described herein may bind to (e.g., specifically bind to) a target antigen of interest, or a specific region or an antigenic epitope therein. Table 3 above lists exemplary target antigens of interest and exemplary antibodies specific to such.

(b) Immunotherapy of Genetically Engineered Hematopoietic Cells Expressing CAR Polypeptides The genetically engineered hematopoietic cells (e.g., hematopoietic stem cells, immune cells, such as T cells or natural killer cells) described herein, co-expressing a Krebs cycle modulating polypeptide and a CAR polypeptide can be used in immune therapy such as T-cell therapy or NK-cell therapy for inhibiting diseased cells expressing an antigen to which the CAR polypeptide targets, directly or indirectly (e.g., via a therapeutic agent conjugated to a tag to which the CAR polypeptide binds). The Krebs cycle modulating polypeptide co-expressed with a CAR polypeptide in immune cells would facilitate the cell-based immune therapy by allowing the cells to grow and/or function effectively in a low glucose, low amino acid, low pH, and/or a hypoxic environment, for example, in a tumor microenvironment. Clinical safety may be further enhanced by using mRNA electroporation to express the Krebs cycle modulating polypeptides and/or the CAR polypeptides transiently, to limit any potential non-tumor specific reactivity.

The methods described herein may comprise introducing into the subject a therapeutically effective amount of genetically engineered host cells such as hematopoietic cells, for example, immune cells (e.g., T lymphocytes or NK cells), which co-express a Krebs cycle modulating polypeptide and a CAR polypeptide of the disclosure. The subject (e.g., a human patient such as a human cancer patient) may additionally have been treated or is being treated with an anti-cancer or anti-infection therapy including, but not limited to, an anti-cancer therapeutic agent or anti-infection agent. The CAR has an antigen-binding domain that may bind any target antigen. Such a target antigen may be any molecule that is associated with a disease or condition, including, but are not limited to, tumor antigens, pathogenic antigens (e.g., bacterial, fungal, or viral), or antigens present on diseased cells, such as those described herein.

Host cells (e.g., hematopoietic cells, for example, immune cells such as T cells and NK cells) expressing Krebs cycle modulating polypeptides and CAR polypeptides described herein are useful for inhibiting cells expressing a target antigen and/or for enhancing growth and/or proliferation of immune cells in a low-glucose environment, a low amino acid environment, a low pH environment, and/or a hypoxic environment, for example, in a tumor microenvironment. In some embodiments, the subject is a mammal, such as a human, monkey, mouse, rabbit, or domestic mammal. In some embodiments, the subject is a human. In some embodiments, the subject is a human cancer patient. In some embodiments, the subject has additionally been treated or is being treated with any of the therapeutic antibodies described herein.

To practice the method described herein, an effective amount of the hematopoietic cells, for example, immune cells (NK cells and/or T lymphocytes) expressing any of the Krebs cycle modulating polypeptides and the CAR polypeptides described herein, or compositions thereof may be administered to a subject in need of the treatment via a suitable route, such as intravenous administration. As used herein, an effective amount refers to the amount of the respective agent (e.g., the NK cells and/or T lymphocytes expressing Krebs cycle modulating polypeptides, CAR polypeptides, or compositions thereof) that upon administration confers a therapeutic effect on the subject. Determination of whether an amount of the cells or compositions described herein achieved the therapeutic effect would be evident to one of skill in the art. Effective amounts vary, as recognized by those skilled in the art, depending on the particular condition being treated, the severity of the condition, the individual patient parameters including age, physical condition, size, gender, sex, and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human. In some embodiments, the subject in need of treatment is a human cancer patient. In some embodiments, the subject in need of treatment suffers from one or more pathogenic infections (e.g., viral, bacterial, and/or fungal infections).

The methods of the disclosure may be used for treatment of any cancer or any pathogen. Specific non-limiting examples of cancers which can be treated by the methods of the disclosure include, for example, lymphoma, breast cancer, gastric cancer, neuroblastoma, osteosarcoma, lung cancer, skin cancer, prostate cancer, colorectal cancer, renal cell carcinoma, ovarian cancer, rhabdomyosarcoma, leukemia, mesothelioma, pancreatic cancer, head and neck cancer, retinoblastoma, glioma, glioblastoma, thyroid cancer, hepatocellular cancer, esophageal cancer, and cervical cancer. In certain embodiments, the cancer may be a solid tumor.

The methods of this disclosure may also be used for treating infectious diseases, which may be caused by bacterial infection, viral infection, or fungus infection. In such instances, genetically engineered immune cells expressing a CAR polypeptide specific to a pathogenic antigen, (e.g., an antigen associated with the bacterium, virus, or fungus that causes the infection) can be used to eliminate infected cells. Specific non-limiting examples of pathogenic antigens include, but are not limited to, bacterial, viral, and/or fungal antigens.

In some embodiments, the immune cells are administered to a subject in an amount effective in inhibiting cells expressing the target antigen by least 20% and/or by at least 2-fold, e.g., inhibiting cells expressing the target antigen by 50%, 80%, 100%, 2-fold, 5-fold, 10-fold, 20-fold, 50-fold, 100-fold, or more.

Additional therapeutic agents (e.g., antibody-based immunotherapeutic agents) may be used to treat, alleviate, or reduce the symptoms of any disease or disorder for which the therapeutic agent is considered useful in a subject.

The efficacy of the cell-based immunotherapy as described herein may be assessed by any method known in the art and would be evident to a skilled medical professional. For example, the efficacy of the cell-based immunotherapy may be assessed by survival of the subject or tumor or cancer burden in the subject or tissue or sample thereof. In some embodiments, the immune cells are administered to a subject in need of the treatment in an amount effective in enhancing the efficacy of an cell-based immunotherapy by at least 20% and/or by at least 2-fold, e.g., enhancing the efficacy of an antibody-based immunotherapy by 50%, 80%, 100%, 2-fold, 5-fold, 10-fold, 20-fold, 50-fold, 100-fold or more, as compared to the efficacy in the absence of the immune cells expressing the Krebs cycle modulating polypeptide and/or the CAR polypeptide.

In any of the compositions or methods described herein, the immune cells (e.g., NK and/or T cells) may be autologous to the subject, i.e., the immune cells may be obtained from the subject in need of the treatment, genetically engineered for expression of the Krebs cycle modulating polypeptides and/or the CAR polypeptides, and then administered to the same subject. In one specific embodiment, prior to re-introduction into the subject, the autologous immune cells (e.g., T lymphocytes or NK cells) are activated and/or expanded ex vivo. Administration of autologous cells to a subject may result in reduced rejection of the host cells as compared to administration of non-autologous cells.

Alternatively, the host cells are allogeneic cells, i.e., the cells are obtained from a first subject, genetically engineered for expression of the Krebs cycle modulating polypeptide and/or the chimeric receptor polypeptide (e.g., ACTR polypeptide or CAR polypeptide), and administered to a second subject that is different from the first subject but of the same species. For example, allogeneic immune cells may be derived from a human donor and administered to a human recipient who is different from the donor. In a specific embodiment, the T lymphocytes are allogeneic T lymphocytes in which the expression of the endogenous T cell receptor has been inhibited or eliminated. In one specific embodiment, prior to introduction into the subject, the allogeneic T lymphocytes are activated and/or expanded ex vivo. T lymphocytes can be activated by any method known in the art, e.g., in the presence of anti-CD3/CD28, IL-2, phytohemoagglutinin, engineered artificial stimulatory cells or particles, or a combination thereof.

NK cells can be activated by any method known in the art, e.g., in the presence of one or more agents selected from the group consisting of CD137 ligand protein, CD137 antibody, IL-15 protein, IL-15 receptor antibody, IL-2 protein, IL-12 protein, IL-21 protein, and K562 cell line, and/or engineered artificial stimulatory cells or particles. See, e.g., U.S. Pat. Nos. 7,435,596 and 8,026,097 for the description of useful methods for expanding NK cells. For example, NK cells used in the compositions or methods of the disclosure may be preferentially expanded by exposure to cells that lack or poorly express major histocompatibility complex I and/or II molecules and which have been genetically modified to express membrane bound IL-15 and 4-1BB ligand (CDl37L). Such cell lines include, but are not necessarily limited to, K562 [ATCC, CCL 243; Lozzio et al., *Blood* 45(3): 321-334 (1975); Klein et al., *Int. J Cancer* 18: 421-431 (1976)], and the Wilms tumor cell line HFWT (Fehniger et al., *Int Rev Immunol* 20(3-4):503-534 (2001); Harada H, et al., *Exp Hematol* 32(7):614-621 (2004)), the uterine endometrium tumor cell line HHUA, the melanoma cell line HMV-II, the hepatoblastoma cell line HuH-6, the lung small cell carcinoma cell lines Lu-130 and Lu-134-A, the neuroblastoma cell lines NB 19 and N1369, the embryonal carcinoma cell line from testis NEC 14, the cervix carcinoma cell line TCO-2, and the bone marrow-metastasized neuroblastoma cell line TNB 1 [Harada, et al., *Jpn. J. Cancer Res* 93: 313-319 (2002)]. Preferably the cell line used lacks or poorly expresses both MHC I and II molecules, such as the K562 and HFWT cell lines. A solid support may be used instead of a cell line. Such support should preferably have attached on its surface at least one molecule capable of binding to NK cells and inducing a primary activation event and/or a proliferative response or capable of binding a molecule having such an affect thereby acting as a scaffold. The support may have attached to its surface the CD137 ligand protein, a CD137 antibody, the IL-15 protein or an IL-15 receptor antibody. Preferably, the support will have IL-15 receptor antibody and CD137 antibody bound on its surface.

In one embodiment of the described compositions or methods, introduction (or re-introduction) of T lymphocytes, NK cells, or T lymphocytes and NK cells to the subject is followed by administering to the subject a therapeutically effective amount of IL-2.

In accordance with the present disclosure, patients can be treated by infusing therapeutically effective doses of immune cells such as T lymphocytes or NK cells comprising a Krebs cycle modulating polypeptide and/or a CAR polypeptide of the disclosure in the range of about $10^5$ to $10^{10}$ or more cells per kilogram of body weight (cells/Kg). The infusion can be repeated as often and as many times as the patient can tolerate until the desired response is achieved. The appropriate infusion dose and schedule will vary from patient to patient, but can be determined by the treating physician for a particular patient. Typically, initial doses of approximately $10^6$ cells/Kg will be infused, escalating to $10^8$ or more cells/Kg. IL-2 can be co-administered to expand infused cells. The amount of IL-2 can about $1-5\times10^6$ international units per square meter of body surface.

The term "about" or "approximately" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

The efficacy of the compositions or methods described herein may be assessed by any method known in the art and would be evident to a skilled medical professional. For example, the efficacy of the compositions or methods described herein may be assessed by survival of the subject or cancer or pathogen burden in the subject or tissue or sample thereof. In some embodiments, the compositions and methods described herein may be assessed based on the safety or toxicity of the therapy (e.g., administration of the immune cells expressing the Krebs cycle modulating polypeptides and the CAR polypeptides) in the subject, for example, by the overall health of the subject and/or the presence of adverse events or severe adverse events.

(c) Other Immunotherapies

In some embodiments, the genetically-engineered immune cells, expressing one or more of the Krebs cycle modulating polypeptides (e.g., GOT such as GOT1 or GOT2), may be derived from natural immune cells specific to diseased cells (e.g., cancer cells or pathogen infected cells). Such genetically-engineered immune cells (e.g., tumor-infiltrating lymphocytes or TILs) may not co-express any chimeric receptor polypeptide and can be used to destroy the target disease cells, e.g., cancer cells. The genetically-engineered TILs, expressing one or more Krebs cycle modulating polypeptides but not chimeric receptors, may be co-used with a bispecific antibody capable of binding to the target tumor cells and the TILs (BiTE).

In some embodiments, the genetically-engineered immune cells, expressing one or more of the Krebs cycle modulating polypeptides (e.g., GOT such as GOT1 or GOT2), may be $T_{reg}$ cells. Such $T_{reg}$ cells may co-express an chimeric receptor polypeptide as disclosed herein. Alternatively, the $T_{reg}$ cells may not co-express any chimeric receptor polypeptide and can be used for the intended therapy.

V. Combination Treatments

The compositions and methods described in the present disclosure may be utilized in conjunction with other types of therapy for cancer, such as chemotherapy, surgery, radiation, gene therapy, and so forth, or anti-infection therapy. Such therapies can be administered simultaneously or sequentially (in any order) with the immunotherapy according to the present disclosure. When co-administered with an additional therapeutic agent, suitable therapeutically effective dosages for each agent may be lowered due to the additive action or synergy.

In some instances, the immune cells (e.g., T lymphocytes and/or NK cells) expressing any of the Krebs cycle modulating polypeptides and/or the chimeric receptor polypeptides disclosed herein may be administered to a subject who has been treated or is being treated with an additional therapeutic agent (e.g., an additional anti-cancer therapeutic agent). For example, the immune cells may be administered to a human subject simultaneously with the additional therapeutic agent. Alternatively, the immune cells may be administered to a human subject before the additional therapeutic agent. Alternatively, the immune cells may be administered to a human subject after the additional therapeutic agent.

Genetically engineered immune cells (e.g., T cells or NK cells) that co-express a Krebs cycle modulating polypeptide and a CAR polypeptide specific to a tag can be co-used with a therapeutic agent conjugated to the tag. Via the therapeutic agent, which is capable of binding to an antigen associated with diseased cells such as tumor cells, such genetically engineered immune cells can be engaged with the diseased cells and inhibit their growth. Any of the antibodies listed in Table 1 above, or others specific to the same target antigen also listed in Table 1 can be conjugated to a suitable tag (e.g., those described herein) and be co-used with immune cells co-expressing the Krebs cycle modulating polypeptide and a CAR polypeptide specific to the tag.

The treatments of the disclosure can be combined with other immunomodulatory treatments such as, e.g., therapeutic vaccines (including but not limited to GVAX, DC-based vaccines, etc.), checkpoint inhibitors (including but not limited to agents that block CTLA4, PD1, LAG3, TIM3, etc.) or activators (including but not limited to agents that enhance 41BB, OX40, etc.).

Non-limiting examples of other therapeutic agents useful for combination with the immunotherapy of the disclosure include: (i) anti-angiogenic agents (e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000)); (ii) a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof; and (iii) chemotherapeutic compounds such as, e.g., pyrimidine analogs (5-fluorouracil, floxuridine, capecitabine, gemcitabine and cytarabine), purine analogs, folate antagonists and related inhibitors (mercaptopurine, thioguanine, to pentostatin and 2-chloro-deoxyadenosine (cladribine)); antiproliferative/antimitotic agents including natural products such as *vinca* alkaloids (vinblastine, vincristine, and vinorelbine), microtubule disruptors such as taxane (paclitaxel, docetaxel), vincristine, vinblastine, nocodazole, epothilones, and navelbine, epidipodophyllotoxins (etoposide and teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamine oxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycin, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (brefeldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); AKT inhibitors (such as MK-2206 2HC1, Perifosine (KRX-0401), GSK690693, Ipatasertib (GDC-0068), AZD5363, uprosertib, afuresertib, or triciribine); mTOR inhibitors, topoisomerase inhibitors (doxorubicin (adriamycin), amsacrine, camptothecin, daunorubicin, dactinomycin, eniposide, epirubicin, etoposide, idarubicin, mitoxantrone, topotecan, and irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

For examples of additional useful agents see also Physician's Desk Reference, 59.sup.th edition, (2005), Thomson P D R, Montvale N.J.; Gennaro et al., Eds. Remington's The Science and Practice of Pharmacy 20th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

The administration of an additional therapeutic agent can be performed by any suitable route, including systemic administration as well as administration directly to the site of the disease (e.g., to a tumor).

In some embodiments, the method involves administering the additional therapeutic agent (e.g., an antibody) to the subject in one dose. In some embodiments, the method involves administering the additional therapeutic agent (e.g., an antibody) to the subject in multiple doses (e.g., at least 2, 3, 4, 5, 6, 7, or 8 doses). In some embodiments, the additional therapeutic agent (e.g., an antibody) is administered to the subject in multiple doses, with the first dose of the additional therapeutic agent (e.g., an antibody) administered to the subject about 1, 2, 3, 4, 5, 6, or 7 days prior to administration of the immune cells expressing the Krebs cycle modulating polypeptide and/or the CAR polypeptide. In some embodiments, the first dose of the additional therapeutic agent (e.g., an antibody) is administered to the subject between about 24-48 hours prior to the administration of the immune cells expressing the Krebs cycle modulating polypeptide and/or the CAR polypeptide. In some instances, the additional therapeutic agent can be an antibody specific to a target antigen of interest, for example, those listed in Table 1 and others that are specific to the same target.

In some embodiments, the additional therapeutic agent (e.g., an antibody) is administered to the subject prior to administration of the immune cells expressing the Krebs cycle modulating polypeptide and/or the CAR polypeptide and then subsequently about every two weeks. In some embodiments, the first two doses of the additional therapeutic agent (e.g., an antibody) are administered about one week (e.g., about 6, 7, 8, or 9 days) apart. In certain embodiments, the third and following doses are administered about every two weeks.

In any of the embodiments described herein, the timing of the administration of the additional therapeutic agent (e.g., an antibody) is approximate and includes three days prior to and three days following the indicated day (e.g., administration every three weeks encompasses administration on day 18, day 19, day 20, day 21, day 22, day 23, or day 24).

The efficacy of the methods described herein may be assessed by any method known in the art and would be evident to a skilled medical professional and/or those described herein. For example, the efficacy of the antibody-based immunotherapy may be assessed by survival of the subject or cancer burden in the subject or tissue or sample thereof. In some embodiments, the antibody-based immunotherapy is assessed based on the safety or toxicity of the therapy in the subject, for example by the overall health of the subject and/or the presence of adverse events or severe adverse events.

VI. Kits for Therapeutic Use

The present disclosure also provides kits for use of the compositions described herein. For example, the present disclosure also provides kits comprising a population of immune cells (e.g., T lymphocytes or NK cells, constructed in vitro or in vivo) that express a Krebs cycle modulating polypeptide and optionally a chimeric receptor polypeptide for use in inhibiting the growth of diseased cells, e.g., tumor cells and/or enhancing immune cell growth and/or proliferation in a low glucose environment, a low amino acid environment, a low-pH environment, and/or hypoxic environment, for example, in a tumor microenvironment. The kit may further comprise a therapeutic agent or a therapeutic agent conjugated to a tag (e.g., those described herein), to which the chimeric receptor polypeptide expressed on the immune cells bind. Such kits may include one or more containers comprising the population of the genetically engineered immune cells as described herein (e.g., T lymphocytes and/or NK cells), which co-express a Krebs cycle modulating polypeptide and a chimeric receptor polypeptide such as those described herein, and optionally a therapeutic agent or a therapeutic agent conjugated to a tag.

In some embodiments, the kit described herein comprises Krebs cycle modulating polypeptide-expressing and chimeric receptor polypeptide-expressing immune cells, which are expanded in vitro, and an antibody specific to a cell surface antibody that is present on activated T cells, for example, an anti-CD5 antibody, an anti-CD38 antibody or an anti-CD7 antibody. The Krebs cycle modulating polypeptide-expressing and chimeric receptor polypeptide-expressing immune cells may express any of the chimeric receptor polypeptide constructs known in the art or disclosed herein.

Alternatively, the kit disclosed herein may comprise a nucleic acid or a nucleic acid set as described herein, which collectively encodes any of the chimeric receptor polypeptides and any of the Krebs cycle modulating polypeptides as also described herein.

In some embodiments, the kit can additionally comprise instructions for use in any of the methods described herein. The included instructions may comprise a description of administration of the first and second pharmaceutical compositions to a subject to achieve the intended activity, e.g., inhibiting target cell growth in a subject, and/or enhancing the growth and/or proliferation of immune cells in a low-glucose environment, a low amino acid (e.g., a low glutamine environment) environment, a low pH environment, and/or a hypoxic environment (e.g., a low glucose, low amino acid, low pH or hyposic tumor microenvironment). The kit may further comprise a description of selecting a subject suitable for treatment based on identifying whether the subject is in need of the treatment. In some embodiments, the instructions comprise a description of administering the population of genetically engineered immune cells and optionally a description of administering the tag-conjugated therapeutic agent.

The instructions relating to the use of the immune cells and optionally the tag-conjugated therapeutic agent as described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. At least one active agent in the second pharmaceutical composition is an antibody as described herein. At least one active agent in the first pharmaceutical composition is a population of immune cells (e.g., T lymphocytes or NK cells) that express a chimeric receptor polypeptide and a Krebs cycle modulating polypeptide as described herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; Oligonucleotide Synthesis (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Impact of Expressing a Krebs Cycle Modulating Polypeptide on T Cell Function in Lower Glucose Environments A Krebs cycle modulating polypeptide transgene is co-expressed in the same T cell with an ACTR polypeptide. The transgene is, for example, PHGDG, PCK1, IDH1, IDH1, MDH1, MDH2, GOT1, GOT2, PSAT1, GDH1, GPT1, or GLS (e.g., SEQ ID NOs:81-92). The T cells are transduced with a virus encoding the ACTR polypeptide and the glucose importation polypeptide separated, for example, by a P2A ribosomal skip sequence. The T cells are mixed at a given effector-to-target (E:T) ratio with tumor target cells, such as IGROV-1 cells, and a tumor-targeting antibody such as an anti-FOLR1 antibody. Reactions are then incubated at 37° C. in a 5% $CO_2$ incubator for a period of time (e.g., 6-8 days) at different starting concentrations of glucose (e.g., 0-20 mM). T cell function is then evaluated, for example, using cytokine production or T cell proliferation assays or for resistance to chronic stimulation. Cytokine production (e.g., IL-2 and/or IFN-gamma) is measured from the reaction supernatant. For proliferation experiments, co-cultures are harvested and stained with an anti-CD3 antibody and a live-dead cell stain. The number of live, CD3-positive cells is evaluated by flow cytometry as a measure of T cell proliferation. T cells expressing a Krebs cycle modulating polypeptide in addition to the ACTR polypeptide show enhanced T cell function relative to T cells expressing ACTR alone including, for example, enhanced cytokine production or enhanced proliferation. This enhanced function may be more pronounced at lower glucose concentrations. These experiments demonstrate that expressing a Krebs cycle modulating polypeptide in T cells has a positive impact on T cell activity.

Example 2: Impact of Expressing a Krebs Cycle Modulating Polypeptide Gene on T Cell Function in Environments with Higher Soluble Inhibitor Concentrations A Krebs cycle modulating polypeptide transgene is co-expressed in the same T cell with an ACTR polypeptide. The transgene is, for example, PHGDG, PCK1, IDH1, IDH1, MDH1, MDH2, GOT1, GOT2, PSAT1, GDH1, GPT1, or GLS (e.g., SEQ ID NOs: 81-92). The T cells are transduced with virus encoding the ACTR polypeptide and the Krebs cycle modulating polypeptide separated, for example, by a P2A ribosomal skip sequence. Transduced T cells are mixed at a given effector-to-target (E:T) ratio with tumor target cells, such as IGROV-1 cells, and a tumor-targeting antibody such as an anti-FOLR1 antibody, in media containing different concentrations of soluble inhibitors that are present in the tumor microenvironment (e.g., TGF-beta, $PGE_2$, kynurenine, and/or adenosine). Reactions are then incubated at 37° C. in a 5% $CO_2$ incubator for a period of time (e.g., 6-8 days). T cell function is then evaluated, for example, using cytokine production or T cell proliferation assays or for resistance to chronic stimulation. Cytokine production (e.g., IL-2 and/or IFN-gamma) is measured from the reaction supernatant. For proliferation experiments, co-cultures are harvested and stained with an anti-CD3 antibody and a live-dead cell stain. The number of live, CD3-positive cells is evaluated by flow cytometry as a measure of T cell proliferation. T cells expressing a Krebs cycle modulating polypeptide in addition to the ACTR polypeptide show enhanced T cell function relative to T cells expressing ACTR alone including, for example, enhanced cytokine production or enhanced proliferation. This enhanced function may be achieved at higher soluble inhibitor concentrations. These experiments demonstrate that expressing a Krebs cycle modulating polypeptide in T cells has a positive impact on T cell activity.

Example 3: Impact of Expressing a Krebs Cycle Modulating Polypeptide on T Cell Function in Environments with Greater Immunosuppressive Cell Presence A Krebs cycle modulating polypeptide transgene is co-expressed in the same T cell with an ACTR polypeptide. The transgene is, for example, PHGDG, PCK1, IDH1, IDH1, MDH1, MDH2, GOT1, GOT2, PSAT1, GDH1, GPT1, or GLS (e.g., SEQ ID NOs: 81-92). The T cells are transduced with virus encoding the ACTR polypeptide and the Krebs cycle modulating polypeptide separated, for example, by a P2A ribosomal skip sequence. Transduced T cells are mixed at a given effector-to-target (E:T) ratio with tumor target cells, such as IGROV-1 cells, and a tumor-targeting antibody such as an anti-FOLR1 antibody, in the presence of immunosuppressive cells (e.g., myeloid-derived suppressor cells and/or regulatory T cells). Reactions are then incubated at 37° C. in a 5% $CO_2$ incubator for a period of time (e.g., 3-10 days). T cell function is then evaluated, for example, using cytokine production or T cell proliferation assays or for resistance to chronic stimulation. Cytokine production (e.g., IL-2 and/or IFN-gamma) is measured from the reaction supernatant. For proliferation experiments, co-cultures are harvested and stained with an anti-CD3 antibody and a live-dead cell stain. The number of live, CD3-positive cells is evaluated by flow cytometry as a measure of T cell proliferation. T cells expressing a Krebs cycle modulating polypeptide in addition to the ACTR polypeptide show enhanced T cell function relative to T cells expressing ACTR alone including, for example, enhanced cytokine production or enhanced proliferation. This enhanced function may be achieved in the presence of increased amounts (e.g., greater number or percentage) of immunosuppressive cells. These experiments demonstrate that expressing a Krebs cycle modulating polypeptide in T cells has a positive impact on T cell activity.

Example 4: Impact of Expressing a Krebs Cycle Modulating Polypeptide on T Cell Function on Tumor Models A Krebs cycle modulating polypeptide transgene is co-expressed in the same T cell with an ACTR polypeptide. The transgene is, for example, PHGDG, PCK1, IDH1, IDH1, MDH1, MDH2, GOT1, GOT2, PSAT1, GDH1, GPT1, or GLS (e.g., SEQ ID NOs: 81-92). The T cells are transduced with virus encoding the ACTR polypeptide and the Krebs cycle modulating polypeptide separated, for example, by a P2A ribosomal skip sequence. Transduced T cells are evaluated for anti-tumor activity in mouse tumor models. For these experiments, a tumor cell line, for example IGROV-1, is inoculated into NSG™ (NOD scid gamma, NOD.Cg-Prkdc$^{scid}$ IL2rg$^{tm1Wjl}$/SzJ, Strain 005557) mice. Tumor-bearing mice are subsequently dosed with a tumor-targeting antibody and T cells expressing ACTR alone or ACTR and a Krebs cycle modulating polypeptide. Tumor growth is monitored throughout the course of the experiment. In combination with a tumor-targeting antibody, T cells expressing a Krebs cycle modulating polypeptide in addition to an ACTR polypeptide show enhanced anti-tumor activity relative to T cells expressing an ACTR polypeptide alone. Additionally, in combination with a tumor-targeting antibody, T cells expressing a Krebs cycle modulating polypeptide in addition to an ACTR polypeptide may show enhanced T cell activity including, for example, enhanced proliferation, enhanced T cell persistence, and/or enhanced cytokine production relative to T cells expressing the ACTR polypeptide alone. These experiments demonstrate that expressing a Krebs cycle modulating polypeptide in ACTR-expressing T cells has a positive impact on T cell function in vivo.

Example 5: Impact of Reduced Glucose Concentrations on T Cell Function

Gamma-retrovirus encoding an exemplary GPC3-targeting CAR expression construct of SEQ ID NO: 104 was generated via recombinant technology and used to infect primary human T-cells for generating cells that express a GPC3-targeting CAR polypeptide on their cell surface. A six-day flow-based proliferation assay was then used to test the functionality of the GPC3-targeting CAR expressing cells. Specifically, 200,000 untransduced mock T-cells or T-cells expressing the GPC3-targeting CAR construct were incubated together at a ratio of 4:1 (effector cells/CAR-expressing T cells to target cells) with either 50,000 GPC3+ hepatocellular carcinoma JHH7 or Hep3B tumor cells. The co-culture was incubated at 37° C. in a 5% $CO_2$ incubator for six days in the presence of different concentrations of glucose. At the end of six days, co-cultures were harvested and stained with an anti-CD3 antibody. The number of CD3-positive cells was evaluated by flow cytometry as a measure of T cell proliferation. At lower glucose concentrations, less CAR-T proliferation was observed (FIG. 1). These experiments demonstrate that low glucose environments may have a negative impact on CAR-T cell proliferation activity.

Example 6: Impact of Expressing a Krebs Cycle Modulating Gene on T Cell Function Using a GPC3-Targeting CAR-T Expression Construct Gamma-retrovirus encoding an exemplary GPC3-targeting CAR polypeptide expression construct (SEQ ID NO: 104) was generated via recombinant technology and used to infect primary human T-cells to generate cells expressing a GPC3-targeting CAR polypeptide on their cell surface. Additionally, gamma-retroviruses encoding an exemplary GPC3-targeting CAR polypeptide and a Krebs cycle modulating polypeptide (GOT1 or GOT2) (SEQ ID NOs: 87 and 88, respectively) were generated via recombinant technology and used to infect primary human T-cells to generate cells that expressed a GPC3-targeting polypeptide and a Krebs cycle modulating polypeptide. In the constructs encoding both the CAR polypeptide and the Krebs cycle modulating polypeptide, the two polypeptides were separated by a P2A ribosomal skip sequence. The variants expressed were anti-GPC3 CAR+GOT1 and anti-GPC3 CAR+GOT2. A six-day flow-based proliferation assay was then used to test the functionality of the GPC3-targeting CAR expressing cells. Specifically, 200,000 untransduced mock T-cells, T-cells expressing a GPC3-targeting CAR polypeptide, or T-cells expressing a GPC3-targeting CAR polypeptide and a Krebs cycle modulating polypeptide were incubated together at a ratio of 4:1 (effector CAR-expressing T cells to target cells) with 50,000 GPC3$^+$ hepatocellular carcinoma JHH7 tumor cells. The co-culture was incubated at 37° C. in a 5% $CO_2$ for six days in the presence of 1.25 mM glucose (tumor-relevant) and 10 mM glucose (approximate peripheral blood levels). At the end of six days, co-cultures were harvested and stained with anti-CD3 antibody.

The number of CD3-positive cells was evaluated by flow cytometry as a measure of T cell proliferation. T cells expressing the Krebs cycle modulating polypeptides in addition to the CAR polypeptide demonstrated enhanced T cell proliferation relative to T cells expressing the CAR construct alone (FIGS. 2A, 2B, 3A, and 3B). This enhanced proliferation also occurred at tumor-relevant low glucose concentrations. These experiments demonstrated that expressing Krebs cycle modulating polypeptides in T cells has a positive impact on CAR-T cell proliferation activity.

Example 7: Impact of Expressing a Krebs Cycle Modulating Gene on T Cell Function in Lower Glucose Environments A Krebs cycle modulating transgene is co-expressed in the same T cell with a chimeric antigen receptor (CAR) polypeptide. The transgene is, for example, GPT1, GLS, PCK1, GOT1, GOT2, IDH1, IDH2, MDH1, MDH2, PHGDH, PSAT1, or GDH1 (e.g. SEQ ID NOs: 81-92). The T cells are transduced with a virus encoding the CAR polypeptide and the Krebs cycle metabolite polypeptide separated, for example, by a P2A ribosomal skip sequence. The T cells are mixed at a given effector-to-target (E:T) ratio with tumor target cells, such as HepG2 cells. Reactions are then incubated at 37° C. in a 5% $CO_2$ incubator for a period of time (e.g., 6-8 days) at different starting concentrations of glucose (e.g., 0-20 mM). T cell function is then evaluated, for example, using cytokine production or T cell proliferation assays. Cytokine production (e.g., IL-2 and/or IFN-gamma) is measured from the reaction supernatant. For proliferation experiments, co-cultures are harvested and stained with an anti-CD3 antibody and a live-dead cell stain. The number of live, CD-3 positive cells is evaluated by flow cytometry as a measure of T cell proliferation.

T cells expressing a Krebs cycle modulating polypeptide in addition to the CAR polypeptide are expected to show enhanced T cell function relative to T cells expressing CAR alone including, for example, enhanced cytokine production or enhanced proliferation. This enhanced function may be more pronounced at lower glucose concentrations.

Example 8: Impact of Expressing a Krebs Cycle Modulating Gene on T Cell Function in Environments with Higher Soluble Inhibitor Concentrations A Krebs cycle modulating transgene is co-expressed in the same T cell with a chimeric antigen receptor (CAR) polypeptide. The transgene is, for example, GPT1, GLS, PCK1, GOT1, GOT2, IDH1, IDH2, MDH1, MDH2, PHGDH, PSAT1, or GDH1 (e.g., SEQ ID NOs: 81-92). The T cells are transduced with virus encoding the CAR polypeptide and the Krebs cycle modulating polypeptide separated, for example, by a P2A ribosomal skip sequence. Transduced T cells are mixed at a given effector-to-target (E:T) ratio with tumor target cells, such as HepG2 cells, in media containing different concentrations of soluble inhibitors that are present in the tumor microenvironment (e.g., TGF-beta, $PGE_2$, and/or adenosine). Reactions are then incubated at 37° C. in a 5% $CO_2$ incubator for a period of time (e.g., 6-8 days). T cell function is then evaluated, for example, using cytokine production or T cell proliferation assays. Cytokine production (e.g., IL-2 and/or IFN-gamma) is measured from the reaction supernatant. For proliferation experiments, co-cultures are harvested and stained with an anti-CD3 antibody and a live-dead cell stain. The number of live, CD3-positive cell is evaluated by flow cytometry as a measure of T cell proliferation.

T cells expressing a Krebs cycle modulating polypeptide in addition to the CAR polypeptide are expected to show enhanced T cell function relative to T cells expressing CAR alone including, for example, enhanced cytokine production or enhanced proliferation. This enhanced function may be achieved at higher soluble inhibitor concentrations.

Example 9: Impact of Expressing a Krebs Cycle Modulating Gene on T Cell Function in Environments with Greater Immunosuppressive Cell Presence A Krebs cycle metabolite shunting transgene is co-expressed in the same T cell with a chimeric antigen receptor (CAR) polypeptide. The transgene is, for example, GPT1, GLS, PCK1, GOT1, GOT2, IDH1, IDH2, MDH1, MDH2, PHGDH, PSAT1, or GDH1 (e.g., SEQ ID NOs: 81-92). The T cells are transduced with virus encoding the CAR polypeptide and the Krebs cycle metabolite shunting polypeptide separated, for example, by a P2A ribosomal skip sequence. Transduced T cells are mixed at a given effector-to-target (E:T) ratio with tumor target cells, such as HepG2 cells, in the presence of immunosuppressive cells (e.g., myeloid-derived suppressor cells and/or regulatory T cells) marked with a fluorescent label. Reactions are then incubated at 37° C. in a 5% $CO_2$ incubator for a period of time (e.g., 3-10 days). T cell function is then evaluated, for example, using cytokine production or T cell proliferation assays. Cytokine production (e.g., IL-2 and/or IFN-gamma) is measured from the reaction supernatant. For proliferation experiments, co-cultures are harvested and stained with an anti-CD3 antibody and a live-dead cell stain. The number of live, CD3-positive, unlabeled cells is evaluated by flow cytometry as a measure of T cell proliferation.

T cells expressing a Krebs cycle modulating polypeptide in addition to the CAR polypeptide are expected to show enhanced T cell function relative to T cells expressing CAR alone including, for example, enhanced cytokine production or enhanced proliferation. This enhanced function may be achieved in the presence of increased amounts (e.g., greater number or percentage) of immunosuppressive cells.

Example 10: Impact of Expressing a Krebs Cycle Modulating Polypeptide on T Cell Function in a Mouse Tumor Model Using a GPC3-Targeting CAR-T Expression Construct A Krebs cycle modulating polypeptide (GOT2) (SEQ ID NO: 88) was co-expressed in the same T cells with a GPC3-targeting CAR-T polypeptide (SEQ ID NO:104). Gamma-retrovirus encoding the GPC3-targeting CAR-T expression construct was generated and used to infect primary human T-cells to generate cells that expressed a GPC3-targeting CAR-T on their cell surface. The T cells were also transduced with virus encoding the anti-GPC3 CAR polypeptide and GOT2 separated by a P2A ribosomal skip sequence.

The CAR transduced T cells were evaluated for anti-tumor activity in a mouse tumor model. For these experiments, the hepatocellular carcinoma tumor cell line, JHH7, was inoculated into NSG™ (NOD scid gamma, NOD.Cg-Prkdc$^{scid}$ IL2rg$^{tmWjl}$/SzJ, Strain 005557) mice. Treatment with anti-GPC3 CAR-expressing T cells was initiated when tumor volumes reached approximately 50 mm$^3$ (day 8 post inoculation). Mice were randomized into treatment groups of 5 mice each based on tumor volume, and treated with T cells expressing the GPC3-targeted CAR at a dose of 5×10$^6$ CAR+ T cells on days 8 and 15 post inoculation. The total T cell dose varied based on the CAR transduction efficiency of each construct.

Figure 4:
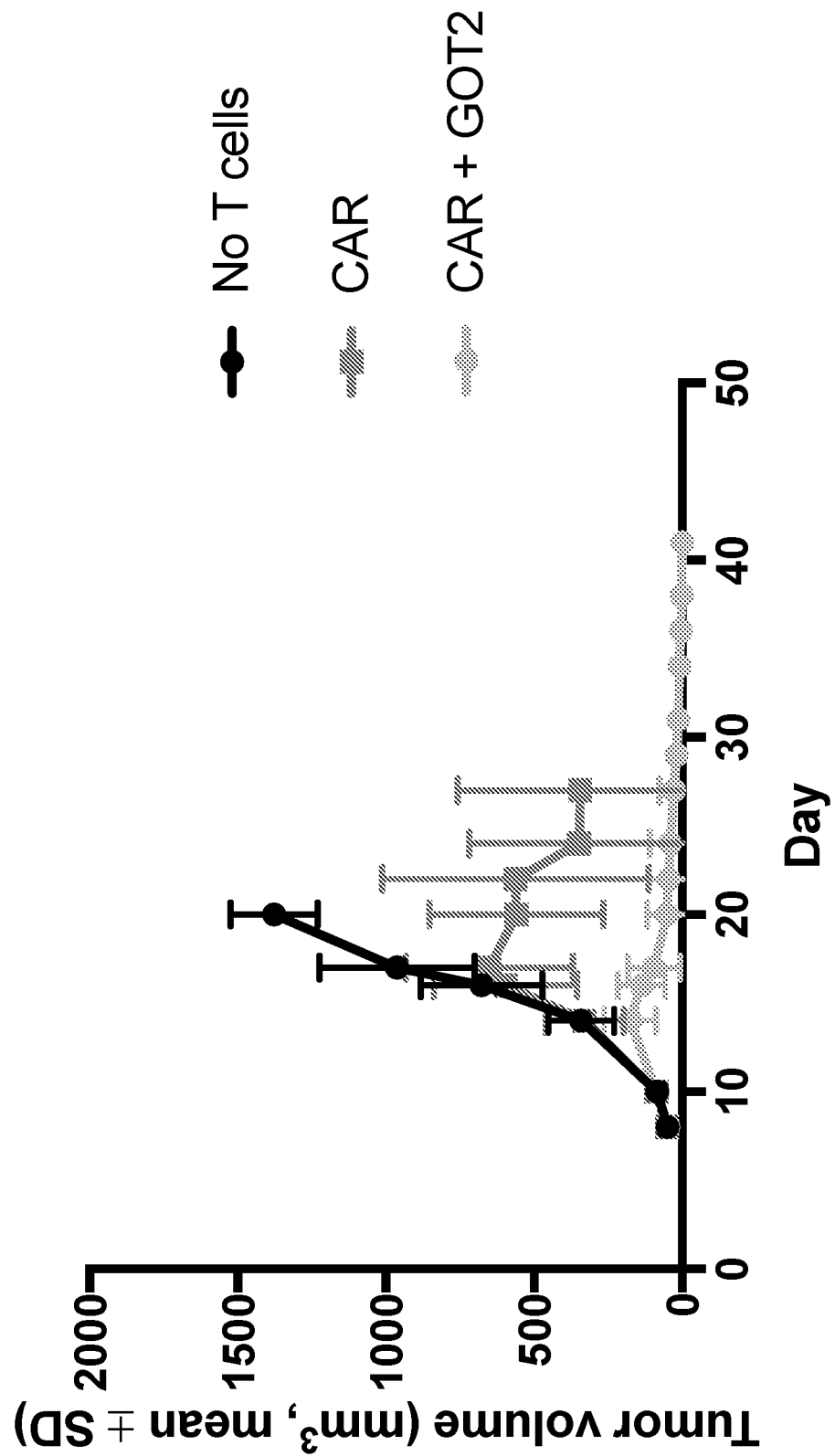
FIG. 4 is a chart showing JHH7 xenograft tumor inhibition activity of T cells expressing a GPC3-targeting CAR and T cells co-expressing the GPC3-targeting CAR (SEQ ID NO:104) and GOT2 (SEQ ID NO:88).

Tumor volume and body weights were measured two-to-three times weekly for the duration of the experiment. CAR-T cells co-expressing GOT2 demonstrated enhanced anti-tumor efficacy relative to the T cells only expressing the GPC3 CAR construct (FIG. 4). These experiments demonstrated that expressing the Krebs cycle modulating polypeptide in CAR-T cells had a positive impact on CAR-T cell anti-tumor efficacy in a mouse xenograft model of hepatocellular carcinoma.

The CAR transduced T cells were evaluated for anti-tumor activity in a mouse tumor model. For these experiments, the hepatocellular carcinoma tumor cell line, Hep3B, was inoculated into NSG™ (NOD scid gamma, NOD.Cg-Prkdc$^{scid}$ IL2rg$^{tmWjl}$/SzJ, Strain 005557) mice. Treatment with anti-GPC3 CAR-expressing T cells was initiated when tumor volumes reached approximately 100 mm$^3$ (day 20 post inoculation). Mice were randomized into treatment groups of 5 mice each based on tumor volume, and treated with T cells expressing the GPC3-targeted CAR at a dose of 1×10$^6$ CAR+ T cells on days 20 and 27 post inoculation. The total T cell dose varied based on the CAR transduction efficiency of each construct.

Figure 6:
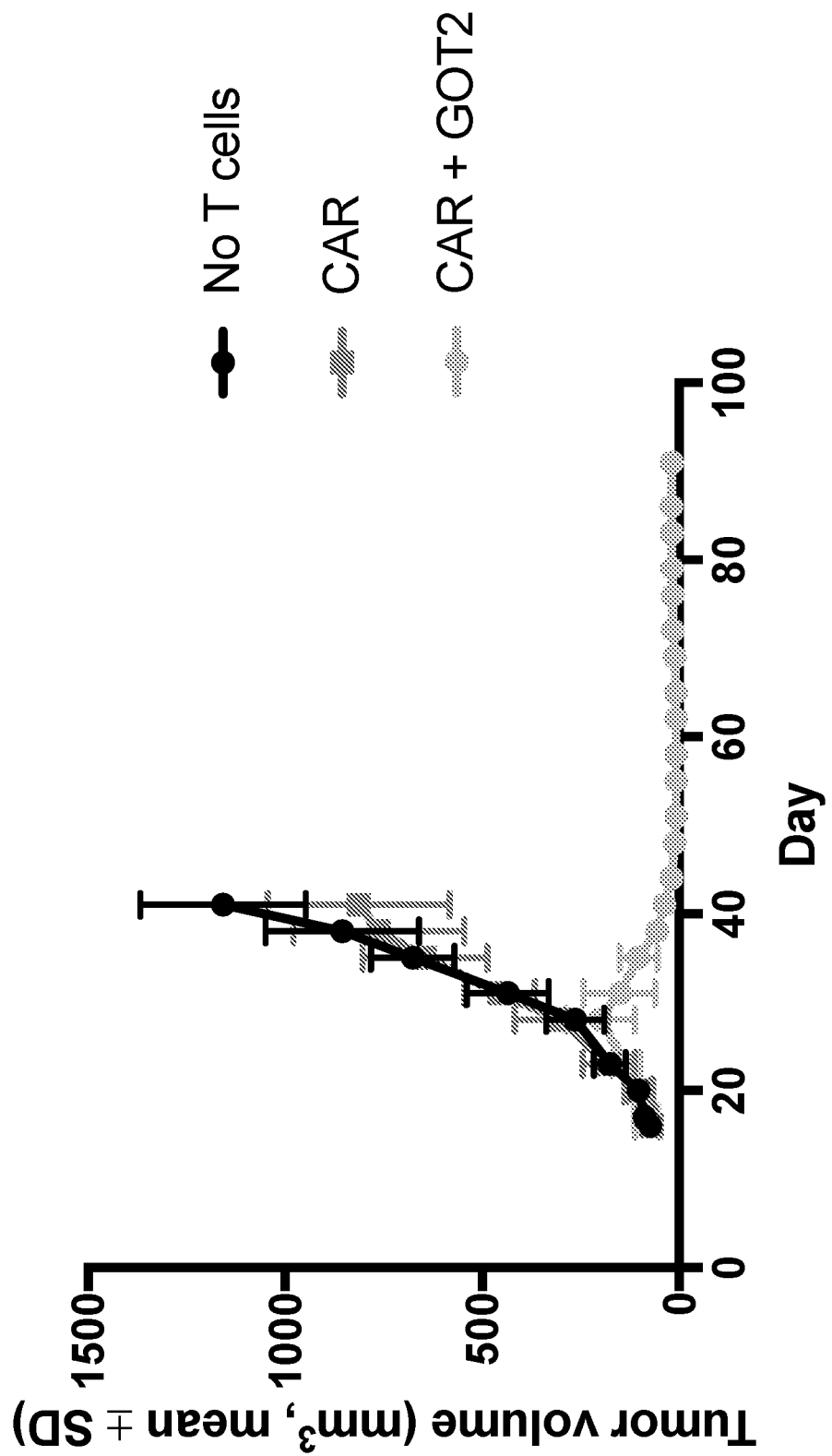
FIG. 6 is a chart showing Hep3B xenograft tumor inhibition activity of T cells expressing a GPC3-targeting CAR and T cells co-expressing the GPC3-targeting CAR (SEQ ID NO: 104) and GOT2 (SEQ ID NO: 88).

Tumor volume and body weights were measured two-to-three times weekly for the duration of the experiment. CAR-T cells co-expressing GOT2 demonstrated enhanced anti-tumor efficacy relative to the T cells only expressing the GPC3 CAR construct (FIG. 6). These experiments demonstrated that expressing the Krebs cycle modulating polypeptide in CAR-T cells had a positive impact on CAR-T cell anti-tumor efficacy in a mouse xenograft model of hepatocellular carcinoma.

The CAR transduced T cells were evaluated for anti-tumor activity in a mouse tumor model. For these experiments, the small cell lung cancer tumor cell line, NCI-H446, was inoculated into NSG™ (NOD scid gamma, NOD.Cg-Prkdc$^{scid}$ IL2rg$^{tmWjl}$/SzJ, Strain 005557) mice. Treatment with anti-GPC3 CAR-expressing T cells was initiated when tumor volumes reached approximately 100 mm$^3$ (day 18 post inoculation). Mice were randomized into treatment groups of 5 mice each based on tumor volume, and treated with T cells expressing the GPC3-targeted CAR at a dose of 5×10$^6$ CAR+ T cells on days 18 and 25 post inoculation. The total T cell dose varied based on the CAR transduction efficiency of each construct.

Figure 5:
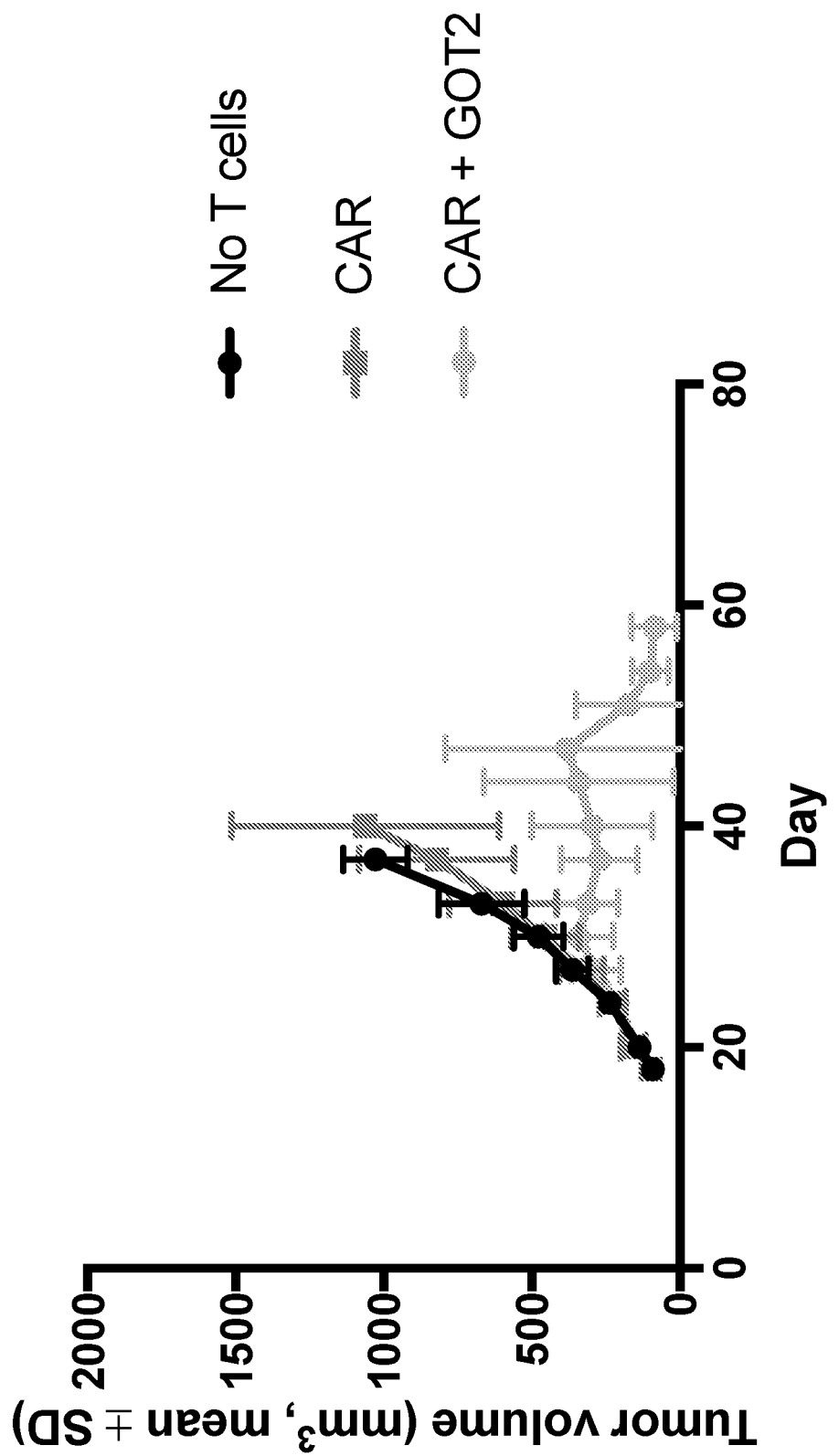
FIG. 5 is a chart showing NCI-H446 xenograft tumor inhibition activity of T cells expressing a GPC3-targeting CAR and T cells co-expressing the GPC3-targeting CAR (SEQ ID NO: 104) and GOT2 (SEQ ID NO: 88).

Tumor volume and body weights were measured two-to-three times weekly for the duration of the experiment. CAR-T cells co-expressing GOT2 demonstrated enhanced anti-tumor efficacy relative to the T cells only expressing the GPC3 CAR construct (FIG. 5). These experiments demonstrated that expressing the Krebs cycle modulating polypeptide in CAR-T cells had a positive impact on CAR-T cell anti-tumor efficacy in a mouse xenograft model of small cell lung cancer.

Example 11: Impact of Expressing a Krebs Cycle Modulating Polypeptide on T Cell Expansion in a Mouse Tumor Model Using a GPC3-Targeting CAR-T Expression Construct A Krebs cycle modulating polypeptide (GOT2) (SEQ ID NO: 88) was co-expressed in the same T cells with a GPC3-targeting CAR-T polypeptide (SEQ ID NO:104). Gamma-retrovirus encoding the GPC3-targeting CAR-T expression construct was generated and used to infect primary human T-cells to generate cells that expressed a GPC3-targeting CAR-T on their cell surface. The T cells were also transduced with virus encoding the anti-GPC3 CAR polypeptide and GOT2 separated by a P2A ribosomal skip sequence.

The CAR-transduced T cells were evaluated for expansion and in a mouse tumor model. For these experiments, the hepatocellular carcinoma tumor cell line, Hep3B, was inoculated into NSG™ (NOD scid gamma, NOD.Cg-Prkdc$^{scid}$ IL2rg$^{tm Wjl}$/SzJ, Strain 005557) mice. Treatment with anti-GPC3 CAR-expressing T cells was initiated when tumor volumes reached approximately 100 mm$^3$ (day 20 post inoculation). Mice were randomized into treatment groups of 5 mice each based on tumor volume, and treated with T cells expressing the GPC3-targeted CAR at a dose of 1×10$^6$ CAR+ T cells on days 20 and 27 post inoculation. The total T cell dose varied based on the CAR transduction efficiency of each construct.

Peripheral blood was collected and stained with an anti-CD3 and an anti-CAR antibody. The number of CD3-positive and CAR-positive cells was evaluated by flow cytometry as a measure of T cell expansion and CAR activity. CAR-T cells co-expressing GOT2 demonstrated enhanced T cell expansion relative to the T cells only expressing the GPC3 CAR construct (FIG. 7). These experiments demonstrated that expressing the Krebs cycle modulating polypeptide in CAR-T cells had a positive impact on CAR-T cell expansion in a mouse xenograft model of hepatocellular carcinoma.

Figure 8B:
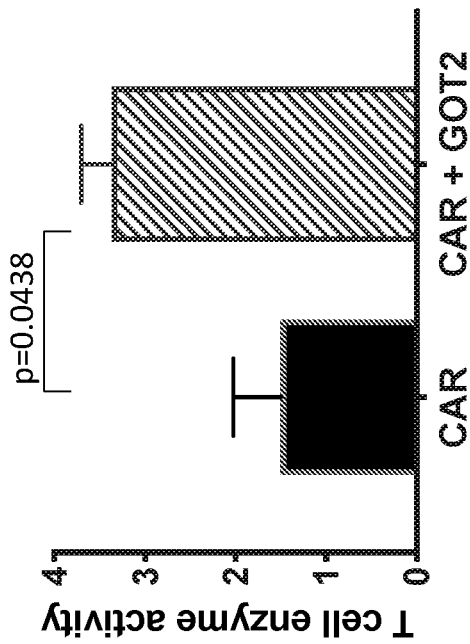
FIG. 8A and FIG. 8B show protein expression and aminotransferase activity in T cells co-expressing anti-GPC3 CAR and GOT2.
Figure 8A:
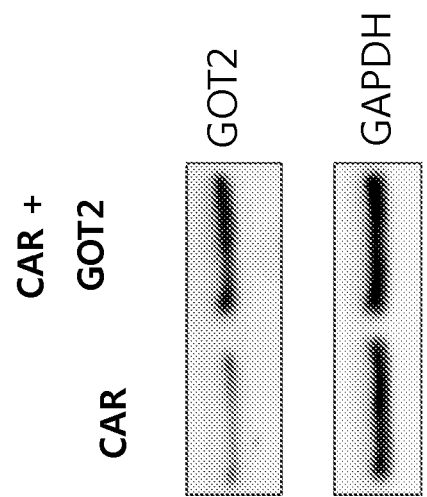

Example 12: Co-Expression of a Krebs Cycle Modulating Gene (GOT2) and a GPC3-Targeting CAR in T Cells Increases Aspartate Aminotransferase Enzyme Activity Gamma-retrovirus encoding an exemplary GPC3-targeting CAR polypeptide expression construct (SEQ ID NO: 104) was generated via recombinant technology and used to infect primary human T-cells to generate cells expressing a GPC3-targeting CAR polypeptide on their cell surface. Additionally, gamma-retrovirus encoding an exemplary GPC3-targeting CAR polypeptide and a Krebs cycle modulating polypeptide (GOT2) (SEQ ID NO:88) was generated via recombinant technology and used to infect primary human T-cells to generate cells that expressed a GPC3-targeting polypeptide and GOT2, with the two polypeptides separated by a P2A ribosomal skip sequence. Expression of GOT2 was confirmed using western blot. CAR transduced T cells were mixed at a 4:1 effector-to-target ratio with GPC3+ hepatocellular carcinoma Hep3B tumor cells and incubated at 37° C., 5% $CO_2$ for 4 days. Following incubation, cell lysates were prepared from 1×10$^6$ cells, cell lysate was combined with Bolt LDS sample buffer (Invitrogen) and 100 nM DTT and run on two separate gels. Proteins from the gels were then transferred onto nitrocellulose membranes (Transblot turbo transfer pack from BioRad). Blots were probed overnight for GOT2 expression using rabbit anti-human GOT2 antibody (Origene) and then probed with HRP-conjugated anti-rabbit antibody or for GAPDH expression using mouse anti-human GAPDH (Biolegend) and then probed with HRP-conjugated anti-mouse IgG secondary antibody. GOT2 expression was greater in T cells transduced with the CAR+GOT2 construct relative to the parental CAR (FIG. 8A) Transduced T cells were mixed at a 4:1 effector-to-target ratio with GPC3+ hepatocellular carcinoma Hep3B tumor cells and incubated at 37° C., 5% $CO_2$ for 8 days. Aspartate aminotransferase (AST) enzyme activity was measured using an Aspartate Aminotransferase Activity Assay Kit (Abcam) according to manufacturer's protocol. AST activity is calculated by measuring the amount of glutamate generated per minute at 37° C. In this example, AST activity was calculated at 50 minutes after addition of substrate. T cells expressing the Krebs-cycle-modulating-polypeptide GOT2 in addition to the CAR polypeptide demonstrated increased AST activity following activation with tumor cells. (FIG. 8B). These experiments demonstrate that expressing a Krebs cycle modulating polypeptide in T cells has a positive impact on T cell function.

Figure 9A:
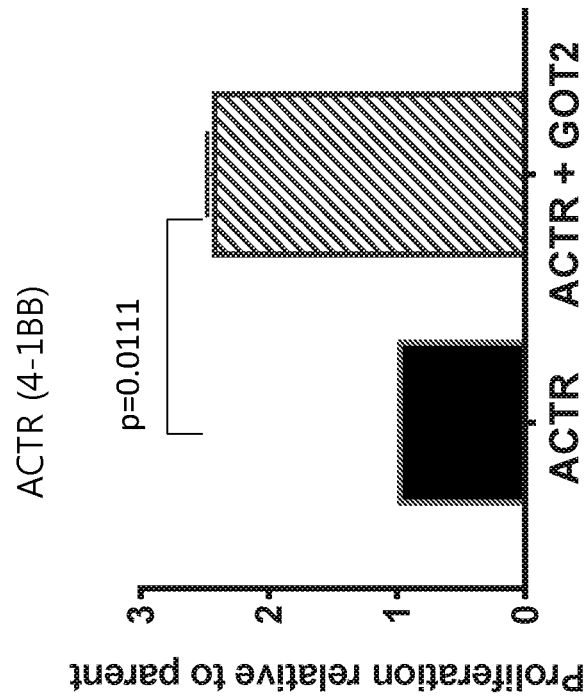
FIG. 9A and FIG. 9B are diagrams that show T cells co-expressing GOT2 (SEQ ID NO: 88) and anti-GPC3 CAR (SEQ ID NO: 104) or ACTR (SEQ ID NO: 1) show enhanced proliferation relative to T cells expressing CAR or ACTR alone.
Figure 9B:
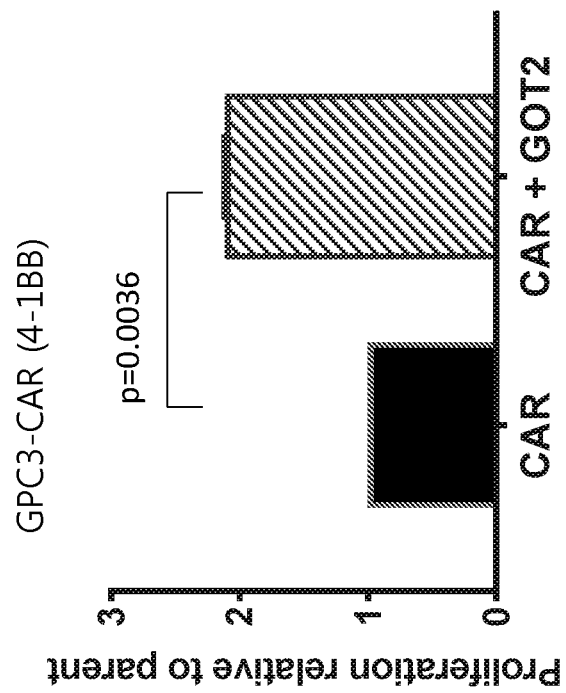

Example 13: Co-Expression of a Krebs Cycle Modulating Gene (GOT2) and Either a GPC3-Targeting CAR or ACTR in T Cells Enhances Proliferation A Krebs cycle modulating polypeptide (GOT2) (SEQ ID NO: 10) was co-expressed in the same T cells with a GPC3-targeting CAR-T polypeptide (SEQ ID NO:1). The T cells were transduced with virus encoding the CAR polypeptide alone or CAR and GOT2 separated by a P2A ribosomal skip sequence. T cells expressing GPC3-targeting CAR and co-expressing GPC3-CAR and GOT2 were labeled with cell trace violet, fluorescently labeling cellular proteins, and then mixed at a 2:1 effector-to-target ratio with GPC3+ hepatocellular carcinoma Hep3B tumor cells. On day 6 after activation, cells were stained with anti-CD3 and cell trace violet dilution was measured by flow cytometry on day 6 after activation to measure proliferation. The inverse of cell trace violet mean fluorescence intensity of CD3+ cells of T cells co-expressing CAR and GOT2 was expressed relative to mean inverse fluorescence intensity of T cells expressing CAR alone. T cells expressing GOT2 in combination with the CAR polypeptide demonstrated increased cell divisions relative to T cells expressing the CAR alone. FIG. 9A A Krebs cycle modulating polypeptide (GOT2) (SEQ ID NO: 10) was co-expressed in the same T cells with an ACTR polypeptide (SEQ ID NO:1). The T cells were transduced with virus encoding the ACTR polypeptide alone or ACTR and GOT2 separated by a P2A ribosomal skip sequence. T cells expressing ACTR and co-expressing ACTR and GOT2 were mixed at a 2:1 effector-to-target ratio with GPC3+ hepatocellular carcinoma HepG2 tumor cells and 1 µg/mL anti-GPC3 antibody GC33 (see Nakano, K et al. Anticancer Drugs. 2010 November; 21(10):907-16). On day 3 after activation, T cell counts were measured by flow cytometry after staining with an anti-CD3 antibody. Total counts of CD3+ cells of T cells co-expressing ACTR and GOT2 was expressed relative to total CD3+ T cell counts of T cells expressing ACTR alone. T cells expressing the GOT2 in addition to the ACTR polypeptide demonstrated increased T cell count. FIG. 9B.

These experiments demonstrate that expressing a Krebs cycle modulating polypeptide in T cells has a positive impact on T cell proliferation.

Figure 10C:
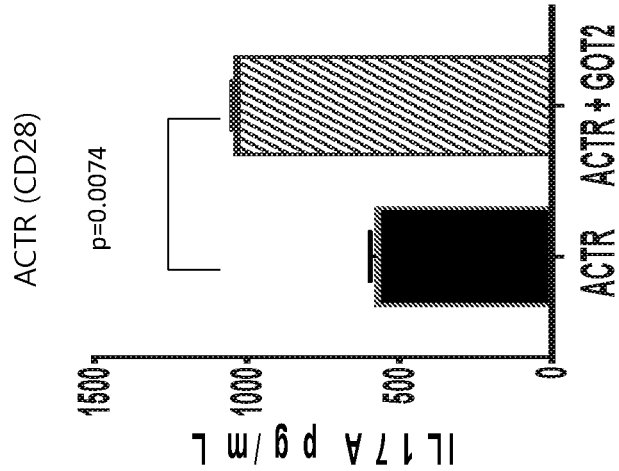
FIGS. 10A-10C are diagrams that show T cells co-expressing GOT2 (SEQ ID NO: 88) and anti-GPC3 CAR (SEQ ID NO: 104) or ACTR (SEQ ID NO: 1 and SEQ ID NO: 57) show enhanced IL-17A production relative to T cells expressing CAR or ACTR alone.
Figure 10B:
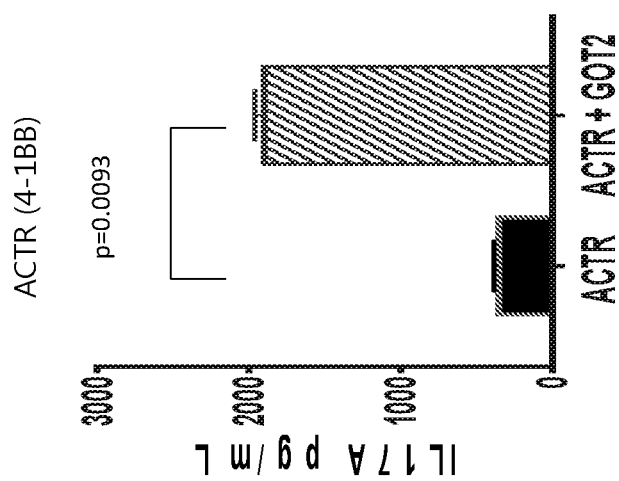
Figure 10A:
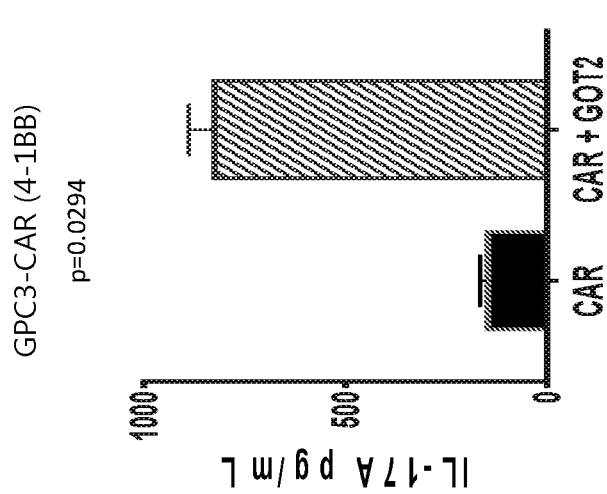

Example 14: Co-Expression of a Krebs Cycle Modulating Gene (GOT2) and Either a GPC3-Targeting CAR or ACTR in T Cells Enhances IL-17A Cytokine Production A Krebs cycle modulating polypeptide (GOT2) (SEQ ID NO: 88) was co-expressed in T cells with a GPC3-targeting CAR-T polypeptide (SEQ ID NO:104) or was co-expressed T cells with an ACTR-4-1BB polypeptide (SEQ ID NO:1) or an ACTR-CD28 polypeptide (SEQ ID NO: 57). The T cells were transduced with virus encoding the CAR or ACTR polypeptide alone or CAR or ACTR and GOT2 separated by a P2A ribosomal skip sequence. Transduced T cells were mixed at a 2:1 effector-to-target ratio with GPC3+ hepatocellular carcinoma HepG2 tumor cells; in experiments with ACTR T cells, the anti-GPC3 antibody GC33 (1 µg/mL) was added. The cells were incubated for 24 hours at 37° C. in a 5% $CO_2$ incubator. Following the incubation, 1004 of cell culture supernatant was collected and IL-17A was measured using an MSD ELISA (Meso Scale Discovery, Pacific BioLabs) according to the manufacturer's instructions. IL-17A production is plotted as a function of expression construct (FIGS. 10A-10C). T cells co-expressing GOT2 and CAR (FIG. 10A) or ACTR polypeptides (FIGS. 10B-10C) demonstrated the enhanced ability to produce IL-17A relative to T cells expressing CAR or ACTR alone. These experiments demonstrate that expressing a Krebs cycle modulating polypeptide in T cells has a positive impact on IL-17A cytokine production.

Example 15: Co-Expression of a Krebs Cycle Modulating Gene (GOT2) and Either a GPC3-Targeting CAR or ACTR Enhances CD4+ T Cell Polyfunctionality A Krebs cycle modulating polypeptide (GOT2) (SEQ ID NO: 88) was co-expressed in the same T cells with a GPC3-targeting CAR-T polypeptide (SEQ ID NO:104) or was co-expressed in the same T cells with an ACTR polypeptide containing either a 4-1BB (SEQ ID NO:1) or CD28 (SEQ ID NO:57) primary costimulatory domain. The T cells were transduced with virus encoding the CAR or ACTR polypeptide alone or CAR or ACTR and GOT2 separated by a P2A ribosomal skip sequence. Transduced T cells were mixed at a 1:1 effector-to-target ratio with GPC3+ hepatocellular carcinoma HepG2 tumor cells; in experiments with ACTR T cells, the anti-GPC3 antibody GC33 (1 µg/mL) was added. The cells were incubated in the presence of protein transport inhibitors, Brefeldin A (5 µg/mL) and Monensin (2 µM), for 6 hours at 37° C. in a 5% $CO_2$ incubator. Following the incubation, co-cultures were stained with anti-CD4 and anti-CD8 antibodies for both CAR and ACTR T cells; ACTR T cells were also stained with an anti-CD16 antibody. The cells were subsequently fixed, permeabilized, and stained with anti-IFNγ, anti-IL-2, anti-TNFα, and anti-IL-17A antibodies to quantify intracellular cytokine production.

The frequency of CD4+ T cells producing multiple cytokines was quantified by flow cytometry. T cells expressing GOT2 in addition to the CAR or ACTR polypeptides had a higher frequency of CD4+ T cells producing greater than one, two, or three cytokines simultaneously relative to T cells expressing CAR or ACTR alone, demonstrating greater polyfunctionality in the GOT2-expressing cells (FIGS. 11A-11C). These experiments demonstrate that expressing a Krebs cycle modulating polypeptide in T cells has a positive impact on CD4 T cell polyfunctionality.

Figures 12A, 12B, 12C:
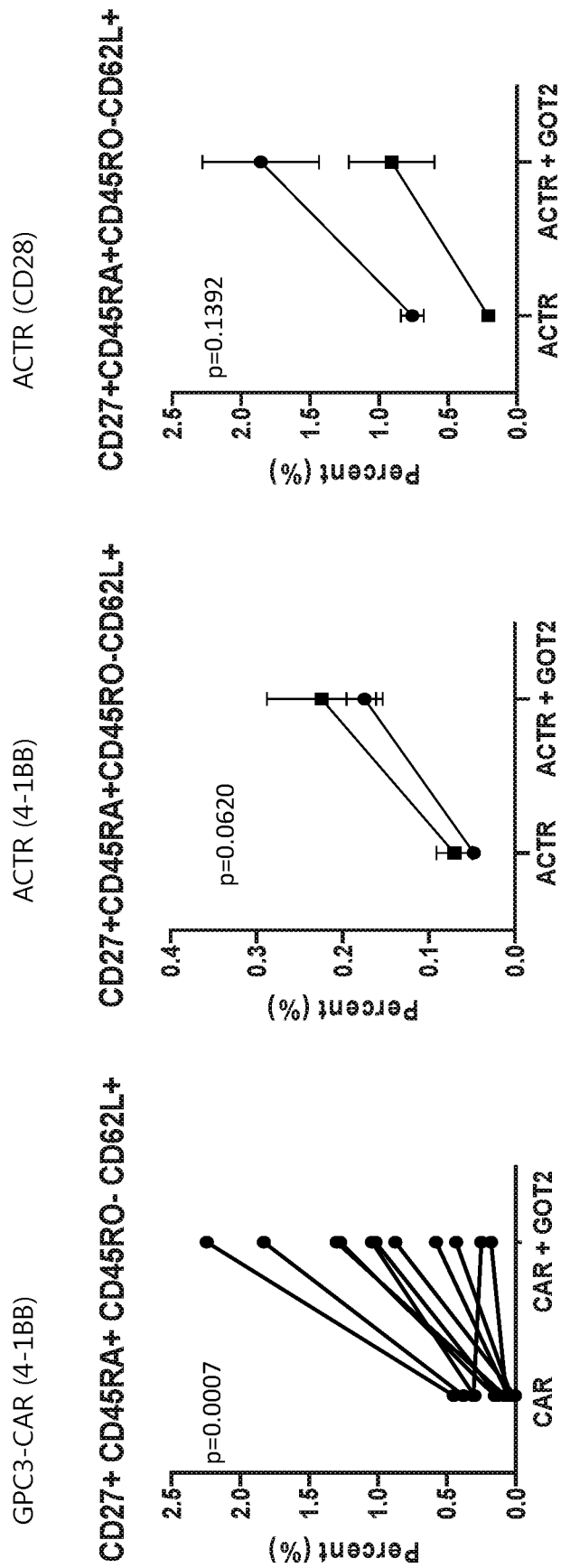
FIGS. 12A-12C are diagrams that show T cells co-expressing GOT2 (SEQ ID NO: 88) and anti-GPC3 CAR (SEQ ID NO: 104) or ACTR (SEQ ID NO: 1 and SEQ ID NO: 57) showed a greater population of less-differentiated, naïve-like CD8+ T cells relative to T cells expressing CAR or ACTR alone.
Figure 13:
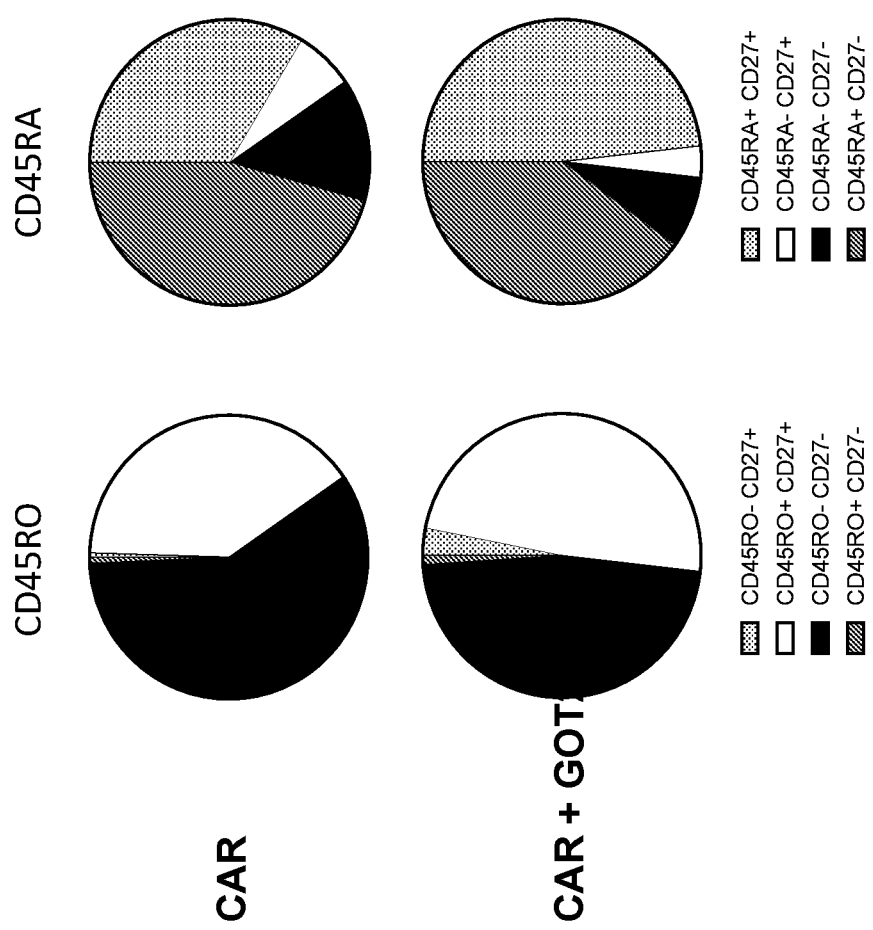
FIG. 13 is a diagram that shows T cells co-expressing GOT2 (SEQ ID NO: 88) and anti-GPC3 CAR (SEQ ID NO: 104) demonstrated a less-differentiated (younger) CD8+ T cell phenotype relative to T cells expressing CAR alone. CAR T cells generated from 11 healthy donors were stained for a panel of surface markers and analyzed by flow cytometry. Cells were gated on CD8+/CAR+. The populations staining CD27+CD45RO+, CD27+RO−, CD27+CD45RA+ or CD27+CD45RA− indicate a less-differentiated phenotype. These subsets were enriched in CAR T cells co-expressing GOT2 relative to T cells expressing CAR alone.

Example 16: Co-Expression of a Krebs Cycle Modulating Gene (GOT2) and Either a GPC3-Targeting CAR or ACTR Increases Frequency of CD8+ Cells with Less-Differentiated, Naïve-Like Phenotype A Krebs cycle modulating polypeptide (GOT2) (SEQ ID NO: 88) was co-expressed in the same T cells with a GPC3-targeting CAR-T polypeptide (SEQ ID NO:104) or was co-expressed in the same T cells with an ACTR polypeptide containing either a 4-1BB (SEQ ID NO:1) or CD28 (SEQ ID NO:57) primary costimulatory domain. The T cells were transduced with virus encoding the CAR or ACTR polypeptide alone or CAR or ACTR and GOT2 separated by a P2A ribosomal skip sequence. T cell phenotype of CAR constructs from 11 healthy donors and of ACTR constructs for two healthy donors was assessed by flow cytometry. For these experiments, cells were thawed and stained with anti-CD3, anti-CD4, anti-CD8, anti-CD45RA, anti-CD45RO, anti-CD27 and anti-CD62L antibodies for both CAR- and ACTR-expressing T cells. CAR T cells were also stained with recombinant GPC3 protein to detect the CAR polypeptide and ACTR T cells were also stained with an anti-CD16 antibody to detect the ACTR polypeptide. The frequency of CD8+ CAR+ or ACTR+ T cells that stained positive for CD27, CD45RA, CD62L and negative for CD45RO was higher in T cells that also co-expressed GOT2 relative to the cognate parent, demonstrating that GOT2-expressing cells have a more naïve-like CD8+ population (FIGS. 12A-12C). Overall, the phenotype of CD8+ CAR or ACTR T cells co-expressing GOT2 show a greater proportion of cells with phenotypic markers of less differentiated (younger) phenotype (CD27+/CD45RO+, CD27+/CD45 RO−, CD27+/CD45RA+, CD27+/CD45RA−) relative to parent CAR (FIG. 13). These experiments demonstrate that expressing a Krebs cycle modulating polypeptide in T cells has a positive impact on CD8 phenotype.

Figure 14:
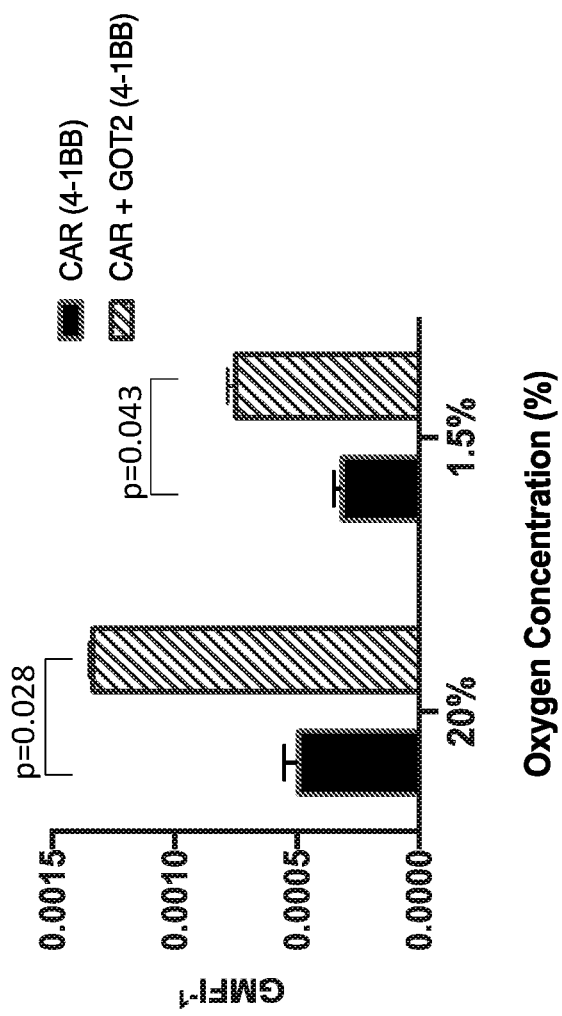
FIG. 14 is a diagram that shows T cells co-expressing GOT2 (SEQ ID NO: 88) and anti-GPC3 CAR (SEQ ID NO: 104) demonstrated a proliferative advantage relative to T cells expressing CAR alone under chronic antigen stimulation and hypoxia. CAR T cells were activated with Hep3B GPC3-expressing tumor cells for 3 days; and then re-stimulated with fresh target cells for 3 days under normoxic (20% oxygen) or hypoxic (1.5%) conditions to simulate the tumor microenvironment stress of chronic antigen stimulation with and without the additional stress of hypoxia. Proliferation was then assessed by flow cytometry of CD3+ T cells using intracellular cell trace violet dilution as a measure of cell division and the inverse of mean fluorescence is plotted.

Example 17: Co-Expression of a Krebs Cycle Modulating Gene (GOT2) and a GPC3-Targeting CAR in T Cells Improves Proliferation Under Chronic Antigen Stimulation and Hypoxia A Krebs cycle modulating polypeptide (GOT2) (SEQ ID NO: 88) was co-expressed in the same T cells with a GPC3-targeting CAR-T polypeptide (SEQ ID NO:104). The T cells were transduced with virus encoding the CAR polypeptide alone or CAR and GOT2 separated by a P2A ribosomal skip sequence. T cells expressing GPC3-targeting CAR and T cells co-expressing GPC3-CAR and GOT2 cells were labeled with cell trace violet, fluorescently labeling cellular proteins, and then mixed at a 2:1 effector-to-target ratio with GPC3+ hepatocellular carcinoma Hep3B tumor cells. On day 3 after activation, cells were washed, and then mixed at a 2:1 effector-to-target ratio with fresh GPC3+ hepatocellular carcinoma Hep3B tumor cells as a second antigen stimulation. Cells were incubated under normoxic (20% oxygen) or hypoxic (1.5% oxygen) conditions for 3 additional days, and then stained with anti-CD3 and cell trace violet dilution was measured by flow cytometry to measure proliferation, expressed as inverse of cell trace violet mean fluorescence intensity ($MFI^{-1}$). T cells expressing GOT2 in addition to the CAR polypeptide demonstrated increased proliferation under chronic antigen stimulation, under both the normoxic and hypoxic conditions (FIG. 14), simulating multiple stresses of the tumor microenvironment. These experiments demonstrate that expressing a Krebs cycle modulating polypeptide in T cells provides a proliferative advantage under unfavorable conditions present in the solid tumor microenvironment.

Example 18: Co-Expression of a Krebs Cycle Modulating Gene (GOT2) and a GPC3-Targeting CAR in T Cells Improves Proliferation in Limiting Glucose Conditions A Krebs cycle modulating polypeptide (GOT2) (SEQ ID NO: 88) was co-expressed in the same T cells with a GPC3-targeting CAR-T polypeptide containing a 4-1BB (SEQ ID NO:104) or CD28 (SEQ ID NO: 105) costimulatory domain. The T cells were transduced with virus encoding the CAR polypeptide alone or CAR and GOT2 separated by a P2A ribosomal skip sequence. T cells transduced with the GPC3-targeting CAR-T polypeptide were isolated with AlexaFluor 647-conjugated GPC3 recombinant protein and anti-AlexaFluor647 microbeads (Miltenyi Biotec) and allowed to rest in RPMI+10% FBS overnight. Transduced T cells were then labeled with cell trace violet and mixed at a 2:1 effector-to-target ratio with GPC3+ hepatocellular carcinoma HepG2 tumor cells. Co-cultures were incubated in the presence of high (10 mM) or low (1.25 mM) glucose to mimic the limited nutrient availability in the tumor microenvironment. After 7 days at 37° C. in a 5% $CO_2$ incubator, the cells were stained with an anti-CD3 antibody and cell division was assessed by cell trace violet dilution via flow cytometry.

Figure 15:
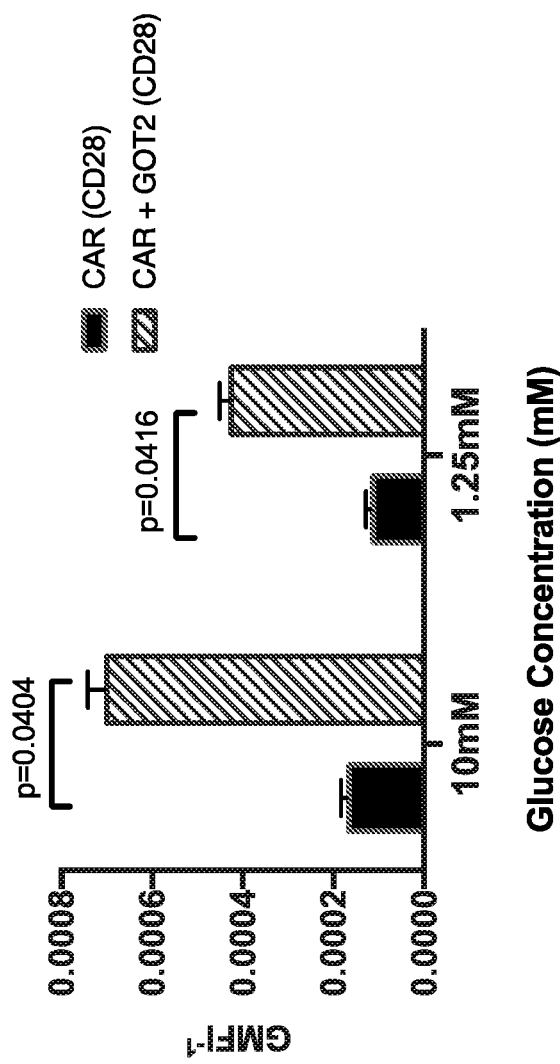
FIG. 15 is a diagram that shows T cells co-expressing GOT2 (SEQ ID NO: 88) and anti-GPC3 CAR (SEQ ID NO: 104) demonstrated a proliferative advantage relative to T cells expressing CAR alone under limiting glucose. CAR T cells were activated with HepG2 GPC3-expressing tumor cells in the presence of 10 mM or 1.25 mM glucose for 7 days. Proliferation was then assessed by flow cytometry using intracellular cell trace violet dilution as a measure of cell division and the inverse of mean fluorescence is plotted. CARs expressing GOT2 had a proliferative advantage in under both glucose conditions.

T cells co-expressing GOT2 and the CAR polypeptide demonstrated greater proliferation in both 10 mM and 1.25 mM glucose relative to T cells expressing CAR alone, as indicated by decreased cell trace violet fluorescence intensity. The inverse of cell trace violet fluorescence intensity was plotted as a function of glucose condition and T cell type (FIG. 15). These experiments demonstrate that expressing a Krebs cycle modulating polypeptide in T cells has a positive impact on T cell proliferation in CAR-T cells that contain 4-1BB or CD28 costimulatory domains and in high and low glucose conditions.

Figure 16:
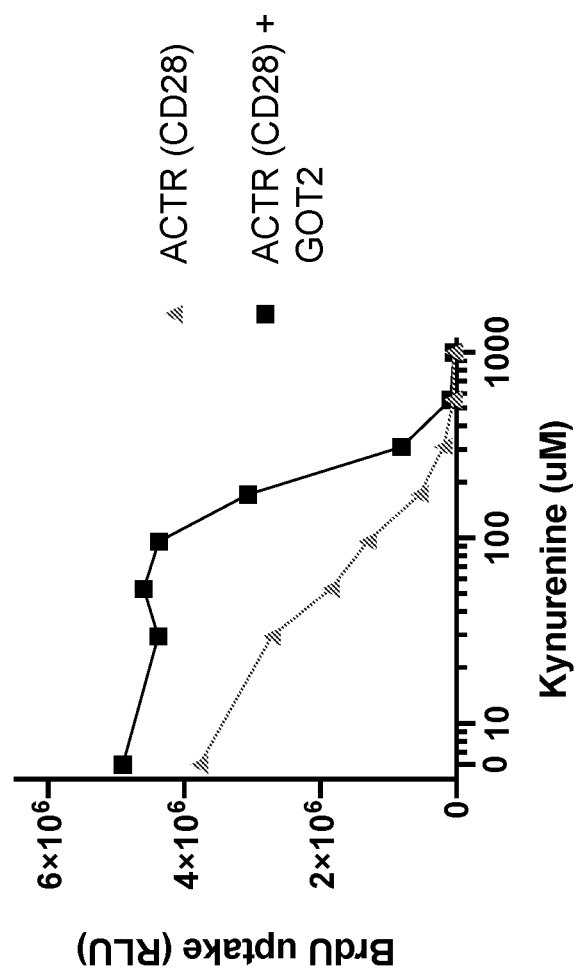
FIG. 16 is a diagram that shows T cells co-expressing GOT2 (SEQ ID NO: 88) and ACTR (SEQ ID NO: 57) demonstrated enhanced proliferation in the presence of the T cell inhibitor kynurenine relative to T cells expressing ACTR alone.

Example 19: Co-Expression of a Krebs Cycle Modulating Gene (GOT2) and a GPC3-Targeting CAR in T Cells Improves Proliferation in the Presence of the T Cell Inhibitor Kynurenine A Krebs cycle modulating polypeptide (GOT2) (SEQ ID NO: 88) was co-expressed in the same T cells with an ACTR polypeptide (SEQ ID NO:57) containing a CD28 primary costimulatory domain and compared in functional assays with T cells expressing the ACTR polypeptide alone. The T cells were transduced with virus encoding the ACTR polypeptide alone or ACTR and GOT2 separated by a P2A ribosomal skip sequence. T cells were mixed at a 4:1 effector-to-target ratio with folate receptor alpha expressing (FOLR+) ovarian carcinoma IGROV-1 tumor cells (fixed in paraformaldehyde) with the addition of anti-FOLR antibody (5 μg/mL). Co-cultures were incubated for 6 days at 37° C. in a 5% $CO_2$ incubator. Following incubation, half of the cells were transferred to a new plate, pulsed with BrdU (Millipore Sigma), incubated for ~16 hrs at 37° C. in a 5% $CO_2$ incubator, and analyzed for BrdU uptake following the manufacturer's directions using an EnVision plate reader (Perkin Elmer) to detect chemiluminescence. T cells co-expressing GOT2 and ACTR demonstrated improved proliferation, as shown by increased BrdU uptake, both in the absence of and in the presence of kynurenine relative to T cells expressing ACTR alone. These experiments demonstrate that expressing a Krebs cycle modulating polypeptide in T cells provides a proliferative advantage in the presence of inhibitory molecules found in the solid tumor microenvironment. FIG. 16.

Example 20: Co-Expression of a Krebs Cycle Modulating Gene (GOT2) and a GPC3-Targeting CAR in T Cells Results in Diminished Sustained Inhibitory Receptor Expression on T Cells Isolated from GPC3+ Solid Tumor Xenografts A Krebs cycle modulating polypeptide (GOT2) (SEQ ID NO: 88) was co-expressed in the same T cells with a GPC3-targeting CAR-T polypeptide (SEQ ID NO:104). The T cells were transduced with virus encoding the CAR polypeptide alone or CAR and GOT2 separated by a P2A ribosomal skip sequence.

The ex vivo phenotype of CAR T cells was evaluated after injection into a mouse tumor model. For these experiments, the GPC3+ hepatocellular carcinoma tumor cell line, JHH7 was inoculated into NSG™ (NOD scid gamma, NOD.Cg-Prkdc$^{scid}$ IL2rg$^{tm Wjl}$/SzJ, Strain 005557) mice. Treatment with T cells was initiated when tumor volumes reached approximately 100 mm$^3$ (day 11 post inoculation). Mice were randomized into treatment groups of 5 mice each based on tumor volume, and treated with T cells expressing the GPC3-targeted CAR or T cells co-expressing the GPC3-targeted CAR and GOT2 at a dose of 5×10$^6$ CAR+ T cells on day 11 post inoculation.

Subcutaneous tumors were harvested from JHH7 tumor bearing mice on day 2, 7, and 14 post T cell dosing. Tumors were minced with a razor blade and enzymatically digested using a human tumor dissociation kit (Miltenyi Biotec) for 1 hour at 37° C. Digested tumors were passed through a 70 μm cell strainer prior to seeding in a 96 well plate for cell staining.

Immunodeficient mice bearing established JHH7 GPC3-expressing subcutaneous tumors were treated with a single intravenous injection of 5×10$^6$ T cells co-expressing CAR and GOT2 or T cells expressing CAR alone. Cohorts of animals were euthanized on days 2, 7 and 14 and T cells were isolated from tumors through manual and enzymatic digestion. Flow cytometry was performed, and mean fluorescence intensity of CD69, CD25, and ICOS activation molecules was quantified on CD4+ and CD8+ T cell subsets. T cell phenotype was assessed by flow cytometry following red blood cell lysis and cell staining. For these experiments, cells isolated from tumors were stained with anti-CD3, anti-CD4, anti-CD8, anti-PD-1, anti-TIM-3, anti-CD69, anti-CD25, and anti-ICOS antibodies. The mean fluorescence intensity of CD69, CD25, and ICOS activation molecules were quantified on CD4+ and CD8+ T cell subsets isolated from the tumor on day 2 (CD69) or day 7 (CD25, ICOS) and plotted for each T cell type. As shown in FIGS. 17A-17C, T cells expressing co-expressing GOT2 and the CAR polypeptide demonstrated increased expression of CD69, CD25, and ICOS activation markers relative to T cells expressing the CAR alone.

Figure 18A:
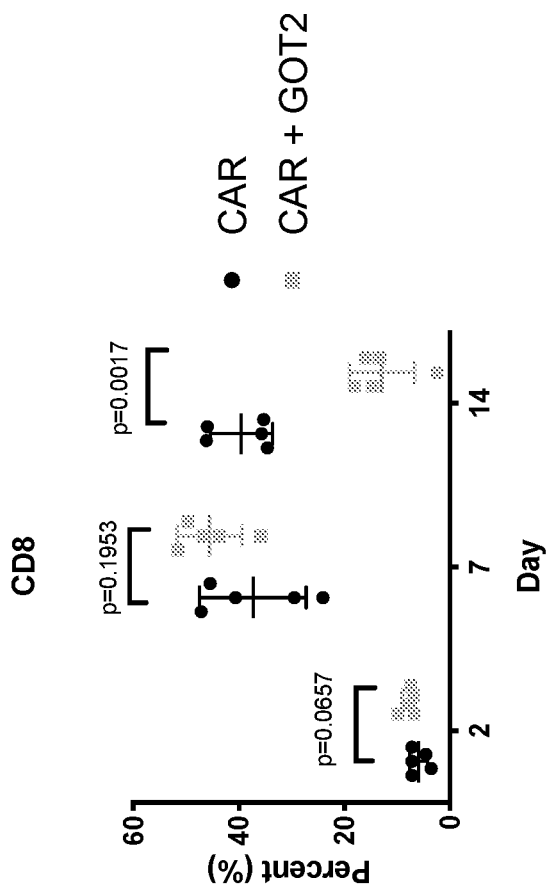
FIG. 18A and FIG. 18B are diagrams that show T cells co-expressing GOT2 (SEQ ID NO: 88) and anti-GPC3 CAR (SEQ ID NO: 104) demonstrated greater resistance to exhaustion in tumors relative to T cells expressing CAR alone.
Figure 18B:
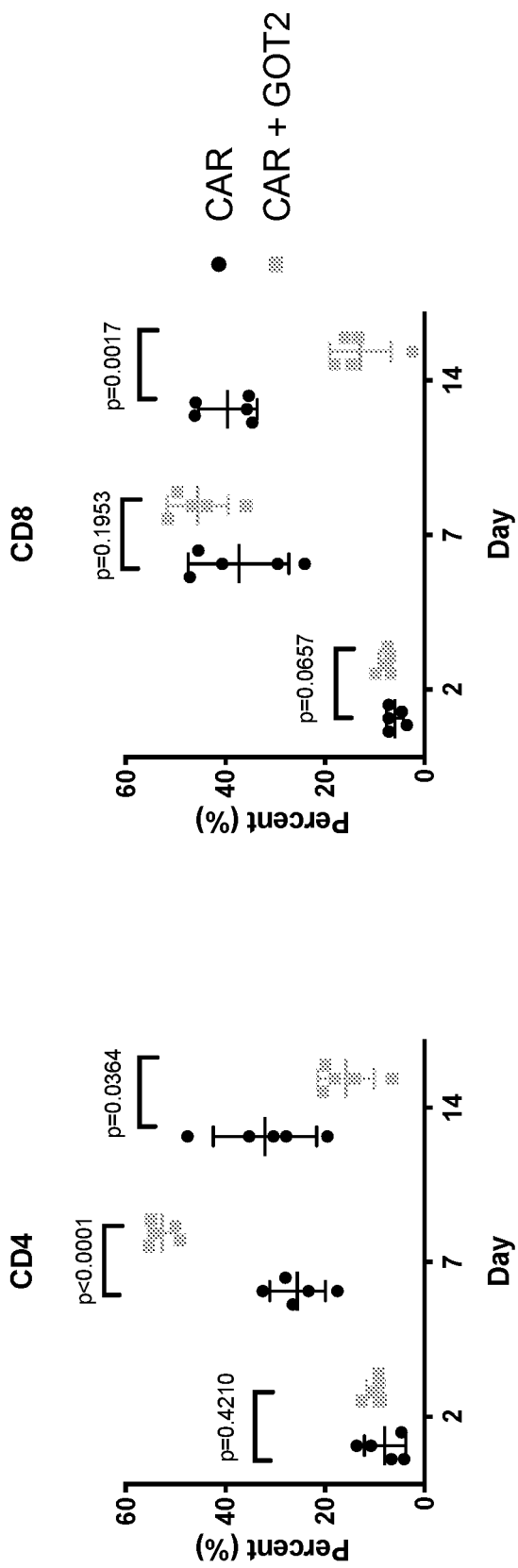

Immunodeficient mice bearing established JHH7 GPC3-expressing subcutaneous tumors were treated with a single intravenous injection of 5×10$^6$ T cells co-expressing CAR and GOT2 or T cells expressing CAR alone. Cohorts of animals were euthanized on days 2, 7 and 14 and T cells were isolated from tumors and spleen through manual and enzymatic digestion. Flow cytometry was performed, and the frequency of T cells co-expressing PD-1 and TIM-3 inhibitory molecules was quantified on CD4+ and CD8+ T cell subsets. The frequency of T cells co-expressing PD-1 and TIM-3 inhibitory molecules were quantified on CD4+ and CD8+ T cell subsets isolated from the tumor and plotted for each T cell type as a function of timepoint. T cells co-expressing CAR and GOT2 showed comparable or higher frequency of PD-1+TIM-3+ T cells on day 7 relative to T cells expressing CAR alone, but lower frequency of PD-1+TIM-3+ T cells on day 14. FIGS. 18A-18B. These results show that T cells co-expressing CAR and GOT2 are more resistant to sustained expression of inhibitory receptors relative to T cells expressing CAR alone. These experiments demonstrate that expressing a Krebs cycle modulating polypeptide in T cells enhances activation and limits sustained inhibitory receptor expression of T cell in the solid tumor microenvironment.

Example 21: Co-Expression of a Krebs Cycle Modulating Gene (GOT2) and a GPC3-Targeting CAR in T Cells Results in Resistance to Sustained Inhibitory Receptor Expression on T Cells Isolated from GPC3+ Solid Tumor Xenografts A Krebs cycle modulating polypeptide (GOT2) (SEQ ID NO: 88) was co-expressed in the same T cells with a GPC3-targeting CAR-T polypeptide (SEQ ID NO:104). The T cells were transduced with virus encoding the CAR polypeptide alone or CAR and GOT2 separated by a P2A ribosomal skip sequence.

The ex vivo phenotype of CART cells was evaluated after injection into a mouse tumor model. For these experiments, the GPC3+ hepatocellular carcinoma tumor cell line, JHH7 was inoculated into NSG™ (NOD scid gamma, NOD.Cg-Prkdc$^{scid}$ IL2rg$^{tmWj1}$/SzJ, Strain 005557) mice. Treatment with T cells was initiated when tumor volumes reached approximately 80 mm$^3$ (day 10 post inoculation). Mice were randomized into treatment groups of 3 mice each based on tumor volume, and treated with T cells expressing the GPC3-targeted CAR or T cells co-expressing the GPC3-targeted CAR and GOT2 at a dose of 5×10$^6$ CAR+ T cells on day 11 post inoculation.

Subcutaneous tumors and spleen tissues were harvested from JHH7 tumor bearing mice on day 1, 6, and 13 post T cell dosing. Tumors were minced with a razor blade and enzymatically digested using a human tumor dissociation kit (Miltenyi Biotec) for 1 hour at 37° C. Spleens were dissociated mechanically using the end of a syringe plunger. Digested tumors and spleens were passed through a 70 μm cell strainer prior to seeding in a 96 well plate for cell staining.

Immunodeficient mice bearing established JHH7 GPC3-expressing subcutaneous tumors were treated with a single intravenous injection of 5×10$^6$ T cells co-expressing CAR and GOT2 or T cells expressing CAR alone. Cohorts of animals were euthanized on days 6 and 13, and T cells were isolated from tumors and spleen through manual and enzymatic digestion. Flow cytometry was performed, and the frequency of T cells co-expressing PD-1 and TIM-3 inhibitory molecules was quantified on CD4+ and CD8+ T cell subsets.

T cell phenotype was assessed by flow cytometry following red blood cell lysis and cell staining. For these experiments, cells were stained with anti-CD3, anti-CD4, anti-CD8, anti-PD-1, and anti-TIM-3 antibodies. The frequency of T cells co-expressing PD-1 and TIM-3 was quantified on CD4+ and CD8+ T cell subsets. T cells in CD4+ and CD8+ subsets co-expressing CAR and GOT2 demonstrated comparable to higher frequency of PD-1+TIM-3+ T cells on day 6 relative to T cells expressing CAR alone, indicating activation, but a diminished frequency of expression after prolonged exposure to the tumor microenvironment (day 13) compared T cells expressing CAR alone, indicating a resistance to sustained inhibitory receptor expression. T cells isolated from the spleen did not show PD-1+TIM-3+ expression at either day 6 or 13, demonstrating the specificity of activation to GPC3-expressing tumor only. FIGS. 19A-19D. T cells co-expressing CAR and GOT2 showed higher frequency of PD-1+TIM-3+ T cells on day 6 relative to T cells expressing CAR alone. FIGS. 19A and 18B. On the other hand, T cells co-expressing CAR and GOT2 showed lower frequency of PD-1+TIM-3+ T cells on day 13, after prolonged exposure to the tumor microenvironment, indicating a resistance to sustained inhibitory receptor expression, compared to T cells expressing CAR alone. FIGS. 19C and 19D. T cells isolated from the spleen did not show PD-1+TIM-3+ expression at either day 6 or 13, demonstrating the specificity of T cell activation in GPC3-expressing tumor only. FIGS. 19A-19D.

These experiments demonstrate that expressing a Krebs cycle modulating polypeptide in T cells provides resistance sustained inhibitory receptor expression in the solid tumor microenvironment.

Example 22: Co-Expression of a Krebs Cycle Modulating Gene (GOT2) and a GPC3-Targeting CAR in T Cells Results in Sustained T Cell Functionality after Exposure to the Tumor Microenvironment In Vivo A Krebs cycle modulating polypeptide (GOT2) (SEQ ID NO: 88) was co-expressed in the same T cells with a GPC3-targeting CAR-T polypeptide (SEQ ID NO:104). The T cells were transduced with virus encoding the CAR polypeptide alone or CAR and GOT2 separated by a P2A ribosomal skip sequence.

The function of CAR transduced cells was evaluated in a mouse tumor model. For these experiments, the GPC3+ hepatocellular carcinoma tumor cell line, JHH7 was inoculated into NSG™ (NOD scid gamma, NOD.Cg-Prkdc$^{scid}$ IL2rg$^{tmWj1}$/SzJ, Strain 005557) mice. Treatment with T cells was initiated when tumor volumes reached approximately 80 mm$^3$ (day 10 post inoculation). Mice were randomized into treatment groups of 3 mice each based on tumor volume, and treated with T cells expressing the GPC3-targeted CAR at a dose of 5×10$^6$ CAR+ T cells on day 11 post inoculation.

Subcutaneous tumors were harvested from JHH7 tumor bearing mice on day 3 post CAR dose. Tumors were minced with a razor blade and enzymatically digested using a human tumor dissociation kit (Miltenyi Biotec) for 1 hour at 37° C. Digested tumors were passed through a 70 μm cell strainer prior to seeding in a 24 well plate (1×10$^6$ cells/1 mL volume). Following incubation for 18 hours at 37° C. in a 5% CO$_2$ incubator, cell supernatants were collected for cytokine analysis. The concentration of IFNγ and IL-17A in the cell supernatants was determined using homogenous time resolved fluorescence assay (Cisbio) and Meso Scale Discovery V-Plex assay technology, respectively. Both assays were performed according to the manufacturer's protocol.

Figure 20B:
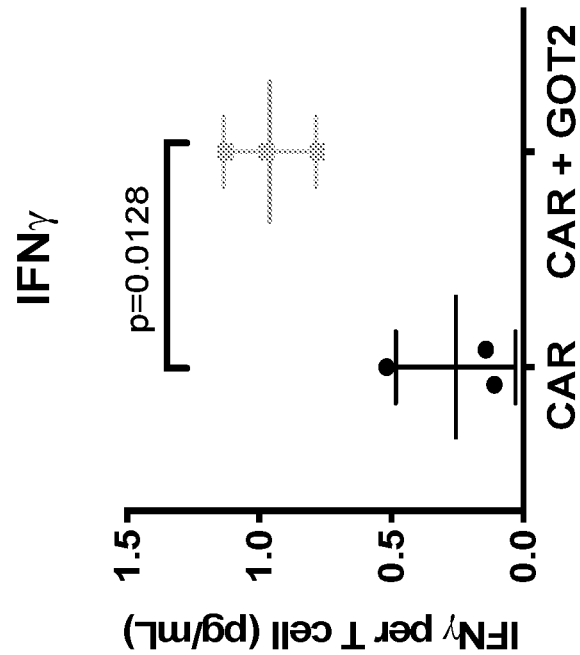
FIG. 20A and FIG. 20B are diagrams that show T cells co-expressing GOT2 (SEQ ID NO: 88) and anti-GPC3 CAR (SEQ ID NO: 104) demonstrate greater function after exposure to tumors in vivo relative to T cells expressing CAR alone.
Figure 20A:
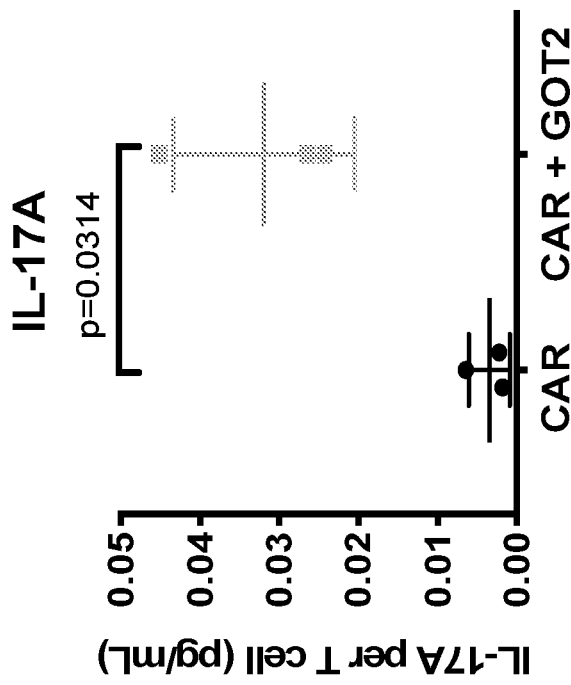

T cells within tumors from mice dosed with T cells co-expressing GOT2 and CAR demonstrated increased IFNγ and IL-17A production relative to T cells within tumors from mice dosed with T cells expressing CAR alone. FIGS. 20A-20B. These experiments demonstrate that expressing a Krebs cycle modulating polypeptide in T cells has a positive impact on T cell function in the tumor microenvironment.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one of skill in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of" will refer to the inclusion of exactly one element of a number or list of elements. In general, the term "or" as used herein to shall only be interpreted as indicating exclusive alternatives (i.e., "one or the other but not both") when preceded by terms of exclusivity, such as "either," "one of," "only one of" or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A genetically engineered hematopoietic cell, which has a modulated Krebs cycle as compared with a native hematopoietic cell of the same hematopoietic cell type;
   wherein the genetically engineered hematopoietic cell expresses:
   (i) a Krebs cycle modulating polypeptide, which is glutamic-oxaloacetic transaminase (GOT), isocitrate dehydrogenase (IDH), malate dehydrogenase (MDH), phosphoglycerate dehydrogenase (PHGDH), phosphoserine aminotransferase (PSAT1), glutamate dehydrogenase (GDH1), glutamate-pyruvate transaminase 1 (GPT1), or glutaminase (GLS); and
   (ii) a chimeric receptor polypeptide, which comprises
      (a) an extracellular target binding domain;
      (b) a transmembrane domain; and
      (c) a cytoplasmic signaling domain; and
   wherein the Krebs cycle modulating polypeptide is encoded by an exogenous nucleic acid; and wherein the transmembrane domain is from a membrane protein selected from the group consisting of CD8α, CD8β, CD137, CD27, CD28, CD34, CD4, FcεR1γ, CD16, CD134, CD32, CD64, CD45, CD5, CD9, CD22, CD37, CD80, CD86, CD40, CD154, VEGFR2, FAS, and FDFR2B.

2. The genetically engineered hematopoietic cell of claim 1, wherein the Krebs cycle modulating polypeptide is GOT, which is GOT1 or GOT2.

3. The genetically engineered hematopoietic cell of claim 1, wherein the chimeric receptor polypeptide is a chimeric receptor antigen (CAR) polypeptide, in which (a) is an extracellular antigen binding domain.

4. The genetically engineered hematopoietic cell of claim 1, wherein the chimeric receptor polypeptide further comprises at least one co-stimulatory signaling domain.

5. The genetically engineered hematopoietic cell of claim 1, wherein the chimeric receptor polypeptide further comprises a hinge domain, which is located at the C-terminus of (a) and the N-terminus of (b); and/or
   wherein the chimeric receptor polypeptide further comprises a signal peptide at its N-terminus.

6. The genetically engineered hematopoietic cell of claim 1, wherein the extracellular target binding domain of (a) in the CAR polypeptide is a single chain antibody fragment.

7. The genetically engineered hematopoietic cell of claim 4, wherein the at least one co-stimulatory signaling domain is of a co-stimulatory molecule selected from the group consisting of 4-1BB, CD28, $CD28_{LL \to GG}$ variant, OX40, ICOS, CD27, GITR, ICOS, HVEM, TIM1, LFA1, and CD2.

8. The genetically engineered hematopoietic cell of claim 7, wherein the at least one co-stimulatory signaling domain is a CD28 co-stimulatory signaling domain or a 4-1BB co-stimulatory signaling domain.

9. The genetically engineered hematopoietic cell of claim 1, wherein the cytoplasmic signaling domain of (c) is a cytoplasmic domain of CD3ζ or FcεR1γ.

10. The genetically engineered hematopoietic cell of claim 5, wherein the hinge domain is of CD28, CD16A, CD8α, or IgG.

11. The genetically engineered hematopoietic cell of claim 6, wherein the chimeric receptor polypeptide is a CAR polypeptide, which comprises (i) a CD28 co-stimulatory domain in combination with a CD28 transmembrane domain, a CD28 hinge domain, or a combination thereof, or (ii) a 4-1BB co-stimulatory domain in combination with a CD8α transmembrane domain, a CD8 hinge domain, or a combination thereof.

12. The genetically engineered hematopoietic cell of claim 6, wherein the CAR polypeptide comprises the amino acid sequence of SEQ ID NOs: 104 or 105.

13. The genetically engineered hematopoietic cell of claim 1, wherein the hematopoietic cell is a hematopoietic stem cell or an immune cell.

14. The genetically engineered hematopoietic cell of claim 13, wherein the hematopoietic cell is the immune cell, which is a T cell in which the expression of an endogenous T cell receptor, an endogenous major histocompatibility complex, an endogenous beta-2-microglobulin, or a combination thereof has been inhibited or eliminated.

15. The genetically engineered hematopoietic cell of claim 1, wherein the hematopoietic cell is an immune cell, which is derived from peripheral blood mononuclear cells (PBMC), hematopoietic stem cells (HSCs), or induced pluripotent stem cells (iPSCs).

16. The genetically engineered hematopoietic cell of claim 1, wherein the hematopoietic cell comprises a nucleic acid or nucleic acid set, which collectively comprises:

(A) a first nucleotide sequence encoding the Krebs cycle metabolite modulating polypeptide; and (B) a second nucleotide sequence encoding the chimeric receptor polypeptide.

17. The genetically engineered hematopoietic cell of claim 16, wherein the nucleic acid or the nucleic acid set is an RNA molecule or a set of RNA molecules; or wherein the nucleic acid or the nucleic acid set is comprised within a vector or a set of vectors.

18. The genetically engineered hematopoietic cell of claim 16, wherein the hematopoietic cell comprises the nucleic acid, which comprises both the first nucleotide sequence and the second nucleotide sequence.

19. The genetically engineered hematopoietic cell of claim 18, wherein the nucleic acid further comprises a third nucleotide sequence located between the first nucleotide sequence and the second nucleotide sequence, wherein the third nucleotide sequence encodes a ribosomal skipping site, an internal ribosome entry site (IRES), or a second promoter.

20. The genetically engineered hematopoietic cell of claim 18, wherein the third nucleotide sequence encodes a ribosomal skipping site, which is a P2A peptide.

21. A pharmaceutical composition, comprising a genetically engineered hematopoietic cell of claim 1, and a pharmaceutically acceptable carrier.

22. A method for inhibiting cells expressing a target antigen in a subject, the method comprising administering to a subject in need thereof a population of the genetically engineered hematopoietic cells set forth in claim 1.

23. The method of claim 22, wherein the subject is a human patient suffering from a cancer and the target antigen is a tumor antigen.

* * * * *